(12) United States Patent
Goldsbrough et al.

(10) Patent No.: US 7,217,857 B2
(45) Date of Patent: May 15, 2007

(54) ISOFORMS OF STARCH BRANCHING ENZYME II (SBE-IIA AND SBE-IIB) FROM WHEAT

(75) Inventors: Andrew Goldsbrough, Histon (GB); Steve Colliver, Brickhill (GB)

(73) Assignee: Monsanto UK Ltd (GB)

( * ) Notice: Subject to any disclaimer, the term of this patent is extended or adjusted under 35 U.S.C. 154(b) by 346 days.

(21) Appl. No.: 10/818,770

(22) Filed: Apr. 6, 2004

(65) Prior Publication Data

US 2004/0216188 A1 Oct. 28, 2004

Related U.S. Application Data

(62) Division of application No. 09/786,480, filed as application No. PCT/GB99/03011 on Sep. 9, 1999, now Pat. No. 6,730,825.

(30) Foreign Application Priority Data

Sep. 10, 1998 (EP) .................... 98307337

(51) Int. Cl.
*A01H 3/00* (2006.01)
*C12N 15/82* (2006.01)
*C12N 15/11* (2006.01)
*C12N 15/00* (2006.01)
*C12N 15/29* (2006.01)
*C12N 5/04* (2006.01)

(52) U.S. Cl. .............. 800/284; 800/278; 800/285; 800/286; 800/320.3; 435/468; 435/419; 435/320.1; 435/275; 536/23.1; 536/23.2; 536/23.6; 536/24.5

(58) Field of Classification Search .................... None
See application file for complete search history.

(56) References Cited

FOREIGN PATENT DOCUMENTS

| WO | WO 97/22703 | 6/1997 |
|---|---|---|
| WO | WO9722703 | * 6/1997 |
| WO | WO 99/14314 | 3/1999 |

OTHER PUBLICATIONS

Sun et al 1998 Plant Physiology 118:37-49.*
Sun et al GenBank accession AF064561.*
Tetlow et al 2004 Journal of Experimental Botony 55:2131-2145.*
Wang et al 1997 The Plant Journal 11:1121-1126.*
Sweetlove et al 1996 Journal of Biochemistry 320:493-498.*
Sun et al., "The two genes encoding starch-branching enzymes IIa and IIb are differentially expressed" *Plant Physiol.* 118:37-48 (1998).
Nair et al., "Isolation, characterization and expression of a starch branching enzyme II cDNA from wheat", *Plant Science* 122:153-163 (1997).
Chibber et al., "Genetic Engineering of Wheat for Starch Modification", *Proceedings: International Wheat Quality Conference*, Manhattan, KS, pp. 249-259 (Aug. 1997).
Kossmann et al., Transgenic Plants as a Tool to Understand Starch Biosynthesis, *Carbohydrate Bioengineering*, pp. 271-278, Petersen et al., Eds,, Elsevier Science B.V., Amsterdam (1995).
Allen et al., Accession No. ABK15494, "Wheat starch branching enzyme IIb cDNA" (May 2002).

* cited by examiner

*Primary Examiner*—David T. Fox
*Assistant Examiner*—Brent T Page
(74) *Attorney, Agent, or Firm*—Howrey LLP

(57) ABSTRACT

A class of wheat SBEII genes, called SBEII-1, can be used to influence properties of starch produced by a plant, including the gelatinization temperature of the starch. Such a starch is useful, for example, in certain industrial applications for the preparation or processing of foodstuffs such as bakery products.

13 Claims, 56 Drawing Sheets

Fig.2(iii).

Fig.3(iii).

Percent Similarity

| | 1 | 2 | 3 | 4 | 5 | 6 | | |
|---|---|---|---|---|---|---|---|---|
| 1 | ■ | 91.0 | 94.4 | 59.0 | 60.0 | 59.5 | 1 | B2.seq |
| 2 | 4.5 | ■ | 89.2 | 58.8 | 59.9 | 59.6 | 2 | B4.seq |
| 3 | 2.4 | 4.6 | ■ | 59.3 | 59.6 | 59.8 | 3 | B10.seq |
| 4 | 32.6 | 32.3 | 34.3 | ■ | 95.5 | 95.7 | 4 | A2.seq |
| 5 | 30.5 | 29.7 | 32.0 | 2.1 | ■ | 96.8 | 5 | B1.seq |
| 6 | 31.6 | 30.9 | 32.6 | 2.4 | 2.7 | ■ | 6 | B11.seq |
| | 1 | 2 | 3 | 4 | 5 | 6 | | |

Percent Divergence

Fig. 4A.

Percent Similarity

| | 1 | 2 | 3 | 4 | | |
|---|---|---|---|---|---|---|
| 1 | ■ | 88.7 | 81.7 | 85.0 | 1 | MaizeIIb.pro |
| 2 | 10.8 | ■ | 82.2 | 82.6 | 2 | B6.pro |
| 3 | 17.9 | 17.5 | ■ | 86.9 | 3 | B11.pro |
| 4 | 14.6 | 17.0 | 12.7 | ■ | 4 | MaizeIIa.pro |
| | 1 | 2 | 3 | 4 | | |

Percent Divergence

Fig. 4.

```
1    M Y D F M A L D R P S T P T I D R G I A L H K M I R L I T M    MaizeIIb.pro SEQ ID No:30
1    M Y D F M A L N G P S T P N I D R G I A L H K M I R L I T M    B6.pro SEQ ID No:7
1    M Y D F M A L D R P S T P R I D R G I A L H K M I R L V T M    B11.pro SEQ ID No:28
1    M Y D F M A L D R P S T P R I D R G I A L H K M I R L V T M    MaizeIIa.pro SEQ ID No:29

31   G L G G E G Y L N F M G N E F G H P E W I D F P R G P Q R L    MaizeIIb.pro
31   G L G G E G Y L N F M G N E F G H P E W I D F P R G P Q V L    B6.pro
31   G L G G E G Y L N F M G N E F G H P E W I D F P R G P Q T L    B11.pro
31   G L G G E G Y L N F M G N E F G H P E W I D F P R G P Q S L    MaizeIIa.pro 61   P S G K F I P G N N N S Y D K C R R R F D L G D A D Y L R Y    MaizeIIb.pro
61   P S G K F I P G N S N S Y D K C R R R F D L G D A E F L R Y    B6.pro
61   P T G K V L P G N N N S Y D K C R R R F D L G D A D F L R Y    B11.pro
61   P N G S V I P G N N N S F D K C R R R F D L G D A D Y L R Y    MaizeIIa.pro 91   H G M Q E F D Q A M Q H L E Q K Y E F M T S D H Q Y I S R K    MaizeIIb.pro
91   H G M Q Q F D Q A M Q H L E E K Y G F M T S D H Q Y V S R K    B6.pro
91   R G M Q E F D Q A M Q H L E E K Y G F M T S E H Q Y V S R K    B11.pro
91   R G M Q E F D Q A M Q H L E G K Y E F M T S D H S Y F S R K    MaizeIIa.pro 121  H E E D K V I V F E K G D L V F V N F H C N N S Y F D Y R     MaizeIIb.pro
121  H E E D K V I V F E K G D L V F V N F H W S N S Y F D Y R     B6.pro
121  H E E D K V I I F E R G D L V F V N F H W S N S F F D Y R     B11.pro
121  H E E D K V I I F E R G D L V F V N F H W S N S Y F D Y R     MaizeIIa.pro 151  I G C R K P G V Y K V V L D S D A G L F G G F S R I H H A A   MaizeIIb.pro
151  V G C L K P G K Y K V V L D S D A G L F G G F G R I H H T A   B6.pro
151  V G C S K P G K Y K V A L D S D D A L F G G F S R L D H D V   B11.pro
151  V G C F K P G K Y K I V L D S D D G L F G G F S R L D H D A   MaizeIIa.pro 181  E H F T A D C S H D N R P Y S F S V Y T P S R T C V V Y A P   MaizeIIb.pro
181  E H F T S D C Q H D N R P H S F S V Y T P S R T C V V Y A P   B6.pro
181  D Y F T T E H P H D N R P R S F L V Y T P S R T A V V Y A L   B11.pro
181  E Y F T A D W P H D N R P C S F S V Y A P S R T A V V Y A P   MaizeIIa.pro 211  V - - - E .                                                   MaizeIIb.pro
211  M - - - N .                                                   B6.pro
211  T - - - E .                                                   B11.pro
211  A G A E D E                                                   MaizeIIa.pro
```

Decoration 'Decoration #1': Shade (with solid black) residues that differ from MaizeIIb.pro.

Fig.5.

```
         10         20         30         40         50         60
ACTAACAGCA AGGTGCAGCA TACGGGTGCG GCTAGTAGCA GCTAGTAGCA AGAAAAATCG  60
TACGGTCAAT ACAGCCAGGT GCAAGTTTTA ATAAGGATTT TTTGCTTCAA CGAGTCCTGG  120
ATAGACAAGA CAACATGATG TGTGGCGTG  TGCTCCCAAT CCCAGGGCG  TTGTGAAGAA  180
AACATGCTCA TCTGTGTTAT GATTTTATGG ATCAGGACG  AAACTTCCCC CAAATACCCA  240
TGCCTCCTTA AATCTTTGTG GCCGTAAACC ATTGCTAGTG TCCTCTAAAT TGACAGTTTA  300
         310        320        330        340        350        360
GCATAGAGGT TTTACTTTG  TATCTCTTT  TTGACAGTTTA GACTTTATTC CTCAAATAAT  360
CGACCAGTCG TTTACTCG   378   (SEQ ID No : 8)
```

Fig. 7.

```
         10         20         30         40         50         60
         |          |          |          |          |          |
ACTAAACAGC AAGTGCAGC ATACGCATGC ACGCTGTTGT TGCTAGCACT AGCAAGAAAA   60
AATCGTATGG TCAATACAAC CAGGTGCAAG GATGATGTGC GTTTAATAAG GGTTTTGCT  120
CTGGATAGAC AAGACAACAT GATGATGTGC TCTGTGCTCC CAAATTCCCA GGGGTTGXG  180
XGGAAACAT GCTCATCTGT GTTATCATTT TATGGATCAG XGXGGAAACC TCCCCAAAT   240
ACCCATGCCT CCTTAAACTT TTGTGGTCCT AAACCATGGC TACTATCCTC TAAATTGGCA  300
         310        320        330        340        350        360
         |          |          |          |          |          |
GTTTAGCATA GAGGTTTTAC TTTTGTAAAT AGTTAATAGA CTCTATTCCT             360
CAAATAATTG ACATGTCCTT TACAAGAAGA TGAGAAATAA AATCAGGGAT TGAAGAATCC  420
CAAAAGCT   428    (SEQ ID No : 10)
```

Fig. 8(iii).

```
409 GTTGTTTACTCGAAGNTGAGAAATAAAATC  B10-3'.seq
367 GTCGTTTTACTCG                    B2-3'.seq
375 GTCGTCTTTACAAGAAGATGAGAAATAAAATC B4-3'.seq
209 CGCTTTC                          ZMSBE2b-3'.seq 439 AGAGATTGNAG                       B10-3'.seq
378                                   B2-3'.seq
405 AGGGATTGAAGAAATCCCAAAAGCT         B4-3'.seq
216                               CT  ZMSBE2b-3'.seq
```

Decoration 'Decoration #1': Shade (with solid black) residues that differ from B10-3'.seq.

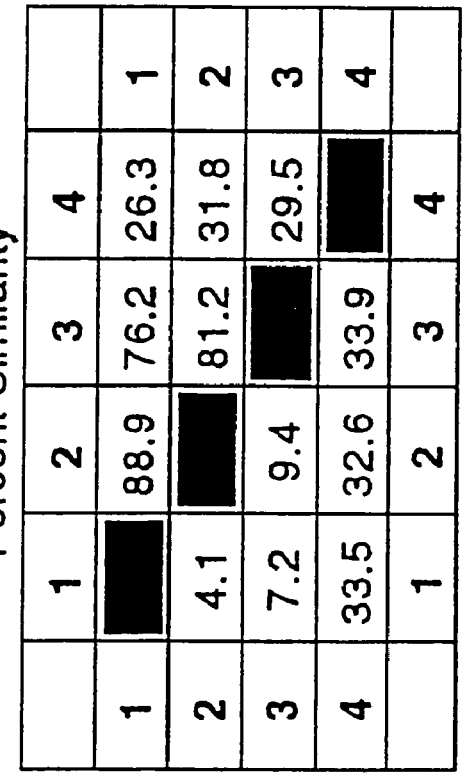

Fig. 8A.

Percent Similarity / Percent Divergence

| | 1 | 2 | 3 | 4 | |
| --- | --- | --- | --- | --- | --- |
| 1 | | 88.9 | 76.2 | 26.3 | B10-3'.seq |
| 2 | 4.1 | | 81.2 | 31.8 | B2-3'.seq |
| 3 | 7.2 | 9.4 | | 29.5 | B4-3'.seq |
| 4 | 33.5 | 32.6 | 33.9 | | ZMSBE2b-3'.seq |
| | 1 | 2 | 3 | 4 | |

Fig. 10(i).

```
CATYGACGGCCAGTGACTTCGAGCTCGGTACCCGGGATCCGATTGGTGTGTGGGAGATGTTCTTGCCAAACAATGCAGATGGTTCGCC  90  SEQ ID No:1
 I  D  G  Q  .  L  R  A  R  Y  P  G  I  R  F  G  V  W  E  M  F  L  P  N  N  A  D  G  S  P      SEQ ID No:2

ACCAATTCCTCACGGCTCACGGGTGAAGGTGAGAATGGATATACTCCATCTGGGATAAAGGATTCAATTCCTGCTTGGATCAAGTACTCCGT  180
 P  I  P  H  G  S  R  V  K  V  R  H  D  T  P  S  G  I  K  D  S  I  P  A  W  I  K  Y  S  V

GCAGACTCCAGGAGAGATATACCATACACAATGGAATATATTATGATCTCCCGAAGAGAGAAGTATGTATTCAAGCATCCTCAACCTAAACG  270
 Q  T  P  G  Q  I  P  Y  N  G  L  Y  Y  Q  P  P  E  E  K  Y  V  F  K  H  P  Q  P  K  R

ACCAAAATCATTGCGGATATATGAAACACATGTTGGCATGAGTAGCCCGGAACCAAAGATCAACACATGCAAACTTCAGGGATGAGGT  360
 Q  T  P  G  Q  I  P  Y  N  G  L  Y  Y  Q  P  P  E  E  K  Y  V  F  K  H  P  Q  P  K  R (further lines)
 P  K  S  L  R  I  Y  E  T  H  V  G  H  S  S  P  E  P  K  I  N  T  Y  A  N  F  R  D  E  V GCTTCCAAGAATTAAAAGACTTGGATACAATGCAGTGCAAATAATGGCAATCCAGGAGCACTCATACTATGGAAGCTTTGGGTACCATGT  450
 L  P  R  I  K  R  L  G  Y  N  A  V  Q  I  M  A  I  Q  E  H  S  Y  Y  G  S  F  G  Y  H  V TACCAATTTCTTTGCACCAAGTAGCCGTTTTGGGTCCCCAGAAGATTAAAATCTTTGATTGATAGAGCTCACGAGCTTGGCTTGGTTGT  540
 T  N  F  F  A  P  S  S  R  F  G  S  P  E  D  L  K  S  L  I  D  R  A  H  E  L  G  L  V  V CCTCATGGATGTTGTTCACAGTAGCAATCACTGGATGTGGGATTCCCGTGTGTTAACTATGGAATAAGGAAGTTATAAGGTTTCTACTTTCCAATGCAAG  630
 L  M  D  V  V  H  S  H  A  S  N  T  L  D  G  L  N  G  F  D  G  T  D  T  H  Y  F  H  G CGGTTCACGGGGCCATCACTGGATGTGGGATTCCCGTGTGTTAACTATGGAATAAGGAAGTTATAAGGTTTCTACTTTCCAATGCAAG  720
 G  S  R  G  H  H  W  W  D  S  R  V  F  N  Y  G  N  K  E  V  I  R  F  L  L  S  N  A  R ATGGTGGCTAGAGGAGTATAAGTTTGATGGTTTCCGATTCGATGGCGCGACCTCCATGATGTATACCCATCATGGATTACAAGTAACCTT  810
 W  W  L  E  E  Y  K  F  D  G  F  R  F  D  G  A  T  S  M  M  Y  T  H  H  G  L  Q  V  T  F
```

Fig. 10(ii).

```
TACAGGAAGCTACCATGAATATTTGGCTTTGCCACTGATGTAGATGCGTCGTTACTTGATGCTGATGAATGATCTAATTCATGGGTT  900
         T  G  S  Y  H  E  Y  F  G  F  A  T  D  V  D  A  V  V  Y  L  M  L  M  N  D  L  I  H  G  F

TTATCCTGAAGCCGTAACTATCGGTGAAGATGTTAGTGGAATGCCTACACATTTGCCCTTCCTGTTCAAGTTGGTGGGGTTGGTTTTGACTA  990
Y  P  E  A  V  T  I  G  E  D  V  S  G  M  P  T  F  A  L  P  V  Q  V  G  G  V  G  F  D  Y

TCGCTTACATATGGCTGTTGCCGACAAATGATTGAACTTCTCAAAGGAAACGATGAAGCTTGGGAGATGGGTAATATTGTGCACACACT  1080
         R  L  H  M  A  V  A  D  K  W  I  E  L  L  K  G  N  D  E  A  W  E  M  G  N  I  V  H  T  L

AACAAACAGAAGGTGGCCGAAAAGTGTGTTACTTATGCTGAAAGTCACGATCAAGCACTGGTTGGAGACAAGACTATTGCATTCTGGTT  1170
T  N  R  R  W  P  E  K  C  V  T  Y  A  E  S  H  D  Q  A  L  V  G  D  K  T  I  A  F  W  L

GATGGACAAGGATATGTATGATTTCATGGCTCTGAACGACCTTGACACCTAGTATTGATCGTGAATAGCACTGCATAAAATGATTAG  1260
         M  D  K  M  Y  D  F  M  A  L  N  G  P  S  T  P  S  I  D  R  G  I  A  L  H  K  M  I  R

ACTTATCACAATGGGTTAGGAGGAGAGGGTTATCTTAACTTTATGGAAATGAGTTCGGGCATCCTGAATGATAGACTTTCCAAGAGG  1350
L  I  T  M  G  L  G  G  E  G  Y  L  N  F  M  G  N  E  F  G  H  P  E  W  I  Q  F  P  R  G

CCCACAAGTACTTCCAACTGGTAAGTTCATCCCAGGAAACAACAACAGTTACGACAAAATGCCGTCGAAGATTTGACCAGGTGATGCAGA  1440
P  Q  V  L  P  T  G  K  F  I  P  G  N  N  S  Y  Q  K  C  R  R  R  F  D  Q  G  D  A  E

AITTCTTAGGTATCATGGTATGCAGCAGTTTGATCAGGCGATGCAGCATCTTGAGGAAAAATATGGCTTTATGACATCAGACCACCAGTA  1530
         F  L  R  Y  H  G  M  Q  Q  F  D  Q  A  M  Q  H  L  E  E  K  Y  G  F  M  T  S  D  H  Q  Y

CGTATCTCGGAAACATGAGGAAGATAAGGTGATCGTGTTTGAAAAAGGGGACTTGGTATTTGTGTTCAACTTCCACTGGAGTAATAGCTA  1620
V  S  R  K  H  E  E  D  K  V  I  V  F  E  K  G  D  L  V  F  V  F  N  F  H  W  S  N  S  Y
```

Fig. 10(iii).

```
TTCGACTACCGGGTTGGCTGTGTTAAAGCCTGGGAAGTACAAGGTTGTCTTAGACTCAGACGCCCGACTCTTTGGTGGATTTGGTAGGAT  1710
 F  D  Y  R  V  G  C  L  K  P  G  K  Y  K  V  V  L  D  S  D  A  G  L  F  G  G  F  G  R  I

CCATCACACTGCAGAGCACTTCACTTCTGACTGCCAACATGACAACAGGCCCCATTCGTTCTCAGTGTACACTCCTAGCAGAACCTGTGT  1800
 H  H  T  A  E  H  F  T  S  D  C  Q  H  D  N  R  P  H  S  F  S  V  Y  T  P  S  R  T  C  V

TGTCTATGCTCCAATGAACTAAACAGCAAAGTGCAGCATACGCCATGCACGCTGTTGTTGCTAGCACTAGCAAGAAAATCGTATGGTCA  1890
 V  Y  A  P  M  N  .  T  A  K  C  S  I  R  M  H  A  V  V  A  S  T  S  K  K  K  S  Y  G  Q

ATACAACCAGGTGCAAGGTTTAATAAGGGTTTGCTTCAACGAGTCCTGGATAGACAAGACAACATGATGTGCTCTGTGCTCCAAAT  1980
 Y  N  Q  V  Q  G  L  I  R  V  C  F  N  E  S  W  I  D  K  T  T  .  C  A  L  C  S  Q  I

TCCCAGGGCGTTGTGGAGAAAAAATGCTCATCTGTGTTATTTTATGGATCAGGANGAAACCTCCCCCAAANACCCTTTTTTTTGAA  2070
 P  Q  G  V  V  E  K  N  A  H  L  C  Y  F  M  D  Q  Q  ?  N  L  P  Q  ?  P  L  F  F  L  K

AGGNGGATAGGCCCCGGTNTCTGCATNTGGATGCCTCCTTAAATNTTTGTAGCCATAAACCATTGCTAGTGTCCTNTAAATTGACAGTT  2160
 G  G  .  A  P  G  ?  C  ?  W  M  P  P  .  ?  F  V  A  I  N  H  C  .  C  P  ?  N  .  Q  F

TAGAATAGNGGTTNTACTTTTGTATTTNTTTTTGACAGTTAGACTGTATTCCTCAAATAATCGACATGTTGTTACTCGAAGNTGAGAA  2250
 R  I  ?  ?  L  L  Y  F  F  D  S  .  T  V  F  L  K  .  S  T  C  C  L  L  E  ?  E  K

ATAAAATCAGAGATTGNAGNAAAAAAAAAAAAAAAAAAAAAAAAAAAAA  2307
 .  N  Q  R  L  ?  ?  K  K  K  K  K  K  K  K  K  N
```

Fig. 11(iii).

```
         XX    XX    LX       XXX    XXXXXXXXXXXXXKKKK-       Majority
         1010       1020              1030              1040
2170                        .TMLEYGGN--G--A...KK                TASBE1D2
2764  LSVCKKKKKRHEDEDAL PHRPLLAISPAAP-LPSRC.PAR                 TASBEI
2204  ----TVFLK.S-TCC L-----EDEK.NQRLKKKKKKKKKK                 OsbeII-1All
2905  ----LH--VNI----------IF...VIP.KKKKKK                      Wheat SBEII-2
```

Decoration 'Decoration #1': Shade (with solid black) residues that match the Consensus exactly.

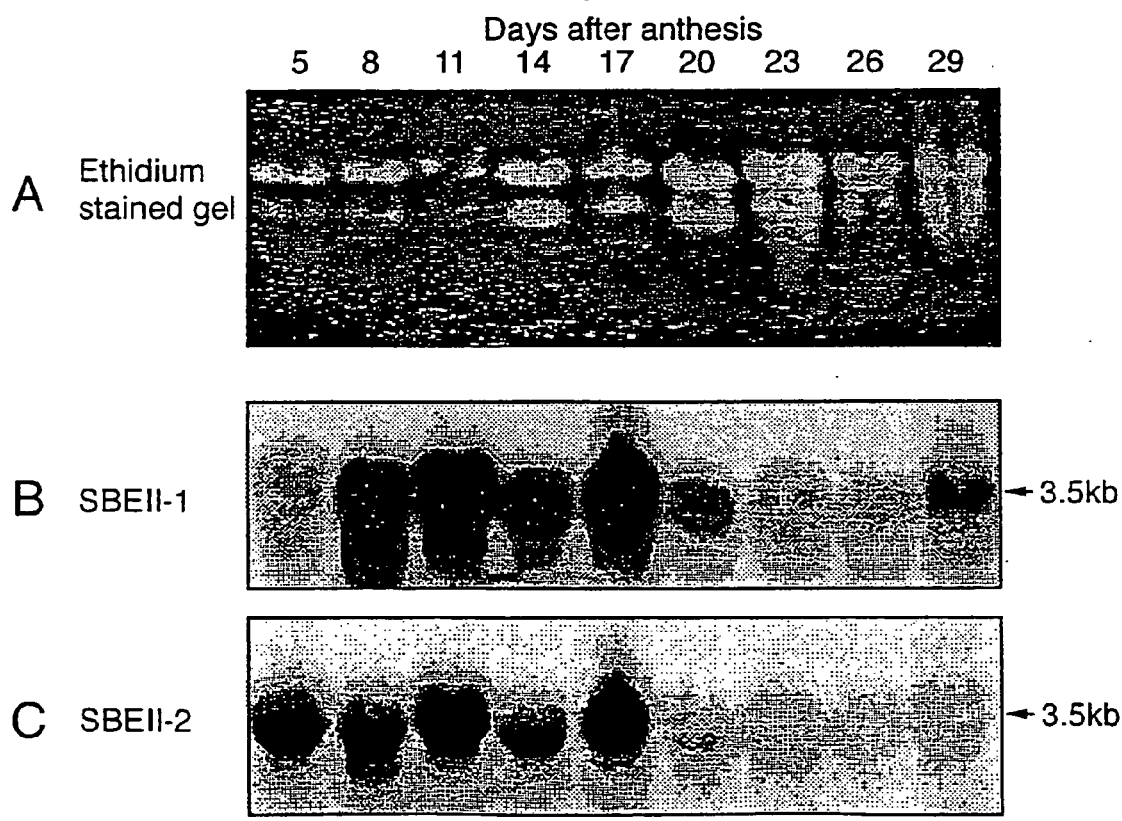

Fig. 13A.

```
         10        20        30        40        50        60        70
AAGCTTGCATGCCTGCAGGTCGACTCTAGAGGATCCCCGGGTAGTTGGGAGCCTACCCAGATTTCATG    70
ATTAACTGTGCTATTGAATTGTTGAAAATGGTTGTCTGTCGTATCCGACGATAACGGAAACCCGTCC   140
GAAATTCAATGGGCATGGCATAGATATAGATTTGTACCCACTACTAGTGTCGCAGGCGATATTGG     210
TTGCAACCGCAGATATAGTTTCGGGAAAAGGATTAGGCTCAGCTCCATCCCTAGACCCACTTGTGT    280
GTGGGGGGTCTACCCTTCAAAGGAAAAAAAACTACACACAGTGCATATAAGAAGATGAATATTCCAAA  350

360       370       380       390       400       410       420
ATTCAGCAGTCAAGAAGCCCTGATAAACTGTCTGGCATAGCTAGTACTTTATACACTTCAAGACCAAAAG 420
AAATCACTAAGTACAGATTTAGTGACTCGTAAGTACAGATATCATCTTACAAGGCCCAGCCCAGCGACC  490
TATTACACAGCCCGCTCGGGCCCGACGTCGGGACACATCTTCTTCCCCCCTTTGGTGAAGCTCTGCTC   560
GCAGCTGTCCGGCTTGCGTTCGTGGCAGATTCATCTCATCTCGTCGTCGTCGTCTTCCTGGG         630
TAGCTTGTGCAGTGACATGGTCTGAGCAGCTTAAAATTGCTCGTAGACGAGAGTACCAGCA           700

710       720       730       740       750       760       770
CAGCACGTTGCGGATTTCTCTGCCCTGTGAAGTGCAACGTCTAGGATTGTCACACGCCTTGGTCGCGTCGA  770
TGCGGTGGTGAGCAGCAGCAACAGCAACAGTCGGCGGCCCAAAGTTGGCTTCCGTGTCTTCGTCGTACG   840
CGCGCGCCCGGGACACGCAGAGAGCGGAGAGCGGAGCCGTGCACGGGAGGTGGTGTGCAAGTGCAGCCG   910
CGCGCCCCGCGCCCGGTGGGCGCCCAACCCACGAGCGGGCAACCCAAAAAGTACCCACGAAGGCGCCAAAGCGATCC 980
AAGCTCCGGAACGCATCAGCCACAAGCAGCCGAGAACCGAACCGGTGGGCGACGCGTCGTGGGACGGACG 1050
```

Fig.13A(Cont).

```
     1060       1070       1080       1090       1100       1110       1120
      |          |          |          |          |          |          |
CGGGCGACGCGCTTCCAAACGGGGCCACGTACGCGCCGGCCGTGTGCGTGCTGCGTGCGGCAAGG       1120
CGAGGCAGCCCCCGATCGGGAAAGCGTTTGGGGCGGAGCGTGCGGGTCAGTCGCTGGTGCGCA       1190
GTGCCGGGGGAACGGGGTATCGTGGGGCGCGGGAGAGAGCGTGGCAGGCCGAGAGCAGCGCG       1260
GCCGGGTCACGCAACGCGCCCCACGTACTGCCCTCCCCGCGCTAGAAATACCGAGGCCTGGA       1330
CCGGGGGCCCCCGTCACATCCATCGACCGATCGCCACAGCCAACACGGCCACCCCGCCGAGGCG      1400
      1410       1420       1430       1440       1450       1460       1470
       |          |          |          |          |          |          |
ACGGCGACAGCCGCCAGGAGGAGGAATAAACTCACTGCCAGCCCAGTGAAGGGGAGAAGTGTACTGCTCC 1470
GTCGACTCTAGAGGATCC 1488   (SEQ ID NO:55)
```

Fig. 26.

```
         10         20         30         40         50         60
GAGCTCCGTT TCGCATGATT GAACAAGATG GATTGCACGC AGGTTCTCCG GCCGCTTGGG    60
TGGAGAGGCT ATTCGGCTAT GACTGGGCAC AACAGACAAT CGGCTGCTCT GATGCCGCCG   120
TGTTCCGGCT GTCAGCGCAG GGGCGCCCGG TTCTTTTTGT CAAGACCGAC CTGTCCGGTG   180
CCCTGAATGA ACTGCAGGAC GAGGCAGCGC GGCTATCGTG GCTGGCCACG ACGGGCGTTC   240
CTTGCGCAGC TGTGCTCGAC GTTGTCACTG AAGCGGGAAG GGACTGGCTG CTATTGGGCG   300

310        320        330        340        350        360
AAGTGCCGGG GCAGGATCTC CTGTCATCTC ACCTTGCTCC TGCCGAGAAA GTATCCATCA   360
TGGCTGATGC AATGCGGCGG CTGCATACGC TTGATCCGGC TACCTGCCCA TTCGACCACC   420
AAGCGAAACA TCGCATCGAG CGAGCACGTA CTCGGATGGA AGCCGGTCTT GTCGATCAGG   480
ATGATCTGGA CGAAGAGCAT CAGGGGCTCG CGCCAGCCGA ACTGTTCGCC AGGCTCAAGG   540
CGGCCATGCC CGACGGCGAG GATCTCGTCG TGACCCATGG CGATGCCTGC TTGCCGAATA   600

610        620        630        640        650        660
TCATGGTGGA AAATGGCCGC TTTTCTGGAT TCATCGACTG TGGCCGGCTG GGTGTGGGCG   660
ACCGCTATCA GGACATAGCG TTGGCTACCC GTGATATTGC TGAAGAGCTT GGCGGCGAAT   720
GGGCTGACCG CTTCCTCGTG CTTTACGGTA TCGCCGCTCC CGATTCGCAG CGCATCGCCT   780
TCTATCGCCT TCTTGACGAG TTCTTCTGAG Ctc 813 (SEQ ID No:35)
```

Fig.29(i).

Pst I

Xba I

```
TTAGCTGAATCCGGCGGGCATGGCAAGGTAGACTGCAGTGCAGCCGGTGACCCGGTCGTGCCCCTCTGAGAGATAATGAGCA
----+----+----+----+----+----+----+----+----+----+----+----+----+----+----+----+      80
AATCGACTTAGGCCGCCCGTACCGTTCCATCTGACGTCACGTCGGCCACTGGGCCAGCACGGGAGAGATCTCTATTACTCGT

TTGCATGTCTAAGTTATAAAAAATTACCACATATTTTTTTGTCACACTTGTTTGAAGTGCAGTTTATCTATCTTTTATAC
----+----+----+----+----+----+----+----+----+----+----+----+----+----+----+----+     160
AACGTACAGATTCAATATTTTTAATGGTGTATAAAAAAACAGTGTGAACAAACTTCACGTCAAATAGATAGAAATATG

Sca I

ATATATTTAAACTTTACTCTACGAATAATAATCTATAGTACTACACAATAATATCAGTGTTTTAGAGAATCATATAAATG
----+----+----+----+----+----+----+----+----+----+----+----+----+----+----+----+     240
TATATAAATTTGAAATGAGAATGCTTATTATTAGATATCATGATTATATAGTCACAAAATCTCTTAGTATATTTAC

AACAGTTAGACACATGGTCTAAAGGACAATTGAGTATTTGACAACAGGACTCTACAGTTTTATCTTTTTAGTGTGCATGTG
----+----+----+----+----+----+----+----+----+----+----+----+----+----+----+----+     320
TTGTCAATCTGTACCAGATTCCTGTTAACTCATAAACAAACTGTTCCTGAGATGTCAAAATAGAAAAATCACACGTACAC

TTCTCCCTTTTTTTTGCAAATAGCTTCACCTATATAATACTTCATCCATTTATTAGTACATCCATTTAGGGTTTAGG
----+----+----+----+----+----+----+----+----+----+----+----+----+----+----+----+     400
AAGAGGAAAAAAAACGTTTATCGAAGTGGATATATTACATCTATTTTATTCTATTTTAGCCTCTAAATTAAGAAAACTAAAACT

GTTAATGGTTTTTATAGACTAATTTTTTTAGTACATCTATTTTATTCTATTTTAGCCTCTAAATTAAGAAAACTAAAACT
----+----+----+----+----+----+----+----+----+----+----+----+----+----+----+----+     480
CAATTACCAAAAAATATCTGATTAAAAAAATCATGTAGATAAAAATCGGAGATTAATTCTTTTGATTTTGA

CTATTTTAGTTTTTTATTTAATAATTTAGATATAAAATAAATTATTTTATCTATTTTATTTCACTGATTTTAATTTCCTTT
----+----+----+----+----+----+----+----+----+----+----+----+----+----+----+----+     560
GATAAAATCAAAAAATAAATTATTAAATCTATATTTTATCTTATTTATTTAAACAAATACCCTTT
```

Fig.29(ii).

```
                                                                          Sal I
AAGAAATTAAAAAAACTAAGGAAACATTTTTCTTGTTTCGAGTAGATAATGCCAGCCTGTTAAACGCCGTCGACGCAGTC
TTCTTTAATTTTTTGATTCCTTTGTAAAAAGAACAAAGCTCATCTATTACGGTCGGACAGCTGCGGCAGCTGCGTCAG   640

TAACGGACACCAACCAGCGAACCAGCGTCGCGTCGGGCCAAGCGAACGACAGCGGCACGGGCATCTCTGTCGCTCCTC
ATTGCCTGTGTGGTTGGTCGCTTGGTCGCTCGCAGCGACGCAGCCCGGTTCGCCTCGTGCCGTAGAGACAGCAGGACGAG   720
    Kpn I
GGTACCGGACTTCGTCCGCTGTCGGCATCCAGAAATTGCGTGGCGGAGCGGCAGACGTGAGCGGCACGGCAGGCGGCCT
CCATGGCCTGAAGCAGCAGGACACAGCCGTAGGTCTTTAACGCACCGGCCGCTCGCCGTGCCGTCGCCGTCCGCCGGA   800

CCTCCTCCTCTCACGGCACCGGCCAGCTACGGGGATTCCTTTCCACCCGCTCCTTCGCTTTCCCTTCGCCCGCCGTA
GGAGGAGAGAGTGCCGTGGCCGTCGATGCCCCCCTAAGGAAAGGGTGGCGAGGAAGCGAAGAGGAGCGGGGCAT   880

ATAAATAGACACCCCCTCCACACCCTCTTTCCCAACCTCGTTGTTCGGAGCCGCACACACAACCAGATCTCCCC
TATTTATCTGTGGGGGAGGTGTGGGAGAAAGGGTTGGAGCACACAACAAGCCTCGCGTGTGTGTGTCTAGAGGGG   960

Xba I
CAAATCCACCCGTCGGCACCTCAAGGTACGCGCTCGTCTCCCCCCCCCTCTACCTTCTCTAGATCGGCGT
GTTTAGGTGGGCAGCCGTGGAGGCGAAGTTCCATGCGCGAGCAGGAGGGGGAGAGATGAAGAGATCTAGCCGCA   1040
  Ncol
  Sty I    Apa I
TCCGGTCCATGGTTAGGGCCCGGTAGTTCTACTTCTGTTCATGTTTGTGTTAGATCCGTGTTTGTGTTAGATCCGTGCTG
AGGCCAGGTACCAATCCCGGGCCATCAAGATGAAGACAAGTACAAACACAATCTAGGCACAAACACAATCTAGGCACGAC   1120
```

Fig. 29(iii).

```
                                        Afl III
                                        .....
CTAGCGTTCGTACACGGATGCGACCTGTACGTCAGACACGTTCTGATTGCTAACTTGCCAGTGTTCTCTTTGGGAATC
----+----+----+----+----+----+----+----+----+----+----+----+----+----+----+ 1200
GATCGCAAGCATGTGCCTACGCTGGACATGCAGTCTGTGCAAGACTAACGATTGAACGGTCACAAAGAGAAACCCTTAG

Cla I
                .....
CTGGGATGGCTCTAGCCGTTCCGCAGACGGGATCGATTTCATGATTTTTTTGTTCGTTGCATAGGGTTTGGTTTGCCC
----+----+----+----+----+----+----+----+----+----+----+----+----+----+----+ 1280
GACCCTACCGAGATCGGCAAGGCGTCTGCCCTAGCTAAAGTACTAAAAAAACAAGCAACGTATCCCAAACAAACGGG

TTTTCCTTTATTTCAATATATGCCGTGCACTTGTTTGTCGGGTCATCTTTTCATGCTTTTTTTGTCTTGGTTGTGATGA
----+----+----+----+----+----+----+----+----+----+----+----+----+----+----+ 1360
AAAAGGAAATAAAGTTATATACGGCACGTGAACAAACAGCCCAGTAGAAAAGTACGAAAAAAACAGAACCAACACTACT

Xba I       EcoR I
                .....       .....
TGTGGTCGTTGGGCGGTTCGTTCTAGATCGGAGTAGAATTCTGTTTCAAACTACCTGGTGGATTTATTAATTTTGGATC
----+----+----+----+----+----+----+----+----+----+----+----+----+----+----+ 1440
ACACCAGACAACCCGCCAAGCTAGCTAGCCTCATCTTAAGACAAAGTTTGATGGACCACCTAAATAATTAAAACCTAG

Cla I               Afl III
                                                .....               .....
TGTATGTGTGTGCCATACATATTCATATAGTTACGAATTGAAGATGATGGAAATATCGATCTAGGATAGGTATACATG
----+----+----+----+----+----+----+----+----+----+----+----+----+----+----+ 1520
ACATACACACACGGTATGTATAAGTATCAATGCTTAACTTCTACTACCTTTATAGCTAGATCCTATCCATATGTAC

Nsi I
        .....
TTGATGCGGGTTTTACTGATGCATATACAGAGATGCTTTTGTTCGCTTGGTTGTGATGATGTGGTGTTGGGCGGTCG
----+----+----+----+----+----+----+----+----+----+----+----+----+----+----+ 1600
AACTACGCCCAAAATGACTACGTATATGTCTACGAAAACAAGCGAACCAACACTACTACCACCAACCCGCCAGC
```

Fig.29(iv).

```
                Xba I
TTCATTCGTTCTAGATCGGAGTAGAATACTGTTTCAAACTACCTGGTGTATTTATTAATTTTGGAACTGTATGTGTGT
----+----+----+----+----+----+----+----+----+----+----+----+----+----+----+----  1680
AAGTAAGCAAGATCTAGCCTCATCTTATGACAAAGTTTGATGGACCACATAAATAATTAAAACCTTGACATACACACA

Cla I            Afl III
CATACATCTTCATAGTTACGAGTTTAAGATGGAAATATCGATCTAGGATAGTATACATGTTGATGTGGGTTTTAC
----+----+----+----+----+----+----+----+----+----+----+----+----+----+----+----  1760
GTATGTAGAAGTATCAATGCTCAAATTCTACCTCCTTTATAGCTAGATCCTATCCATATGTACAACTACACCCAAAATG

Nsi I
TGATGCATATACATGATGGCATATGCAGCATCTATTCATATGCTCTAACCTTGAGTACCTATCTTATTATAATAAACAAGT
----+----+----+----+----+----+----+----+----+----+----+----+----+----+----+----  1840
ACTACGTATATGTACTACCGTATACGTCGTAGATAAGTATACGAGATTGGAACTCATGGATAGATAATATTATTTGTTCA

ATGTTTTATAATTATTTTGATCTTGATATACTTGGATGATGGCATATATGCAGCAGCTATATGTGGATTTTTTTAGCCCTGC
----+----+----+----+----+----+----+----+----+----+----+----+----+----+----+----  1920
TACAAAATATTAATAAAACTAGAACTATATGAACCTACTACCGTATACGTCGTCGATATACACCTAAAAAAATCGGGACG

Pst I
CTTCATACGCTATTTATTGCTTGGTACTGTTCTTTTTGTCGATGCTCACCCTGTTGTTGGTGTTACTTCTGCAGATGC
----+----+----+----+----+----+----+----+----+----+----+----+----+----+----+----  2000
GAAGTATGCGGATAAATAAACGAACCATGACAAGAAAAACAGCTACGAGTGGGACAACAAAACCACAATGAAGACGTCTACG

AGATCTTTGTGAAAACCCTGACTGGCAAGACTATCACC
----+----+----+----+----  2038    (SEQ ID No : 52)
TCTAGAAACACTTTTGGGACTGACCGTTCTGATAGTGG
```

Fig.36.
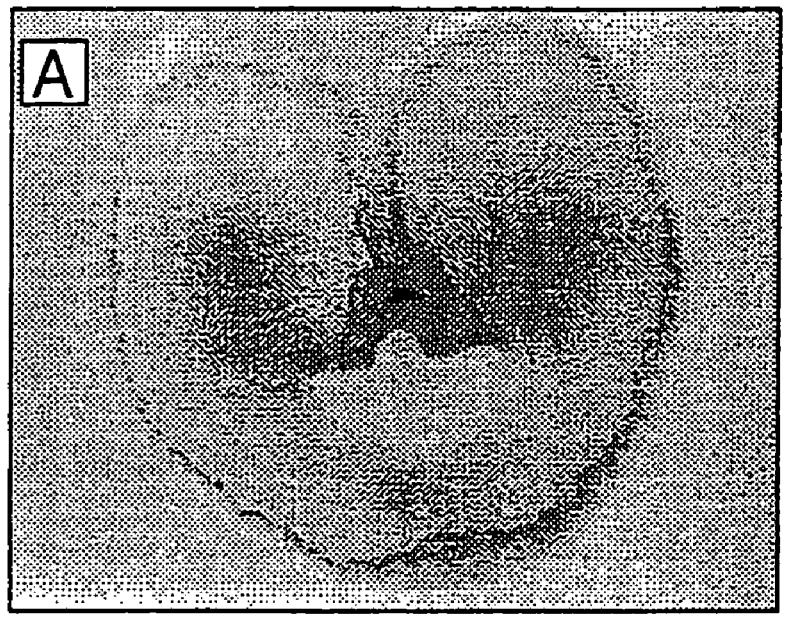
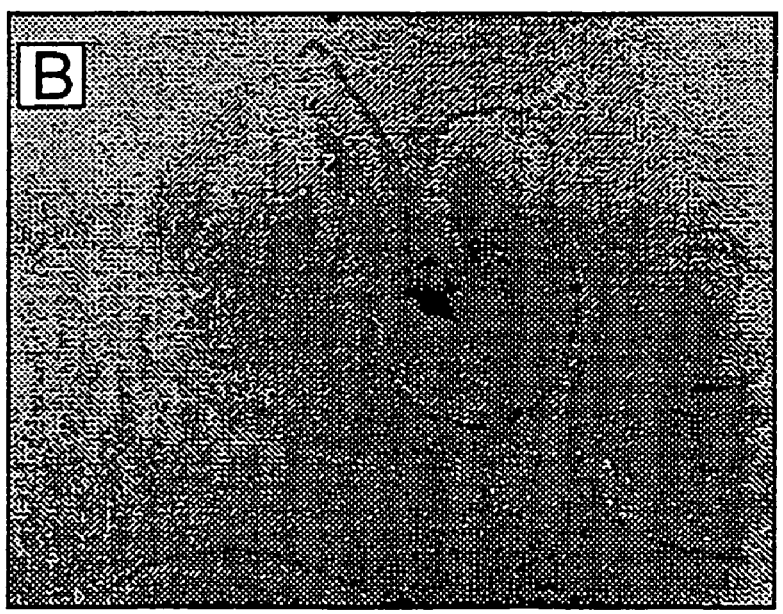

Endogenous SBEII-1 bands

1kb SBEII-1 plasmid band

SEQUENCE LISTING

```
<160> NUMBER OF SEQ ID NOS: 55

<210> SEQ ID NO 1
<211> LENGTH: 2307
<212> TYPE: DNA
<213> ORGANISM: Triticum aestivum
<220> FEATURE:
<221> NAME/KEY: misc_feature
<222> LOCATION: (2036)..(2270)
<223> OTHER INFORMATION: N = any nucleotide

<400> SEQUENCE: 1
catygacggc cagtgacttc gagctcggta cccggggatc cgatttggtg tgtgggagat      60
gttcttgcca aacaatgcag atggttcgcc accaattcct cacggctcac gggtgaaggt     120
gagaatggat actccatctg ggataaagga ttcaattcct gcttggatca agtactccgt     180
gcagactcca ggagatatac catacaatgg aatatattat gatcctcccg aagaggagaa     240
gtatgtattc aagcatcctc aacctaaacg accaaaatca ttgcggatat atgaaacaca     300
tgttggcatg agtagcccgg aaccaaagat caacacatat gcaaacttca gggatgaggt     360
gcttccaaga attaaaagac ttggatacaa tgcagtgcaa ataatggcaa tccaggagca     420
ctcatactat ggaagctttg ggtaccatgt taccaatttc tttgcaccaa gtagccgttt     480
tgggtcccca gaagatttaa aatctttgat tgatagagct cacgagcttg gcttggttgt     540
cctcatggat gttgttcaca gtcacgcgtc aaataatacc ttggacgggt tgaatggttt     600
tgatggcacg gatacacatt acttccatgg cggttcacgg ggccatcact ggatgtggga     660
ttcccgtgtg tttaactatg ggaataagga agttataagg tttctacttt ccaatgcaag     720
atggtggcta gaggagtata gtttgatgg tttccgattc gatggcgcga cctccatgat     780
gtatacccat catggattac aagtaacctt tacaggaagc taccatgaat attttggctt     840
tgccactgat gtagatgcgg tcgtttactt gatgctgatg aatgatctaa ttcatggtt      900 ttatcctgaa gccgtaacta tcggtgaaga tgttagtgga atgcctacat tgccccttcc     960
```

-continued

```
tgttcaagtt ggtggggttg gttttgacta tcgcttacat atggctgttg ccgacaaatg    1020
gattgaactt ctcaaaggaa acgatgaagc ttgggagatg ggtaatattg tgcacacact    1080
aacaaacaga aggtggccgg aaaagtgtgt tacttatgct gaaagtcacg atcaagcact    1140
ggttggagac aagactattg cattctggtt gatggacaag gatatgtatg atttcatggc    1200
tctgaacgga ccttcgacac ctagtattga tcgtggaata gcactgcata aaatgattag    1260
acttatcaca atgggtttag gaggagaggg ttatcttaac tttatgggaa atgagttcgg    1320
gcatcctgaa tggatagact ttccaagagg cccacaagta cttccaactg gtaagttcat    1380
cccaggaaac aacaacagtt acgacaaatg ccgtcgaaga tttgaccagg gtgatgcaga    1440
atttcttagg tatcatggta tgcagcagtt tgatcaggcg atgcagcatc ttgaggaaaa    1500
atatggcttt atgacatcag accaccagta cgtatctcgg aaacatgagg aagataaggt    1560
gatcgtgttt gaaaaggggg acttggtatt tgtgttcaac ttccactgga gtaatagcta    1620
tttcgactac cgggttggct gtttaaagcc tgggaagtac aaggttgtct tagactcaga    1680
cgccggactc tttggtggat ttggtaggat ccatcacact gcagagcact tcacttctga    1740
ctgccaacat gacaacaggc cccattcgtt ctcagtgtac actcctagca gaacctgtgt    1800
tgtctatgct ccaatgaact aaacagcaaa gtgcagcata cgcatgcacg ctgttgttgc    1860
tagcactagc aagaaaaaat cgtatggtca atacaaccag gtgcaaggtt taataagggt    1920
ttgcttcaac gagtcctgga tagacaagac aacatgatga tgtgctctgt gctcccaaat    1980
tcccagggcg ttgtggagaa aaaatgctca tctgtgttat tttatggatc agggangaaa    2040
cctcccccaa anaccccttt ttttttttgaa aggnggatag gccccggnt tctgcatntg    2100 gatgcctcct taaatntttg tagccataaa ccattgctag tgtcctntaa attgacagtt    2160
tagaatagng gttntacttt tgtatttnt ttttgacagt tagactgtat tcctcaaata    2220
atcgacatgt tgtttactcg aagntgagaa ataaaatcag agattgnagn aaaaaaaaaa    2280
aaaaaaaaaa aaaaaaaaaa aaaaaaa                                        2307
```

<210> SEQ ID NO 2
<211> LENGTH: 758
<212> TYPE: PRT
<213> ORGANISM: Triticum aestivum
<220> FEATURE:
<221> NAME/KEY: PEPTIDE
<222> LOCATION: (675)..(746)
<223> OTHER INFORMATION: Xaa = any amino acid
<220> FEATURE:
<221> NAME/KEY: MISC_FEATURE
<222> LOCATION: (675)..(746)
<223> OTHER INFORMATION: Xaa = any amino acid

<400> SEQUENCE: 2

```
Ile Asp Gly Gln Leu Arg Ala Arg Tyr Pro Gly Ile Arg Phe Gly Val
1               5                  10                  15

Trp Glu Met Phe Leu Pro Asn Asn Ala Asp Gly Ser Pro Pro Ile Pro
            20                  25                  30

His Gly Ser Arg Val Lys Val Arg Met Asp Thr Pro Ser Gly Ile Lys
        35                  40                  45

Asp Ser Ile Pro Ala Trp Ile Lys Tyr Ser Val Gln Thr Pro Gly Asp
    50                  55                  60

Ile Pro Tyr Asn Gly Ile Tyr Tyr Asp Pro Pro Glu Glu Lys Tyr
65                  70                  75                  80

Val Phe Lys His Pro Gln Pro Lys Arg Pro Lys Ser Leu Arg Ile Tyr
```

-continued

```
                    85                  90                  95
Glu Thr His Val Gly Met Ser Ser Pro Glu Pro Lys Ile Asn Thr Tyr
                100                 105                 110
Ala Asn Phe Arg Asp Glu Val Leu Pro Arg Ile Lys Arg Leu Gly Tyr
                115                 120                 125
Asn Ala Val Gln Ile Met Ala Ile Gln Glu His Ser Tyr Tyr Gly Ser
130                 135                 140
Phe Gly Tyr His Val Thr Asn Phe Phe Ala Pro Ser Ser Arg Phe Gly
145                 150                 155                 160
Ser Pro Glu Asp Leu Lys Ser Leu Ile Asp Arg Ala His Glu Leu Gly
                165                 170                 175
Leu Val Val Leu Met Asp Val Val His Ser His Ala Ser Asn Asn Thr
                180                 185                 190
Leu Asp Gly Leu Asn Gly Phe Asp Gly Thr Asp Thr His Tyr Phe His
                195                 200                 205
Gly Gly Ser Arg Gly His His Trp Met Trp Asp Ser Arg Val Phe Asn
                210                 215                 220
Tyr Gly Asn Lys Glu Val Ile Arg Phe Leu Leu Ser Asn Ala Arg Trp
225                 230                 235                 240
Trp Leu Glu Glu Tyr Lys Phe Asp Gly Phe Arg Phe Asp Gly Ala Thr
                245                 250                 255
Ser Met Met Tyr Thr His His Gly Leu Gln Val Thr Phe Thr Gly Ser
                260                 265                 270
Tyr His Glu Tyr Phe Gly Phe Ala Thr Asp Val Asp Ala Val Val Tyr
                275                 280                 285
Leu Met Leu Met Asn Asp Leu Ile His Gly Phe Tyr Pro Glu Ala Val
                290                 295                 300
Thr Ile Gly Glu Asp Val Ser Gly Met Pro Thr Phe Ala Leu Pro Val
305                 310                 315                 320
Gln Val Gly Gly Val Gly Phe Asp Tyr Arg Leu His Met Ala Val Ala
                325                 330                 335
Asp Lys Trp Ile Glu Leu Leu Lys Gly Asn Asp Glu Ala Trp Glu Met
                340                 345                 350
Gly Asn Ile Val His Thr Leu Thr Asn Arg Arg Trp Pro Glu Lys Cys
                355                 360                 365
Val Thr Tyr Ala Glu Ser His Asp Gln Ala Leu Val Gly Asp Lys Thr
                370                 375                 380
Ile Ala Phe Trp Leu Met Asp Lys Asp Met Tyr Asp Phe Met Ala Leu
385                 390                 395                 400
Asn Gly Pro Ser Thr Pro Ser Ile Asp Arg Gly Ile Ala Leu His Lys
                405                 410                 415
Met Ile Arg Leu Ile Thr Met Gly Leu Gly Gly Glu Gly Tyr Leu Asn
                420                 425                 430
Phe Met Gly Asn Glu Phe Gly His Pro Glu Trp Ile Asp Phe Pro Arg
                435                 440                 445
Gly Pro Gln Val Leu Pro Thr Gly Lys Phe Ile Pro Gly Asn Asn Asn
450                 455                 460
Ser Tyr Asp Lys Cys Arg Arg Arg Phe Asp Gln Gly Asp Ala Glu Phe
465                 470                 475                 480
Leu Arg Tyr His Gly Met Gln Gln Phe Asp Gln Ala Met Gln His Leu
                485                 490                 495
Glu Glu Lys Tyr Gly Phe Met Thr Ser Asp His Gln Tyr Val Ser Arg
                500                 505                 510
```

Lys His Glu Glu Asp Lys Val Ile Val Phe Glu Lys Gly Asp Leu Val
            515                 520                 525

Phe Val Phe Asn Phe His Trp Ser Asn Ser Tyr Phe Asp Tyr Arg Val
            530                 535                 540

Gly Cys Leu Lys Pro Gly Lys Tyr Lys Val Val Leu Asp Ser Asp Ala
545                 550                 555                 560

Gly Leu Phe Gly Gly Phe Gly Arg Ile His Thr Ala Glu His Phe
            565                 570                 575

Thr Ser Asp Cys Gln His Asp Asn Arg Pro His Ser Phe Ser Val Tyr
            580                 585                 590

Thr Pro Ser Arg Thr Cys Val Val Tyr Ala Pro Met Asn Thr Ala Lys
            595                 600                 605

Cys Ser Ile Arg Met His Ala Val Val Ala Ser Thr Ser Lys Lys Lys
            610                 615                 620

Ser Tyr Gly Gln Tyr Asn Gln Val Gln Gly Leu Ile Arg Val Cys Phe
625                 630                 635                 640

Asn Glu Ser Trp Ile Asp Lys Thr Thr Cys Ala Leu Cys Ser Gln Ile
            645                 650                 655

Pro Arg Ala Leu Trp Arg Lys Asn Ala His Leu Cys Tyr Phe Met Asp
            660                 665                 670

Gln Gly Xaa Asn Leu Pro Gln Xaa Pro Leu Phe Phe Leu Lys Gly Gly
            675                 680                 685

Ala Pro Gly Xaa Cys Xaa Trp Met Pro Pro Xaa Phe Val Ala Ile Asn
            690                 695                 700

His Cys Cys Pro Xaa Asn Gln Phe Arg Ile Xaa Val Xaa Leu Leu Tyr
705                 710                 715                 720

Phe Xaa Phe Asp Ser Thr Val Phe Leu Lys Ser Thr Cys Cys Leu Leu
            725                 730                 735

Glu Xaa Glu Lys Asn Gln Arg Leu Xaa Xaa Lys Lys Lys Lys Lys
            740                 745                 750

Lys Lys Lys Lys Lys Asn
        755

<210> SEQ ID NO 3
<211> LENGTH: 1036
<212> TYPE: DNA
<213> ORGANISM: Triticum aestivum
<220> FEATURE:
<221> NAME/KEY: misc_feature
<222> LOCATION: (77)..(1036)
<223> OTHER INFORMATION: N = any nucleotide

<400> SEQUENCE: 3

```
atgtatgatt tcatggctct gaacggacct tcgacgccta atattgatcg tggaatagca      60
ctgcataaaa tgattanact tatcacaatg ggtttaggcg agagggtta tcttaacttt      120 atgggaaatg agttcgggca tcctgaatgg atagactttc caagaggccc acaagtactt     180
ccaagtggta agttcatccc aggaaacagc aacagttacg acaaatgccg tcgaagattt     240
gacctgggtg atgcagaatt tcttaggtat catggtatgc agcagtttga tcaggcaatg     300
cagcatcttg aggaaaaata tggttttatg acatcagacc accagtacgt atctcggaaa     360
cacgaggaag ataaggtgat cgtgtttgaa aaaggggact tggtatttgt gttcaacttc     420
cactggagta atagctattt cgactaccgg tcggctgtt taaagcctgg gaagtacaag      480
gtggtcttag actcagacgc tggactcttt ggtggatttg gtaggatcca tcacactgca     540
```

```
gagcacttca cttctgactg ccaacatgac aacaggcccc attcgttctc agtgtacact    600
cctagcagaa cctgtgttgt ctatgctcca atgaactaac agcaaggtgc agcatacgcg    660
tgcgcgctgt tgttgctagt agcaagaaaa atcgtacggt caatacagcc aggtgcaagg    720
tttaataagg attttttgct tcaacgagtc ctggatagac aagacaacat gatgttgtgg    780
cgtgtgctcc caatcccag ggcgttgtga agaaaacatg ctcatctgtg ttatgatttt     840
atggatcagc gacgaaactt cccccaaata cccatgcctc cttaaatctt tgtggccgta    900
aaccattgct agtgtcctct aaattgacag tttagcatag aggtttttact tttgtatctt   960 cttttttgaca gttagacttt attcctcaaa taatcgacca gtcgtttact cgaaaaaaaa  1020
aaaaaaaaaa aaaan                                                    1036
```

<210> SEQ ID NO 4
<211> LENGTH: 1087
<212> TYPE: DNA
<213> ORGANISM: Triticum aestivum
<220> FEATURE:
<221> NAME/KEY: misc_feature
<222> LOCATION: (201)..(857)
<223> OTHER INFORMATION: N = any nucleotide

<400> SEQUENCE: 4

```
atgtatgatt tcatggctct gaacggacct tcgacaccta atattgatcg tggaatagca     60
ctgcataaaa tgattagact tatcacaatg ggtttaggag gagagggtta tcttaacttt    120
atgggaaatg agttcgggca tcctgaatgg atagactttc caagaggccc acaagtactt    180
ccaactggta agttcatccc nngaaacaac aacagttacg acaaatgccg tcgaaaattt    240 gacctggggtg atgcagaatt tcttaggtat catggtatgc agcagtttga tcaggcgatg    300
cagcatcttg aggaaaaata tggctttatg acatcagacc accagtacgt atctcggaaa    360
catgaggaag ataaggtgat cgtgtttgaa aaaggggact tggtatttgt gttcaacttc    420
cactggagta atagctattt cggctaccgg gttggctgtt taaagcctgg gaagtacaag    480
gttgtcttag actcagacgc cggactctt ggtggatttg gtaggatcca tcacactgca    540
gagcacttca cttctgactg ccaacatgac aacaggcccc attcgttctc agtgtacact    600
cctagcagaa cctgtgttgt ctatgctcca atgaactaaa cagcaaagtg cagcatacgc    660
atgcacgctg ttgttgctag cactagcaag aaaaaatcgt atggtcaata caaccaggtg    720
caaggtttaa taagggtttt tgcttcaacg agtcctggat agacaagaca acatgatgat    780
gtgctctgtg ctcccaaatt cccagggcgt tgngnggaaa acatgctcat ctgtgttatc    840
attttatgga tcagngngga aacctccccc aaatacccat gcctccttaa acttttgtgg    900
tcctaaacca tggctactat cctctaaatt ggcagtttag catagaggtt ttactttgt    960 aaatttttt tgacagttaa tagactctat tcctcaaata attgacatgt cctttacaag   1020
aagatgagaa ataaaatcag ggattgaaga atcccaaaag ctaaaaaaaa aaaaaaaaaa  1080
aaaaaaa                                                            1087
```

<210> SEQ ID NO 5
<211> LENGTH: 1120
<212> TYPE: DNA
<213> ORGANISM: Triticum aestivum
<220> FEATURE:
<221> NAME/KEY: misc_feature
<222> LOCATION: (802)..(1083)
<223> OTHER INFORMATION: N = any nucleotide

<400> SEQUENCE: 5

```
atgtatgatt tcatggcgct gaacggacct tcgacgccta atattgatcg tggaatagca      60
ctgcataaaa tgattagact tatcacaatg ggtctaggag gagagggtta tcttaacttt     120
atgggaaatg agttcgggca tcctgaatgg atagactttc aagaggccc acaagtactt      180 ccaagtggta agttcatccc aggaaacaac aacagttacg acaaatgccg tcgaagattt     240
gacctgggtg atgcagaatt tcttaggtat catggtatgc agcagtttga tcaggcaatg     300
cagcatcttg aggaaaaata tggttttatg acatcagacc accagtacgt ttctcggaaa     360
catgaggaag ataaggtgat cgtgtttgaa aaggggact tggtatttgt gttcaacttc      420
cactggagta gtagctattt cgactaccgg gtcggctgtt taaagcctgg gaagtacaag     480
gtggtcttag actcggacgc tggactcttt ggtggatttg gtaggatcca tcacactgca     540
gagcacttca cttctgactg ccaacatgac aacaggcccc attcattctc agtgtacact     600
cctagcagaa cctgtgttgt ctatgctcca atgaactaac agcaaagtgc agcatacgcg     660
tgcgcgctgt tgttgctagt agcaagaaaa atcgtatggt caatacaacc aggtgcaagg     720
tttaataagg attttttgctt caacgagtcc tggatagaca agacaacatg atgttgtgct     780
gtgtgctccc aatccccagg gngttgtgaa gaaaacatgc tcatctgtgt tatttttatgg    840 atcagggang aaacctcccc caaanacccc ttttttttt gaaaggngga taggcccccg      900
gtntctgcat ntggatgcct ccttaaatnt ttgtagccat aaaccattgc tagtgtcctn     960
taaattgaca gtttagaata ngggttntac ttttgtattt tnttttttgac agttagactg   1020 tattcctcaa ataatcgaca tgttgtttac tcgaagntga gaaataaaat cagagattgn   1080
agnaaaaaaa aaaaaaaaaa aaaaaaaaa aaaaaaaaa                            1120

<210> SEQ ID NO 6
<211> LENGTH: 979
<212> TYPE: DNA
<213> ORGANISM: Triticum aestivum
<220> FEATURE:
<221> NAME/KEY: misc_feature
<222> LOCATION: (763)..(763)
<223> OTHER INFORMATION: N = any nucleotide

<400> SEQUENCE: 6
atatgtatga tttcatggct ctggataggc cttcaactcc tcgcattgat cgtggcatag     60
cattacataa aatgatcagg cttgtcacca tgggtttagg tggtgaaggc tatcttaact    120
tcatgggaaa tgagtttggg catcctgaat ggatagattt ccaagaggc ccacaaactc     180 ttccaaccgg caaagttctc cctggaaata acaatagtta tgataaatgc cgccatagat    240
ttgatcttgg agatgcagat tttcttagat atcgtggtat gcaagagttc gatcaggcaa    300
tgcagcatct tgaggaaaaa tatgggttta tgacatctga gcaccagtat gtttcacgga    360
aacatgagga gataaggtg atcttcttcg aaagaggaga tttggtattt gttttcaact    420
tccactggag caatagcttt tttgactacc gtgttgggtg ttccaagcct gggaagtaca    480
aggtggcctt ggactccgac gatgcactct ttggtggatt cagcaggctt gatcatgatg    540
tcgactactt cacaaccgaa catccgcatg acaacaggcc gcactctttc tcggtgtaca    600
ctccgagcag aactgcggtc gtgtatgccc ttacagagta agaaccagca gcggcttgtt    660
acaaggcaaa gagagaactc cagagagctc gtggatcgtg agcgaagcga cgggcaacgg    720
cgcgaggctg ctccaagcgc catgactggg aggggatcgt gcntcttccc cagatgccag    780
gaggagcaga tggataggta gcttgttggt gagcgctcga aagaaaatgg acgggcctgg    840
```

-continued

```
gtgtttgttg tgctgcactg aaccctcctc ctatcttgca cattcccggt tgttttgta      900 catataacta ataattgccc gtgcgcttca acatgaacat ataaatattc taataggtta      960
aaaaaaaaaa aaaaaaaaa                                                   979
```

<210> SEQ ID NO 7
<211> LENGTH: 212
<212> TYPE: PRT
<213> ORGANISM: Triticum aestivum

<400> SEQUENCE: 7

```
Met Tyr Asp Phe Met Ala Leu Asn Gly Pro Ser Thr Pro Asn Ile Asp
1               5                   10                  15

Arg Gly Ile Ala Leu His Lys Met Ile Arg Leu Ile Thr Met Gly Leu
            20                  25                  30

Gly Gly Glu Gly Tyr Leu Asn Phe Met Gly Asn Glu Phe Gly His Pro
        35                  40                  45

Glu Trp Ile Asp Phe Pro Arg Gly Pro Gln Val Leu Pro Ser Gly Lys
    50                  55                  60

Phe Ile Pro Gly Asn Ser Asn Ser Tyr Asp Lys Cys Arg Arg Arg Phe
65                  70                  75                  80

Asp Leu Gly Asp Ala Glu Phe Leu Arg Tyr His Gly Met Gln Gln Phe
                85                  90                  95

Asp Gln Ala Met Gln His Leu Glu Glu Lys Tyr Gly Phe Met Thr Ser
            100                 105                 110

Asp His Gln Tyr Val Ser Arg Lys His Glu Glu Asp Lys Val Ile Val
        115                 120                 125

Phe Glu Lys Gly Asp Leu Val Phe Val Phe Asn Phe His Trp Ser Asn
    130                 135                 140

Ser Tyr Phe Asp Tyr Arg Val Gly Cys Leu Lys Pro Gly Lys Tyr Lys
145                 150                 155                 160

Val Val Leu Asp Ser Asp Ala Gly Leu Phe Gly Gly Phe Gly Arg Ile
                165                 170                 175

His His Thr Ala Glu His Phe Ser Asp Cys Gln His Asp Asn Arg
            180                 185                 190

Pro His Ser Phe Ser Val Tyr Thr Pro Ser Arg Thr Cys Val Val Tyr
        195                 200                 205

Ala Pro Met Asn
    210
```

<210> SEQ ID NO 8
<211> LENGTH: 378
<212> TYPE: DNA
<213> ORGANISM: Triticum aestivum

<400> SEQUENCE: 8

```
actaacagca aggtgcagca tacgcgtgcg cgctgttgtt gctagtagca agaaaaatcg       60
tacggtcaat acagccaggt gcaaggttta ataaggattt tttgcttcaa cgagtcctgg      120
atagacaaga caacatgatg ttgtggcgtg tgctcccaat ccccagggcg ttgtgaagaa      180 acatgctca tctgtgttat gattttatgg atcagcgacg aaacttcccc caaataccca      240
tgcctcctta atctttgtg gccgtaaacc attgctagtg tcctctaaat tgacagttta      300
gcatagaggt tttactttg tatcttcttt ttgacagtta gactttattc ctcaaataat      360
cgaccagtcg tttactcg                                                    378
```

<210> SEQ ID NO 9
<211> LENGTH: 449
<212> TYPE: DNA
<213> ORGANISM: Triticum aestivum
<220> FEATURE:
<221> NAME/KEY: misc_feature
<222> LOCATION: (169)..(447)
<223> OTHER INFORMATION: N = any nucleotide

<400> SEQUENCE: 9

```
aactaacagc aaagtgcagc atacgcgtgc gcgctgttgt tgctagtagc aagaaaaatc      60
gtatggtcaa taaccaggt gcaaggttt aataaggatt tttgcttcaa cgagtcctgg     120
atagacaaga caacatgatg ttgtgctgtg tgctcccaat ccccagggng ttgtgaagaa    180
aacatgctca tctgtgttat tttatggatc agggangaaa cctcccccaa anccccttt    240
ttttttttgaa aggnggatag gccccggtn tctgcatntg gatgcctcct taaatntttg    300
tagccataaa ccattgctag tgtcctntaa attgacagtt tagaatagng gttntacttt    360
tgtatttttnt ttttgacagt tagactgtat tcctcaaata atcgacatgt tgtttactcg    420
aagntgagaa ataaaatcag agattgnag                                       449
```

<210> SEQ ID NO 10
<211> LENGTH: 428
<212> TYPE: DNA
<213> ORGANISM: Triticum aestivum
<220> FEATURE:
<221> NAME/KEY: misc_feature
<222> LOCATION: (178)..(223)
<223> OTHER INFORMATION: N = any nucleotide

<400> SEQUENCE: 10

```
actaaacagc aaagtgcagc atacgcatgc acgctgttgt tgctagcact agcaagaaaa      60
atcgtatgg tcaatacaac caggtgcaag gtttaataag gttttttgct tcaacgagtc     120
ctggatagac aagacaacat gatgatgtgc tctgtgctcc caattcccca gggcgttgng    180
nggaaaacat gctcatctgt gttatcattt tatggatcag ngnggaaacc tcccccaaat    240
acccatgcct ccttaaactt ttgtggtcct aaaccatggc tactatcctc taaattggca    300
gtttagcata gaggtttac ttttgtaaat ttttttgac agttaataga ctctattcct     360
caaataattg acatgtcctt tacaagaaga tgagaaataa atcagggat tgaagaatcc    420
caaaagct                                                              428
```

<210> SEQ ID NO 11
<211> LENGTH: 592
<212> TYPE: PRT
<213> ORGANISM: Triticum aestivum

<400> SEQUENCE: 11

```
Phe Gly Val Trp Glu Met Phe Leu Pro Asn Asn Ala Asp Gly Ser Pro
1               5                   10                  15

Pro Ile Pro His Gly Ser Arg Val Lys Val Arg Met Asp Thr Pro Ser
            20                  25                  30

Gly Ile Lys Asp Ser Ile Pro Ala Trp Ile Lys Tyr Ser Val Gln Thr
        35                  40                  45

Pro Gly Asp Ile Pro Tyr Asn Gly Ile Tyr Tyr Asp Pro Pro Glu Glu
    50                  55                  60

Glu Lys Tyr Val Phe Lys His Pro Gln Pro Lys Arg Pro Lys Ser Leu
65                  70                  75                  80

Arg Ile Tyr Glu Thr His Val Gly Met Ser Ser Pro Glu Pro Lys Ile
```

-continued

```
                85                  90                  95
Asn Thr Tyr Ala Asn Phe Arg Asp Glu Val Leu Pro Arg Ile Lys Arg
            100                 105                 110
Leu Gly Tyr Asn Ala Val Gln Ile Met Ala Ile Gln Glu His Ser Tyr
        115                 120                 125
Tyr Gly Ser Phe Gly Tyr His Val Thr Asn Phe Phe Ala Pro Ser Ser
    130                 135                 140
Arg Phe Gly Ser Pro Glu Asp Leu Lys Ser Leu Ile Asp Arg Ala His
145                 150                 155                 160
Glu Leu Gly Leu Val Val Leu Met Asp Val Val His Ser His Ala Ser
                165                 170                 175
Asn Asn Thr Leu Asp Gly Leu Asn Gly Phe Asp Gly Thr Asp Thr His
            180                 185                 190
Tyr Phe His Gly Gly Ser Arg Gly His His Trp Met Trp Asp Ser Arg
        195                 200                 205
Val Phe Asn Tyr Gly Asn Lys Glu Val Ile Arg Phe Leu Leu Ser Asn
    210                 215                 220
Ala Arg Trp Trp Leu Glu Glu Tyr Lys Phe Asp Gly Phe Arg Phe Asp
225                 230                 235                 240
Gly Ala Thr Ser Met Met Tyr Thr His His Gly Leu Gln Val Thr Phe
                245                 250                 255
Thr Gly Ser Tyr His Glu Tyr Phe Gly Phe Ala Thr Asp Val Asp Ala
            260                 265                 270
Val Val Tyr Leu Met Leu Met Asn Asp Leu Ile His Gly Phe Tyr Pro
        275                 280                 285
Glu Ala Val Thr Ile Gly Glu Asp Val Ser Gly Met Pro Thr Phe Ala
    290                 295                 300
Leu Pro Val Gln Val Gly Gly Val Gly Phe Asp Tyr Arg Leu His Met
305                 310                 315                 320
Ala Val Ala Asp Lys Trp Ile Glu Leu Leu Lys Gly Asn Asp Glu Ala
                325                 330                 335
Trp Glu Met Gly Asn Ile Val His Thr Leu Thr Asn Arg Arg Trp Pro
            340                 345                 350
Glu Lys Cys Val Thr Tyr Ala Glu Ser His Asp Gln Ala Leu Val Gly
        355                 360                 365
Asp Lys Thr Ile Ala Phe Trp Leu Met Asp Lys Asp Met Tyr Asp Phe
    370                 375                 380
Met Ala Leu Asn Gly Pro Ser Thr Pro Ser Ile Asp Arg Gly Ile Ala
385                 390                 395                 400
Leu His Lys Met Ile Arg Leu Ile Thr Met Gly Leu Gly Gly Glu Gly
                405                 410                 415
Tyr Leu Asn Phe Met Gly Asn Glu Phe Gly His Pro Glu Trp Ile Asp
            420                 425                 430
Phe Pro Arg Gly Pro Gln Val Leu Pro Thr Gly Lys Phe Ile Pro Gly
        435                 440                 445
Asn Asn Asn Ser Tyr Asp Lys Cys Arg Arg Phe Asp Gln Gly Asp
    450                 455                 460
Ala Glu Phe Leu Arg Tyr His Gly Met Gln Gln Phe Asp Gln Ala Met
465                 470                 475                 480
Gln His Leu Glu Glu Lys Tyr Gly Phe Met Thr Ser Asp His Gln Tyr
                485                 490                 495
Val Ser Arg Lys His Glu Glu Asp Lys Val Ile Val Phe Glu Lys Gly
            500                 505                 510
```

-continued

Asp Leu Val Phe Val Phe Asn Phe His Trp Ser Asn Ser Tyr Phe Asp
          515                 520                 525

Tyr Arg Val Gly Cys Leu Lys Pro Gly Lys Tyr Lys Val Val Leu Asp
     530                 535                 540

Ser Asp Ala Gly Leu Phe Gly Gly Phe Gly Arg Ile His His Thr Ala
545                 550                 555                 560

Glu His Phe Thr Ser Asp Cys Gln His Asp Asn Arg Pro His Ser Phe
                565                 570                 575

Ser Val Tyr Thr Pro Ser Arg Thr Cys Val Val Tyr Ala Pro Met Asn
          580                 585                 590

<210> SEQ ID NO 12
<211> LENGTH: 771
<212> TYPE: PRT
<213> ORGANISM: Triticum aestivum

<400> SEQUENCE: 12

Ser Arg Ala Ala Ser Pro Gly Lys Val Leu Val Pro Asp Gly Glu Ser
1                5                  10                  15

Asp Asp Leu Ala Ser Pro Ala Gln Pro Glu Glu Leu Gln Ile Pro Glu
            20                  25                  30

Asp Ile Glu Glu Gln Thr Ala Glu Val Asn Met Thr Gly Gly Thr Ala
        35                  40                  45

Glu Lys Leu Glu Ser Ser Glu Pro Thr Gln Gly Ile Val Glu Thr Ile
    50                  55                  60

Thr Asp Gly Val Thr Lys Gly Val Lys Glu Leu Val Val Gly Glu Lys
65                  70                  75                  80

Pro Arg Val Val Pro Lys Pro Gly Asp Gly Gln Lys Ile Tyr Glu Ile
                85                  90                  95

Asp Pro Thr Leu Lys Asp Phe Arg Ser His Leu Asp Tyr Arg Tyr Ser
            100                 105                 110

Glu Tyr Arg Arg Ile Arg Ala Ala Ile Asp Gln His Glu Gly Gly Leu
        115                 120                 125

Glu Ala Phe Ser Arg Gly Tyr Glu Lys Leu Gly Phe Thr Arg Ser Ala
    130                 135                 140

Glu Gly Ile Thr Tyr Arg Glu Trp Ala Pro Gly Ala His Ser Ala Ala
145                 150                 155                 160

Leu Val Gly Asp Phe Asn Asn Trp Asn Pro Asn Ala Asp Thr Met Thr
                165                 170                 175

Arg Asp Asp Tyr Gly Val Trp Glu Ile Phe Leu Pro Asn Asn Ala Asp
            180                 185                 190

Gly Ser Pro Ala Ile Pro His Gly Ser Arg Val Lys Ile Arg Met Asp
        195                 200                 205

Thr Pro Ser Gly Val Lys Asp Ser Ile Ser Ala Trp Ile Lys Phe Ser
    210                 215                 220

Val Gln Ala Pro Gly Glu Ile Pro Phe Asn Gly Ile Tyr Tyr Asp Pro
225                 230                 235                 240

Pro Glu Glu Glu Lys Tyr Val Phe Gln His Pro Gln Pro Lys Arg Pro
                245                 250                 255

Glu Ser Leu Arg Ile Tyr Glu Ser His Ile Gly Met Ser Ser Pro Glu
            260                 265                 270

Pro Lys Ile Asn Ser Tyr Ala Asn Phe Arg Asp Glu Val Leu Pro Arg
        275                 280                 285

Ile Lys Arg Leu Gly Tyr Asn Ala Val Gln Ile Met Ala Ile Gln Glu

```
               290                 295                 300
His Ser Tyr Tyr Ala Ser Phe Gly Tyr His Val Thr Asn Phe Phe Ala
305                 310                 315                 320

Pro Ser Ser Arg Phe Gly Thr Pro Glu Asp Leu Lys Ser Leu Ile Asp
                325                 330                 335

Arg Ala His Glu Leu Gly Leu Ile Val Leu Met Asp Ile Val His Ser
                340                 345                 350

His Ser Ser Asn Asn Thr Leu Asp Gly Leu Asn Gly Phe Asp Gly Thr
                355                 360                 365

Asp Thr His Tyr Phe His Gly Gly Pro Arg Gly His His Trp Met Trp
370                 375                 380

Asp Ser Arg Leu Phe Asn Tyr Gly Ser Trp Glu Val Leu Arg Phe Leu
385                 390                 395                 400

Leu Ser Asn Ala Arg Trp Trp Leu Glu Glu Tyr Lys Phe Asp Gly Phe
                405                 410                 415

Arg Phe Asp Gly Val Thr Ser Met Met Tyr Thr His His Gly Leu Gln
                420                 425                 430

Met Thr Phe Thr Gly Asn Tyr Gly Glu Tyr Phe Gly Phe Ala Thr Asp
                435                 440                 445

Val Asp Ala Val Val Tyr Leu Met Leu Val Asn Asp Leu Ile His Gly
450                 455                 460

Leu His Pro Asp Ala Val Ser Ile Gly Glu Asp Val Ser Gly Met Pro
465                 470                 475                 480

Thr Phe Cys Ile Pro Val Pro Asp Gly Val Gly Leu Asp Tyr Arg
                485                 490                 495

Leu His Met Ala Val Ala Asp Lys Trp Ile Glu Leu Leu Lys Gln Ser
                500                 505                 510

Asp Glu Ser Trp Lys Met Gly Asp Ile Val His Thr Leu Thr Asn Arg
                515                 520                 525

Arg Trp Leu Glu Lys Cys Val Thr Tyr Ala Glu Ser His Asp Gln Ala
                530                 535                 540

Leu Val Gly Asp Lys Thr Ile Ala Phe Trp Leu Met Asp Lys Asp Met
545                 550                 555                 560

Tyr Asp Phe Met Ala Leu Asp Arg Pro Ser Thr Pro Arg Ile Asp Arg
                565                 570                 575

Gly Ile Ala Leu His Lys Met Ile Arg Leu Val Thr Met Gly Leu Gly
                580                 585                 590

Gly Glu Gly Tyr Leu Asn Phe Met Gly Asn Glu Phe Gly His Pro Glu
                595                 600                 605

Trp Ile Asp Phe Pro Arg Gly Pro Gln Thr Leu Pro Thr Gly Lys Val
                610                 615                 620

Leu Pro Gly Asn Asn Asn Ser Tyr Asp Lys Cys Arg Arg Arg Phe Asp
625                 630                 635                 640

Leu Gly Asp Ala Asp Phe Leu Arg Tyr His Gly Met Gln Glu Phe Asp
                645                 650                 655

Gln Ala Met Gln His Leu Glu Glu Lys Tyr Gly Phe Met Thr Ser Glu
                660                 665                 670

His Gln Tyr Val Ser Arg Lys His Glu Glu Asp Lys Val Ile Ile Phe
                675                 680                 685

Glu Arg Gly Asp Leu Val Phe Val Phe Asn Phe His Trp Ser Asn Ser
                690                 695                 700

Phe Phe Asp Tyr Arg Val Gly Cys Ser Arg Pro Gly Lys Tyr Lys Val
705                 710                 715                 720
```

-continued

```
Ala Leu Asp Ser Asp Asp Ala Leu Phe Gly Gly Phe Ser Arg Leu Asp
                725                 730                 735

His Asp Val Asp Tyr Phe Thr Thr Glu His Pro His Asp Asn Arg Pro
            740                 745                 750

Arg Ser Phe Ser Val Tyr Thr Pro Ser Arg Thr Ala Val Val Tyr Ala
        755                 760                 765

Leu Thr Glu
    770

<210> SEQ ID NO 13
<211> LENGTH: 797
<212> TYPE: PRT
<213> ORGANISM: Zea mays

<400> SEQUENCE: 13

Ser Cys Ala Gly Ala Pro Gly Lys Val Leu Val Pro Gly Gly Gly Ser
1               5                   10                  15

Asp Asp Leu Leu Ser Ser Ala Glu Pro Val Val Asp Thr Gln Pro Glu
            20                  25                  30

Glu Leu Gln Ile Pro Glu Ala Glu Leu Thr Val Glu Lys Thr Ser Ser
        35                  40                  45

Ser Pro Thr Gln Thr Thr Ser Ala Val Ala Glu Ala Ser Ser Gly Val
    50                  55                  60

Glu Ala Glu Glu Arg Pro Glu Leu Ser Ser Glu Val Ile Gly Val Gly
65                  70                  75                  80

Gly Thr Gly Gly Thr Lys Ile Asp Gly Ala Gly Ile Lys Ala Lys Ala
                85                  90                  95

Pro Leu Val Glu Glu Lys Pro Arg Val Ile Pro Pro Gly Asp Gly
            100                 105                 110

Gln Arg Ile Tyr Glu Ile Asp Pro Met Leu Glu Gly Phe Arg Gly His
        115                 120                 125

Leu Asp Tyr Arg Tyr Ser Glu Tyr Lys Arg Leu Arg Ala Ala Ile Asp
    130                 135                 140

Gln His Glu Gly Gly Leu Asp Ala Phe Ser Arg Gly Tyr Glu Lys Leu
145                 150                 155                 160

Gly Phe Thr Arg Ser Ala Glu Gly Ile Thr Tyr Arg Glu Trp Ala Pro
                165                 170                 175

Gly Ala Tyr Ser Ala Ala Leu Val Gly Asp Phe Asn Asn Trp Asn Pro
            180                 185                 190

Asn Ala Asp Ala Met Ala Arg Asn Glu Tyr Gly Val Trp Glu Ile Phe
        195                 200                 205

Leu Pro Asn Asn Ala Asp Gly Ser Pro Ala Ile Pro His Gly Ser Arg
    210                 215                 220

Val Lys Ile Arg Met Asp Thr Pro Ser Gly Val Lys Asp Ser Ile Pro
225                 230                 235                 240

Ala Trp Ile Lys Phe Ser Val Gln Ala Pro Gly Glu Ile Pro Tyr Asn
                245                 250                 255

Gly Ile Tyr Tyr Asp Pro Pro Glu Glu Lys Tyr Val Phe Lys His
            260                 265                 270

Pro Gln Pro Lys Arg Pro Lys Ser Leu Arg Ile Tyr Glu Ser His Val
        275                 280                 285

Gly Met Ser Ser Pro Glu Pro Lys Ile Asn Thr Tyr Ala Asn Phe Arg
    290                 295                 300

Asp Glu Val Leu Pro Arg Ile Lys Lys Leu Gly Tyr Asn Ala Val Gln
```

```
                    305                 310                 315                 320
Ile Met Ala Ile Gln Glu His Ser Tyr Tyr Ala Ser Phe Gly Tyr His
                    325                 330                 335

Val Thr Asn Phe Phe Ala Pro Ser Ser Arg Phe Gly Thr Pro Glu Asp
                    340                 345                 350

Leu Lys Ser Leu Ile Asp Lys Ala His Glu Leu Gly Leu Leu Val Leu
                    355                 360                 365

Met Asp Ile Val His Ser His Ser Ser Asn Asn Thr Leu Asp Gly Leu
                    370                 375                 380

Asn Gly Phe Asp Gly Thr Asp Thr His Tyr Phe His Gly Gly Pro Arg
385                 390                 395                 400

Gly His His Trp Met Trp Asp Ser Arg Leu Phe Asn Tyr Gly Ser Trp
                    405                 410                 415

Glu Val Leu Arg Phe Leu Leu Ser Asn Ala Arg Trp Trp Leu Glu Glu
                    420                 425                 430

Tyr Lys Phe Asp Gly Phe Arg Phe Asp Gly Val Thr Ser Met Met Tyr
                    435                 440                 445

Thr His His Gly Leu Gln Val Thr Phe Thr Gly Asn Tyr Gly Glu Tyr
                    450                 455                 460

Phe Gly Phe Ala Thr Asp Val Asp Ala Val Tyr Leu Met Leu Val
465                 470                 475                 480

Asn Asp Leu Ile Arg Gly Leu Tyr Pro Glu Ala Val Ser Ile Gly Glu
                    485                 490                 495

Asp Val Ser Gly Met Pro Thr Phe Cys Ile Pro Val Gln Asp Gly Gly
                    500                 505                 510

Val Gly Phe Asp Tyr Arg Leu His Met Ala Val Pro Asp Lys Trp Ile
                    515                 520                 525

Glu Leu Leu Lys Gln Ser Asp Glu Tyr Trp Glu Met Gly Asp Ile Val
                    530                 535                 540

His Thr Leu Thr Asn Arg Arg Trp Leu Glu Lys Cys Val Thr Tyr Cys
545                 550                 555                 560

Glu Ser His Asp Gln Ala Leu Val Gly Asp Lys Thr Ile Ala Phe Trp
                    565                 570                 575

Leu Met Asp Lys Asp Met Tyr Asp Phe Met Ala Leu Asp Arg Pro Ser
                    580                 585                 590

Thr Pro Arg Ile Asp Arg Gly Ile Ala Leu His Lys Met Ile Arg Leu
                    595                 600                 605

Val Thr Met Gly Leu Gly Gly Glu Gly Tyr Leu Asn Phe Met Gly Asn
                    610                 615                 620

Glu Phe Gly His Pro Glu Trp Ile Asp Phe Pro Arg Gly Pro Gln Ser
625                 630                 635                 640

Leu Pro Asn Gly Ser Val Ile Pro Gly Asn Asn Asn Ser Phe Asp Lys
                    645                 650                 655

Cys Arg Arg Arg Phe Asp Leu Gly Asp Ala Asp Tyr Leu Arg Tyr Arg
                    660                 665                 670

Gly Met Gln Glu Phe Asp Gln Ala Met Gln His Leu Glu Gly Lys Tyr
                    675                 680                 685

Glu Phe Met Thr Ser Asp His Ser Tyr Val Ser Arg Lys His Glu Glu
                    690                 695                 700

Asp Lys Val Ile Ile Phe Glu Arg Gly Asp Leu Val Phe Val Phe Asn
705                 710                 715                 720

Phe His Trp Ser Asn Ser Tyr Phe Asp Tyr Arg Val Gly Cys Phe Lys
                    725                 730                 735
```

```
Pro Gly Lys Tyr Lys Ile Val Leu Asp Ser Asp Gly Leu Phe Gly
            740                 745                 750
Gly Phe Ser Arg Leu Asp His Asp Ala Glu Tyr Phe Thr Ala Asp Trp
        755                 760                 765
Pro His Asp Asn Arg Pro Cys Ser Phe Ser Val Tyr Ala Pro Ser Arg
770                 775                 780
Thr Ala Val Val Tyr Ala Pro Ala Gly Ala Glu Asp Glu
785                 790                 795

<210> SEQ ID NO 14
<211> LENGTH: 747
<212> TYPE: PRT
<213> ORGANISM: Zea mays

<400> SEQUENCE: 14

Ala Ala Ala Ala Ala Arg Lys Ala Val Met Val Pro Glu Gly Glu Asn
1               5                   10                  15
Asp Gly Leu Ala Ser Arg Ala Asp Ser Ala Gln Phe Gln Ser Asp Glu
            20                  25                  30
Leu Glu Val Pro Asp Ile Ser Glu Thr Thr Cys Gly Ala Gly Val
        35                  40                  45
Ala Asp Ala Gln Ala Leu Asn Arg Val Arg Val Pro Pro Ser
50                  55                  60
Asp Gly Gln Lys Ile Phe Gln Ile Asp Pro Met Leu Gln Gly Tyr Lys
65                  70                  75                  80
Tyr His Leu Glu Tyr Arg Tyr Ser Leu Tyr Arg Arg Ile Arg Ser Asp
                85                  90                  95
Ile Asp Glu His Glu Gly Gly Leu Glu Ala Phe Ser Arg Ser Tyr Glu
            100                 105                 110
Lys Phe Gly Phe Asn Ala Ser Ala Glu Gly Ile Thr Tyr Arg Glu Trp
        115                 120                 125
Ala Pro Gly Ala Phe Ser Ala Ala Leu Val Gly Asp Val Asn Asn Trp
    130                 135                 140
Asp Pro Asn Ala Asp Arg Met Ser Lys Asn Glu Phe Gly Val Trp Glu
145                 150                 155                 160
Ile Phe Leu Pro Asn Asn Ala Asp Gly Thr Ser Pro Ile Pro His Gly
                165                 170                 175
Ser Arg Val Lys Val Arg Met Asp Thr Pro Ser Gly Ile Lys Asp Ser
            180                 185                 190
Ile Pro Ala Trp Ile Lys Tyr Ser Val Gln Ala Pro Gly Glu Ile Pro
        195                 200                 205
Tyr Asp Gly Ile Tyr Tyr Asp Pro Pro Glu Glu Val Lys Tyr Val Phe
    210                 215                 220
Arg His Ala Gln Pro Lys Arg Pro Lys Ser Leu Arg Ile Tyr Glu Thr
225                 230                 235                 240
His Val Gly Met Ser Ser Pro Glu Pro Lys Ile Asn Thr Tyr Val Asn
                245                 250                 255
Phe Arg Asp Glu Val Leu Pro Arg Ile Lys Lys Leu Gly Tyr Asn Ala
            260                 265                 270
Val Gln Ile Met Ala Ile Gln Glu His Ser Tyr Tyr Gly Ser Phe Gly
        275                 280                 285
Tyr His Val Thr Asn Phe Phe Ala Pro Ser Ser Arg Phe Gly Thr Pro
    290                 295                 300
Glu Asp Leu Lys Ser Leu Ile Asp Arg Ala His Glu Leu Gly Leu Leu
```

-continued

```
            305                 310                 315                 320
Val Leu Met Asp Val His Ser His Ala Ser Ser Asn Thr Leu Asp
                325                 330                 335
Gly Leu Asn Gly Phe Asp Gly Thr Asp Thr His Tyr Phe His Ser Gly
                340                 345                 350
Pro Arg Gly His His Trp Met Trp Asp Ser Arg Leu Phe Asn Tyr Gly
                355                 360                 365
Asn Trp Glu Val Leu Arg Phe Leu Ser Asn Ala Arg Trp Trp Leu
    370                 375                 380
Glu Glu Tyr Lys Phe Asp Gly Phe Arg Phe Asp Gly Val Thr Ser Met
385                 390                 395                 400
Met Tyr Thr His His Gly Leu Gln Val Thr Phe Thr Gly Asn Phe Asn
                405                 410                 415
Glu Tyr Phe Gly Phe Ala Thr Asp Val Asp Ala Val Val Tyr Leu Met
                420                 425                 430
Leu Val Asn Asp Leu Ile His Gly Leu Tyr Pro Glu Ala Val Thr Ile
                435                 440                 445
Gly Glu Asp Val Ser Gly Met Pro Thr Phe Ala Leu Pro Val His Asp
    450                 455                 460
Gly Gly Val Gly Phe Asp Tyr Arg Met His Met Ala Val Ala Asp Lys
465                 470                 475                 480
Trp Ile Asp Leu Leu Lys Gln Ser Asp Glu Thr Trp Lys Met Gly Asp
                485                 490                 495
Ile Val His Thr Leu Thr Asn Arg Arg Trp Leu Glu Lys Cys Val Thr
                500                 505                 510
Tyr Ala Glu Ser His Asp Gln Ala Leu Val Gly Asp Lys Thr Ile Ala
                515                 520                 525
Phe Trp Leu Met Asp Lys Asp Met Tyr Asp Phe Met Ala Leu Asp Arg
    530                 535                 540
Pro Ser Thr Pro Thr Ile Asp Arg Gly Ile Ala Leu His Lys Met Ile
545                 550                 555                 560
Arg Leu Ile Thr Met Gly Leu Gly Gly Glu Gly Tyr Leu Asn Phe Met
                565                 570                 575
Gly Asn Glu Phe Gly His Pro Glu Trp Ile Asp Phe Pro Arg Gly Pro
                580                 585                 590
Gln Arg Leu Pro Ser Gly Lys Phe Ile Pro Gly Asn Asn Ser Tyr
                595                 600                 605
Asp Lys Cys Arg Arg Phe Asp Leu Gly Asp Ala Asp Tyr Leu Arg
                610                 615                 620
Tyr His Gly Met Gln Glu Phe Asp Gln Ala Met Gln His Leu Glu Gln
625                 630                 635                 640
Lys Tyr Glu Phe Met Thr Ser Asp His Gln Tyr Ile Ser Arg Lys His
                645                 650                 655
Glu Glu Asp Lys Val Ile Val Phe Glu Lys Gly Asp Leu Val Phe Val
                660                 665                 670
Phe Asn Phe His Cys Asn Asn Ser Tyr Phe Asp Tyr Arg Ile Gly Cys
                675                 680                 685
Arg Lys Pro Gly Val Tyr Lys Val Val Leu Asp Ser Asp Ala Gly Leu
    690                 695                 700
Phe Gly Gly Phe Ser Arg Ile His His Ala Ala Glu His Phe Thr Ala
705                 710                 715                 720
Asp Cys Ser His Asp Asn Arg Pro Tyr Ser Phe Ser Val Tyr Thr Pro
                725                 730                 735
```

```
Ser Arg Thr Cys Val Val Tyr Ala Pro Val Glu
        740                 745

<210> SEQ ID NO 15
<211> LENGTH: 50
<212> TYPE: PRT
<213> ORGANISM: Hordeum vulgare

<400> SEQUENCE: 15

Asn Asp Leu Gly Ile Trp Glu Ile Phe Leu Pro Asn Asn Ala Asp Gly
1               5                   10                  15

Ser Pro Pro Ile Pro His Gly Ser Arg Val Lys Val Arg Met Asp Thr
            20                  25                  30

Pro Ser Gly Thr Lys Asp Ser Ile Pro Ala Trp Ile Lys Phe Ser Val
        35                  40                  45

Gln Ala
    50

<210> SEQ ID NO 16
<211> LENGTH: 50
<212> TYPE: PRT
<213> ORGANISM: Hordeum vulgare

<400> SEQUENCE: 16

Asp Asp Tyr Gly Val Trp Glu Ile Phe Leu Pro Asn Asn Ala Asp Gly
1               5                   10                  15

Ser Pro Ala Ile Pro His Gly Ser Arg Val Lys Ile Arg Met Asp Thr
            20                  25                  30

Pro Ser Gly Val Lys Asp Ser Ile Ser Ala Trp Ile Lys Phe Ser Val
        35                  40                  45

Gln Ala
    50

<210> SEQ ID NO 17
<211> LENGTH: 760
<212> TYPE: PRT
<213> ORGANISM: Oryza sativa

<400> SEQUENCE: 17

Ala Ala Gly Ala Ser Gly Glu Val Met Ile Pro Glu Gly Glu Ser Asp
1               5                   10                  15

Gly Met Pro Val Ser Ala Gly Ser Asp Asp Leu Gln Leu Pro Ala Leu
            20                  25                  30

Asp Asp Glu Leu Ser Thr Glu Val Gly Ala Glu Val Glu Ile Glu Ser
        35                  40                  45

Ser Gly Ala Ser Asp Val Glu Gly Val Lys Arg Val Val Glu Glu Leu
    50                  55                  60

Ala Ala Glu Gln Lys Pro Arg Val Pro Pro Thr Gly Asp Gly Gln
65                  70                  75                  80

Lys Ile Phe Gln Met Asp Ser Met Leu Asn Gly Tyr Lys Tyr His Leu
                85                  90                  95

Glu Tyr Arg Tyr Ser Leu Tyr Arg Arg Leu Arg Ser Asp Ile Asp Gln
            100                 105                 110

Tyr Glu Gly Gly Leu Glu Thr Phe Ser Arg Gly Tyr Glu Lys Phe Gly
        115                 120                 125

Phe Asn His Ser Ala Glu Gly Val Thr Tyr Arg Glu Trp Ala Pro Gly
    130                 135                 140
```

```
Ala His Ser Ala Ala Leu Val Gly Asp Phe Asn Asn Trp Asn Pro Asn
145                 150                 155                 160

Ala Asp Arg Met Ser Lys Asn Glu Phe Gly Val Trp Glu Ile Phe Leu
            165                 170                 175

Pro Asn Asn Ala Asp Gly Ser Ser Pro Ile Pro His Gly Ser Arg Val
        180                 185                 190

Lys Val Arg Met Glu Thr Pro Ser Gly Ile Lys Asp Ser Ile Pro Ala
    195                 200                 205

Trp Ile Lys Tyr Ser Val Gln Ala Ala Gly Glu Ile Pro Tyr Asn Gly
210                 215                 220

Ile Tyr Tyr Asp Pro Glu Glu Glu Lys Tyr Ile Phe Lys His Pro
225                 230                 235                 240

Gln Pro Lys Arg Pro Lys Ser Leu Arg Ile Tyr Glu Thr His Val Gly
            245                 250                 255

Met Ser Ser Thr Glu Pro Lys Ile Asn Thr Tyr Ala Asn Phe Arg Asp
        260                 265                 270

Glu Val Leu Pro Arg Ile Lys Lys Leu Gly Tyr Asn Ala Val Gln Ile
    275                 280                 285

Met Ala Ile Gln Glu His Ala Tyr Tyr Gly Ser Phe Gly Tyr His Val
290                 295                 300

Thr Asn Phe Phe Ala Pro Ser Ser Arg Phe Gly Thr Pro Glu Asp Leu
305                 310                 315                 320

Lys Ser Leu Ile Asp Lys Ala His Glu Leu Gly Leu Val Val Leu Met
            325                 330                 335

Asp Val Val His Ser His Ala Ser Asn Asn Thr Leu Asp Gly Leu Asn
        340                 345                 350

Gly Phe Asp Gly Thr Asp Thr His Tyr Phe His Ser Gly Ser Arg Gly
    355                 360                 365

His His Trp Met Trp Asp Ser Arg Leu Phe Asn Tyr Gly Asn Trp Glu
370                 375                 380

Val Leu Arg Phe Leu Leu Ser Asn Ala Arg Trp Trp Leu Glu Glu Tyr
385                 390                 395                 400

Lys Phe Asp Gly Phe Arg Phe Asp Gly Val Thr Ser Met Met Tyr Thr
            405                 410                 415

His His Gly Leu Gln Val Ala Phe Thr Gly Asn Tyr Ser Glu Tyr Phe
        420                 425                 430

Gly Phe Ala Thr Asp Ala Asp Ala Val Val Tyr Leu Met Leu Val Asn
    435                 440                 445

Asp Leu Ile His Gly Leu Tyr Pro Glu Ala Ile Thr Ile Gly Glu Asp
450                 455                 460

Val Ser Gly Met Pro Thr Phe Ala Leu Pro Val Gln Asp Gly Gly Val
465                 470                 475                 480

Gly Phe Asp Tyr Arg Leu His Met Ala Val Pro Asp Lys Trp Ile Glu
            485                 490                 495

Leu Leu Lys Gln Ser Asp Glu Ser Trp Lys Met Gly Asp Ile Val His
        500                 505                 510

Thr Leu Thr Asn Arg Arg Trp Ser Glu Lys Cys Val Thr Tyr Ala Glu
    515                 520                 525

Ser His Asp Gln Ala Leu Val Gly Asp Lys Thr Ile Ala Phe Trp Leu
530                 535                 540

Met Asp Lys Asp Met Tyr Asp Phe Met Ala Leu Asp Arg Pro Ala Thr
545                 550                 555                 560

Pro Ser Ile Asp Arg Gly Ile Ala Leu His Lys Met Ile Arg Leu Ile
```

```
                565                 570                 575
Thr Met Gly Leu Gly Gly Glu Gly Tyr Leu Asn Phe Met Gly Asn Glu
            580                 585                 590

Phe Gly His Pro Glu Trp Ile Asp Phe Pro Arg Ala Pro Gln Val Leu
            595                 600                 605

Pro Asn Gly Lys Phe Ile Pro Gly Asn Asn Asn Ser Tyr Asp Lys Cys
            610                 615                 620

Arg Arg Arg Phe Asp Leu Gly Asp Ala Asp Tyr Leu Arg Tyr Arg Gly
625                 630                 635                 640

Met Leu Glu Phe Asp Arg Ala Met Gln Ser Leu Glu Glu Lys Tyr Gly
            645                 650                 655

Phe Met Thr Ser Asp His Gln Tyr Ile Ser Arg Lys His Glu Glu Asp
            660                 665                 670

Lys Met Ile Ile Phe Glu Lys Gly Asp Leu Val Phe Val Phe Asn Phe
            675                 680                 685

His Trp Ser Asn Ser Tyr Phe Asp Tyr Arg Val Gly Cys Leu Lys Pro
            690                 695                 700

Gly Lys Tyr Lys Val Val Leu Asp Ser Asp Ala Gly Leu Phe Gly Gly
705                 710                 715                 720

Phe Gly Arg Ile His His Thr Ala Glu His Phe Thr Ala Asp Cys Ser
            725                 730                 735

His Asp Asn Arg Pro Tyr Ser Phe Ser Val Tyr Ser Pro Ser Arg Thr
            740                 745                 750

Cys Val Val Tyr Ala Pro Ala Glu
            755                 760

<210> SEQ ID NO 18
<211> LENGTH: 844
<212> TYPE: PRT
<213> ORGANISM: Oryza sativa

<400> SEQUENCE: 18

Val Glu Ala Glu Arg Gly Gly Cys Arg Gly Ile Arg Ser Gly Cys Gly
1               5                   10                  15

Ala Gly Glu Met Ala Ala Pro Ala Ser Ala Val Pro Gly Ser Ala Ala
            20                  25                  30

Gly Leu Arg Ala Gly Ala Val Arg Phe Pro Val Pro Ala Gly Ala Arg
        35                  40                  45

Ser Trp Arg Ala Ala Ala Glu Leu Pro Thr Ser Arg Ser Leu Leu Ser
    50                  55                  60

Gly Arg Arg Phe Pro Gly Ala Val Arg Val Gly Ser Gly Gly Arg
65                  70                  75                  80

Val Ala Val Arg Ala Ala Gly Ala Ser Gly Glu Val Met Ile Pro Glu
                85                  90                  95

Gly Glu Ser Asp Gly Met Pro Val Ser Ala Gly Ser Asp Asp Leu Gln
            100                 105                 110

Leu Pro Ala Leu Asp Asp Glu Leu Ser Thr Glu Val Gly Ala Glu Val
        115                 120                 125

Glu Ile Glu Ser Ser Gly Ala Ser Asp Val Glu Gly Val Lys Arg Val
    130                 135                 140

Val Glu Glu Leu Ala Ala Glu Gln Lys Pro Arg Val Val Pro Pro Thr
145                 150                 155                 160

Gly Asp Gly Gln Lys Ile Phe Gln Met Asp Ser Met Leu Asn Gly Tyr
                165                 170                 175
```

```
Lys Tyr His Leu Glu Tyr Arg Tyr Ser Leu Tyr Arg Arg Leu Arg Ser
            180                 185                 190

Asp Ile Asp Gln Tyr Glu Gly Gly Leu Glu Thr Phe Ser Arg Gly Tyr
            195                 200                 205

Glu Lys Phe Gly Phe Asn His Ser Ala Glu Gly Val Thr Tyr Arg Glu
            210                 215                 220

Trp Ala Pro Gly Ala His Ser Ala Ala Leu Val Gly Asp Phe Asn Asn
225                 230                 235                 240

Trp Asn Pro Asn Ala Asp Arg Met Ser Lys Asn Glu Phe Gly Val Trp
                245                 250                 255

Glu Ile Phe Leu Pro Asn Asn Ala Asp Gly Ser Ser Pro Ile Pro His
            260                 265                 270

Gly Ser Arg Val Lys Val Arg Met Glu Thr Pro Ser Gly Ile Lys Asp
            275                 280                 285

Ser Ile Pro Ala Trp Ile Lys Tyr Ser Val Gln Ala Ala Gly Glu Ile
            290                 295                 300

Pro Tyr Asn Gly Ile Tyr Tyr Asp Pro Pro Glu Glu Glu Lys Tyr Ile
305                 310                 315                 320

Phe Lys His Pro Gln Pro Lys Arg Pro Lys Ser Leu Arg Ile Tyr Glu
                325                 330                 335

Thr His Val Gly Met Ser Ser Thr Glu Pro Lys Ile Asn Thr Tyr Ala
            340                 345                 350

Asn Phe Arg Asp Glu Val Leu Pro Arg Ile Lys Lys Leu Gly Tyr Asn
            355                 360                 365

Ala Val Gln Ile Met Ala Ile Gln Glu His Ala Tyr Tyr Gly Ser Phe
            370                 375                 380

Gly Tyr His Val Thr Asn Phe Phe Ala Pro Ser Ser Arg Phe Gly Thr
385                 390                 395                 400

Pro Glu Asp Leu Lys Ser Leu Ile Asp Lys Ala His Glu Leu Gly Leu
                405                 410                 415

Val Val Leu Met Asp Val Val His Ser His Ala Ser Asn Asn Thr Leu
            420                 425                 430

Asp Gly Leu Asn Gly Phe Asp Gly Thr Asp Thr His Tyr Phe His Ser
            435                 440                 445

Gly Ser Arg Gly His His Trp Met Trp Asp Ser Arg Leu Phe Asn Tyr
450                 455                 460

Gly Asn Trp Glu Val Leu Arg Phe Leu Leu Ser Asn Ala Arg Trp Trp
465                 470                 475                 480

Leu Glu Glu Tyr Lys Phe Asp Gly Phe Arg Phe Asp Gly Val Thr Ser
                485                 490                 495

Met Met Tyr Thr His His Gly Leu Gln Val Ala Phe Thr Gly Asn Tyr
            500                 505                 510

Ser Glu Tyr Phe Gly Phe Ala Thr Asp Ala Asp Ala Val Val Tyr Leu
            515                 520                 525

Met Leu Val Asn Asp Leu Ile His Gly Leu Tyr Pro Glu Ala Ile Thr
            530                 535                 540

Ile Gly Glu Asp Val Ser Gly Met Pro Thr Phe Ala Leu Pro Val Gln
545                 550                 555                 560

Asp Gly Gly Val Gly Phe Asp Tyr Arg Leu His Met Ala Val Pro Asp
                565                 570                 575

Lys Trp Ile Glu Leu Leu Lys Gln Ser Asp Glu Ser Trp Lys Met Gly
            580                 585                 590

Asp Ile Val His Thr Leu Thr Asn Arg Arg Trp Ser Glu Lys Cys Val
```

```
                595                 600                 605
Thr Tyr Ala Glu Ser His Asp Gln Ala Leu Val Gly Asp Lys Thr Ile
            610                 615                 620

Ala Phe Trp Leu Met Asp Lys Asp Met Tyr Asp Phe Met Ala Leu Asp
625                 630                 635                 640

Arg Pro Ala Thr Pro Ser Ile Asp Arg Gly Ile Ala Leu His Lys Met
                645                 650                 655

Ile Arg Leu Ile Thr Met Gly Leu Gly Gly Glu Gly Tyr Leu Asn Phe
            660                 665                 670

Met Gly Asn Glu Phe Gly His Pro Glu Trp Ile Asp Phe Pro Arg Ala
        675                 680                 685

Pro Gln Val Leu Pro Asn Gly Lys Phe Ile Pro Gly Asn Asn Asn Ser
    690                 695                 700

Tyr Asp Lys Cys Arg Arg Phe Asp Leu Gly Asp Ala Asp Tyr Leu
705                 710                 715                 720

Arg Tyr Arg Gly Met Leu Glu Phe Asp Arg Ala Met Gln Ser Leu Glu
                725                 730                 735

Glu Lys Tyr Gly Phe Met Thr Ser Asp His Gln Tyr Ile Ser Arg Lys
            740                 745                 750

His Glu Glu Asp Lys Met Ile Ile Phe Glu Lys Gly Asp Leu Val Phe
        755                 760                 765

Val Phe Asn Phe His Trp Ser Asn Ser Tyr Phe Asp Tyr Arg Val Gly
    770                 775                 780

Cys Leu Lys Pro Gly Lys Tyr Lys Val Val Leu Asp Ser Asp Ala Gly
785                 790                 795                 800

Leu Phe Gly Gly Phe Gly Arg Ile His His Thr Ala Glu His Phe Thr
                805                 810                 815

Ala Asp Cys Ser His Asp Asn Arg Pro Tyr Ser Phe Ser Val Tyr Ser
            820                 825                 830

Pro Ser Arg Thr Cys Val Val Tyr Ala Pro Ala Glu
        835                 840

<210> SEQ ID NO 19
<211> LENGTH: 857
<212> TYPE: PRT
<213> ORGANISM: Pisum sativum

<400> SEQUENCE: 19

Lys Val Leu Ile Pro Glu Asp Gln Asp Asn Ser Val Ser Leu Ala Asp
1               5                   10                  15

Gln Leu Glu Asn Pro Asp Ile Thr Ser Glu Asp Ala Gln Asn Leu Glu
            20                  25                  30

Asp Leu Thr Met Lys Asp Gly Asn Lys Tyr Asn Ile Asp Glu Ser Thr
        35                  40                  45

Ser Ser Tyr Arg Glu Val Gly Asp Glu Lys Gly Ser Val Thr Ser Ser
    50                  55                  60

Ser Leu Val Asp Val Asn Thr Asp Thr Gln Ala Lys Lys Thr Ser Val
65                  70                  75                  80

His Ser Asp Lys Lys Val Lys Val Asp Lys Pro Lys Ile Ile Pro Pro
                85                  90                  95

Pro Gly Thr Gly Gln Lys Ile Tyr Glu Ile Asp Pro Leu Leu Gln Ala
            100                 105                 110

His Arg Gln His Leu Asp Phe Arg Tyr Gly Gln Tyr Lys Arg Ile Arg
        115                 120                 125
```

-continued

```
Glu Glu Ile Asp Lys Tyr Gly Gly Leu Asp Ala Phe Ser Arg Gly
    130                 135                 140
Tyr Glu Lys Phe Gly Phe Thr Arg Ser Ala Thr Gly Ile Thr Tyr Arg
145                 150                 155                 160
Glu Trp Ala Pro Gly Ala Lys Ser Ala Ala Leu Val Gly Asp Phe Asn
                165                 170                 175
Asn Trp Asn Pro Asn Ala Asp Val Met Thr Lys Asp Ala Phe Gly Val
            180                 185                 190
Trp Glu Ile Phe Leu Pro Asn Asn Ala Asp Gly Ser Pro Pro Ile Pro
        195                 200                 205
His Gly Ser Arg Val Lys Ile His Met Asp Thr Pro Ser Gly Ile Lys
    210                 215                 220
Asp Ser Ile Pro Ala Trp Ile Lys Phe Ser Val Gln Ala Pro Gly Glu
225                 230                 235                 240
Ile Pro Tyr Asn Gly Ile Tyr Tyr Asp Pro Pro Glu Glu Lys Tyr
                245                 250                 255
Val Phe Lys His Pro Gln Pro Lys Arg Pro Gln Ser Ile Arg Ile Tyr
            260                 265                 270
Glu Ser His Ile Gly Met Ser Ser Pro Glu Pro Lys Ile Asn Thr Tyr
    275                 280                 285
Ala Asn Phe Arg Asp Asp Val Leu Pro Arg Ile Lys Lys Leu Gly Tyr
    290                 295                 300
Asn Ala Val Gln Ile Met Ala Ile Gln Glu His Ser Tyr Tyr Ala Ser
305                 310                 315                 320
Phe Gly Tyr His Val Thr Asn Phe Phe Ala Pro Ser Ser Arg Phe Gly
                325                 330                 335
Thr Pro Glu Asp Leu Lys Ser Leu Ile Asp Arg Ala His Glu Leu Gly
            340                 345                 350
Leu Leu Val Leu Met Asp Ile Val His Ser His Ser Ser Asn Asn Thr
        355                 360                 365
Leu Asp Gly Leu Asn Met Phe Asp Gly Thr Asp Gly His Tyr Phe His
    370                 375                 380
Pro Gly Ser Arg Gly Tyr His Trp Met Trp Asp Ser Arg Leu Phe Asn
385                 390                 395                 400
Tyr Gly Ser Trp Glu Val Leu Arg Tyr Leu Leu Ser Asn Ala Arg Trp
                405                 410                 415
Trp Leu Asp Glu Tyr Lys Phe Asp Gly Phe Arg Phe Asp Gly Val Thr
            420                 425                 430
Ser Met Met Tyr Thr His His Gly Leu Gln Val Ser Phe Thr Gly Asn
        435                 440                 445
Tyr Ser Glu Tyr Phe Gly Leu Ala Thr Asp Val Glu Ala Val Val Tyr
    450                 455                 460
Met Met Leu Val Asn Asp Leu Ile His Gly Leu Phe Pro Glu Ala Val
465                 470                 475                 480
Ser Ile Gly Glu Asp Val Ser Gly Met Pro Thr Phe Cys Leu Pro Thr
                485                 490                 495
Gln Asp Gly Gly Ile Gly Phe Asn Tyr Arg Leu His Met Ala Val Ala
            500                 505                 510
Asp Lys Trp Ile Glu Leu Leu Lys Lys Gln Asp Glu Asp Trp Arg Met
        515                 520                 525
Gly Asp Ile Val His Thr Leu Thr Asn Arg Arg Trp Leu Glu Lys Cys
    530                 535                 540
Val Val Tyr Ala Glu Ser His Asp Gln Ala Leu Val Gly Asp Lys Thr
```

```
                545                 550                 555                 560

Leu Ala Phe Trp Leu Met Asp Lys Asp Met Tyr Asp Phe Met Ala Leu
                565                 570                 575

Asp Arg Pro Ser Thr Pro Leu Ile Asp Arg Gly Ile Ala Leu His Lys
                580                 585                 590

Met Ile Arg Leu Ile Thr Met Gly Leu Gly Gly Glu Gly Tyr Leu Asn
                595                 600                 605

Phe Met Gly Asn Glu Phe Gly His Pro Glu Trp Ile Asp Phe Pro Arg
                610                 615                 620

Gly Glu Gln His Leu Pro Asn Gly Lys Ile Val Pro Gly Asn Asn Asn
625                 630                 635                 640

Ser Tyr Asp Lys Cys Arg Arg Phe Asp Leu Gly Asp Ala Asp Tyr
                645                 650                 655

Leu Arg Tyr His Gly Met Gln Glu Phe Asp Arg Ala Met Gln His Leu
                660                 665                 670

Glu Glu Arg Tyr Gly Phe Met Thr Ser Glu His Gln Tyr Ile Ser Arg
                675                 680                 685

Lys Asn Glu Gly Asp Arg Val Ile Ile Phe Glu Arg Asp Asn Leu Val
                690                 695                 700

Phe Val Phe Asn Phe His Trp Thr Asn Ser Tyr Ser Asp Tyr Lys Val
705                 710                 715                 720

Gly Cys Leu Lys Pro Gly Lys Tyr Lys Ile Val Leu Asp Ser Asp Asp
                725                 730                 735

Thr Leu Phe Gly Gly Phe Asn Arg Leu Asn His Thr Ala Glu Tyr Phe
                740                 745                 750

Thr Ser Glu Gly Trp Tyr Asp Asp Arg Pro Arg Ser Phe Leu Val Tyr
                755                 760                 765

Ala Pro Ser Arg Thr Ala Val Val Tyr Ala Leu Ala Asp Gly Val Glu
                770                 775                 780

Ser Glu Pro Ile Glu Leu Ser Asp Gly Val Glu Ser Glu Pro Ile Glu
785                 790                 795                 800

Leu Ser Val Gly Val Glu Ser Glu Pro Ile Glu Leu Ser Val Glu Glu
                805                 810                 815

Ala Glu Ser Glu Pro Ile Glu Arg Ser Val Glu Glu Val Glu Ser Glu
                820                 825                 830

Thr Thr Gln Gln Ser Val Glu Val Glu Ser Glu Thr Thr Gln Gln Ser
                835                 840                 845

Val Glu Val Glu Ser Glu Thr Thr Gln
    850                 855

<210> SEQ ID NO 20
<211> LENGTH: 779
<212> TYPE: PRT
<213> ORGANISM: Solanum tuberosum

<400> SEQUENCE: 20

Thr Met Ala Pro Leu Glu Glu Asp Val Lys Thr Glu Asn Ile Gly Leu
1               5                   10                  15

Leu Asn Leu Asp Pro Thr Leu Glu Pro Tyr Leu Asp His Phe Arg His
                20                  25                  30

Arg Met Lys Arg Tyr Val Asp Gln Lys Met Leu Ile Glu Lys Tyr Glu
            35                  40                  45

Gly Pro Leu Glu Glu Phe Ala Gln Gly Tyr Leu Lys Phe Gly Phe Asn
        50                  55                  60
```

-continued

```
Arg Glu Asp Gly Cys Ile Val Tyr Arg Glu Trp Ala Pro Ala Ala Gln
 65                  70                  75                  80

Glu Asp Glu Val Ile Gly Asp Phe Asn Gly Trp Asn Gly Ser Asn His
                 85                  90                  95

Met Met Glu Lys Asp Gln Phe Gly Val Trp Ser Ile Arg Ile Pro Asp
            100                 105                 110

Val Asp Ser Lys Pro Val Ile Pro His Asn Ser Arg Val Lys Phe Arg
            115                 120                 125

Phe Lys His Gly Asn Gly Val Trp Val Asp Arg Ile Pro Ala Trp Ile
        130                 135                 140

Lys Tyr Ala Thr Ala Asp Ala Thr Lys Phe Ala Ala Pro Tyr Asp Gly
145                 150                 155                 160

Val Tyr Trp Asp Pro Pro Ser Glu Arg Tyr His Phe Lys Tyr Pro
                165                 170                 175

Arg Pro Pro Lys Pro Arg Ala Pro Arg Ile Tyr Glu Ala His Val Gly
            180                 185                 190

Met Ser Ser Glu Pro Arg Val Asn Ser Tyr Arg Glu Phe Ala Asp
            195                 200                 205

Asp Val Leu Pro Arg Ile Lys Ala Asn Asn Tyr Asn Thr Val Gln Leu
    210                 215                 220

Met Ala Ile Met Glu His Ser Tyr Tyr Gly Ser Phe Gly Tyr His Val
225                 230                 235                 240

Thr Asn Phe Phe Ala Val Ser Ser Arg Tyr Gly Asn Pro Glu Asp Leu
                245                 250                 255

Lys Tyr Leu Ile Asp Lys Ala His Ser Leu Gly Leu Gln Val Leu Val
            260                 265                 270

Asp Val Val His Ser His Ala Ser Asn Asn Val Thr Asp Gly Leu Asn
        275                 280                 285

Gly Phe Asp Ile Gly Gln Gly Ser Gln Glu Ser Tyr Phe His Ala Gly
    290                 295                 300

Glu Arg Gly Tyr His Lys Leu Trp Asp Ser Arg Leu Phe Asn Tyr Ala
305                 310                 315                 320

Asn Trp Glu Val Leu Arg Phe Leu Leu Ser Asn Leu Arg Trp Trp Leu
                325                 330                 335

Glu Glu Tyr Asn Phe Asp Gly Phe Arg Phe Asp Gly Ile Thr Ser Met
            340                 345                 350

Leu Tyr Val His His Gly Ile Asn Met Gly Phe Thr Gly Asn Tyr Asn
        355                 360                 365

Glu Tyr Phe Ser Glu Ala Thr Asp Val Asp Ala Val Val Tyr Leu Met
    370                 375                 380

Leu Ala Asn Asn Leu Ile His Lys Ile Phe Pro Asp Ala Thr Val Ile
385                 390                 395                 400

Ala Glu Asp Val Ser Gly Met Pro Gly Leu Gly Arg Pro Val Ser Glu
                405                 410                 415

Gly Gly Ile Gly Phe Asp Tyr Arg Leu Ala Met Ala Ile Pro Asp Lys
            420                 425                 430

Trp Ile Asp Tyr Leu Lys Asn Lys Asn Asp Glu Asp Trp Ser Met Lys
        435                 440                 445

Glu Val Thr Ser Ser Leu Thr Asn Arg Arg Tyr Thr Glu Lys Cys Ile
    450                 455                 460

Ala Tyr Ala Glu Ser His Asp Gln Ser Ile Val Gly Asp Lys Thr Ile
465                 470                 475                 480

Ala Phe Leu Leu Met Asp Lys Glu Met Tyr Ser Gly Met Ser Cys Leu
```

```
                485                 490                 495
Thr Asp Ala Ser Pro Val Val Asp Arg Gly Ile Ala Leu His Lys Met
            500                 505                 510
Ile His Phe Phe Thr Met Ala Leu Gly Gly Glu Gly Tyr Leu Asn Phe
        515                 520                 525
Met Gly Asn Glu Phe Gly His Pro Glu Trp Ile Asp Phe Pro Arg Glu
    530                 535                 540
Gly Asn Asn Trp Ser Tyr Asp Lys Cys Arg Arg Gln Trp Asn Leu Ala
545                 550                 555                 560
Asp Ser Glu His Leu Arg Tyr Lys Phe Met Asn Ala Phe Asp Arg Ala
            565                 570                 575
Met Asn Ser Leu Asp Glu Lys Phe Ser Phe Leu Ala Ser Gly Lys Gln
        580                 585                 590
Ile Val Ser Ser Met Asp Asp Asn Lys Val Val Phe Glu Arg
    595                 600                 605
Gly Asp Leu Val Phe Val Phe Asn Phe His Pro Lys Asn Thr Tyr Glu
    610                 615                 620
Gly Tyr Lys Val Gly Cys Asp Leu Pro Gly Lys Tyr Arg Val Ala Leu
625                 630                 635                 640
Asp Ser Asp Ala Trp Glu Phe Gly His Gly Arg Thr Gly His Asp
            645                 650                 655
Val Asp His Phe Thr Ser Pro Glu Gly Ile Pro Gly Val Pro Glu Thr
        660                 665                 670
Asn Phe Asn Gly Arg Gln Ile Pro Ser Lys Cys Cys Leu Leu Arg Glu
    675                 680                 685
His Val Trp Leu Ile Thr Glu Leu Met Asn Ala Cys Gln Lys Leu Lys
    690                 695                 700
Ile Thr Arg Gln Thr Phe Val Val Ser Tyr Tyr Gln Gln Pro Ile Ser
705                 710                 715                 720
Arg Arg Val Thr Arg Asn Leu Lys Ile Arg Tyr Leu Gln Ile Ser Val
            725                 730                 735
Thr Leu Thr Asn Ala Cys Gln Lys Leu Lys Phe Thr Arg Gln Thr Phe
        740                 745                 750
Leu Val Ser Tyr Tyr Gln Gln Pro Ile Leu Arg Arg Val Thr Arg Lys
    755                 760                 765
Leu Lys Asp Ser Leu Ser Thr Asn Ile Ser Thr
    770                 775

<210> SEQ ID NO 21
<211> LENGTH: 762
<212> TYPE: PRT
<213> ORGANISM: Triticum aestivum

<400> SEQUENCE: 21

Thr Met Ala Thr Ala Glu Asp Gly Val Gly Asp Leu Pro Ile Tyr Asp
1               5                   10                  15
Leu Asp Pro Lys Phe Ala Gly Phe Lys Glu His Phe Ser Tyr Arg Met
            20                  25                  30
Lys Lys Tyr Leu Asp Gln Lys His Ser Ile Glu Lys His Glu Gly Gly
        35                  40                  45
Leu Glu Glu Phe Ser Lys Gly Tyr Leu Lys Phe Gly Ile Asn Thr Glu
    50                  55                  60
Asn Asp Ala Thr Val Tyr Arg Glu Trp Ala Pro Ala Ala Met Asp Ala
65                  70                  75                  80
```

-continued

```
Gln Leu Ile Gly Asp Phe Asn Asn Trp Asn Gly Ser Gly His Arg Met
                 85                  90                  95
Thr Lys Asp Asn Tyr Gly Val Trp Ser Ile Arg Ile Ser His Val Asn
            100                 105                 110
Gly Lys Pro Ala Ile Pro His Asn Ser Lys Val Lys Phe Arg Phe His
            115                 120                 125
Arg Gly Asp Gly Leu Trp Val Asp Arg Val Pro Ala Trp Ile Arg Tyr
        130                 135                 140
Ala Thr Phe Asp Ala Ser Lys Phe Gly Ala Pro Tyr Asp Gly Val His
145                 150                 155                 160
Trp Asp Pro Pro Ser Gly Glu Arg Tyr Val Phe Lys His Pro Arg Pro
                165                 170                 175
Arg Lys Pro Asp Ala Pro Arg Ile Tyr Glu Ala His Val Gly Met Ser
            180                 185                 190
Gly Glu Lys Pro Glu Val Ser Thr Tyr Arg Glu Phe Ala Asp Asn Val
        195                 200                 205
Leu Pro Arg Ile Lys Ala Asn Asn Tyr Asn Thr Val Gln Leu Met Ala
    210                 215                 220
Ile Met Glu His Ser Tyr Tyr Ala Ser Phe Gly Tyr His Val Thr Asn
225                 230                 235                 240
Phe Phe Ala Val Ser Ser Arg Ser Gly Thr Pro Glu Asp Leu Lys Tyr
                245                 250                 255
Leu Val Asp Lys Ala His Ser Leu Gly Leu Arg Val Leu Met Asp Val
            260                 265                 270
Val His Ser His Ala Ser Ser Asn Lys Thr Asp Gly Leu Asn Gly Tyr
        275                 280                 285
Asp Val Gly Gln Asn Thr Gln Glu Ser Tyr Phe His Thr Gly Glu Arg
    290                 295                 300
Gly Tyr His Lys Leu Trp Asp Ser Arg Leu Phe Asn Tyr Ala Asn Trp
305                 310                 315                 320
Glu Val Leu Arg Phe Leu Leu Ser Asn Leu Arg Tyr Trp Met Asp Glu
                325                 330                 335
Phe Met Phe Asp Gly Phe Arg Phe Asp Gly Val Thr Ser Met Leu Tyr
            340                 345                 350
Asn His His Gly Ile Asn Met Ser Phe Ala Gly Ser Tyr Lys Glu Tyr
        355                 360                 365
Phe Gly Leu Asp Thr Asp Val Asp Ala Val Val Tyr Leu Met Leu Ala
    370                 375                 380
Asn His Leu Met His Lys Leu Leu Pro Glu Ala Thr Val Val Ala Glu
385                 390                 395                 400
Asp Val Ser Gly Met Pro Val Leu Cys Arg Ser Val Asp Glu Gly Gly
                405                 410                 415
Val Gly Phe Asp Tyr Arg Leu Ala Met Ala Ile Pro Asp Arg Trp Ile
            420                 425                 430
Asp Tyr Leu Lys Asn Lys Asp Asp Leu Glu Trp Ser Met Ser Gly Ile
        435                 440                 445
Ala His Thr Leu Thr Asn Arg Arg Tyr Thr Glu Lys Cys Ile Ala Tyr
    450                 455                 460
Ala Glu Ser His Asp Gln Ser Ile Val Gly Asp Lys Thr Met Ala Phe
465                 470                 475                 480
Leu Leu Met Asp Lys Glu Met Tyr Thr Gly Met Ser Asp Leu Gln Pro
                485                 490                 495
Ala Ser Pro Thr Ile Asp Arg Gly Ile Ala Leu Gln Lys Met Ile His
```

```
                    500                 505                 510
Phe Ile Thr Met Ala Leu Gly Gly Asp Gly Tyr Leu Asn Phe Met Gly
            515                 520                 525
Asn Glu Phe Gly His Pro Glu Trp Ile Asp Phe Pro Arg Glu Gly Asn
    530                 535                 540
Asn Trp Ser Tyr Asp Lys Cys Arg Arg Gln Trp Ser Leu Ala Asp Ile
545                 550                 555                 560
Asp His Leu Arg Tyr Lys Tyr Met Asn Ala Phe Asp Gln Ala Met Asn
                565                 570                 575
Ala Leu Asp Asp Lys Phe Ser Phe Leu Ser Ser Lys Gln Ile Val
            580                 585                 590
Ser Asp Met Asn Glu Lys Lys Ile Ile Val Phe Glu Arg Gly Asp
            595                 600                 605
Leu Val Phe Val Phe Asn Phe His Pro Ser Lys Thr Tyr Asp Gly Tyr
            610                 615                 620
Lys Val Gly Cys Asp Leu Pro Gly Lys Tyr Lys Val Ala Leu Asp Ser
625                 630                 635                 640
Asp Ala Leu Met Phe Gly Gly His Gly Arg Val Ala His Asp Asn Asp
                645                 650                 655
His Phe Thr Ser Pro Glu Gly Val Pro Gly Val Pro Glu Thr Asn Phe
            660                 665                 670
Asn Asn Arg Pro Asn Ser Phe Lys Ile Leu Ser Pro Ser Arg Thr Cys
            675                 680                 685
Val Ala Tyr Tyr Arg Val Glu Glu Lys Ala Glu Lys Pro Lys Asp Glu
            690                 695                 700
Gly Ala Ala Ser Trp Gly Lys Thr Ala Leu Gly Tyr Ile Asp Val Glu
705                 710                 715                 720
Ala Thr Gly Val Lys Asp Ala Ala Asp Gly Glu Ala Thr Ser Gly Ser
                725                 730                 735
Glu Lys Ala Ser Thr Gly Gly Asp Ser Ser Lys Lys Gly Ile Asn Phe
            740                 745                 750
Val Phe Leu Ser Pro Asp Lys Asp Asn Lys
            755                 760

<210> SEQ ID NO 22
<211> LENGTH: 703
<212> TYPE: PRT
<213> ORGANISM: Triticum aestivum

<400> SEQUENCE: 22

Ser Pro Pro Thr Leu Thr Ser Pro Pro Ser Ala Val Pro Ser Thr
1               5                   10                  15
Thr Met Leu Cys Leu Ser Ser Leu Leu Pro Arg Pro Ser Ala Ala
                20                  25                  30
Ala Asp Arg Pro Leu Pro Gly Ile Ile Ala Gly Gly Gly Gly Lys
            35                  40                  45
Arg Leu Ser Val Val Pro Ser Val Pro Phe Leu Leu Arg Trp Leu Trp
    50                  55                  60
Pro Arg Lys Ala Lys Ser Lys Ser Phe Val Ser Val Thr Ala Arg Gly
65                  70                  75                  80
Asn Lys Ile Ala Ala Thr Thr Gly Tyr Gly Ser Asp His Leu Pro Ile
                85                  90                  95
Tyr Asp Leu Asp Leu Lys Leu Ala Glu Phe Lys Asp His Phe Asp Tyr
            100                 105                 110
```

```
Thr Arg Asn Arg Tyr Ile Glu Gln Lys His Leu Ile Glu Lys His Glu
            115                 120                 125

Gly Ser Leu Glu Glu Phe Ser Lys Gly Tyr Leu Lys Phe Gly Ile Asn
        130                 135                 140

Thr Glu His Gly Ala Ser Val Tyr Arg Glu Trp Ala Pro Ala Ala Glu
145                 150                 155                 160

Glu Ala Gln Leu Val Gly Asp Phe Asn Asn Trp Asn Gly Ser Gly His
                165                 170                 175

Lys Met Ala Lys Asp Asn Phe Gly Val Trp Ser Ile Arg Ile Ser His
            180                 185                 190

Val Asn Gly Lys Pro Ala Ile Pro His Asn Ser Lys Val Lys Phe Arg
        195                 200                 205

Phe Arg His His Gly Val Trp Val Glu Gln Ile Pro Ala Trp Ile Arg
210                 215                 220

Tyr Ala Thr Val Thr Ala Ser Glu Ser Gly Ala Pro Tyr Asp Gly Leu
225                 230                 235                 240

His Trp Asp Pro Pro Ser Ser Glu Arg Tyr Val Phe Asn His Pro Arg
                245                 250                 255

Pro Pro Lys Pro Asp Val Pro Arg Ile Tyr Glu Ala His Val Gly Val
            260                 265                 270

Ser Gly Gly Lys Leu Glu Ala Gly Thr Tyr Arg Glu Phe Pro Asp Asn
        275                 280                 285

Val Leu Pro Cys Leu Arg Ala Thr Asn Tyr Asn Thr Val Gln Leu Met
    290                 295                 300

Gly Ile Met Glu His Ser Asp Ser Ala Ser Phe Gly Tyr His Val Thr
305                 310                 315                 320

Asn Phe Phe Ala Val Ser Ser Arg Ser Gly Thr Pro Glu Asp Leu Lys
                325                 330                 335

Tyr Leu Ile Asp Lys Ala His Ser Leu Gly Leu Arg Val Leu Met Asp
            340                 345                 350

Val Val His Ser His Ala Ser Asn Asn Val Ile Asp Gly Leu Asn Gly
        355                 360                 365

Tyr Asp Val Gly Gln Ser His Glu Ser Tyr Phe Tyr Thr Gly Asp
    370                 375                 380

Lys Gly Tyr Asn Lys Met Trp Asn Gly Arg Met Phe Asn Tyr Ala Asn
385                 390                 395                 400

Trp Glu Val Leu Arg Phe Leu Leu Ser Asn Leu Arg Tyr Trp Met Asp
                405                 410                 415

Glu Phe Met Phe Asp Gly Phe Arg Phe Val Gly Val Thr Ser Met Leu
            420                 425                 430

Tyr Asn His Asn Gly Ile Asn Met Ser Phe Asn Gly Asn Tyr Lys Asp
        435                 440                 445

Tyr Ile Gly Leu Asp Thr Asn Val Asp Ala Phe Val Tyr Met Met Leu
    450                 455                 460

Ala Asn His Leu Met His Lys Leu Phe Pro Glu Ala Ile Val Val Ala
465                 470                 475                 480

Val Asp Val Ser Gly Met Pro Val Leu Cys Trp Pro Val Asp Glu Gly
                485                 490                 495

Gly Leu Gly Phe Asp Tyr Arg Gln Ala Met Thr Ile Pro Asp Arg Trp
            500                 505                 510

Ile Asp Tyr Leu Glu Asn Lys Gly Asp Gln Gln Trp Ser Met Ser Ser
        515                 520                 525

Val Ile Ser Gln Thr Leu Thr Asn Arg Arg Tyr Pro Glu Lys Phe Ile
```

-continued

```
            530                 535                 540
Ala Tyr Ala Glu Arg Gln Asn His Ser Ile Ile Gly Ser Lys Thr Met
545                 550                 555                 560

Ala Phe Leu Leu Met Glu Trp Glu Thr Tyr Ser Gly Met Ser Ala Met
                565                 570                 575

Asp Pro Asp Ser Pro Thr Ile Asp Arg Ala Ile Ala Leu Gln Lys Met
            580                 585                 590

Ile His Phe Ile Thr Met Ala Phe Gly Gly Asp Ser Tyr Leu Lys Phe
        595                 600                 605

Met Gly Asn Glu Tyr Met Asn Ala Phe Val Gln Ala Val Asp Thr Pro
    610                 615                 620

Ser Asp Lys Cys Ser Phe Leu Ser Ser Asn Gln Thr Ala Ser His
625                 630                 635                 640

Met Asn Glu Glu Lys Gly Ser Ala Leu Thr Lys Gly Tyr Thr His
                645                 650                 655

Leu Arg Ser Gly Cys Phe Asp Pro Ser Leu Pro Ser Thr Ser Ser Cys
                660                 665                 670

Ala Phe Leu Gly Pro Ser Asn Gln Ser Pro Phe Ser Lys Pro Phe Ile
            675                 680                 685

Gly Phe Pro Gly Cys Ile Phe Cys Cys Gly Leu Phe Lys Gly Glu
        690                 695                 700

<210> SEQ ID NO 23
<211> LENGTH: 752
<212> TYPE: PRT
<213> ORGANISM: Zea mays

<400> SEQUENCE: 23

Thr Met Ala Thr Ala Lys Gly Asp Val Asp His Leu Pro Ile Tyr Asp
1               5                   10                  15

Leu Asp Pro Lys Leu Glu Ile Phe Lys Asp His Phe Arg Tyr Arg Met
                20                  25                  30

Lys Arg Phe Leu Glu Gln Lys Gly Ser Ile Glu Glu Asn Glu Gly Ser
            35                  40                  45

Leu Glu Ser Phe Ser Lys Gly Tyr Leu Lys Phe Gly Ile Asn Thr Asn
    50                  55                  60

Glu Asp Gly Thr Val Tyr Arg Glu Trp Ala Pro Ala Ala Gln Glu Ala
65                  70                  75                  80

Glu Leu Ile Gly Asp Phe Asn Asp Trp Asn Gly Ala Asn His Lys Met
                85                  90                  95

Glu Lys Asp Lys Phe Gly Val Trp Ser Ile Lys Ile Asp His Val Lys
            100                 105                 110

Gly Lys Pro Ala Ile Pro His Asn Ser Lys Val Lys Phe Arg Phe Leu
        115                 120                 125

His Gly Gly Val Trp Val Asp Arg Ile Pro Ala Leu Ile Arg Tyr Ala
    130                 135                 140

Thr Val Asp Ala Ser Lys Phe Gly Ala Pro Tyr Asp Gly Val His Trp
145                 150                 155                 160

Asp Pro Pro Ala Ser Glu Arg Tyr Thr Phe Lys His Pro Arg Pro Ser
                165                 170                 175

Lys Pro Ala Ala Pro Arg Ile Tyr Glu Ala His Val Gly Met Ser Gly
            180                 185                 190

Glu Lys Pro Ala Val Ser Thr Tyr Arg Glu Phe Ala Asp Asn Val Leu
        195                 200                 205
```

```
Pro Arg Ile Arg Ala Asn Asn Tyr Asn Thr Val Gln Leu Met Ala Val
210                 215                 220
Met Glu His Ser Tyr Tyr Ala Ser Phe Gly Tyr His Val Thr Asn Phe
225                 230                 235                 240
Phe Ala Val Ser Ser Arg Ser Gly Thr Pro Glu Asp Leu Lys Tyr Leu
                245                 250                 255
Val Asp Lys Ala His Ser Leu Gly Leu Arg Val Leu Met Asp Val Val
            260                 265                 270
His Ser His Ala Ser Asn Asn Val Thr Asp Gly Leu Asn Gly Tyr Asp
        275                 280                 285
Val Gly Gln Ser Thr Gln Glu Ser Tyr Phe His Ala Gly Asp Arg Gly
290                 295                 300
Tyr His Lys Leu Trp Asp Ser Arg Leu Phe Asn Tyr Ala Asn Trp Glu
305                 310                 315                 320
Val Leu Arg Phe Leu Leu Ser Asn Leu Arg Tyr Trp Leu Asp Glu Phe
                325                 330                 335
Met Phe Asp Gly Phe Arg Phe Asp Gly Val Thr Ser Met Leu Tyr His
            340                 345                 350
His His Gly Ile Asn Val Gly Phe Thr Gly Asn Tyr Gln Glu Tyr Phe
        355                 360                 365
Ser Leu Asp Thr Ala Val Asp Ala Val Val Tyr Met Met Leu Ala Asn
370                 375                 380
His Leu Met His Lys Leu Leu Pro Glu Ala Thr Val Val Ala Glu Asp
385                 390                 395                 400
Val Ser Gly Met Pro Val Leu Cys Arg Pro Val Asp Glu Gly Gly Val
                405                 410                 415
Gly Phe Asp Tyr Arg Leu Ala Met Ala Ile Pro Asp Arg Trp Ile Asp
            420                 425                 430
Tyr Leu Lys Asn Lys Asp Asp Ser Glu Trp Ser Met Gly Glu Ile Ala
        435                 440                 445
His Thr Leu Thr Asn Arg Arg Tyr Thr Glu Lys Cys Ile Ala Tyr Ala
450                 455                 460
Glu Ser His Asp Gln Ser Ile Val Gly Asp Lys Thr Ile Ala Phe Leu
465                 470                 475                 480
Leu Met Asp Lys Glu Met Tyr Thr Gly Met Ser Asp Leu Gln Pro Ala
                485                 490                 495
Ser Pro Thr Ile Asp Arg Gly Ile Ala Leu Gln Lys Met Ile His Phe
            500                 505                 510
Ile Thr Met Ala Leu Gly Gly Asp Gly Tyr Leu Asn Phe Met Gly Asn
        515                 520                 525
Glu Phe Gly His Pro Glu Trp Ile Asp Phe Pro Arg Glu Gly Asn Asn
530                 535                 540
Trp Ser Tyr Asp Lys Cys Arg Arg Gln Trp Ser Leu Val Asp Thr Asp
545                 550                 555                 560
His Leu Arg Tyr Lys Tyr Met Asn Ala Phe Asp Gln Ala Met Asn Ala
                565                 570                 575
Leu Asp Glu Arg Phe Ser Phe Leu Ser Ser Lys Gln Ile Val Ser
            580                 585                 590
Asp Met Asn Asp Glu Glu Lys Val Ile Val Phe Glu Arg Gly Asp Leu
        595                 600                 605
Val Phe Val Phe Asn Phe His Pro Lys Lys Thr Tyr Glu Gly Tyr Lys
610                 615                 620
Val Gly Cys Asp Leu Pro Gly Lys Tyr Arg Val Ala Leu Asp Ser Asp
```

```
                625                 630                 635                 640
Ala Leu Val Phe Gly Gly His Gly Arg Val Gly His Asp Val Asp His
                    645                 650                 655

Phe Thr Ser Pro Glu Gly Val Pro Gly Val Pro Glu Thr Asn Phe Asn
                    660                 665                 670

Asn Arg Pro Asn Ser Phe Lys Val Leu Ser Pro Pro Arg Thr Cys Val
                    675                 680                 685

Ala Tyr Tyr Arg Val Asp Glu Ala Gly Ala Gly Arg Arg Leu His Ala
                    690                 695                 700

Lys Ala Glu Thr Gly Lys Thr Ser Pro Ala Glu Ser Ile Asp Val Lys
705                 710                 715                 720

Ala Ser Arg Ala Ser Ser Lys Glu Asp Lys Glu Ala Thr Ala Gly Gly
                    725                 730                 735

Lys Lys Gly Trp Lys Phe Ala Arg Gln Pro Ser Asp Gln Asp Thr Lys
                    740                 745                 750

<210> SEQ ID NO 24
<211> LENGTH: 756
<212> TYPE: PRT
<213> ORGANISM: Oryza sativa

<400> SEQUENCE: 24

Thr Met Val Thr Val Val Glu Glu Val Asp His Leu Pro Ile Tyr Asp
1               5                   10                  15

Leu Asp Pro Lys Leu Glu Glu Phe Lys Asp His Phe Asn Tyr Arg Ile
                20                  25                  30

Lys Arg Tyr Leu Asp Gln Lys Cys Leu Ile Glu Lys His Glu Gly Gly
            35                  40                  45

Leu Glu Glu Phe Ser Lys Gly Tyr Leu Lys Phe Gly Ile Asn Thr Val
        50                  55                  60

Asp Gly Ala Thr Ile Tyr Arg Glu Trp Ala Pro Ala Ala Gln Glu Ala
65                  70                  75                  80

Gln Leu Ile Gly Glu Phe Asn Asn Trp Asn Gly Ala Lys His Lys Met
                85                  90                  95

Glu Lys Asp Lys Phe Gly Ile Trp Ser Ile Lys Ile Ser His Val Asn
                100                 105                 110

Gly Lys Pro Ala Ile Pro His Asn Ser Lys Val Lys Phe Arg Phe Arg
            115                 120                 125

His Gly Gly Gly Ala Trp Val Asp Arg Ile Pro Ala Trp Ile Arg Tyr
        130                 135                 140

Ala Thr Phe Asp Ala Ser Lys Phe Gly Ala Pro Tyr Asp Gly Val His
145                 150                 155                 160

Trp Asp Pro Pro Ala Cys Glu Arg Tyr Val Phe Lys His Pro Arg Pro
                165                 170                 175

Pro Lys Pro Asp Ala Pro Arg Ile Tyr Glu Ala His Val Gly Met Ser
                180                 185                 190

Gly Glu Glu Pro Glu Val Ser Thr Tyr Arg Glu Phe Ala Asp Asn Val
            195                 200                 205

Leu Pro Arg Ile Arg Ala Asn Asn Tyr Asn Thr Val Gln Leu Met Ala
        210                 215                 220

Ile Met Glu His Ser Tyr Tyr Ala Ser Phe Gly Tyr His Val Thr Asn
225                 230                 235                 240

Phe Phe Ala Val Ser Ser Arg Ser Gly Thr Pro Glu Asp Leu Lys Tyr
                245                 250                 255
```

-continued

```
Leu Val Asp Lys Ala His Ser Leu Gly Leu Arg Val Leu Met Asp Val
            260                 265                 270

Val His Ser His Ala Ser Asn Asn Val Thr Asp Gly Leu Asn Gly Tyr
            275                 280                 285

Asp Val Gly Gln Asn Thr His Glu Ser Tyr Phe His Thr Gly Asp Arg
            290                 295                 300

Gly Tyr His Lys Leu Trp Asp Ser Arg Leu Phe Asn Tyr Ala Asn Trp
305                 310                 315                 320

Glu Val Leu Arg Phe Leu Leu Ser Asn Leu Arg Tyr Trp Met Asp Glu
                325                 330                 335

Phe Met Phe Asp Gly Phe Arg Phe Asp Gly Val Thr Ser Met Leu Tyr
            340                 345                 350

His His His Gly Ile Asn Lys Gly Phe Thr Gly Asn Tyr Lys Glu Tyr
            355                 360                 365

Phe Ser Leu Asp Thr Asp Val Asp Ala Ile Val Tyr Met Met Leu Ala
370                 375                 380

Asn His Leu Met His Lys Leu Leu Pro Glu Ala Thr Ile Val Ala Glu
385                 390                 395                 400

Asp Val Ser Gly Met Pro Val Leu Cys Arg Pro Val Asp Glu Gly Gly
                405                 410                 415

Val Gly Phe Asp Phe Arg Leu Ala Met Ala Ile Pro Asp Arg Trp Ile
            420                 425                 430

Asp Tyr Leu Lys Asn Lys Glu Asp Arg Lys Trp Ser Met Ser Glu Ile
            435                 440                 445

Val Gln Thr Leu Thr Asn Arg Arg Tyr Thr Glu Lys Cys Ile Ala Tyr
450                 455                 460

Ala Glu Ser His Asp Gln Ser Ile Val Gly Asp Lys Thr Ile Ala Phe
465                 470                 475                 480

Leu Leu Met Asp Lys Glu Met Tyr Thr Gly Met Ser Asp Leu Gln Pro
                485                 490                 495

Ala Ser Pro Thr Ile Asn Arg Gly Ile Ala Leu Gln Lys Met Ile His
            500                 505                 510

Phe Ile Thr Met Ala Leu Gly Gly Asp Gly Tyr Leu Asn Phe Met Gly
            515                 520                 525

Asn Glu Phe Gly His Pro Glu Trp Ile Asp Phe Pro Arg Glu Gly Asn
530                 535                 540

Asn Trp Ser Tyr Asp Lys Cys Arg Arg Gln Trp Ser Leu Val Asp Thr
545                 550                 555                 560

Asp His Leu Arg Tyr Lys Tyr Met Asn Ala Phe Asp Gln Ala Met Asn
                565                 570                 575

Ala Leu Glu Glu Glu Phe Ser Phe Leu Ser Ser Ser Lys Gln Ile Val
            580                 585                 590

Ser Asp Met Asn Glu Lys Asp Lys Val Ile Val Phe Glu Arg Gly Asp
            595                 600                 605

Leu Val Phe Val Phe Asn Phe His Pro Asn Lys Thr Tyr Lys Gly Tyr
            610                 615                 620

Lys Val Gly Cys Asp Leu Pro Gly Lys Tyr Arg Val Ala Leu Asp Ser
625                 630                 635                 640

Asp Ala Leu Val Phe Gly Gly His Gly Arg Val Gly His Asp Val Asp
                645                 650                 655

His Phe Thr Ser Pro Glu Gly Met Pro Gly Val Pro Glu Thr Asn Phe
            660                 665                 670

Asn Asn Arg Pro Asn Ser Phe Lys Val Leu Ser Pro Pro Arg Thr Cys
```

```
                675                 680                 685
Val Ala Tyr Tyr Arg Val Asp Glu Asp Arg Glu Leu Arg Arg Gly
        690                 695                 700

Gly Ala Val Ala Ser Gly Lys Ile Val Thr Glu Tyr Ile Asp Val Glu
705                 710                 715                 720

Ala Thr Ser Gly Glu Thr Ile Ser Gly Gly Trp Lys Gly Ser Glu Lys
                725                 730                 735

Asp Asp Cys Gly Lys Lys Gly Met Lys Phe Val Phe Arg Ser Ser Asp
                740                 745                 750

Glu Asp Cys Lys
        755

<210> SEQ ID NO 25
<211> LENGTH: 762
<212> TYPE: PRT
<213> ORGANISM: Pisum sativum

<400> SEQUENCE: 25

Thr Met Pro Ser Val Glu Glu Asp Phe Glu Asn Ile Gly Ile Leu Asn
1               5                   10                  15

Val Asp Ser Ser Leu Glu Pro Phe Lys Asp His Phe Lys Tyr Arg Leu
                20                  25                  30

Lys Arg Tyr Leu His Gln Lys Lys Leu Ile Glu Glu Tyr Glu Gly Gly
            35                  40                  45

Leu Gln Glu Phe Ala Lys Gly Tyr Leu Lys Phe Gly Phe Asn Arg Glu
    50                  55                  60

Glu Asp Gly Ile Ser Tyr Arg Glu Trp Ala Pro Ala Ala Gln Glu Ala
65                  70                  75                  80

Gln Ile Ile Gly Asp Phe Asn Gly Trp Asn Gly Ser Asn Leu His Met
                85                  90                  95

Glu Lys Asp Gln Phe Gly Val Trp Ser Ile Gln Ile Pro Asp Ala Asp
            100                 105                 110

Gly Asn Pro Ala Ile Pro His Asn Ser Arg Val Lys Phe Arg Phe Lys
        115                 120                 125

His Ser Asp Gly Val Trp Val Asp Arg Ile Pro Ala Trp Ile Lys Tyr
    130                 135                 140

Ala Thr Val Asp Pro Thr Arg Phe Ala Ala Pro Tyr Asp Gly Val Tyr
145                 150                 155                 160

Trp Asp Pro Pro Leu Ser Glu Arg Tyr Gln Phe Lys His Pro Arg Pro
                165                 170                 175

Pro Lys Pro Lys Ala Pro Arg Ile Tyr Glu Ala His Val Gly Met Ser
            180                 185                 190

Ser Ser Glu Pro Arg Ile Asn Ser Tyr Arg Glu Phe Ala Asp Asp Val
        195                 200                 205

Leu Pro Arg Ile Arg Glu Asn Asn Tyr Asn Thr Val Gln Leu Met Ala
    210                 215                 220

Val Met Glu His Ser Tyr Tyr Ala Ser Phe Trp Tyr His Val Thr Lys
225                 230                 235                 240

Pro Phe Phe Ala Val Ser Ser Arg Ser Gly Ser Pro Glu Asp Leu Lys
                245                 250                 255

Tyr Leu Ile Asp Lys Ala His Ser Leu Gly Leu Asn Val Leu Met Asp
            260                 265                 270

Val Ile His Ser His Ala Ser Asn Asn Val Thr Asp Gly Leu Asn Gly
        275                 280                 285
```

-continued

```
Phe Asp Val Gly Gln Ser Ser Gln Gln Ser Tyr Phe His Ala Gly Asp
    290                 295                 300
Arg Gly Tyr His Lys Leu Trp Asp Ser Arg Leu Phe Asn Tyr Ala Asn
305                 310                 315                 320
Trp Lys Ser Ser Phe Leu Leu Ser Asn Leu Arg Trp Trp Leu Glu Glu
                325                 330                 335
Tyr Lys Phe Asp Gly Phe Arg Phe Asp Gly Val Thr Ser Met Leu Tyr
            340                 345                 350
His His His Gly Ile Asn Met Ala Phe Thr Gly Asp Tyr Asn Glu Tyr
        355                 360                 365
Phe Ser Glu Glu Thr Asp Val Asp Ala Val Val Tyr Leu Met Leu Ala
    370                 375                 380
Asn Ser Leu Val His Asp Ile Leu Pro Asp Ala Thr Asp Ile Ala Glu
385                 390                 395                 400
Asp Val Ser Gly Met Pro Gly Leu Gly Arg Pro Val Ser Glu Val Gly
                405                 410                 415
Ile Gly Phe Asp Tyr Arg Leu Ala Met Ala Ile Pro Asp Lys Trp Ile
            420                 425                 430
Asp Tyr Leu Lys Asn Lys Asp Ser Glu Trp Ser Met Lys Glu Ile
        435                 440                 445
Ser Leu Asn Leu Thr Asn Arg Arg Tyr Thr Glu Lys Cys Val Ser Tyr
    450                 455                 460
Ala Glu Ser His Asp Gln Ser Ile Val Gly Asp Lys Thr Ile Ala Phe
465                 470                 475                 480
Leu Leu Met Asp Glu Glu Met Tyr Ser Ser Met Ser Cys Leu Thr Met
                485                 490                 495
Leu Ser Pro Thr Ile Glu Arg Gly Ile Ser Leu His Lys Met Ile His
            500                 505                 510
Phe Ile Thr Leu Ala Leu Gly Gly Glu Gly Tyr Leu Asn Phe Met Gly
        515                 520                 525
Asn Glu Phe Gly His Pro Glu Trp Ile Asp Phe Pro Arg Glu Gly Asn
    530                 535                 540
Gly Trp Ser Tyr Glu Lys Cys Arg Leu Thr Gln Trp Asn Leu Val Asp
545                 550                 555                 560
Thr Asn His Leu Arg Tyr Lys Phe Met Asn Ala Phe Asp Arg Ala Met
                565                 570                 575
Asn Leu Leu Asp Asp Lys Phe Ser Ile Leu Ala Ser Thr Lys Gln Ile
            580                 585                 590
Val Ser Ser Thr Asn Asn Glu Asp Lys Val Ile Val Phe Glu Arg Gly
        595                 600                 605
Asp Leu Val Phe Val Phe Asn Phe His Pro Glu Asn Thr Tyr Glu Gly
    610                 615                 620
Tyr Lys Val Gly Cys Asp Leu Pro Gly Lys Tyr Arg Val Ala Leu Asp
625                 630                 635                 640
Ser Asp Ala Thr Glu Phe Gly Gly His Gly Arg Val Gly His Asp Ala
                645                 650                 655
Asp Gln Phe Thr Ser Pro Glu Gly Ile Pro Gly Ile Pro Glu Thr Asn
            660                 665                 670
Phe Asn Asn Arg Pro Asn Ser Phe Lys Val Leu Ser Pro Pro His Thr
        675                 680                 685
Cys Val Val Tyr Tyr Arg Val Asp Glu Arg Gln Glu Glu Ser Asn Asn
    690                 695                 700
Pro Asn Leu Gly Ser Val Glu Glu Thr Phe Ala Ala Ala Asp Thr Asp
```

```
                705                 710                 715                 720
Val Ala Arg Ile Pro Asp Val Ser Met Glu Ser Glu Asp Ser Asn Leu
                    725                 730                 735
Asp Arg Ile Glu Asp Asn Ser Glu Asp Ala Val Asp Ala Gly Ile Leu
                740                 745                 750
Lys Val Glu Arg Glu Val Val Gly Asp Asn
        755                 760

<210> SEQ ID NO 26
<211> LENGTH: 984
<212> TYPE: DNA
<213> ORGANISM: Triticum aestivum

<400> SEQUENCE: 26
atatgtatga tttcatggct ctggatagac cttcaactcc tcgcattgat cgtggcatag        60
cattacataa aatgatcagg cttgtcacca tgggtttagg tggcgaaggc tatcttaact       120
tcatgggaaa tgagtttggg catcctgaat ggatagattt ccaagaggt ccgcaaactc        180 ttccaaccgg caaagttctc cctggaaata acaatagtta tgataaatgc cgccgtagat       240
ttgatcttgg agatgcagat tttcttagat atcgtggtat gcaagagtcc gaccaggcaa       300
tgcagcatct tgaggaaaaa tatgggttta tgacatctga gcaccagtat gtttcacgga       360
aacatgagga agataaggtg atcatcttcg aaagaggaga tttggtattc gttttcaact       420
tccaccggag caatagcttt tttgactacc gtgttgggtg ttccaggcct gggaagtaca       480
aggtggcctt agactccgac gatgcactct ttggtggatt cagcaggctt gatcatgatg       540
tcgactactt cacaaccgaa catccgcatg acaacaggcc gcgctctttc tcggtgtaca       600
ctccgagcag aactgcggtc gtgtatgccc ttacagagta agaaccagca gctgcttgtt       660
acaaggcaaa gagagaactc cagagagctc gtggatcgtg agcgaagcga cgggcaacgg       720
cgcgaggctg ctctaagcgc catgactggg aggggatcgt gcctcttccc cagatgccag       780
gaggagcaga tggataggta gcttgttggt gagcgctcga agaaaatgg acgggcctgg        840 gtgtttgtcg tgctgcacta ccctcctcct atccttgcaca ttcccggttg tctttgtaca      900
tataactaat aattgcccgt gcgctcaacg tgaacatata aatattctaa taataggtta       960
tcccgtgaaa aaaaaaaaa aaaa                                                984

<210> SEQ ID NO 27
<211> LENGTH: 977
<212> TYPE: DNA
<213> ORGANISM: Triticum aestivum

<400> SEQUENCE: 27
atatgtatga tttcatggct ctggatagac cttcaactcc tcgcattgat cgtggcatag        60
cattacataa aatgatcagg cttgtcacca tgggtttagg tggcgaaggc tatcttaact       120
tcatgggaaa tgagtttggg catcctgaat ggatagattt ccaagaggt ccgcaaactc        180 ttccaaccgg caaagttctc cctggaaata acaatagtta tgataaatgc cgccgtagat       240
ttgatcttgg agatgcagat tttcttagat atcgtggtat gcaagagttc gaccaggcaa       300
tgcagcatct tgaggaaaaa tatgggttta tgacatctga gcaccagtat gtttcacgga       360
aacatgagga agataaggtg atcatcttcg aaagaggaga tttggtattt gttttcaact       420
tccactggag caatagcttt tttgactacc gtgttgggtg ttccaagcct gggaagtaca       480
aggtggcctt agactccgac gatgcactct ttggtggatt cagcaggctt gatcatgatg       540
```

-continued

```
tcgactactt cacaaccgaa catccgcatg acaataggcc gcgctctttc ttggtgtaca      600
ctcctagcag aactgcggtc gtgtatgccc ttacagagta agaaccagca gcggcttgtt      660
acaaggcaaa gagagaactc cagggagctc gtggattgtg agcgaagcga cgggcaactg      720
cgtgaggctg ctctaagcgc catgactggg aggggatcgt gcctcttccc ctgatgccag      780
gaggatcaga tggataggta gcttgttggt gagcgctcga agaaaatgg acgggcctgg       840 gtgtttgtcg tgctgcactt aaccctcctc ctatgttgca cattcccggg tgtttttgta      900
catataacta ataattgccc gtgcgcttca acatgaacat ataaatattc tatataaaaa      960
aaaaaaaaaa aaaaaa                                                     977
```

<210> SEQ ID NO 28
<211> LENGTH: 212
<212> TYPE: PRT
<213> ORGANISM: Triticum aestivum

<400> SEQUENCE: 28

```
Met Tyr Asp Phe Met Ala Leu Asp Arg Pro Ser Thr Pro Arg Ile Asp
1               5                   10                  15

Arg Gly Ile Ala Leu His Lys Met Ile Arg Leu Val Thr Met Gly Leu
            20                  25                  30

Gly Gly Glu Gly Tyr Leu Asn Phe Met Gly Asn Glu Phe Gly His Pro
        35                  40                  45

Glu Trp Ile Asp Phe Pro Arg Gly Pro Gln Thr Leu Pro Thr Gly Lys
    50                  55                  60

Val Leu Pro Gly Asn Asn Ser Tyr Asp Lys Cys Arg Arg Phe
65                  70                  75                  80

Asp Leu Gly Asp Ala Asp Phe Leu Arg Tyr Arg Gly Met Gln Glu Phe
                85                  90                  95

Asp Gln Ala Met Gln His Leu Glu Glu Lys Tyr Gly Phe Met Thr Ser
            100                 105                 110

Glu His Gln Tyr Val Ser Arg Lys His Glu Glu Asp Lys Val Ile Ile
        115                 120                 125

Phe Glu Arg Gly Asp Leu Val Phe Val Phe Asn Phe His Trp Ser Asn
    130                 135                 140

Ser Phe Asp Tyr Arg Val Gly Cys Ser Lys Pro Gly Lys Tyr Lys
145                 150                 155                 160

Val Ala Leu Asp Ser Asp Asp Ala Leu Phe Gly Gly Phe Ser Arg Leu
                165                 170                 175

Asp His Asp Val Asp Tyr Phe Thr Thr Glu His Pro His Asp Asn Arg
            180                 185                 190

Pro Arg Ser Phe Leu Val Tyr Thr Pro Ser Arg Thr Ala Val Val Tyr
        195                 200                 205

Ala Leu Thr Glu
        210
```

<210> SEQ ID NO 29
<211> LENGTH: 212
<212> TYPE: PRT
<213> ORGANISM: Zea mays

<400> SEQUENCE: 29

```
Met Tyr Asp Phe Met Ala Leu Asp Arg Pro Ser Thr Pro Thr Ile Asp
1               5                   10                  15

Arg Gly Ile Ala Leu His Lys Met Ile Arg Leu Ile Thr Met Gly Leu
            20                  25                  30
```

-continued

Gly Gly Glu Gly Tyr Leu Asn Phe Met Gly Asn Glu Phe Gly His Pro
         35                  40                  45

Glu Trp Ile Asp Phe Pro Arg Gly Pro Gln Arg Leu Pro Ser Gly Lys
 50                  55                  60

Phe Ile Pro Gly Asn Asn Asn Ser Tyr Asp Lys Cys Arg Arg Arg Phe
65                  70                  75                  80

Asp Leu Gly Asp Ala Asp Tyr Leu Arg Tyr His Gly Met Gln Glu Phe
                 85                  90                  95

Asp Gln Ala Met Gln His Leu Glu Gln Lys Tyr Glu Phe Met Thr Ser
             100                 105                 110

Asp His Gln Tyr Ile Ser Arg Lys His Glu Glu Asp Lys Val Ile Val
             115                 120                 125

Phe Glu Lys Gly Asp Leu Val Phe Val Phe Asn Phe His Cys Asn Asn
 130                 135                 140

Ser Tyr Phe Asp Tyr Arg Ile Gly Cys Arg Lys Pro Gly Val Tyr Lys
145                 150                 155                 160

Val Val Leu Asp Ser Asp Ala Gly Leu Phe Gly Gly Phe Ser Arg Ile
                165                 170                 175

His His Ala Ala Glu His Phe Thr Ala Asp Cys Ser His Asp Asn Arg
             180                 185                 190

Pro Tyr Ser Phe Ser Val Tyr Thr Pro Ser Arg Thr Cys Val Val Tyr
             195                 200                 205

Ala Pro Val Glu
    210

<210> SEQ ID NO 30
<211> LENGTH: 216
<212> TYPE: PRT
<213> ORGANISM: Zea mays

<400> SEQUENCE: 30

Met Tyr Asp Phe Met Ala Leu Asp Arg Pro Ser Thr Pro Arg Ile Asp
1                5                  10                  15

Arg Gly Ile Ala Leu His Lys Met Ile Arg Leu Val Thr Met Gly Leu
             20                  25                  30

Gly Gly Glu Gly Tyr Leu Asn Phe Met Gly Asn Glu Phe Gly His Pro
         35                  40                  45

Glu Trp Ile Asp Phe Pro Arg Gly Pro Gln Ser Leu Pro Asn Gly Ser
 50                  55                  60

Val Ile Pro Gly Asn Asn Asn Ser Phe Asp Lys Cys Arg Arg Arg Phe
65                  70                  75                  80

Asp Leu Gly Asp Ala Asp Tyr Leu Arg Tyr Arg Gly Met Gln Glu Phe
                 85                  90                  95

Asp Gln Ala Met Gln His Leu Glu Gly Lys Tyr Glu Phe Met Thr Ser
             100                 105                 110

Asp His Ser Tyr Phe Ser Arg Lys His Glu Glu Asp Lys Val Ile Ile
             115                 120                 125

Phe Glu Arg Gly Asp Leu Val Phe Val Phe Asn His Trp Ser Asn
 130                 135                 140

Ser Tyr Phe Asp Tyr Arg Val Gly Cys Phe Lys Pro Gly Lys Tyr Lys
145                 150                 155                 160

Ile Val Leu Asp Ser Asp Asp Gly Leu Phe Gly Gly Phe Ser Arg Leu
                165                 170                 175

Asp His Asp Ala Glu Tyr Phe Thr Ala Asp Trp Pro His Asp Asn Arg

```
                    180                 185                 190
Pro Cys Ser Phe Ser Val Tyr Ala Pro Ser Arg Thr Ala Val Val Tyr
                195                 200                 205
Ala Pro Ala Gly Ala Glu Asp Glu
        210                 215

<210> SEQ ID NO 31
<211> LENGTH: 217
<212> TYPE: DNA
<213> ORGANISM: Zea mays

<400> SEQUENCE: 31
tagcggggta ctcgttgctg cgcggcatgt gtggggctgt cgatgtgagg aaaaaccttc      60
ttccaaaacc ggcagatgca tgcatgcatg ctacaataag gttctgatac tttaatcgat     120
gctggaaagc ccatgcatct cgctgcgttg tcctctctat atatataaga ccttcaaggt     180
gtcaattaaa catagagttt tcgttttttcg ctttcct                             217

<210> SEQ ID NO 32
<211> LENGTH: 686
<212> TYPE: PRT
<213> ORGANISM: Triticum aestivum

<400> SEQUENCE: 32

Met Leu Cys Leu Ser Ser Ser Leu Leu Pro Arg Pro Ser Ala Ala Ala
1               5                   10                  15
Asp Arg Pro Leu Pro Gly Ile Ile Ala Gly Gly Gly Gly Lys Arg
            20                  25                  30
Leu Ser Val Val Pro Ser Val Pro Phe Leu Leu Arg Trp Leu Trp Pro
        35                  40                  45
Arg Lys Ala Lys Ser Lys Ser Phe Val Ser Val Thr Ala Arg Gly Asn
    50                  55                  60
Lys Ile Ala Ala Thr Thr Gly Tyr Gly Ser Asp His Leu Pro Ile Tyr
65                  70                  75                  80
Asp Leu Asp Leu Lys Leu Ala Glu Phe Lys Asp His Phe Asp Tyr Thr
                85                  90                  95
Arg Asn Arg Tyr Ile Glu Gln Lys His Leu Ile Glu Lys His Glu Gly
            100                 105                 110
Ser Leu Glu Glu Phe Ser Lys Gly Tyr Leu Lys Phe Gly Ile Asn Thr
        115                 120                 125
Glu His Gly Ala Ser Val Tyr Arg Glu Trp Ala Pro Ala Ala Glu Glu
    130                 135                 140
Ala Gln Leu Val Gly Asp Phe Asn Asn Trp Asn Gly Ser Gly His Lys
145                 150                 155                 160
Met Ala Lys Asp Asn Phe Gly Val Trp Ser Ile Arg Ile Ser His Val
                165                 170                 175
Asn Gly Lys Pro Ala Ile Pro His Asn Ser Lys Val Lys Phe Arg Phe
            180                 185                 190
Arg His His Gly Val Trp Val Glu Gln Ile Pro Ala Trp Ile Arg Tyr
        195                 200                 205
Ala Thr Val Thr Ala Ser Glu Ser Gly Ala Pro Tyr Asp Gly Leu His
    210                 215                 220
Trp Asp Pro Pro Ser Ser Glu Arg Tyr Val Phe Asn His Pro Arg Pro
225                 230                 235                 240
Pro Lys Pro Asp Val Pro Arg Ile Tyr Glu Ala His Val Gly Val Ser
                245                 250                 255
```

-continued

```
Gly Gly Lys Leu Glu Ala Gly Thr Tyr Arg Glu Phe Pro Asp Asn Val
            260                 265                 270

Leu Pro Cys Leu Arg Ala Thr Asn Tyr Asn Thr Val Gln Leu Met Gly
            275                 280                 285

Ile Met Glu His Ser Asp Ser Ala Ser Phe Gly Tyr His Val Thr Asn
            290                 295                 300

Phe Phe Ala Val Ser Ser Arg Ser Gly Thr Pro Glu Asp Leu Lys Tyr
305                 310                 315                 320

Leu Ile Asp Lys Ala His Ser Leu Gly Leu Arg Val Leu Met Asp Val
                    325                 330                 335

Val His Ser His Ala Ser Asn Asn Val Ile Asp Gly Leu Asn Gly Tyr
                    340                 345                 350

Asp Val Gly Gln Ser Ala His Glu Ser Tyr Phe Tyr Thr Gly Asp Lys
            355                 360                 365

Gly Tyr Asn Lys Met Trp Asn Gly Arg Met Phe Asn Tyr Ala Asn Trp
    370                 375                 380

Glu Val Leu Arg Phe Leu Leu Ser Asn Leu Arg Tyr Trp Met Asp Glu
385                 390                 395                 400

Phe Met Phe Asp Gly Phe Arg Phe Val Gly Val Thr Ser Met Leu Tyr
                    405                 410                 415

Asn His Asn Gly Ile Asn Met Ser Phe Asn Gly Asn Tyr Lys Asp Tyr
            420                 425                 430

Ile Gly Leu Asp Thr Asn Val Asp Ala Phe Val Tyr Met Met Leu Ala
                    435                 440                 445

Asn His Leu Met His Lys Leu Phe Pro Glu Ala Ile Val Val Ala Val
    450                 455                 460

Asp Val Ser Gly Met Pro Val Leu Cys Trp Pro Val Asp Glu Gly Gly
465                 470                 475                 480

Leu Gly Phe Asp Tyr Arg Gln Ala Met Thr Ile Pro Asp Arg Trp Ile
                    485                 490                 495

Asp Tyr Leu Glu Asn Lys Gly Asp Gln Gln Trp Ser Met Ser Ser Val
            500                 505                 510

Ile Ser Gln Thr Leu Thr Asn Arg Arg Tyr Pro Glu Lys Phe Ile Ala
    515                 520                 525

Tyr Ala Glu Arg Gln Asn His Ser Ile Ile Gly Ser Lys Thr Met Ala
    530                 535                 540

Phe Leu Leu Met Glu Trp Glu Thr Tyr Ser Gly Met Ser Ala Met Asp
545                 550                 555                 560

Pro Asp Ser Pro Thr Ile Asp Arg Ala Ile Ala Leu Gln Lys Met Ile
                    565                 570                 575

His Phe Ile Thr Met Ala Phe Gly Gly Asp Ser Tyr Leu Lys Phe Met
            580                 585                 590

Gly Asn Glu Tyr Met Asn Ala Phe Val Gln Ala Val Asp Thr Pro Ser
    595                 600                 605

Asp Lys Cys Ser Phe Leu Ser Ser Asn Gln Thr Ala Ser His Met
610                 615                 620

Asn Glu Glu Glu Lys Gly Ser Ala Leu Thr Lys Gly Tyr Thr His Leu
625                 630                 635                 640

Arg Ser Gly Cys Phe Asp Pro Ser Leu Pro Thr Ser Ser Cys Ala
                    645                 650                 655

Phe Leu Gly Pro Ser Asn Gln Ser Pro Phe Ser Lys Pro Phe Ile Gly
                    660                 665                 670
```

```
Phe Pro Gly Cys Ile Phe Cys Cys Gly Leu Phe Lys Gly Glu
        675                 680                 685

<210> SEQ ID NO 33
<211> LENGTH: 830
<212> TYPE: PRT
<213> ORGANISM: Triticum aestivum

<400> SEQUENCE: 33

Met Leu Cys Leu Thr Ala Pro Ser Cys Ser Pro Ser Leu Pro Pro Arg
1               5                   10                  15

Pro Ser Arg Pro Ala Ala Asp Arg Pro Gly Pro Gly Ile Ser Gly Gly
            20                  25                  30

Gly Asn Val Arg Leu Ser Ala Val Pro Ala Pro Ser Ser Leu Arg Trp
        35                  40                  45

Ser Trp Pro Arg Lys Ala Lys Ser Lys Phe Ser Val Pro Val Ser Ala
50                  55                  60

Pro Arg Asp Tyr Thr Met Ala Thr Ala Glu Asp Gly Val Gly Asp Leu
65                  70                  75                  80

Pro Ile Tyr Asp Leu Asp Pro Lys Phe Ala Gly Phe Lys Glu His Phe
                85                  90                  95

Ser Tyr Arg Met Lys Lys Tyr Leu Asp Gln Lys His Ser Ile Glu Lys
            100                 105                 110

His Glu Gly Gly Leu Glu Glu Phe Ser Lys Gly Tyr Leu Lys Phe Gly
        115                 120                 125

Ile Asn Thr Glu Asn Asp Ala Thr Val Tyr Arg Glu Trp Ala Pro Ala
130                 135                 140

Ala Met Asp Ala Gln Leu Ile Gly Asp Phe Asn Asn Trp Asn Gly Ser
145                 150                 155                 160

Gly His Arg Met Thr Lys Asp Asn Tyr Gly Val Trp Ser Ile Arg Ile
                165                 170                 175

Ser His Val Asn Gly Lys Pro Ala Ile Pro His Asn Ser Lys Val Lys
            180                 185                 190

Phe Arg Phe His Arg Gly Asp Gly Leu Trp Val Asp Arg Val Pro Ala
        195                 200                 205

Trp Ile Arg Tyr Ala Thr Phe Asp Ala Ser Lys Phe Gly Ala Pro Tyr
210                 215                 220

Asp Gly Val His Trp Asp Pro Pro Ser Gly Glu Arg Tyr Val Phe Lys
225                 230                 235                 240

His Pro Arg Pro Arg Lys Pro Asp Ala Pro Arg Ile Tyr Glu Ala His
                245                 250                 255

Val Gly Met Ser Gly Glu Lys Pro Glu Val Ser Thr Tyr Arg Glu Phe
            260                 265                 270

Ala Asp Asn Val Leu Pro Arg Ile Lys Ala Asn Asn Tyr Asn Thr Val
        275                 280                 285

Gln Leu Met Ala Ile Met Glu His Ser Tyr Tyr Ala Ser Phe Gly Tyr
290                 295                 300

His Val Thr Asn Phe Phe Ala Val Ser Ser Arg Ser Gly Thr Pro Glu
305                 310                 315                 320

Asp Leu Lys Tyr Leu Val Asp Lys Ala His Ser Leu Gly Leu Arg Val
                325                 330                 335

Leu Met Asp Val Val His Ser His Ala Ser Ser Asn Lys Thr Asp Gly
            340                 345                 350

Leu Asn Gly Tyr Asp Val Gly Gln Asn Thr Gln Glu Ser Tyr Phe His
        355                 360                 365
```

-continued

```
Thr Gly Glu Arg Gly Tyr His Lys Leu Trp Asp Ser Arg Leu Phe Asn
    370                 375                 380

Tyr Ala Asn Trp Glu Val Leu Arg Phe Leu Leu Ser Asn Leu Arg Tyr
385                 390                 395                 400

Trp Met Asp Glu Phe Met Phe Asp Gly Phe Arg Phe Asp Gly Val Thr
                405                 410                 415

Ser Met Leu Tyr Asn His His Gly Ile Asn Met Ser Phe Ala Gly Ser
            420                 425                 430

Tyr Lys Glu Tyr Phe Gly Leu Asp Thr Asp Val Asp Ala Val Val Tyr
        435                 440                 445

Leu Met Leu Ala Asn His Leu Met His Lys Leu Leu Pro Glu Ala Thr
    450                 455                 460

Val Val Ala Glu Asp Val Ser Gly Met Pro Val Leu Cys Arg Ser Val
465                 470                 475                 480

Asp Glu Gly Gly Val Gly Phe Asp Tyr Arg Leu Ala Met Ala Ile Pro
                485                 490                 495

Asp Arg Trp Ile Asp Tyr Leu Lys Asn Lys Asp Asp Leu Glu Trp Ser
            500                 505                 510

Met Ser Gly Ile Ala His Thr Leu Thr Asn Arg Arg Tyr Thr Glu Lys
        515                 520                 525

Cys Ile Ala Tyr Ala Glu Ser His Asp Gln Ser Ile Val Gly Asp Lys
    530                 535                 540

Thr Met Ala Phe Leu Leu Met Asp Lys Glu Met Tyr Thr Gly Met Ser
545                 550                 555                 560

Asp Leu Gln Pro Ala Ser Pro Thr Ile Asp Arg Gly Ile Ala Leu Gln
                565                 570                 575

Lys Met Ile His Phe Ile Thr Met Ala Leu Gly Gly Asp Gly Tyr Leu
            580                 585                 590

Asn Phe Met Gly Asn Glu Phe Gly His Pro Glu Trp Ile Asp Phe Pro
        595                 600                 605

Arg Glu Gly Asn Asn Trp Ser Tyr Asp Lys Cys Arg Arg Gln Trp Ser
    610                 615                 620

Leu Ala Asp Ile Asp His Leu Arg Tyr Lys Tyr Met Asn Ala Phe Asp
625                 630                 635                 640

Gln Ala Met Asn Ala Leu Asp Asp Lys Phe Ser Phe Leu Ser Ser Ser
                645                 650                 655

Lys Gln Ile Val Ser Asp Met Asn Glu Glu Lys Lys Ile Ile Val Phe
            660                 665                 670

Glu Arg Gly Asp Leu Val Phe Val Phe Asn Phe His Pro Ser Lys Thr
        675                 680                 685

Tyr Asp Gly Tyr Lys Val Gly Cys Asp Leu Pro Gly Lys Tyr Lys Val
    690                 695                 700

Ala Leu Asp Ser Asp Ala Leu Met Phe Gly Gly His Gly Arg Val Ala
705                 710                 715                 720

His Asp Asn Asp His Phe Thr Ser Pro Glu Gly Val Pro Gly Val Pro
                725                 730                 735

Glu Thr Asn Phe Asn Asn Arg Pro Asn Ser Phe Lys Ile Leu Ser Pro
            740                 745                 750

Ser Arg Thr Cys Val Ala Tyr Tyr Arg Val Glu Glu Lys Ala Glu Lys
        755                 760                 765

Pro Lys Asp Glu Gly Ala Ala Ser Trp Gly Lys Thr Ala Leu Gly Tyr
    770                 775                 780
```

Ile Asp Val Glu Ala Thr Gly Val Lys Asp Ala Ala Asp Gly Glu Ala
785                 790                 795                 800

Thr Ser Gly Ser Glu Lys Ala Ser Thr Gly Gly Asp Ser Ser Lys Lys
                805                 810                 815

Gly Ile Asn Phe Val Phe Leu Ser Pro Asp Lys Asp Asn Lys
            820                 825                 830

<210> SEQ ID NO 34
<211> LENGTH: 818
<212> TYPE: PRT
<213> ORGANISM: Triticum aestivum

<400> SEQUENCE: 34

Met Ala Thr Phe Ala Val Ser Gly Trp Thr Leu Gly Val Ala Arg Pro
1               5                   10                  15

Ala Gly Ala Gly Gly Leu Leu Pro Arg Ser Gly Ser Glu Arg Arg
            20                  25                  30

Gly Val Asp Leu Pro Ser Leu Leu Arg Lys Lys Asp Ser Ser
        35                  40                  45

Arg Ala Ala Ser Pro Gly Lys Val Leu Val Pro Asp Gly Glu Ser Asp
50                  55                  60

Asp Leu Ala Ser Pro Ala Gln Pro Glu Glu Leu Gln Ile Pro Glu Asp
65                  70                  75                  80

Ile Glu Glu Gln Thr Ala Glu Val Asn Met Thr Gly Gly Thr Ala Glu
                85                  90                  95

Lys Leu Glu Ser Ser Glu Pro Thr Gln Gly Ile Val Glu Thr Ile Thr
            100                 105                 110

Asp Gly Val Thr Lys Gly Val Lys Glu Leu Val Val Gly Glu Lys Pro
        115                 120                 125

Arg Val Val Pro Lys Pro Gly Asp Gly Gln Lys Ile Tyr Glu Ile Asp
130                 135                 140

Pro Thr Leu Lys Asp Phe Arg Ser His Leu Asp Tyr Arg Tyr Ser Glu
145                 150                 155                 160

Tyr Arg Arg Ile Arg Ala Ala Ile Asp Gln His Glu Gly Gly Leu Glu
                165                 170                 175

Ala Phe Ser Arg Gly Tyr Glu Lys Leu Gly Phe Thr Arg Ser Ala Glu
            180                 185                 190

Gly Ile Thr Tyr Arg Glu Trp Ala Pro Gly Ala His Ser Ala Ala Leu
        195                 200                 205

Val Gly Asp Phe Asn Asn Trp Asn Pro Asn Ala Asp Thr Met Thr Arg
210                 215                 220

Asp Asp Tyr Gly Val Trp Glu Ile Phe Leu Pro Asn Asn Ala Asp Gly
225                 230                 235                 240

Ser Pro Ala Ile Pro His Gly Ser Arg Val Lys Ile Arg Met Asp Thr
                245                 250                 255

Pro Ser Gly Val Lys Asp Ser Ile Ser Ala Trp Ile Lys Phe Ser Val
            260                 265                 270

Gln Ala Pro Gly Glu Ile Pro Phe Asn Gly Ile Tyr Tyr Asp Pro Pro
        275                 280                 285

Glu Glu Glu Lys Tyr Val Phe Gln His Pro Gln Pro Lys Arg Pro Glu
290                 295                 300

Ser Leu Arg Ile Tyr Glu Ser His Ile Gly Met Ser Ser Pro Glu Pro
305                 310                 315                 320

Lys Ile Asn Ser Tyr Ala Asn Phe Arg Asp Glu Val Leu Pro Arg Ile
                325                 330                 335

```
Lys Arg Leu Gly Tyr Asn Ala Val Gln Ile Met Ala Ile Gln Glu His
            340                 345                 350

Ser Tyr Tyr Ala Ser Phe Gly Tyr His Val Thr Asn Phe Phe Ala Pro
        355                 360                 365

Ser Ser Arg Phe Gly Thr Pro Glu Asp Leu Lys Ser Leu Ile Asp Arg
        370                 375                 380

Ala His Glu Leu Gly Leu Ile Val Leu Met Asp Ile Val His Ser His
385                 390                 395                 400

Ser Ser Asn Asn Thr Leu Asp Gly Leu Asn Gly Phe Asp Gly Thr Asp
                405                 410                 415

Thr His Tyr Phe His Gly Gly Pro Arg Gly His His Trp Met Trp Asp
                420                 425                 430

Ser Arg Leu Phe Asn Tyr Gly Ser Trp Glu Val Leu Arg Phe Leu Leu
            435                 440                 445

Ser Asn Ala Arg Trp Trp Leu Glu Glu Tyr Lys Phe Asp Gly Phe Arg
        450                 455                 460

Phe Asp Gly Val Thr Ser Met Met Tyr Thr His His Gly Leu Gln Met
465                 470                 475                 480

Thr Phe Thr Gly Asn Tyr Gly Glu Tyr Phe Gly Phe Ala Thr Asp Val
                485                 490                 495

Asp Ala Val Val Tyr Leu Met Leu Val Asn Asp Leu Ile His Gly Leu
                500                 505                 510

His Pro Asp Ala Val Ser Ile Gly Glu Asp Val Ser Gly Met Pro Thr
            515                 520                 525

Phe Cys Ile Pro Val Pro Asp Gly Gly Val Gly Leu Asp Tyr Arg Leu
        530                 535                 540

His Met Ala Val Ala Asp Lys Trp Ile Glu Leu Leu Lys Gln Ser Asp
545                 550                 555                 560

Glu Ser Trp Lys Met Gly Asp Ile Val His Thr Leu Thr Asn Arg Arg
                565                 570                 575

Trp Leu Glu Lys Cys Val Thr Tyr Ala Glu Ser His Asp Gln Ala Leu
            580                 585                 590

Val Gly Asp Lys Thr Ile Ala Phe Trp Leu Met Asp Lys Asp Met Tyr
        595                 600                 605

Asp Phe Met Ala Leu Asp Arg Pro Ser Thr Pro Arg Ile Asp Arg Gly
        610                 615                 620

Ile Ala Leu His Lys Met Ile Arg Leu Val Thr Met Gly Leu Gly Gly
625                 630                 635                 640

Glu Gly Tyr Leu Asn Phe Met Gly Asn Glu Phe Gly His Pro Glu Trp
                645                 650                 655

Ile Asp Phe Pro Arg Gly Pro Gln Thr Leu Pro Thr Gly Lys Val Leu
        660                 665                 670

Pro Gly Asn Asn Asn Ser Tyr Asp Lys Cys Arg Arg Arg Phe Asp Leu
            675                 680                 685

Gly Asp Ala Asp Phe Leu Arg Tyr His Gly Met Gln Glu Phe Asp Gln
690                 695                 700

Ala Met Gln His Leu Glu Glu Lys Tyr Gly Phe Met Thr Ser Glu His
705                 710                 715                 720

Gln Tyr Val Ser Arg Lys His Glu Glu Asp Lys Val Ile Ile Phe Glu
                725                 730                 735

Arg Gly Asp Leu Val Phe Val Phe Asn Phe His Trp Ser Asn Ser Phe
                740                 745                 750
```

-continued

```
Phe Asp Tyr Arg Val Gly Cys Ser Arg Pro Gly Lys Tyr Lys Val Ala
        755                 760                 765

Leu Asp Ser Asp Asp Ala Leu Phe Gly Gly Phe Ser Arg Leu Asp His
        770                 775                 780

Asp Val Asp Tyr Phe Thr Thr Glu His Pro His Asp Asn Arg Pro Arg
785                 790                 795                 800

Ser Phe Ser Val Tyr Thr Pro Ser Arg Thr Ala Val Val Tyr Ala Leu
                805                 810                 815

Thr Glu
```

<210> SEQ ID NO 35
<211> LENGTH: 813
<212> TYPE: DNA
<213> ORGANISM: Escherichia coli

<400> SEQUENCE: 35

| | | | | | |
|---|---|---|---|---|---|
| gagctccgtt | tcgcatgatt | gaacaagatg | gattgcacgc | aggttctccg | gccgcttggg | 60 |
| tggagaggct | attcggctat | gactgggcac | aacagacaat | cggctgctct | gatgccgccg | 120 |
| tgttccggct | gtcagcgcag | gggcgcccgg | ttcttttttgt | caagaccgac | ctgtccggtg | 180 |
| ccctgaatga | actgcaggac | gaggcagcgc | ggctatcgtg | gctggccacg | acgggcgttc | 240 |
| cttgcgcagc | tgtgctcgac | gttgtcactg | aagcgggaag | ggactggctg | ctattgggcg | 300 |
| aagtgccggg | gcaggatctc | ctgtcatctc | accttgctcc | tgccgagaaa | gtatccatca | 360 |
| tggctgatgc | aatgcggcgg | ctgcatacgc | ttgatccggc | tacctgccca | ttcgaccacc | 420 |
| aagcgaaaca | tcgcatcgag | cgagcacgta | ctcggatgga | agccggtctt | gtcgatcagg | 480 |
| atgatctgga | cgaagagcat | cagggggctcg | cgccagccga | actgttcgcc | aggctcaagg | 540 |
| cgcgcatgcc | cgacggcgag | gatctcgtcg | tgacccatgg | cgatgcctgc | ttgccgaata | 600 |
| tcatggtgga | aaatggccgc | ttttctggat | tcatcgactg | tggccggctg | ggtgtggcgg | 660 |
| accgctatca | ggacatagcg | ttggctaccc | gtgatattgc | tgaagagctt | ggcggcgaat | 720 |
| gggctgaccg | cttcctcgtg | ctttacggta | tcgccgctcc | cgattcgcag | cgcatcgcct | 780 |
| tctatcgcct | tcttgacgag | ttcttctgag | ctc | | | 813 |

<210> SEQ ID NO 36
<211> LENGTH: 7
<212> TYPE: PRT
<213> ORGANISM: Triticum aestivum

<400> SEQUENCE: 36

```
Met Asp Lys Asp Met Tyr Asp
1               5
```

<210> SEQ ID NO 37
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 37
aaggatccgt cgacatcgat aatacgactc actataggga          40

<210> SEQ ID NO 38
<211> LENGTH: 17
<212> TYPE: DNA
<213> ORGANISM: Artificial Sequence
<220> FEATURE:

-continued

<223> OTHER INFORMATION: Synthetic Oligonucleotide

<400> SEQUENCE: 38
aaggatccgt cgacatc                                                  17

<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 39
atggacaagg atatgtatga                                               20

<210> SEQ ID NO 40
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 40
ttttcttcac aacgccctgg g                                             21

<210> SEQ ID NO 41
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 41
tgtttgggag atcttcctcc c                                             21

<210> SEQ ID NO 42
<211> LENGTH: 8
<212> TYPE: PRT
<213> ORGANISM: Triticum aestivum

<400> SEQUENCE: 42

Gly Val Trp Glu Ile Phe Leu Pro
1               5

<210> SEQ ID NO 43
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 43
cgggatcccg                                                          10

<210> SEQ ID NO 44
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 44
gatgagctcc gtttcgcatg attgaacaag atgg                               34

<210> SEQ ID NO 45

```
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 45
gtcgagctca gaagaactcg tcaagaaggc                                    30

<210> SEQ ID NO 46
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 46
cccgacggcg aggatctcgt gctgacc                                       27

<210> SEQ ID NO 47
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 47
catgggtcac gacgagatcc tcgccgtcgg gcatg                              35

<210> SEQ ID NO 48
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 48
attaggtacc ggacttgctc cgctgtcggc                                    30

<210> SEQ ID NO 49
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 49
tataggtacc gaggcagcga cagagatgcc                                    30

<210> SEQ ID NO 50
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 50
agctgaatcc ggcggcatgg c                                             21

<210> SEQ ID NO 51
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 51
```
tgatagtctt gccagtcagg g                                              21

<210> SEQ ID NO 52
<211> LENGTH: 2037
<212> TYPE: DNA
<213> ORGANISM: Zea mays

<400> SEQUENCE: 52
ttagctgaat ccggcggcat ggcaaggtag actgcagtgc agcgtgaccc ggtcgtgccc    60
ctctctagag ataatgagca ttgcatgtct aagttataaa aaattaccac atatttttt    120
tgtcacactt gtttgaagtg cagtttatct atctttatac atatatttaa actttactct   180
acgaataata taatctatag tactacaata atatcagtgt tttagagaat catataaatg    240
aacagttaga catggtctaa aggacaattg gtattttgac aacaggactc tacagttta    300
tcttttagt gtgcatgtgt tctccttttt tttttgcaa atagcttcac ctatataata     360
cttcatccat tttattagta catccattta gggtttaggg ttaatggttt ttatagacta   420
attttttttag tacatctatt ttattctatt ttagcctcta aattaagaaa actaaaactc  480
tatttagtt tttttattta ataatttaga tataaaatag aataaaataa agtgactaaa    540
aattaaacaa ataccctta agaaattaaa aaaactaagg aaacatttt cttgtttcga     600
gtagataatg ccagcctgtt aaacgccgtc gacgcagtct aacggacacc aaccagcgaa    660
ccagcagcgt cgcgtcgggc caagcgaagc agacggcacg gcatctctgt cgctgcctcg    720
gtaccggact tcgtccgctg tcggcatcca gaaattgcgt ggcggagcgg cagacgtgag   780
ccggcacggc aggcggcctc ctcctcctct cacggcaccg gcagctacgg gggattcctt    840
tcccaccgct ccttcgcttt ccttcctcg cccgccgtaa taaatagaca ccccctccac     900
accctctttc cccaaccctcg tgttgttcgg agcgcacaca cacacaacca gatctcccc    960
aaatccaccc gtcggcacct ccgcttcaag gtacgccgct cgtcctcccc ccccctctct    1020
accttctcta gatcggcgtt ccggtccatg gttagggccc ggtagttcta cttctgttca  1080
tgtttgtgtt agatccgtgt ttgtgttaga tccgtgctgc tagcgttcgt acacggatgc   1140
gacctgtacg tcagacacgt tctgattgct aacttgccag tgtttctctt tggggaatcc   1200
tgggatggct ctagccgttc cgcagacggg atcgatttca tgattttttt tgtttcgttg   1260
catagggttt ggtttgcccct tttccttttat ttcaatatat gccgtgcact tgtttgtcgg  1320
gtcatcttt catgcttttt tttgtcttgg ttgtgatgat gtggtctggt tgggcggtcg    1380
ttctagatcg gagtagaatt ctgtttcaaa ctacctggtg gatttattaa ttttggatct   1440
gtatgtgtgt gccatacata ttcatagtta cgaattgaag atgatggatg gaaatatcga    1500
tctaggatag gtatacatgt tgatgcgggt tttactgatg catatacaga gatgcttttg    1560
ttcgcttggt tgtgatgatg tggtgtggtt gggcggtcgt tcattcgttc tagatcggag    1620
tagaatactg tttcaaacta cctggtgtat ttattaattt tggaactgta tgtgtgtgtc   1680
atacatcttc atagttacga gtttaagatg gatggaaata tcgatctagg ataggtatac   1740
atgttgatgt gggttttact gatgcatata catgatggca tatgcagcat ctattcatat   1800
gctctaacct tgagtaccta tctattataa taaacaagta tgttttataa ttattttgat   1860
cttgatatac ttggatgatg gcatatgcag cagctatatg tggatttttt tagccctgcc   1920
ttcatacgct atttatttgc ttggtactgt ttcttttgtc gatgctcacc ctgttgtttg   1980
gtgttacttc tgcagatgca gatctttgtg aaaaccctga ctggcaagac tatcacc      2037

<210> SEQ ID NO 53
<211> LENGTH: 1085
<212> TYPE: DNA
<213> ORGANISM: Triticum aestivum

<400> SEQUENCE: 53

```
atatgtatga tttcatggct ctggatggac cttcgactcc tgctattgat cgtggcatag      60
cattgcataa aatgattagg cttgtcacca tgggtttagg tggagagggt tatcttaact     120
ttatgggaaa tgagtttggg catcctgaat ggatagattt ccaagaggc ccacaagttc      180
ttccaactgg taagtttctc cctggaaata acaatagtta tgataaatgc cgtcgtagat     240
ttgatcttgg tgatgcagat tttcttaggt atcgtggtat gcaggagttt gatcaggcaa     300
tgcagcatct tgaggaaaaa tatgggttta tgacatctga gcaccagtat gtttctcgga     360
aacatgagga agataaggtg atcgtgtttg aaagagggga tttggtattt gttttcaact     420
tccactggag taatagcttt tttgactacc gtgttgggtg tttcaagcct gggaagtaca     480
aggtggtctt agactccgac gctggactct ttggtggatt tggtaggctt gatcatgctg     540
tcgagtactt cacttctgac tgtccgcatg acaacaggcc gcattctttc tcggtgtaca     600
ctcctagcag aacttgtgtt gtgtatgctc ttatggagta agcagcaagt gcagcatacg     660
ctgccgctgt tgttgctagt agcaaggaga gatcgtaggt cactacacca ggtgcagggt     720
ttgatatgga ttttttgcttg agcgagtcct ggatgggcaa gacagcgtga tgctgtgtgt     780
gctcccaaat cgccatggcg ttgggagggg atcgtgcttc tttgtgttat gctttgtgga     840
tcaggatgga actcccctag gtagccttgt tggtgagcgc tcgaaagaaa atggacgggc     900
ctgggtgttt gcttaaattt tgttgcccta aaccctcgct cctatcttgt acattgccgg     960
tttagatagg gtttgttttt gtacattttt ttgatagtta atagacttat tgctcgtgtg    1020
cttgacgttt tacatgaaca tataaatatt ctaaataggt taaaaaaaaa aaaaaaaaa     1080
aaaaa                                                                1085
```

<210> SEQ ID NO 54
<211> LENGTH: 888
<212> TYPE: PRT
<213> ORGANISM: Triticum aestivum
<220> FEATURE:
<221> NAME/KEY: PEPTIDE
<222> LOCATION: (1)..(888)
<223> OTHER INFORMATION: Xaa = any amino acid
<220> FEATURE:
<221> NAME/KEY: MISC_FEATURE
<222> LOCATION: (1)..(888)
<223> OTHER INFORMATION: Xaa = any amino acid

<400> SEQUENCE: 54

```
Met Leu Cys Leu Ser Xaa Ser Leu Leu Pro Arg Pro Ser Arg Ala Ala
1               5                   10                  15

Ala Asp Arg Pro Xaa Leu Pro Gly Ile Xaa Gly Gly Xaa Xaa Arg
            20                  25                  30

Leu Ser Ala Val Pro Ala Pro Xaa Xaa Leu Arg Trp Xaa Trp Pro Arg
        35                  40                  45

Lys Ala Lys Ser Lys Ser Ser Val Pro Val Xaa Ala Xaa Xaa Xaa Xaa
    50                  55                  60

Ile Xaa Ala Thr Xaa Xaa Xaa Gly Val Xaa Xaa Leu Pro Ile Tyr Asp
65                  70                  75                  80

Leu Asp Pro Lys Leu Ala Xaa Phe Lys Xaa His Phe Asp Tyr Arg Xaa
                85                  90                  95
```

```
Xaa Xaa Tyr Xaa Xaa Gln Lys His Xaa Ile Glu Lys His Glu Gly Gly
        100                 105                 110

Leu Glu Glu Phe Ser Lys Gly Tyr Leu Lys Phe Gly Ile Asn Thr Glu
            115                 120                 125

Xaa Xaa Ala Xaa Val Tyr Arg Glu Trp Ala Pro Ala Ala Xaa Xaa Ala
        130                 135                 140

Gln Leu Val Gly Asp Phe Asn Asn Trp Asn Gly Ser Gly His Xaa Met
145                 150                 155                 160

Thr Lys Asp Asn Phe Gly Val Trp Ser Ile Arg Leu Ser Asn Asn Ala
                165                 170                 175

Asp Gly Ser Pro Ala Ile Pro His Gly Ser Lys Val Lys Phe Arg Phe
            180                 185                 190

Asp Thr Pro Ser Gly Val Trp Val Asp Ser Ile Pro Ala Trp Ile Lys
            195                 200                 205

Tyr Ala Val Gln Thr Ala Gly Glu Ile Gly Ala Pro Tyr Asp Gly Ile
        210                 215                 220

His Tyr Asp Pro Pro Ser Glu Glu Lys Tyr Val Phe Lys His Pro Gln
225                 230                 235                 240

Pro Lys Lys Pro Asp Ser Leu Arg Ile Tyr Glu Ala His Val Gly Met
                245                 250                 255

Ser Gly Pro Glu Pro Glu Ile Asn Thr Tyr Ala Glu Phe Arg Asp Glu
            260                 265                 270

Val Leu Pro Arg Ile Lys Ala Leu Gly Tyr Asn Ala Val Gln Leu Met
            275                 280                 285

Ala Ile Gln Glu His Ser Tyr Tyr Ala Ser Phe Gly Tyr His Val Thr
        290                 295                 300

Asn Phe Phe Ala Val Ser Ser Arg Ser Gly Thr Pro Glu Asp Leu Lys
305                 310                 315                 320

Ser Leu Ile Asp Lys Ala His Ser Leu Gly Leu Arg Val Leu Met Asp
                325                 330                 335

Val Val His Ser His Ala Ser Asn Asn Thr Leu Asp Gly Leu Asn Gly
            340                 345                 350

Phe Asp Val Gly Gln Gly Thr Asp Thr Ser Tyr Phe His Gly Gly Xaa
        355                 360                 365

Arg Gly His His Lys Met Trp Asp Ser Arg Leu Phe Asn Tyr Gly Asn
370                 375                 380

Trp Glu Val Leu Arg Phe Leu Leu Ser Asn Ala Arg Tyr Trp Leu Asp
385                 390                 395                 400

Glu Phe Lys Phe Asp Gly Phe Arg Phe Asp Gly Val Thr Ser Met Leu
                405                 410                 415

Tyr Thr His His Gly Leu Asn Met Ser Phe Thr Gly Ser Tyr Lys Glu
            420                 425                 430

Tyr Phe Gly Leu Ala Thr Asp Val Asp Ala Val Val Tyr Leu Met Leu
        435                 440                 445

Ala Asn Asp Leu Ile His Gly Leu Xaa Pro Glu Ala Val Val Val Gly
450                 455                 460

Glu Asp Val Ser Gly Met Pro Val Leu Cys Xaa Pro Val Asp Glu Gly
465                 470                 475                 480

Gly Val Gly Phe Asp Tyr Arg Leu Ala Met Ala Val Ala Asp Lys Trp
                485                 490                 495

Ile Asp Leu Leu Lys Asn Lys Asp Asp Xaa Trp Ser Met Gly Xaa Ile
            500                 505                 510
```

-continued

Val His Thr Leu Thr Asn Arg Arg Tyr Pro Glu Lys Cys Val Ala Tyr
        515                 520                 525

Ala Glu Ser His Asp Gln Ala Leu Val Gly Asp Lys Thr Ile Ala Phe
    530                 535                 540

Leu Leu Met Asp Lys Asp Met Tyr Asp Gly Met Ala Leu Xaa Xaa Pro
545                 550                 555                 560

Ser Ser Pro Thr Ile Asp Arg Gly Ile Ala Leu Gln Lys Met Ile His
                565                 570                 575

Leu Ile Thr Met Gly Leu Gly Gly Asp Gly Tyr Leu Asn Phe Met Gly
            580                 585                 590

Asn Glu Phe Gly His Pro Glu Trp Ile Asp Phe Pro Arg Gly Pro Gln
        595                 600                 605

Leu Pro Thr Gly Lys Pro Gly Asn Asn Asn Ser Tyr Asp Lys Cys Arg
    610                 615                 620

Arg Arg Phe Asp Leu Gly Asp Ala Asp Phe Leu Arg Tyr His Gly Met
625                 630                 635                 640

Asn Ala Phe Asp Gln Ala Met Gln His Leu Glu Asp Lys Tyr Gly Phe
                645                 650                 655

Leu Ser Ser Ser His Gln Tyr Val Ser Arg Lys Asn Glu Glu Asp Lys
            660                 665                 670

Val Ile Val Phe Glu Lys Gly Asp Leu Val Phe Val Phe Asn Phe His
        675                 680                 685

Trp Ser Asn Ser Tyr Phe Asp Tyr Arg Val Gly Cys Xaa Xaa Pro Gly
    690                 695                 700

Lys Tyr Lys Val Ala Leu Asp Ser Asp Ala Xaa Leu Phe Gly Gly Phe
705                 710                 715                 720

Gly Arg Xaa Xaa His Asp Xaa Asp His Phe Thr Ser Glu Xaa Xaa His
                725                 730                 735

Asp Asn Arg Pro Xaa Ser Phe Ser Val Leu Thr Pro Ser Arg Thr Cys
            740                 745                 750

Val Val Tyr Ala Pro Xaa Glu Xaa Ala Ala Xaa Val Thr Lys Xaa Tyr
        755                 760                 765

Xaa Xaa Xaa Xaa Xaa Leu Xaa Arg Xaa Xaa Gly Xaa Xaa Xaa Xaa Xaa
    770                 775                 780

Xaa Phe Leu Xaa Pro Xaa Lys Xaa Xaa Xaa Xaa Xaa Xaa Xaa Xaa Leu
785                 790                 795                 800

Xaa Xaa Xaa Xaa Xaa Xaa Pro Xaa Xaa Xaa Pro Xaa Ile Xaa Phe Xaa
                805                 810                 815

Xaa Xaa Gly Gly Xaa Xaa Xaa Xaa Xaa Xaa Xaa Xaa Xaa Xaa Lys Xaa
            820                 825                 830

Xaa Xaa Xaa Ala Val Xaa Xaa Xaa Xaa Ser Xaa Xaa Xaa Xaa Xaa Xaa
        835                 840                 845

Xaa Ile Leu Xaa Leu Xaa Xaa Xaa Ile Ile Xaa Xaa Xaa Xaa Xaa Xaa
850                 855                 860

Xaa Xaa Leu Xaa Xaa Xaa Xaa Xaa Xaa Xaa Xaa Xaa Xaa Xaa Xaa Xaa
865                 870                 875                 880

Lys Lys Lys Lys Lys Lys Lys Lys
                885

<210> SEQ ID NO 55
<211> LENGTH: 1488
<212> TYPE: DNA
<213> ORGANISM: Zea mays

<400> SEQUENCE: 55

-continued

```
aagcttgcat gcctgcaggt cgactctaga ccaaatttca tggtagttgg gagcctaccc      60
agatttcatg attaactgtg ctattgaatt gttgaaaatg gttgtgtctg tcgtatccga     120
cggataacgg aaacccgtcc gaaattcaat gggcatgggc atagatatag atttgtaccc     180
actactagta tggtcgcagg cggatattgg ttgcaaccgc agatatagtt tcggggaaaa     240
ggattaggct cagctccatc cctagacccc acttgtgtgt gtgggggggt ctacccttca     300
aaaggaaaaa aaactacaca cagtgcatat aagaagatga atattccaaa attcagcagt     360
caagaagccc tgataaactg tctggcatag ctagtacttt atacacttca agaccaaaag     420
aaatcactaa gtacagattt tagtgactcg taagtacaga tatcatctta caaggcccag     480
cccagcgacc tattacacag cccgctcggg cccgcgacgt cgggacacat cttcttcccc     540
cttttggtga agctctgctc gcagctgtcc ggctgcttgg acgttcgtgt ggcagattca     600
tctgtcgtct cgtctcctgt gcttcctggg tagcttgtgc agtggagctg acatggtctg     660
agcaggctta aaatttgctc gtagacgagg agtaccagca cagcacgttg cggatttctc     720
tgcctgtgaa gtgcaacgtc taggattgtc acacgccttg gtcgcgtcga tgcggtggtg     780
agcagagcag caacagctgg gcggcccaaa gttggcttcc gtgtcttcgt cgtacgtacg     840
cgcgcgccgg ggacacgcag agagcggaga gcgagccgtg cacggggag gtggtgtgca      900
agtgcagccg cgcgcccgcg cccgcgcccg gtgggcaacc caaaaagtac ccacgacaag     960
cgaaggcgcc aaagcgatcc aagctccgga acgcatcagc cacaagcagc cgagaaccga   1020
accggtgggc gacgcgtcgt gggacggacg cgggcgacgc ttccaaacgg ggccacgtac   1080
gccggcgtgt gcgtgcgtgc gtgcagacga caagccaagg cgaggcagcc cccgatcggg   1140
aaagcgtttt gggcgcgagc gctggcgtgc gggtcagtcg ctggtgcgca gtgccggggg   1200
gaacgggtat cgtgggggc gcggcggaga agagcgtggc gaggccgaga gcagcgcgcg    1260
gccgggtcac gcaacgcgcc ccacgtactg ccctccccct ccgcgcgcgc tagaaatacc   1320
gaggcctgga ccggggccc ccccgtcaca tccatccatc gaccgatcga tcgccacagc    1380
caacaccacc cgccgaggcg acgcgacagc cgccaggagg aaggaataaa ctcactgcca   1440
gccagtgaag ggggagaagt gtactgctcc gtcgactcta gaggatcc                1488
```

ISOFORMS OF STARCH BRANCHING ENZYME II (SBE-IIA AND SBE-IIB) FROM WHEAT

This application is divisional of application SN 09/786,480 filed Sep. 17, 2001, which is a §371 national stage filing of PCT/GB99/03011, filed Sep. 9, 1999 (published in English on Mar. 23, 2000 as WO 00/15810) and claiming priority to EP 98307337.0 filed Sep. 10, 1998.

FIELD OF THE INVENTION

This invention relates generally to plant starch compositions, and concerns novel nucleotide sequences; polypeptides encoded thereby; vectors and host cells and host organisms comprising one or more of the novel sequences; a method of altering one or more characteristics of a plant; a plant having altered characteristics; starch obtained from such plants; and uses of the starch.

BACKGROUND TO THE INVENTION

The majority of developments in cereal science in the recent past have concentrated primarily on the functionality of the gluten protein sub-units and their role in bakery systems. This has been greatly facilitated by the abundance of natural variation between cultivators for the gluten protein sub-unit components.

In contrast, although flour from commercially grown wheat varieties contains approximately 75–85% starch, the role of starch from a breeding perspective has been overlooked; this is largely due to the difficulty of measuring differences in starch structure. Of the limited amount of work that has been carried out however, there appears to be a lack of natural variation between different wheat cultivars. With the advent of recombinant DNA and gene transfer technologies it is now possible to create new variation in planta, therefore directly modifying starch composition in wheat becomes a realistic target.

Starch is the major form of carbon reserve in plants, constituting 50% or more of the dry weight of many storage organs, e.g. tubers, seeds of cereals. Starch is used in numerous food and industrial applications. In many cases, however, it is necessary to modify the native starches, via chemical or physical means, in order to produce distinct properties to suit particular applications. It would be highly desirable to be able to produce starches with the required properties directly in the plant, thereby removing the need for additional modification. To achieve this via genetic engineering requires knowledge of the metabolic pathway of starch biosynthesis. This includes characterization of genes and encoded gene products which catalyse the synthesis of starch. Knowledge about the regulation of starch biosynthesis raises the possibility of "re-programming" biosynthetic pathways to create starches with novel properties that could have new commercial applications.

The most significant property of starch derives from the ability of the native granular form to lose its order and to swell and absorb water upon suitable treatment, thereby conferring viscosity and texture, in a process known as gelatinisation. Gelatinisation has been defined (W A Atwell et al, 1988) as ". . . the collapse (disruption) of molecular orders within the starch granule manifested in irreversible changes in properties such as granular swelling, native crystallite melting, loss of birefringence, and starch solubilisation. The point of initial gelatinisation and the range over which it occurs is governed by starch concentration, method of observation, granule type, and heterogeneities within the granule population under observation".

14 molecules of water per molecule of anhydrous glucose, i.e. a minimum of 75% water, are necessary for full starch gelatinisation (Donovan, 1979). Starch gelatinisation is usually caused by heat, but can be caused by physical damage and some chaotropic agents, mainly dimethylsulphoxide (DMSO), urea, calcium chloride, strong base and acid.

The various events taking place during gelatinisation can be followed by various methods, including birefringence, X-ray diffraction, differential scanning calorimetry (DSC), $^{13}C$ NMR. Swelling can be monitored by various methods, particularly rheology.

Differential scanning calorimetry (DSC) is a destructive method which records an endothermic event on heating of granules, generally thought to measure the temperature and the endothermic energy (delta H) required for the melting of the native crystallites. Starch gelatinisation temperature is independent of water content above 75% water (described as excess water), but increases when water is limited (Donovan, 1979).

The rate and extent of starch granule swelling upon heating dictate the type of viscosity development of aqueous starch suspensions on heating. Swelling behaviour is therefore of utmost technological importance. Viscosity increase on heating can be conveniently measured by a Brabender amylograph (Brabender is a Trade Mark) (Kennedy and Cabalda, 1991) or using a Rapid Visco analyser (Rapid Visco is a Trade-Mark from Newport Scientific, Australia). FIG. 1 is a typical viscoamylgraph profile for wheat starch, produced in this way, showing changes in starch during and after cooking. As starch granules swell on uptake of water, in, a process known as pasting, their phase volume increases, causing an increase in viscosity. The onset of pasting is indicated at A in FIG. 1. Peak viscosity, indicated at B in FIG. 1, is achieved when maximum phase volume is reached. Shear will then disrupt/cause fragmentation of the swollen granules, causing the viscosity to decrease. Complete dispersion is indicated at C in FIG. 1. This has been confirmed by an oscillatory rheology study of starch pastes at various stages of the viscosity profile (Svegmark and Hermansson, 1990). The viscosity onset temperature and peak viscosity are indicative of the initiation and extent of swelling, respectively. On cooling, leached amylose forms a network in a process involving reassociation of molecules, or retrogradation, causing an increase in viscosity as indicated at D in FIG. 1. Retrogradation (or set-back) viscosity is therefore indicative of the amount of amylose leached out of the granules.

The properties of wheat starch are useful in a large number of applications and also non-food (paper, textiles, adhesives etc.) applications. However, for many applications, properties are not optimum and various chemical and physical modifications well known in the art are undertaken in order to improve useful properties. Two types of property manipulation which would be of use are: the controlled alteration of gelatinisation and pasting temperatures; and starches which suffer less granular fragmentation during pasting than conventional starches.

Currently the only ways of manipulating the gelatinisation and pasting temperatures of starch are by the inclusion of additives such as sugars, polyhydroxy compounds of salts or by extensive physical or chemical pre-treatments. The reduction of granule fragmentation during pasting can be achieved either by extensive physical pre-treatments or by chemical cross-linking. Such processes are inconvenient and inefficient. It is therefore desirable to obtain plants which produce starch which intrinsically possesses such advantageous properties.

Starch consists of two main glucose polysaccharides: amylose and amylopectin. Amylose is a generally linear polymer comprising α-1,4 linked glucose units, while amylopectin is a highly branched polymer consisting of an α-1,4 linked glucan backbone with α-1,6 linked glucan branches. In wheat endosperm amylopectin constitutes approximately 70% of the total starch content, with the balance being amylose. Amylopectin is synthesised through the concerted action of several enzymes, including soluble starch synthase(s) (SSS), starch branching enzyme(s) (SBE), starch de-branching enzyme(s) (DBE). The physical properties of starch are strongly affected by the relative abundance of amylose and amylopectin, therefore SSSs, SBEs and DBEs play a key role in determining both starch quantity and quality. As such, one approach to manipulating starch structure would be to modify the expression of the enzymes involved in starch biosynthesis in the endosperm using a transgenic approach.

SBE catalyses the formation of the α-1,6 linkages, creating branch points in the growing starch molecule, via hydrolysis of an α-1,4 linkage followed by reattachment of the released α-1,4-glucan chain to the same or another glucosyl chain. This reaction also provides a new non-reducing end for further elongation of the original α-1,4-glucan chain.

Multiple isoforms of starch branching enzyme have been described, biochemically, from a number of species including maize (Boyer and Preiss, 1978), rice (Nakamura et al., 1992), pea (Smith, 1988), potato (Khoshnoodi et al., 1993) and wheat (Morell et al., 1997). More recently, genomic and cDNA sequences for SBE have been characterised from several species including maize (Baba et al., 1991; Fisher et al., 1993; Gao et al. 1997) pea (Burton et al., 1995), potato (Kossmann et al., 1991), rice (Nakamura and Yamanouchi, 1992; Mizuno et al., 1993), *Arabidopsis* (Fisher et al., 1996), cassava (Salehuzzaman et al., 1992), and wheat (Rapellin et al., 1997, Nair et al., 1997, Rahman et al., 1997). Sequence alignment of these SBEs revealed a high degree of sequence conservation at the amino acid level and that the SBEs may be grouped into two distinct families, generally known as SBEI and SBEII. Further, analysis indicates that within a species there is generally of the order of 50% homology between the two families, SBEI and SBEII, while there is often greater homology within the two families between species.

Maize is unusual in that the maize SBEII family is thought to comprise two different members, known as SBEIIa and SBEIIb. There has been controversy over whether the SBEIIa and IIb enzymes are in fact a) encoded by genes at two different loci, and b) whether the genes represent different alleles at a single locus. Fisher et al (1996) and Gao et al (1997) have provided evidence that SBEIIa and SBEIIb are encoded by independent genes. However, there is no conclusive evidence that both isoforms exist together in any one maize genotype. The DNA clones for the two published gene sequences were purified from different genotypes of maize and it is thus possible that they represent different alleles of a single locus. In summary, in maize, three distinct SBE genes have been characterised to date (Baba et al., 1991; Fisher et al., 1993; Gao et al., 1997). SBEI is distinct from SBEIIa and SBEIIb in amino acid composition, substrate specificity, kinetic properties, and immunological reactivities, whereas SBEIIa and SBEIIb are similar in these respects (Guan and Preiss, 1993; Preiss 1991; Takeda et al., 1993). At the amino acid level the sequence exhibits approximately 50% homology with the SBEIIa and SBEIIb sequences, whereas SBEIIa and SBEIIb exhibit approximately 80% homology to each other.

Prior to the present invention, maize was unique in having SBEIIa- and SBEIIb-type enzymes. Although *Arabidopsis* has two SBEII family members, the subdivision in *Arabidopsis* does not appear to conform to that seen in maize: the *Arabidopsis* sub-family members do not obviously fall into the IIa and IIb categories as do the maize sequences. Both of the *Arabidopsis* SBEII genes have similar levels of homology to both the maize SBEII genes, SBEIIa and SBEIIb, but the similarities are not sufficient to be able to place the *Arabidopsis* genes into the same SBEIIa and SBEIIb categories as for maize. Indeed, the data, if anything, suggests that the *Arabidopsis* SBEII genes do nor fall into the maize IIa and IIb categories. For barley, two forms of SBEII had been partly characterised. Although these have been called SBEIIa and SBEIIb, only a very limited amount of sequence information had been published (Sun et al, 1995) and it was not possible to infer or conclude that these forms correspond to the IIa and IIb categories of maize. In fact, based on the available barley sequence information both of the barley SBEII sequences (SBEIIa and SBEIIb) would appear to show greater homology to maize SBEIIa than to maize SBEIIb.

For all other plant species for which SBEII sequences have been identified and published, including potato, pea, rice, cassava, wheat and barley, no subdivision of the SBEII family comparable to the SBEIIa and SBEIIb division of maize has been made.

Studies of purified SBEI and SBEII demonstrate that these isoforms differ in their specificity for a substrate with respect to both chain length and degree of branching. In maize, SBEI and SBEII show distinct branching activities in vitro, with SBEI showing a higher rate of branching of an amylose substrate when compared to SBEII whereas both SBEIIa and IIb show higher rates of branching than SBEI when acting upon an amylopectin substrate (Guan and Preiss, 1993). Furthermore, maize SBEI preferentially transfers longer glucan chains (average chain length=24) than SBEII (average chain length=21(IIa) and 22(IIb)) (Takeda et al., 1993). A similar observation has been reported for SBEI and SBEII isoforms from wheat and pea (Morell et al., 1997; Smith, 1988). Mutational studies in maize, rice and pea demonstrate that high amylose mutants in each case are deficient in the branching enzyme activity analogous to maize SBEII (Martin and Smith, 1995; Morell et al., 1995). However, the linkage between the biochemical observations and the genetic evidence suggesting the differences in the roles remains unclear.

The present invention is based on the unexpected discovery of a novel class of SBEII genes in wheat, referred to herein as SBEII-1. The novel SBEII-1 gene sequence has strong homology with the maize SBEIIb gene. The wheat SBEII-1 genes are thought to be functionally equivalent to the maize SBEIIb gene, and on this basis it is believed that manipulation of the wheat SBEII-1 gene is likely to influence starch properties including starch gelatinisation temperature, in a manner analogous to manipulation of the maize SBEIIb gene as described in WO 97/22703.

In summary, although two different SBEII gene sequences are known from maize, *Arabidopsis* and barley, as discussed above, prior to the present invention there was no reason to expect that wheat would show a similar sub-division of SBEII genes as is seen for maize. The two *Arabidopsis* SBEII genes show a different sub-division, and prior to the present invention there was insufficient evidence to determine whether the two barley SBEII sequences belonged to the maize-type sub-division. That is, prior to the present invention there was no reason to expect that wheat would have two similar SBEII members comparable to those of maize. Subsequent to the present invention Sun et al (1998) have presented data which indicates that the barley sequences do indeed sub-divide in a similar manner to the maize SBEIIa and IIb sequences and the wheat SBEII-2 and SBEII-1 sequences discussed in this document.

The present inventors have used the high degree of sequence conservation between several SBE gene sequences to design oligonucleotide primers to motifs which are specific to either SBEI or SBEII families and have used these primers to amplify cDNA sequences from developing endosperm of wheat.

When this work was started, a single partial length wheat SBE cDNA clone had been reported (Mousley, 1994). Multiple sequence alignment of this wheat SBE sequence with other published SBE sequences from a number of plant species revealed a number of motifs which were highly conserved. Oligonucleotide primers designed to be complementary to these motifs were used to clone 3' partial length cDNA clones of wheat SBEII. Alignment of the cDNA clone sequences indicated that the clones could be divided into two classes, which the inventors have designated SBEII-1 and SBEII-2, which showed greater than 90% similarity to members within a class but only 60% similarity between classes. Significantly, comparison between representative sequences from each class with previously identified wheat SBEII clones, pWBE6 (Mousley, 1994) and SBEII (Nair et al., 1997), showed that each appear to be homologues of the SBEII-2 class. The cloning of a wheat SBEII-1 cDNA is novel.

SUMMARY OF THE INVENTION

In one aspect the invention provides a nucleotide sequence encoding substantially the amino acid sequence shown in FIG. 10 (SEQ ID No: 2) or a functional equivalent of said nucleotide sequence.

The term functional equivalent is used in this context to encompass those sequences which differ in their nucleotide composition to that shown in FIG. 10 (SEQ ID No: 1) but which, by virtue of the degeneracy of the genetic code, encode polypeptides having identical or substantially identical amino acid sequences. It is intended that the term should generally apply to, sequences which are sufficiently homologous to the sequence of the invention that they can hybridise to the complement thereof under stringent hybridisation conditions (eg as described by Sambrook et al 1989, ie washing with 0.1×SSC, 0.5% SDS at 68° C.); such equivalents will preferably possess at least 86%, more preferably at least 90%, and most preferably at least 95%, sequence homology (ie sequence similarity) with the sequence of the invention. Sequence homology is suitably determined using the 'MEGALIGN' program of the software package DNAStar (MEGALIGN and DNAStar are Trade Marks). It will be apparent to those skilled in the art that the nucleotide sequence of the invention may also find useful application when present as an "antisense" sequence. Accordingly, functionally equivalent sequences will also include those sequences which can hybridise, under stringent hybridisation conditions, to the sequence of the invention (rather than the complement thereof). Such "antisense" equivalents will preferably possess at least 86%, more preferably at least 90%, and most preferably 95% sequence homology with the complement of the sequence of the invention.

In another aspect, the invention provides a nucleotide sequence comprising substantially the sequence of B2 shown in FIG. 3 (SEQ ID No: 3), or a functional equivalent thereof.

In a further aspect, the invention provides a nucleotide sequence comprising substantially the sequence of B4 shown in FIG. 3 (SEQ ID No: 4), or a functional equivalent thereof.

Another aspect of the invention provides a nucleotide sequence comprising substantially the sequence of B10 shown in FIG. 3 (SEQ ID No: 5), or a functional equivalent thereof.

Yet a further aspect of the invention provides a nucleotide sequence comprising substantially the sequence of B1 shown in FIG. 3 (SEQ ID No: 6), or a functional equivalent thereof.

In another aspect the invention provides a nucleotide sequence encoding substantially the amino acid sequence of B6 shown in FIG. 4 (SEQ ID No: 7), or a functional equivalent thereof.

The term functional equivalent in this context has the same general meaning as discussed above, although equivalents for B2, B4, B10 and B6 will preferably possess at least 90%, more preferably at least 95%, sequence homology with the relevant sequence of the invention, while equivalents for B1 will preferably possess at least 97% sequence homology with the sequence of the invention.

The sequences of the invention are part of novel wheat SBEII genes, with B1 being a novel subclass of the known class of SBEII genes, referred to herein as SBEII-2, with the novel subclass being called SBEII-2B. The remaining sequences are all of a completely new class of wheat SBEII genes, referred to herein as SBEII-1. The sequences have been found to fall into 3 sub-classes, to be discussed below.

The novel wheat SBEII-1 genes that are the subject of this invention have strong sequence homology with the maize SBEIIb gene. The wheat SBEII-1 genes are thought to have similar functional properties to the maize SBEIIb gene. On this basis it is expected that by genetic manipulation of the wheat SBEII-1 gene it will be possible to influence properties of starch produced by a plant, including the gelatinisation temperature and rheological properties of starch, in a manner analogous to manipulation of the maize SBEIIb gene described in WO 97/22703. The content of WO 97/22703 is incorporated herein by reference.

The present invention also includes within its scope a portion of any of the above sequences, comprising at least 500 base pairs and having at least 90% sequence homology to the corresponding portion of the sequence from which it is derived.

Although the coding sequences of the novel wheat SBEII-1 genes have strong sequence homology with the maize SBEIIb gene, there is much greater divergence in the 3' untranslated parts of the sequences, with a maximum of 31.8% homology between the 3' untranslated sequences of wheat SBEII-1 and maize SBEIIb as is apparent from FIG. 8.

In another aspect the invention thus provides a nucleotide sequence comprising substantially the sequence shown in FIG. 5 (SEQ ID No: 8), FIG. 6 (SEQ ID No: 9) or FIG. 7 (SEQ ID No: 10), or a functional equivalent thereof.

The term functional equivalent in this context has the same general meaning as discussed above, but with equivalents preferably at, least 32%, more preferably at least 40%, 50%, 60%, 70%, 80% or 90% sequence homology with the sequence of the relevant Figure.

It is thought such 3' untranslated sequences may be useful, both in sense and antisense function, in manipulation of starch properties by affecting SBE expression in plants, as will be discussed below.

The sequence may include further nucleotides at the 5' or 3' end. For example, for ease of expression, the sequence desirably also comprises an in-frame ATG start code, and may also encode a leader sequence.

The invention also covers a nucleic acid construct comprising a nucleotide sequence or portion thereof in accordance with the invention conveniently operably linked, in sense or antisense orientation, to a promoter sequence.

Also included within the scope of the invention is amino acid sequence encoded by any of the nucleotide sequences of the invention.

The invention also provides vectors, particularly expression vectors, comprising the nucleotide sequence of the invention. The vector will typically comprise a promoter and one or more regulatory signals of the type well known to those skilled in the art. The invention also includes provision of cells transformed (which term encompasses transduction and transfection) with a vector comprising the nucleotide sequence of the invention.

Nucleotide sequences in accordance with the invention may be introduced into plants, particularly but not exclusively wheat plants, and it is expected that this can be used to affect expression of SBE in the plant and hence affect the properties of starch produced by the plant. In particular, use of sequences in antisense orientation is expected to reduce or suppress enzyme expression. Additionally, it has recently been demonstrated in other experimental systems that "sense suppression" can also occur (i.e. expression of an introduced sequence operably linked in the sense orientation can interfere, by some unknown mechanism, with the expression of the native gene), as described by Matzke & Matzke 1995. Any one of the methods mentioned by Matzke & Matzke could, in theory, be used to affect the expression in a host of a homologous-SBE gene.

It is believed that antisense methods are mainly operable by the production of antisense mRNA which hybridises to the sense MRNA, preventing its translation into functional polypeptide, possibly by causing the hybrid RNA to be degraded (e.g. Sheehy et al., 1988; Van der Krol et al.,). Sense suppression also requires homology between the introduced sequence and the target gene, but the exact mechanism is unclear. It is apparent however that, in relation to both antisense and sense suppression, neither a full length nucleotide sequence, nor a "native" sequence is essential. Preferably the "effective portion" used in the method will comprise at least one third of the full length sequence, but by simply trial and error other fragments (smaller or larger) may be found which are functional in altering the characteristics of the plant.

Thus, in a further aspect the invention provides a method of altering the characteristics of a plant, comprising introducing into the plant an effective portion of the sequence of the invention operably linked to a suitable promoter active in the plant so as to affect expression of a gene present in the plant. Conveniently the sequence will be linked in the antisense orientation to the promoter. Preferably the plant is a wheat plant. Conveniently, the characteristic altered relates to the starch content and/or starch composition of the plant (i.e. amount and/or type of starch present in the plant). Preferably the method of altering the characteristics of the plant will also comprise the introduction of one or more further sequences, in addition to an effective portion of the sequence of the invention. The introduced sequence of the invention and the one or more further sequences (which may be sense or antisense sequences) may be operably linked to a single promoter (which would ensure both sequences were transcribed at essentially the same time), or may be operably linked to separate promoters (which may be necessary for optimal expression). Where separate promoters are employed they may be identical to each other or different. Suitable promoters are well known to those skilled in the art and include both constitutive and inducible types. Examples include the CaMV 35S promoter (e.g. single or tandem repeat) and the ubiquitin promoter. Advantageously the promoter will be tissue-specific. Desirably the promoter will cause expression of the operably linked sequence at substantial levels only in the tissue of the plant where starch synthesis and/or starch storage mainly occurs.

The sequence of the invention, and the one or more further sequences if desired, can be introduced into the plant by any one of a number of well-known techniques (e.g. Agrobacterium-mediated transformation, or by "biolistic" methods). The sequences are likely to be most effective in affecting SBE activity in wheat plants, but theoretically could be introduced into any plant. Desirable examples include pea, tomato, maize, rice, barley, sweet potato and cassava plants. Preferably the plant will comprise a natural gene encoding an SBE molecule which exhibits reasonable homology with the introduced nucleic acid sequence of the invention.

In another aspect, the invention provides a plant cell, or a plant or the progeny thereof, which has been altered by the method defined above. The progeny of the altered plant may be obtained, for example, by vegetative propagation, or by crossing the altered plant and reserving the seed so obtained. The invention also covers parts of the altered plant, such as storage organs. Conveniently, for example, the invention covers grain comprising altered starch, said grain being obtained from an altered plant or the progeny thereof. Grain obtained from altered plants (or the progeny thereof) will be particularly useful materials in certain industrial applications and for the preparation and/or processing of foodstuffs and may be used, for example, in bakery products.

In particular relation to wheat plants, the invention provides a wheat plant or part thereof which, in its wild type possesses an effective SBEII-1 gene, but which plant has been altered such that there is either reduced, increased or no effective expression of an SBEII-1 polypeptide within the cells of at least part of the plant. The plant may have been altered by the method defined above, or may have been selected by conventional breeding to be deleted for the SBEII-1 gene, the presence or absence of which can be readily determined by screening samples of the plants with a nucleic acid probe or antibody specific for the wheat gene or gene product respectively.

The invention also provides starch extracted from a plant altered by the method defined above, or from the progeny of such a plant, the starch having altered properties compared to starch extracted from equivalent, but unaltered, plants. The invention further provides a method of making altered starch, comprising altering a plant by the method defined above and extracting therefrom starch having altered properties compared to starch extracted from equivalent, but unaltered, plants. It is believed that use of nucleotide sequences in accordance with the invention will enable the production of starches, particularly wheat starches, having a wide variety of novel properties. For example, it may be anticipated that plants altered to give a reduction in SBEII activity will give rise to a starch with a relatively higher proportion of amylose and a lower proportion of amylopectin compared with that from unaltered plants.

In particular the invention provides the following: a plant (especially a wheat plant) altered by the method defined above, containing starch which, when extracted from the plant, has an elevated gelatinisation onset and/or peak temperature as measured by DSC, compared to starch extracted from a similar, but unaltered, plant; a plant (especially a wheat plant) altered by the method defined above, containing starch which, when extracted from the plant, has a elevated gelatinisation onset temperature (conveniently elevated by at least 3° C., possibly by at least 7° C., by at least 12° C. or possibly even by 15 to 25° C.) as measured by DSC compared to starch extracted from a similar, but unaltered plant; a plant (especially a wheat plant) altered by the method defined above, particularly to reduce expression of SBEII-1 polypeptide, containing starch which, when extracted from a plant, has a higher amylose:amylopectin ratio compared to starch extracted from a similar, but unaltered plant.

The present invention particularly covers starch extracted from a plant altered by the method of the invention, particularly starch having an increased gelatinisation temperature. Such starch is useful, eg in bakery products, having particular benefits in certain situations, and the invention also covers products, particularly bakery products, made from such starch. The invention also covers starch extracted from a plant altered by the method of the invention and having an increased amylose:amylopectin ratio.

BRIEF DESCRIPTION OF THE DRAWINGS

The invention will be further described, by way of illustration, in the following Examples and with reference to the accompanying drawings, in which:

FIG. 2 shows alignment amino acid sequence data of C terminal portions of various known starch branching enzymes (SEQ ID Nos: 12 to 25), obtained from the European Molecular Biology Laboratory (EMBL) database, and for a novel wheat SBEII-1 sequence of the invention (OsbeII-1ALL) (SEQ ID No: 11) from clone 5A1, with consensus residues highlighted;

FIG. 3 shows aligned DNA sequence data for various recombinant clones (B2, B4, B10, A2, B1, B11) (SEQ ID Nos: 3, 4, 5, 26, 6, 27 respectively) containing wheat starch branching enzyme genes, representing two SBE classes, SBEII-1 and SBEII-2, each of which includes three sub-classes A, B and C, with residues differing from the consensus (majority) (SEQ ID No: 53) highlighted;

FIG. 3a is a residue weight table showing the percent similarity and percent divergence of the sequences shown in FIG. 3;

FIG. 4 is an alignment of predicted amino acid sequences for clones B6 (wheat SBEII-1) (SEQ ID No: 7) and B11 (wheat SBEII-2) (SEQ ID No: 28) against the corresponding regions of the maize SBEIIa (SEQ ID No: 29) and SBEIIb (SEQ ID No: 30) amino acid sequences, with residues differing from those of maize SBEIIb highlighted;

FIG. 4a is a residue weight table showing the percent similarity and percent divergence of the sequences shown in FIG. 4;

FIG. 5 shows the 3' untranslated DNA sequence of clone B2 (SEQ ID No: 8) (wheat SBEII-1, sub-class A);

FIG. 7 shows the 3' untranslated DNA sequence of clone B4 (SEQ ID No: 10) (wheat SBEII-1, sub-class C);

FIG. 8 shows aligned DNA sequence data for the 3' untranslated region of clones B10 (SEQ ID No: 9), B2 (SEQ ID No: 8) and B4 (SEQ ID No: 10) and maize SBEIIb (ZMSBE2b) (SEQ ID No: 31), with residues differing from those of the B10 sequence highlighted;

FIG. 8a is a residue weight table showing the percent similarity and percent divergence of the sequences shown in FIG. 8;

FIG. 10 shows the DNA (SEQ ID No: 1) and predicted amino acid sequence (SEQ ID No: 2) of part of SBEII-1 clone 5A1;

FIG. 11 shows aligned amino acid sequence data for the wheat SBEII-1 sequence of the invention, from clone 5A1 (OsbeI-1ALL) (SEQ ID No: 11), wheat SBEI-D2 (SEQ ID No: 32) of Rahman et al 1997 (TASBEID2)., wheat SBE1 of RapeUin et al 1997 (SEQ ID No: 33) (TASBEI) and wheat SBEII-2 of Nair et al 1997 (SEQ ID No: 34) (wheat SBEII-2), with residues exactly matching the consensus (majority) (SEQ ID No: 54) highlighted;

FIG. 11a is a residue weight table showing the percent similarity and percent divergence of the sequences shown in FIG. 11;

FIG. 12 illustrates northern blotting of wheat grains harvested at various different intervals after anthesis and probed with SBEII-1 and SBEII-2 fragments;

FIG. 13a shows the sequence (SEQ ID No: 55) of the promoter (HindIII-BarnH1 fragment) in pWxGS+;

FIG. 26 shows the DNA sequence of the NptII Sac1 fragment of pUNI (SEQ ID No: 35)

FIG. 29 is a partial restriction map of the predicted sequence (SEQ ID No: 52) of a cloned fragment of p97-U3;

FIG. 36 shows histochemical localisation of waxy-GUS expression in endosperm tissue of two independent transgenic wheat lines (in panels A and B) transformed with the plasmid pWxGS+.

DETAILED DESCRIPTION OF THE PREFERRED EMBODIMENTS

EXAMPLES

Amplification and Characterisation of Two Classes of SBEII cDNA Clones

A PCR based cloning strategy was devised for isolating starch branching enzymes from wheat using conserved domains within the known cloned gene sequences. Starch branching enzymes have been cloned from a number of plant species and FIG. 2 shows amino acid sequence data, obtained from the European Molecular Biology Laboratory (EMBL) nucleotide database for various known starch branching enzymes as follows:

Wheat SBEII-2 for *Triticum aestivum* (SEQ ID No: 12)
ZM SBE2a (maize) for *Zea mays* (SEQ ID No: 13)
ZM SBP2b (maize) for *Zea mays* (SEQ ID No: 14)
Barley SBEIIa (SEQ ID No: 15)
Barley SBEIIb (SEQ ID No: 16)
RICBCE3 (rice SBEII type enzyme) for *Oryza sativa* (SEQ ID No: 17)
RICESBE-1/97 (as above, including transit peptide sequence) (SEQ ID No: 18)
PSSBEIGEN (pea SBEI, which is in fact an SBEII-type sequence) for *Pisum sativum* (SEQ ID No: 19)
STSBE (potato SBEI type) for *Solanum tuberosum* (SEQ ID No: 20)
TASBEI (wheat SBEI-2) for *Triticum aestivum* (SEQ ID No: 21)
TASBEI D2 (SEQ ID No: 22)
ZMSBEI (maize SBEI) for *Zea mays* (SEQ ID No: 23)
RICBEI (rice SBEI) for *Oryza sativa* (SEQ ID No: 24)
PSSBEIIGN (pea SBEII, which is in fact an SBEI-type sequence) for *Pisum sativum* (SEQ ID No: 25)

FIG. 2 also shows sequence information for a novel wheat SBEII-1 sequence of the invention, identified as OsbeII-1ALL (SEQ ID No: 11).

Figure 1:
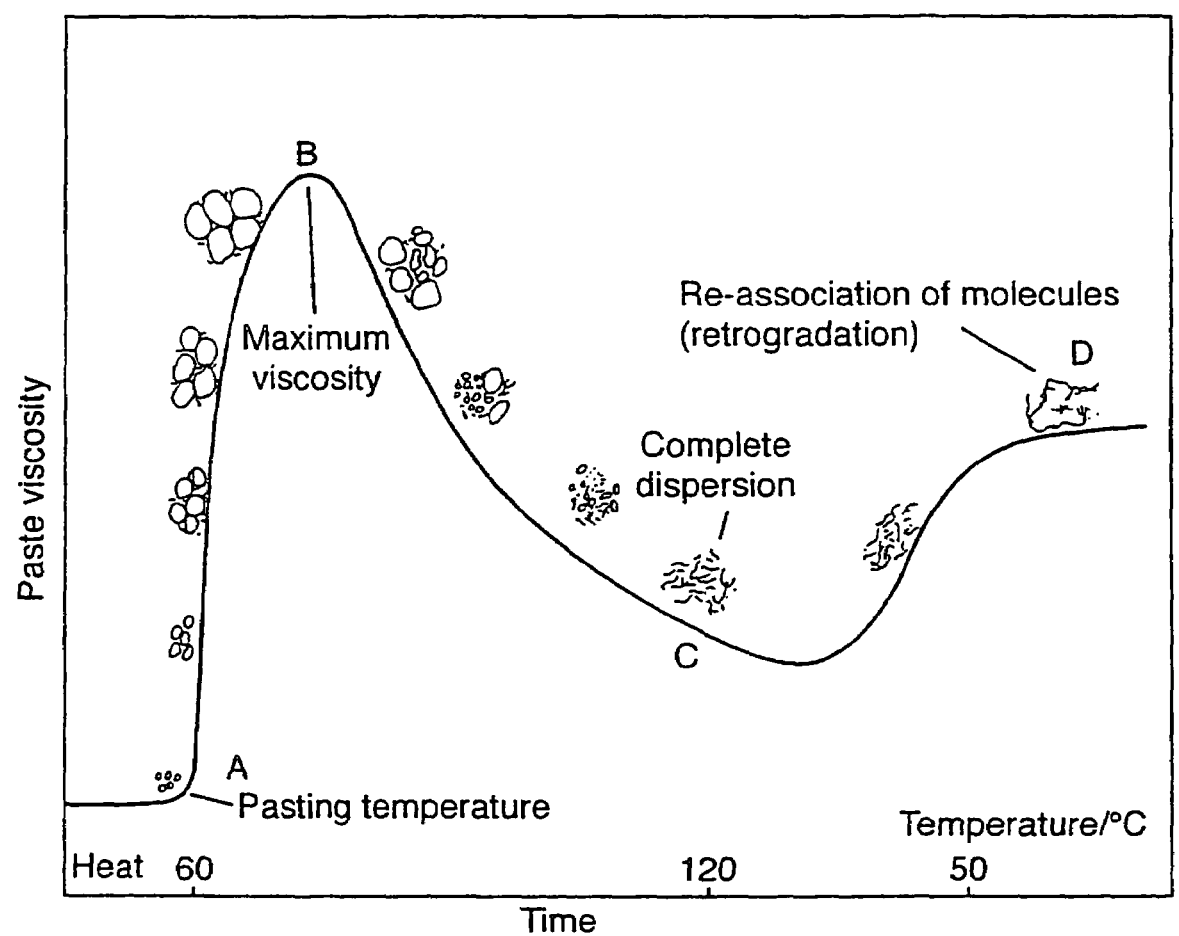
FIG. 1 is a graph of viscosity versus time, showing a viscoamylgraph profile for wheat starch during and after cooking.
Figure 2I:
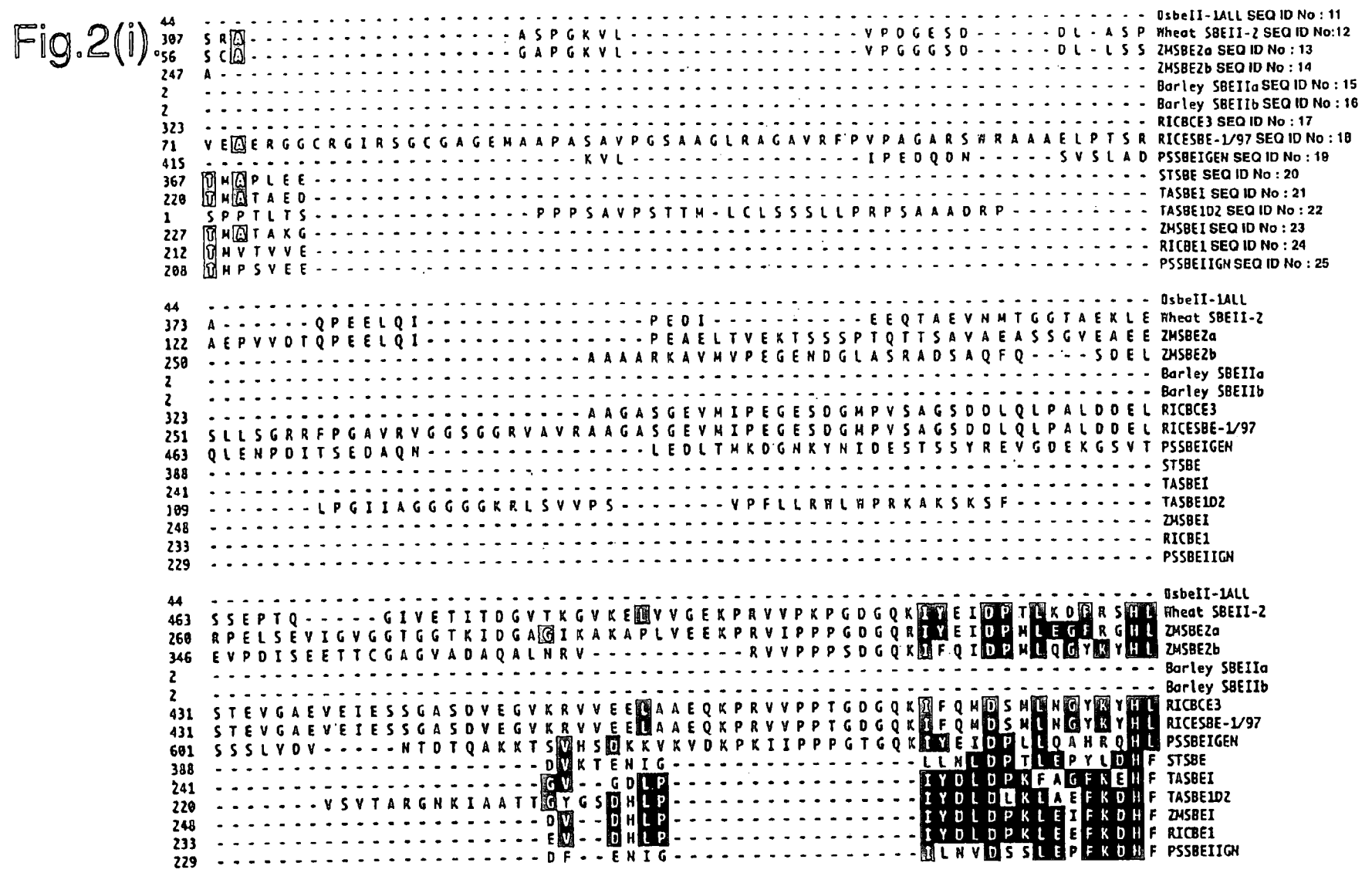
Figure 2II:
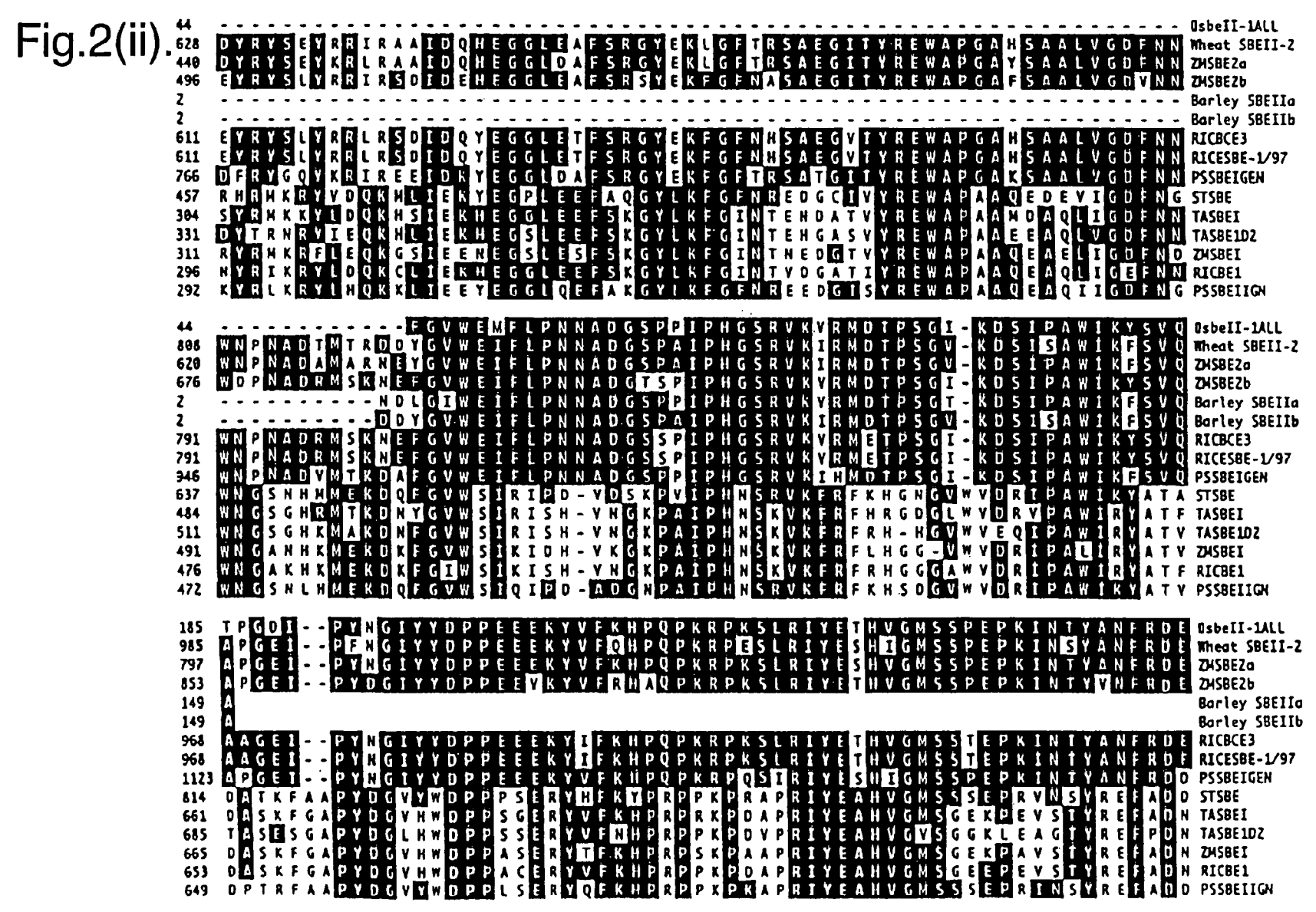
Figure 2III:
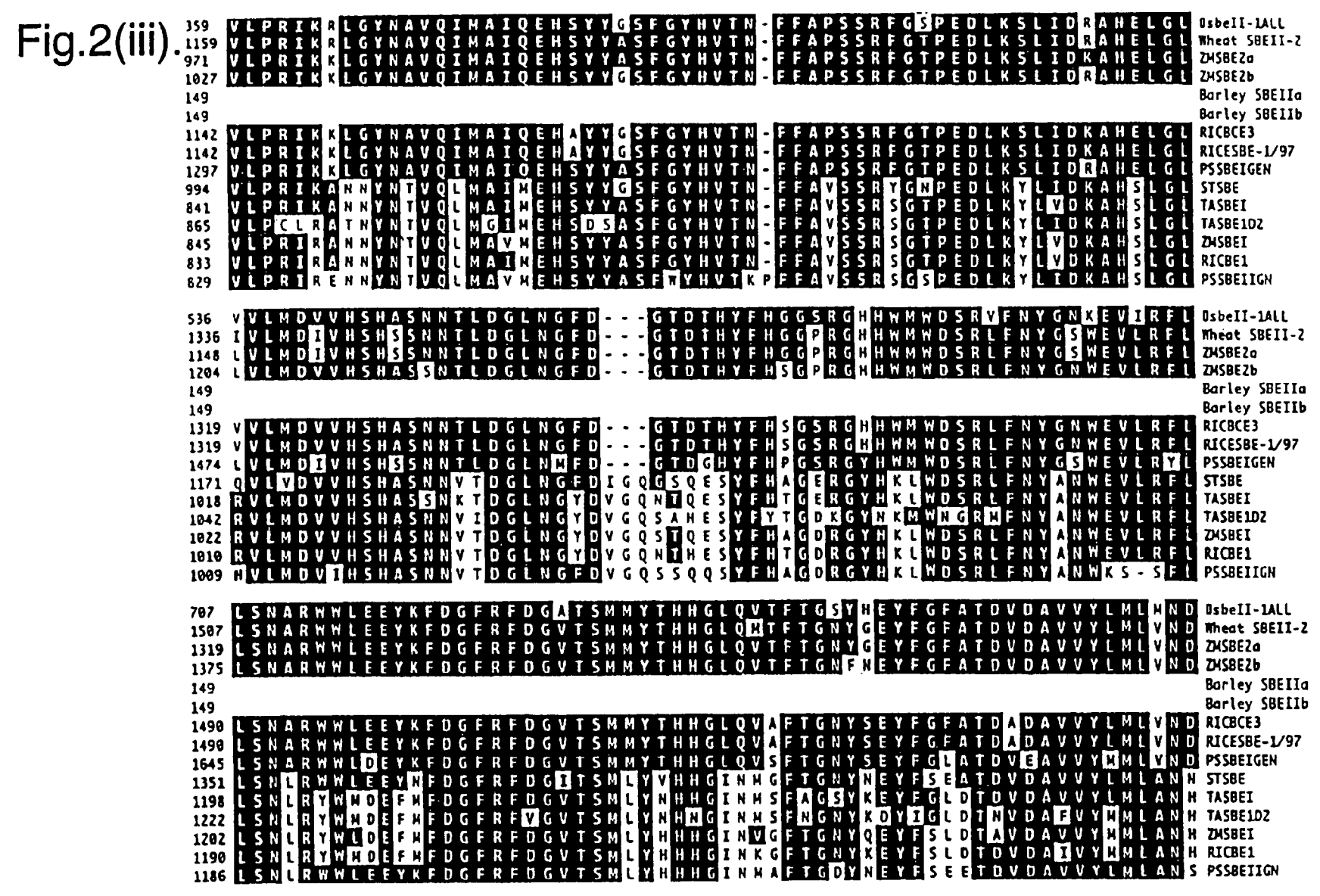
Figure 2IV:
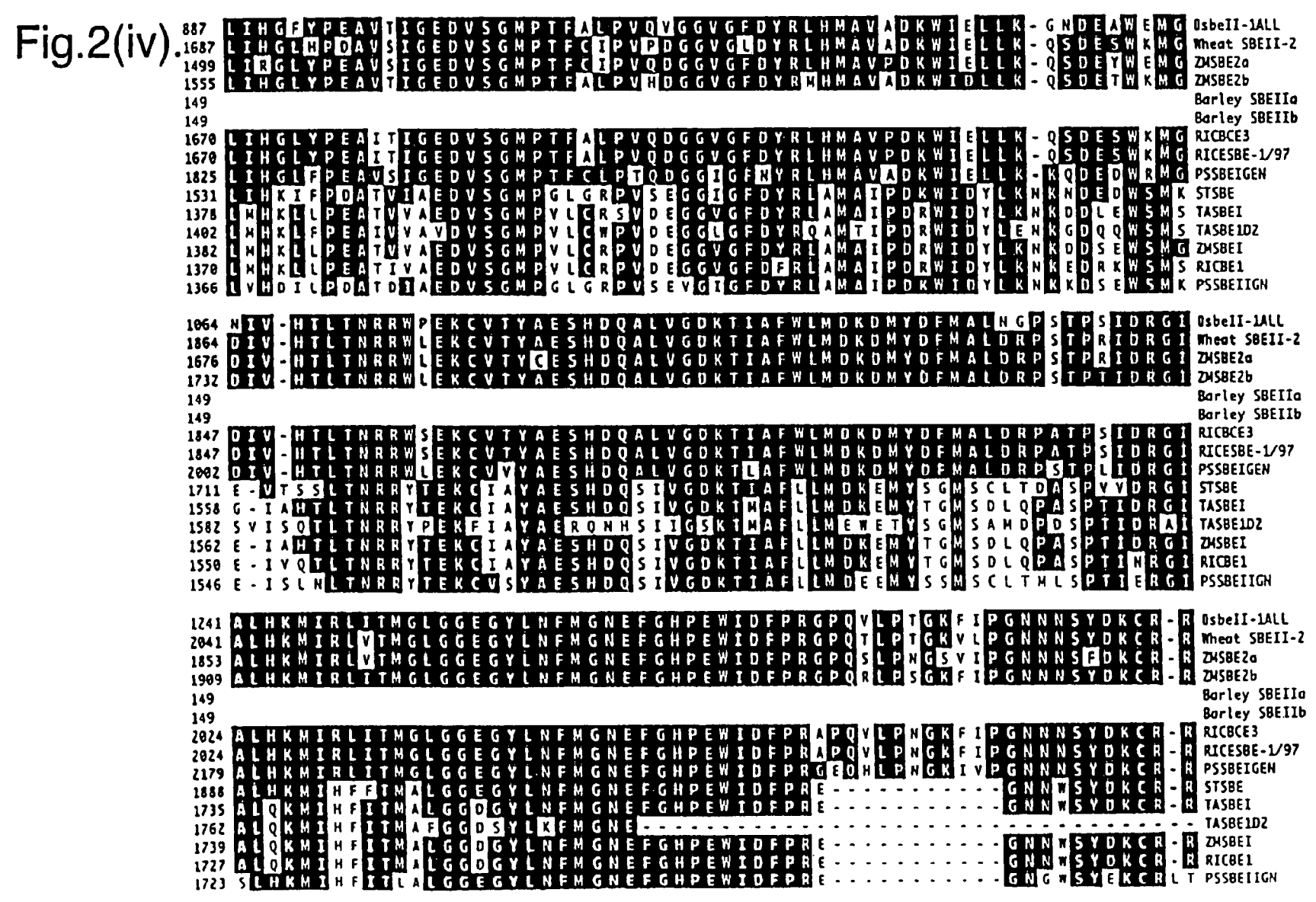
Figure 2V:
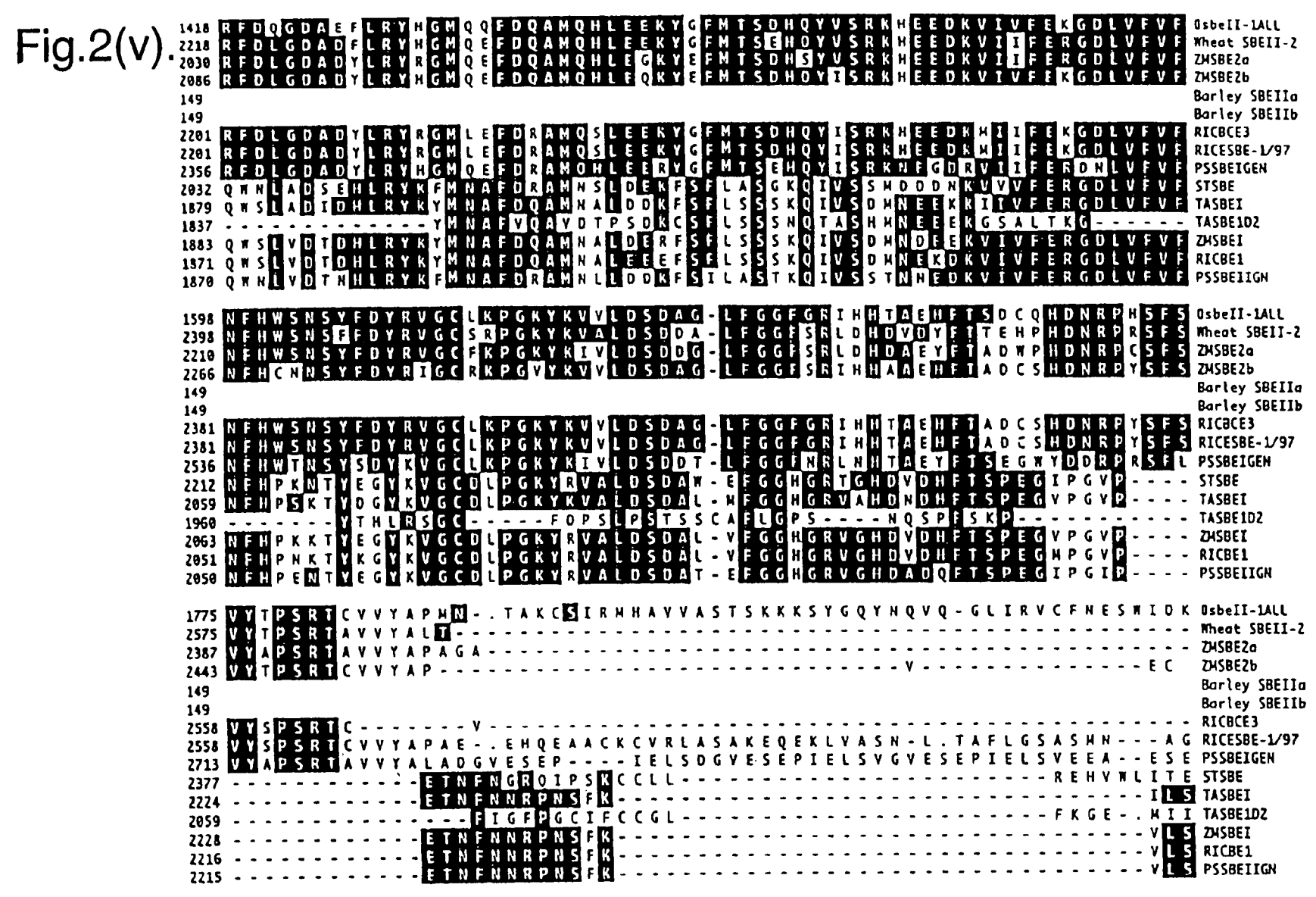
Figure 2VI:
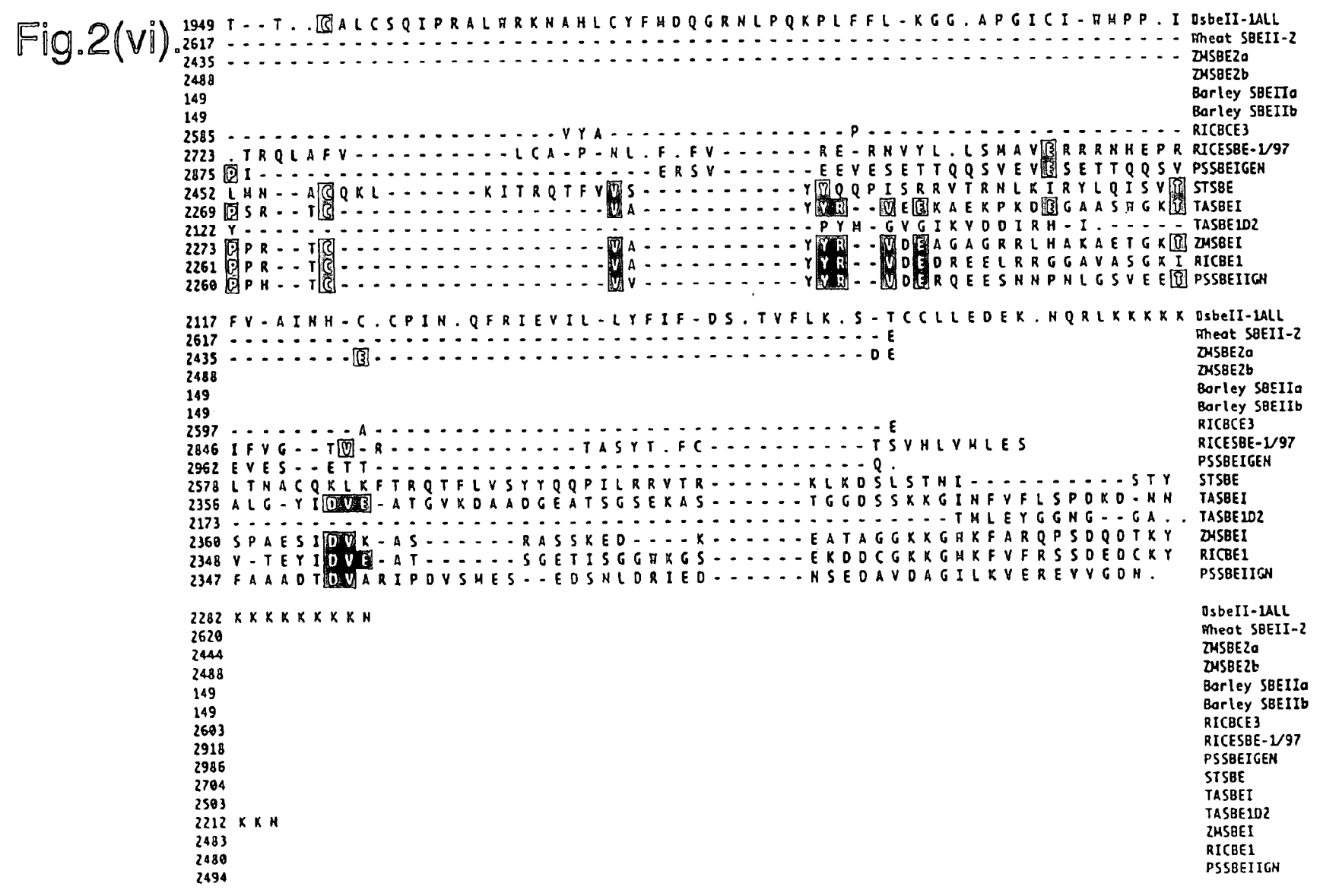
Figure 2A:
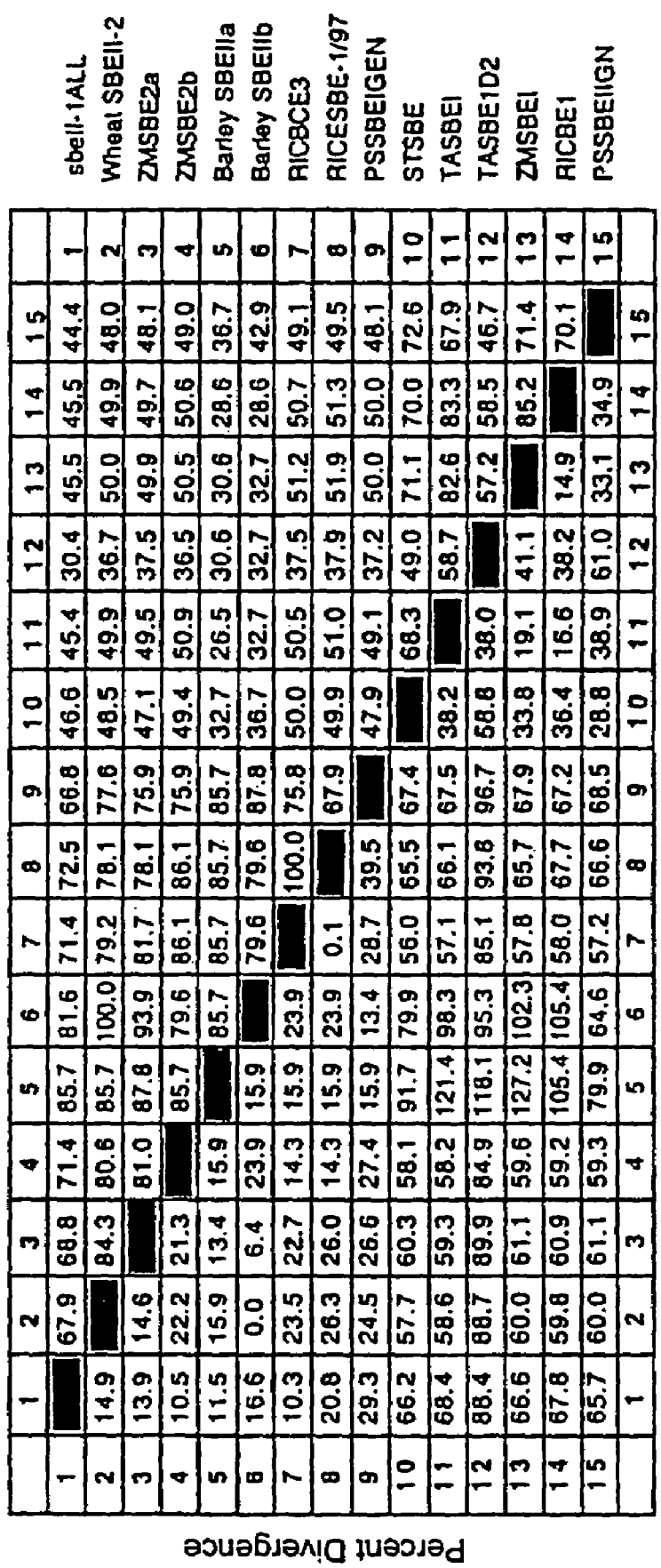
FIG. 2a is a residue weight table showing the percent similarity and percent divergence of the sequences shown in FIG. 2.

The alignment report of FIG. 2, and also FIGS. 3, 4, 8 and 11, was prepared using Clustal method, with PAM 250 residue weight table for amino acid sequences and weighted residue weight table for DNA sequences. Sequence pair distances expressed as % similarity shown in FIGS. 2A and 3A, 4A, 8A and 11A are determined using a 'MEGALIGN' program of DNAStar software, and correspond to sequence homology percentages as specified above.

Alignment of the sequences shown in FIG. 2 reveals several domains which are highly conserved. One such domain, MDKDMYD (SEQ ID No: 36), was almost completely conserved and it was assumed that this domain would also be present in wheat starch branching enzyme genes. This motif was chosen as a target for an oligonucleotide sense primer (SBEA). 3'RACE PCR was carried out on endosperm first strand cDNA using the primers Ro and SBE A.

Two populations of PCR products of approximately 1 kb and 1.2 Kb were cloned into the plasmid vector pT7Blue (Novagen). Plasmid DNA from 36 putative recombinant clones was purified and the insert size estimated by restriction analysis. Fifteen clones harbouring inserts of between approximately 1 Kb and 1.2 Kb were selected for sequencing.

Alignment of the sequence data obtained, using the MEGALIGN program of DNAStar, indicated that the 15 selected clones could be divided on the basis of degrees of homology into two different classes, which we have designated SBEII-1 and SBEII-2. Furthermore, both the SBEII-1 and SBEII-2 classes may each be further subdivided into three sub-classes, based on sequence differences (Table 1). It is thought the subdivision into three sub-classes probably arises because wheat comprises three homoeologous genomes.

TABLE 1

| Class | Sub-Class | Clone Number |
|-------|-----------|--------------|
| SBEII-1 | A | B2, B5, B6, B7, B12 |
| SBEII-1 | B | B10 |
| SBEII-1 | C | A1, A13, B4 |
| SBEII-2 | A | B11 |
| SBEII-2 | B | B1, B9 |
| SBEII-2 | C | A2, C5 |

Figure 3I:
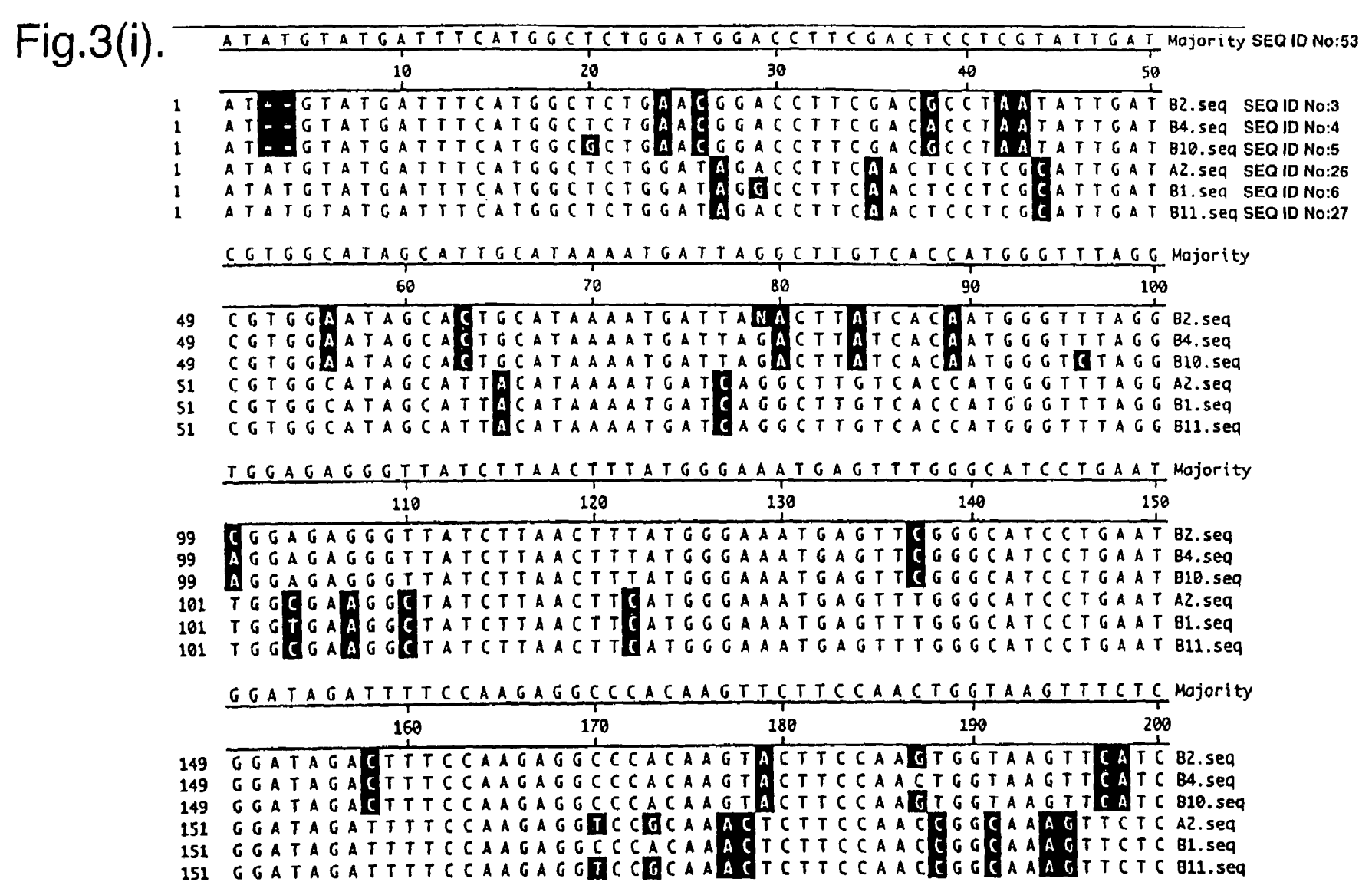
Figure 3II:
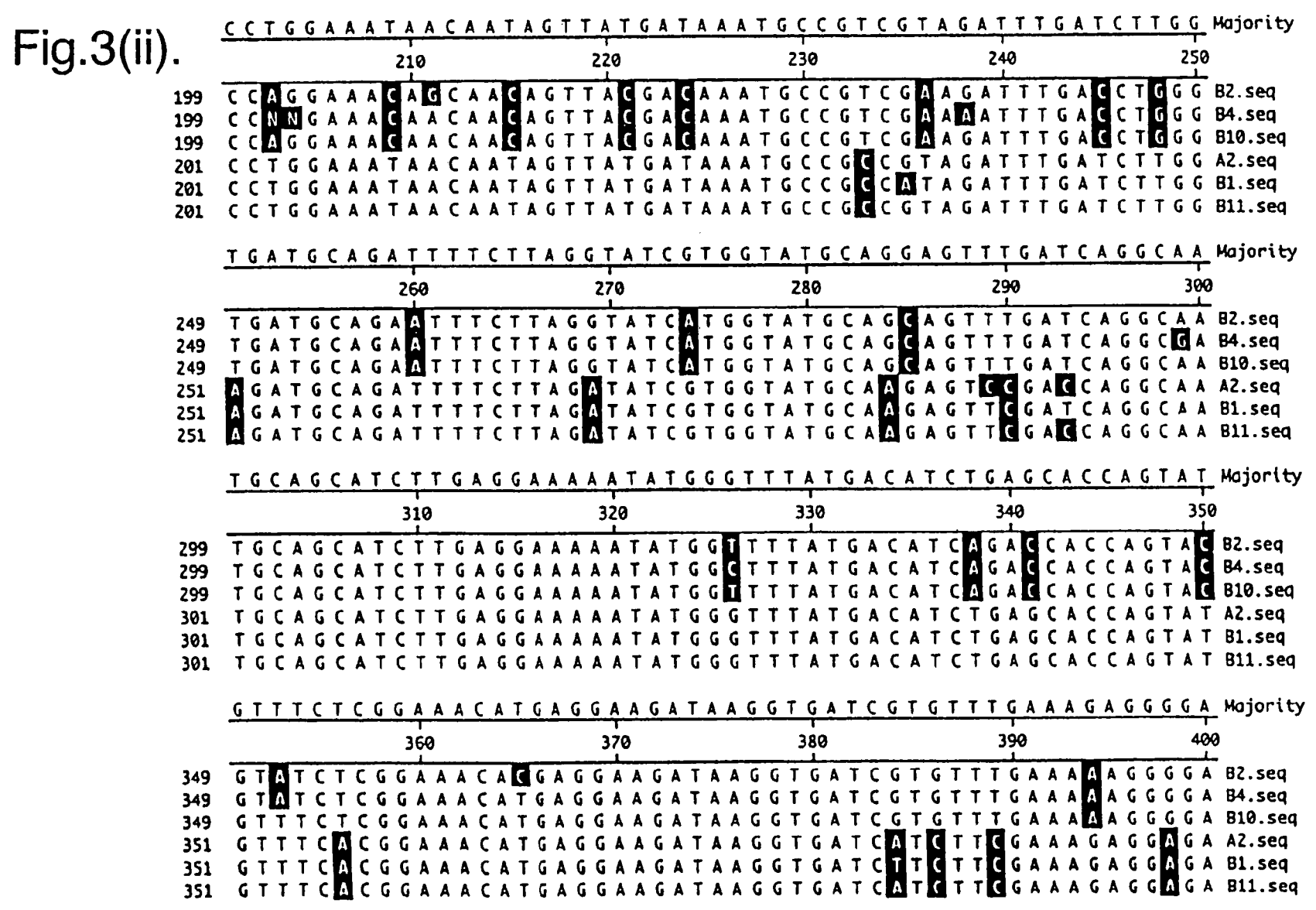
Figure 3III:
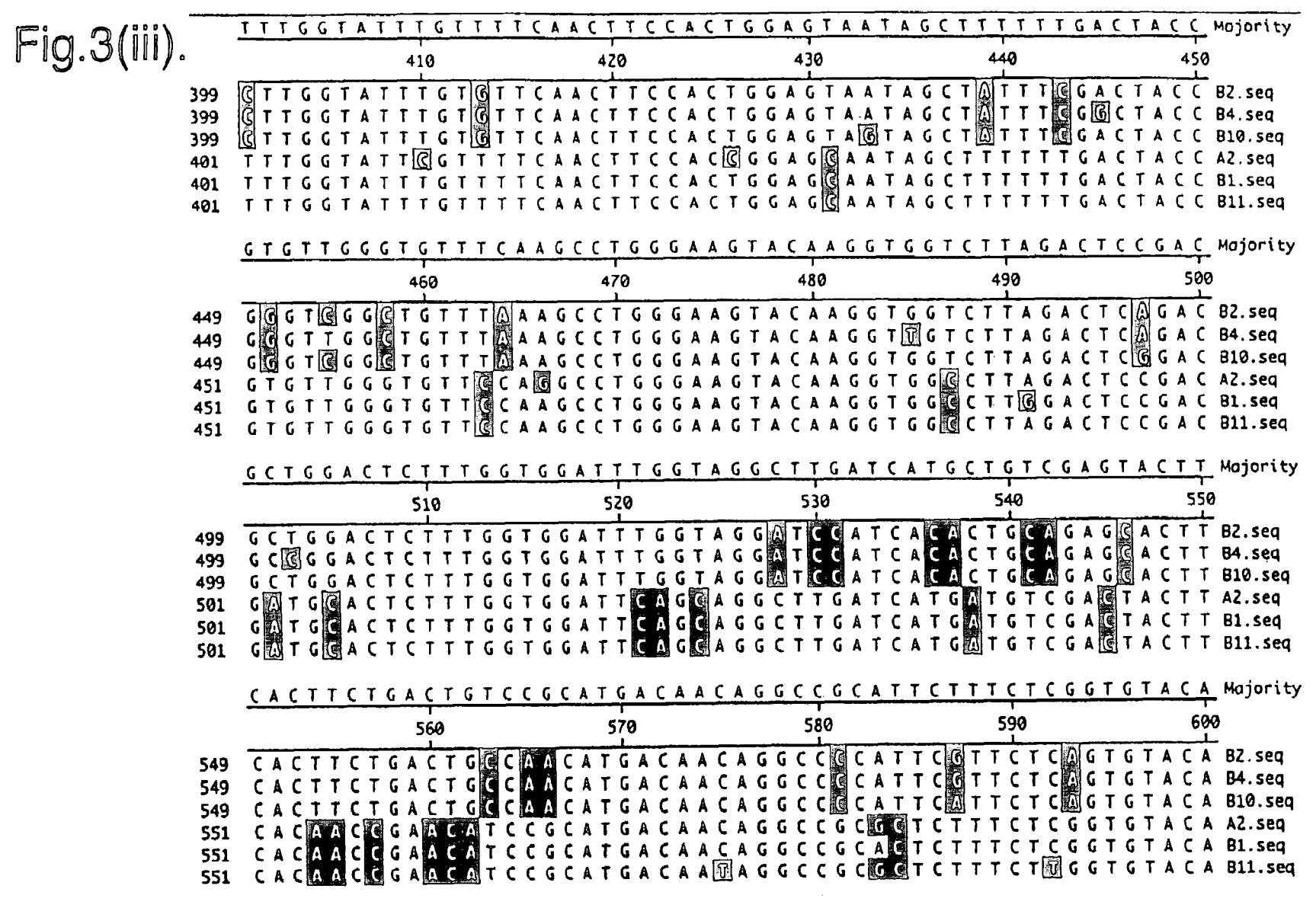
Figure 3IV:
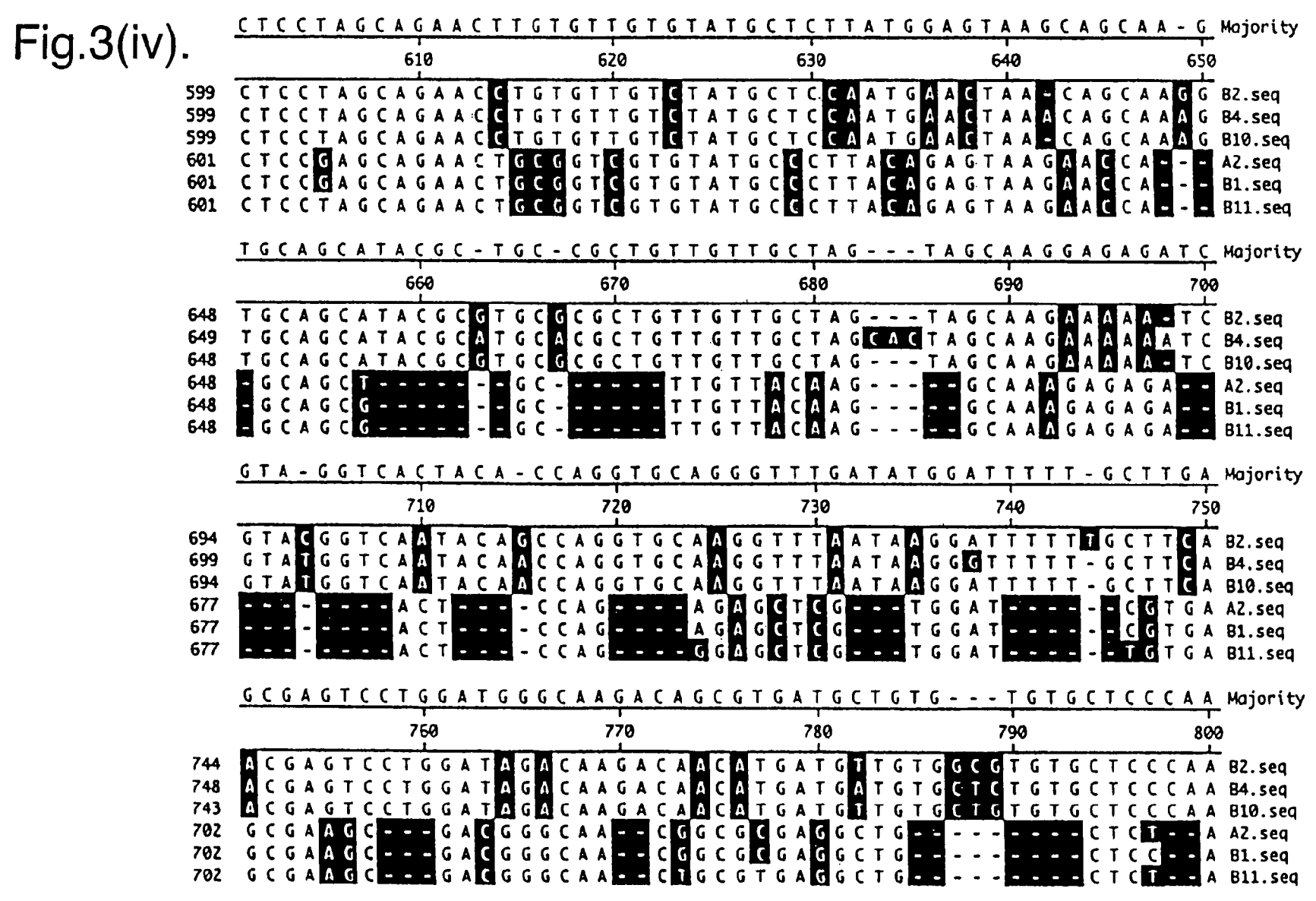
Figure 3V:
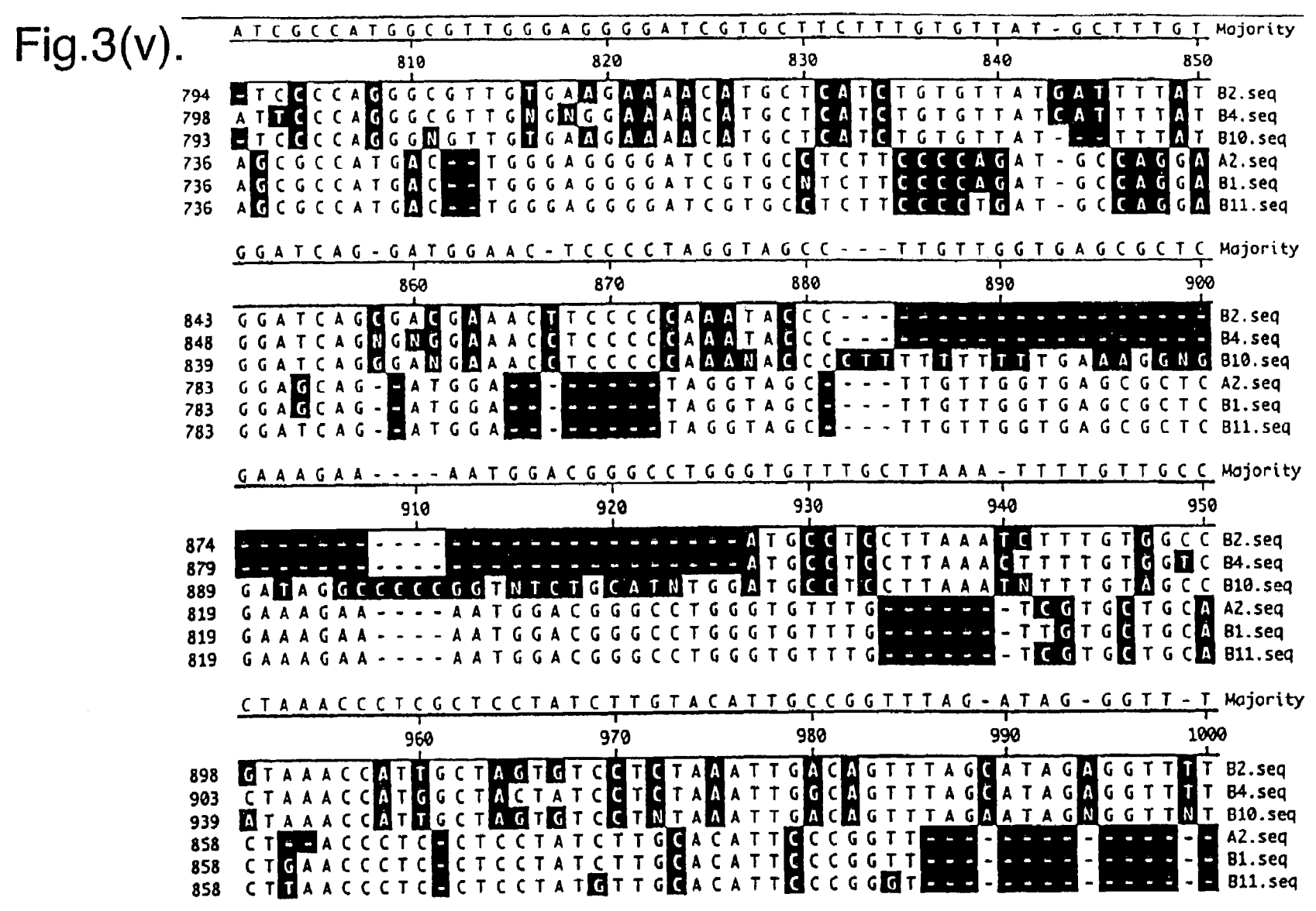
Figure 3VI:
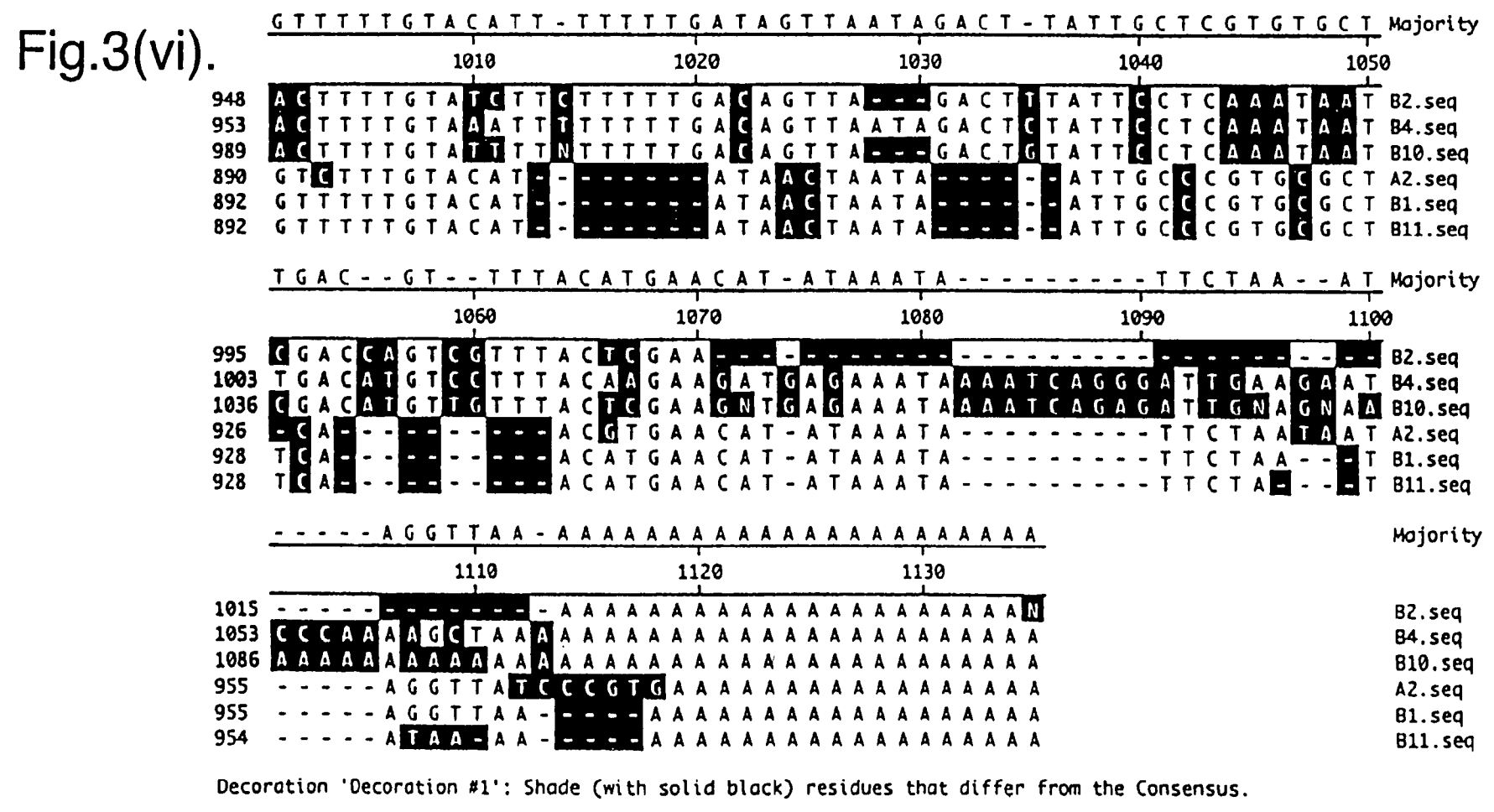

Comparison between sequences within either of the SBEII-1 or SBEII-2 classes showed between 90 and 96.8% similarity. In contrast, sequence similarity between representatives of SBEII-1 and SBEII-2 classes only display between 58.8 and 60.0% homology in the region of comparison (FIGS. 3 and 3a).

Furthermore, we have compared representative sequences from each SBEII-1 and SBEII-2 class with the previously reported wheat SBEII clones, pWBE6 (Mousley, 1994) and the very recently published SBEII (Nair et al., 1997). The results showed that each of the previously isolated SBEII clones are highly homologous (>90%) to our SBEII-2 class (data not shown). Significantly, neither of the previously reported wheat sequence's showed high homology to our SBEII-1 sequence. The isolation and characterisation of three forms of SBEII-1 (SBEII-1, sub-classes A, B & C) is novel. The SBEII-2 sub-class B is also novel, sub-classes A and C corresponding to the sequences previously disclosed by Mousley (1994) and Nair et al (1997) respectively.

Alignment of the predicted amino acid sequences from representative clones, B6 and B11 of the wheat SBEII-1 and SBEII-2 sequences (respectively) against the corresponding regions of the maize SBEIIa and SBEIIb amino acid sequences (FIGS. 4 and 4a) indicate that the wheat SBEII-1 sequence (clone B6) is more similar to the maize SBEIIb sequence (88.7% similarity) than to the wheat SBEII-2 sequence and the maize SBEIIa sequence (82.2% & 82.6% similarity respectively) and similarly that the wheat SBEII-2 sequence is more similar to the maize SBEIIa sequence (86.9% similarity) than to the wheat SBEII-1 and maize SBEIIb sequences (82.2% and 81.7% similarity respectively). We thus hypothesise that the wheat SBEII-1 is phylogenetically more related to the maize SBEIIb and that the wheat SBEII-2 is phylogenetically related to the maize SBEIIa sequences and that the corresponding wheat and maize sequences are likely to exhibit similar functional properties.

Figure 6:
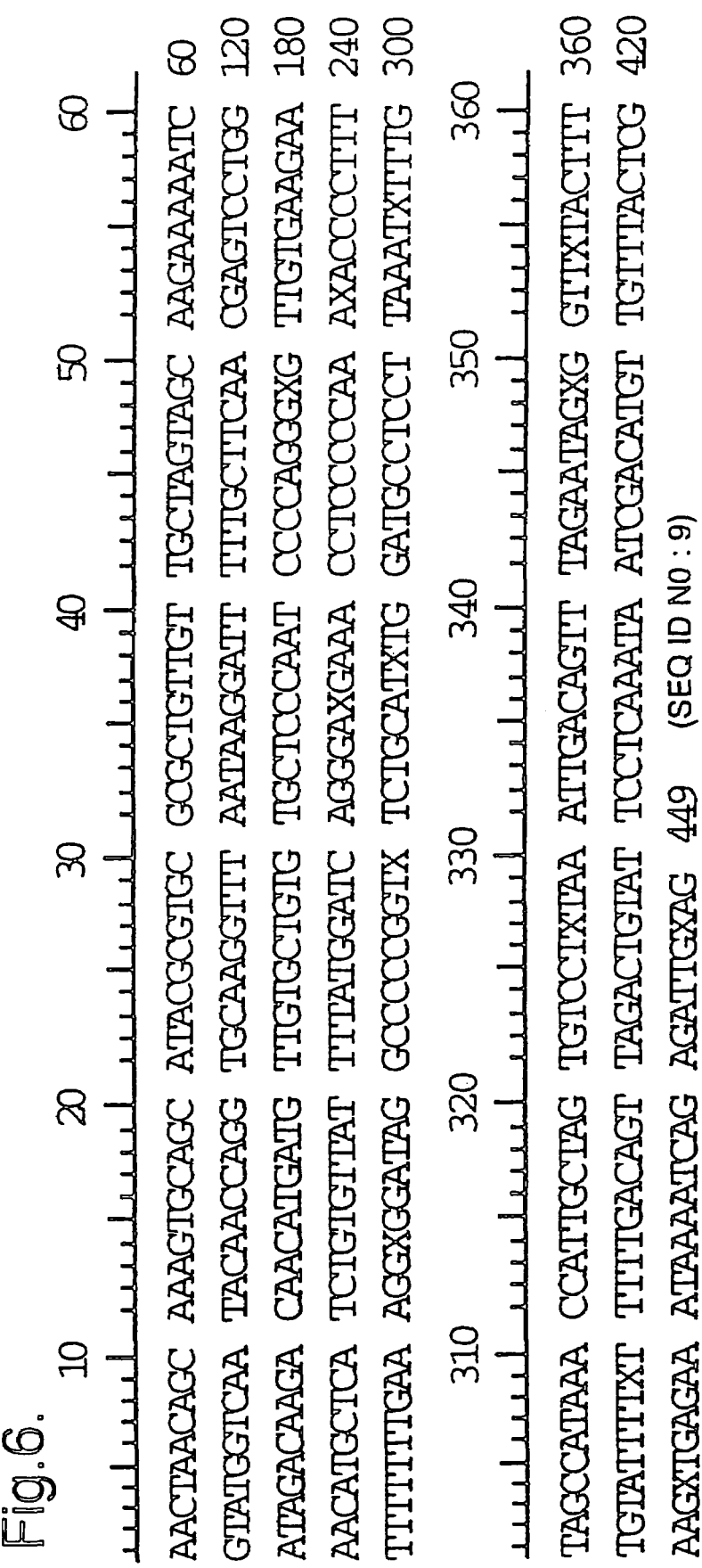
FIG. 6 shows the 3' untranslated DNA sequence of clone B10 (SEQ ID No: 9) (wheat SBEII-1, sub-class B)
Figure 8I:
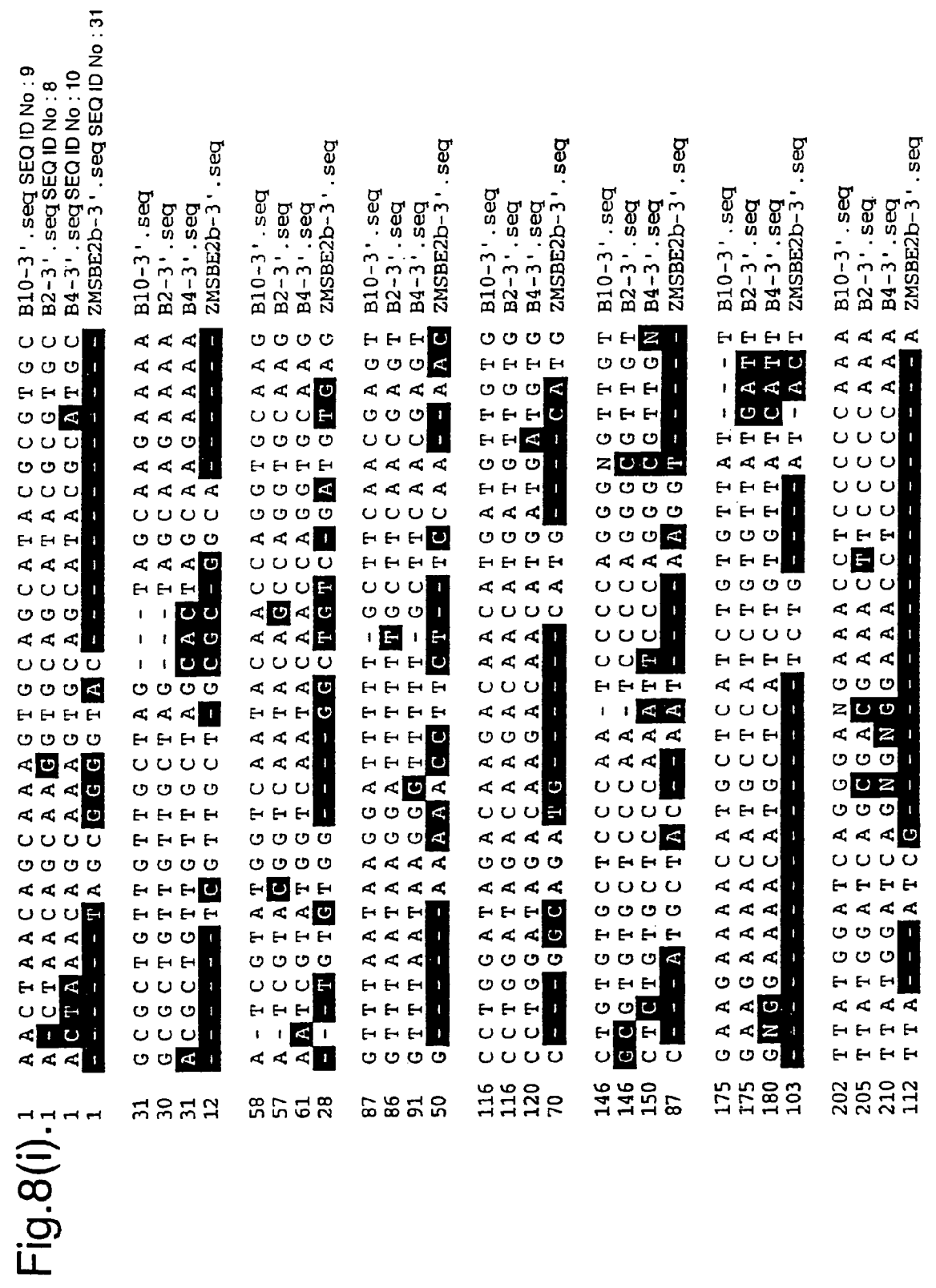
Figure 8II:
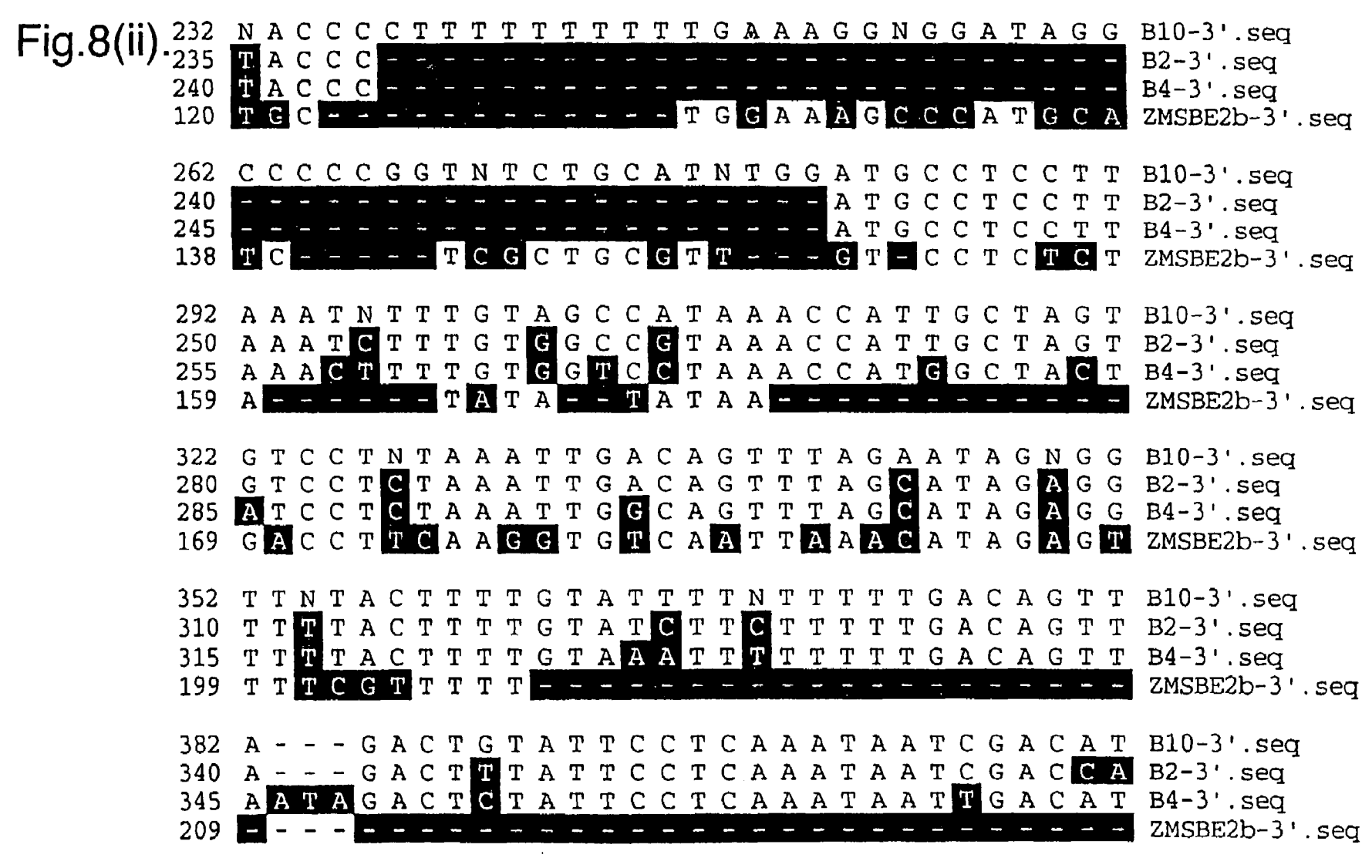

While the coding sequences of clones B2, B10 and B4 have strong sequence homology to the maize SBEIIb gene, there is much greater divergence in the 3' untranslated parts of the sequences. FIGS. 5, 6 and 7 show the 3' untranslated sequences of clones B2, B10 and B4, respectively, and FIG. 8 compares these sequences with the corresponding sequence of maize SBEIIb.

Considering matters in more detail, experimental details were as follows.

Plant Material

*Triticum aestivum* cultivar Rialto was grown in a glass house under supplementary lighting and temperature control to maintain a 16 hour day-length at 18+/−1° C.

Recombinant DNA Manipulations and Sequencing

Standard procedures were performed essentially according to Sambrook et al., (1989). DNA sequencing was performed on an ABI automated sequencer and sequences analysed using DNASTAR software for Macintosh.

RNA Isolation for cDNA Cloning

RNA was extracted from *Triticum aesrivum* cultivar Rialto endosperm, using a Purescript RNA isolation kit (Flowgen) essentially according to the manufacturers recommendations. Briefly, endosperm tissue was frozen in liquid nitrogen and ground, for 2 min, to a fine powder using a dismembrenator (Braun Biotech International). The ground tissue was stored in liquid nitrogen prior to extraction. Approx. 100 mg of ground tissue was transferred to a 1.5 ml microcentrifuge tube and 1.2 ml of 'Lysis buffer' was added to the tissue before mixing by inversion and placing on ice for 10 minutes. Protein and DNA were precipitated from the cell lysate by adding 0.4 ml of 'Protein-DNA Precipitation Solution' and mixing by inversion before centrifuging at 13,000×g at 4° C. for 20 minutes. The supernatant was divided between two fresh 1.5 ml tubes each containing 600 µl of iso-propanol. The RNA precipitate was pelleted by centrifugation at 13,000×g at 4° C. for 10 minutes, the supernatant was discarded and the pellets washed with 70% ethanol by inverting the tube several times. The ethanol was discarded and the pellet air dried for 15–20 minutes before the RNA was resuspended in 7.5 ml of 'RNA Hydration Solution'.

Preparation of Wheat Endosperm cDNA Pool

Wheat endosperm cDNA pool was prepared from total RNA, extracted as described above, using Superscript™ reverse transcriptase (Life Technologies) essentially according to manufacturers instructions. Briefly, five microgrammes of RNA, 10 pMol RoRidT17 [AAGGATCCGTCGACATCGATAATACGACTCACTATAGGGA(T17)] (SEQ ID No: 37) and sterile distilled water to a reaction volume of 12 µl, in a 500 µl microcentrifuge tube, was heated to 70° C. for 10 minutes before being quick chilled on ice. The contents of the tube were collected by brief centrifugation before adding 4 µl 5×First Strand Buffer, 2 µl 0.1M DTT and 1 µl 10 mM dNTPs and, after mixing, incubating at 42° C. for 2 min. 1 µl of Superscript™ was added and, after mixing, incubation continued for 1 hour. The reaction was inactivated by heating to 70° C. for 15 min. 150 µl of $T_{10}E_1$ was added to the reaction mix and the resulting cDNA pool was used as a template for amplification in PCR.

PCR Amplification of SBEII Sequences From Endosperm cDNA Pool

SBEII sequences were amplified from the endosperm cDNA pool using primers Ro [AAGGATCCGTCGACATC] (SEQ ID No: 38), which is complementary to the Ro region of the RoRidT17 primer used to synthesise the cDNA pool, and the SBEII specific primer, SBEA [ATGGACAAGGATATGTATGA] (SEQ ID No: 39). SBEA was designed to be homologous to the MDKDMYD (SEQ ID No: 36) motif which is situated approx. 1 kb from the 3' end of the mature peptide coding sequence. PCR was carried out in a 50 µl reaction, comprising 5 µl of the CDNA pool, 25 pmol Ro, 50 pmol SBEA, 5 µl 5× Taq buffer, 4 µl 25 mM $Mg^{2+}$, 0.5 µl 20 mM dNTPs, and 1.25 u Taq polymerase. All of the reaction components were mixed, except for the Taq polymerase, before being pre-heated to 94° C. for 7 min and then cooled to 75° C. for 5 min. Whilst the reaction mixtures were held at 75° C. the Taq polymerase was added and, after mixing well, the reactions were thermocycled at (94° C.-30 sec, 50° C.-30 sec, 72° C.-1 min)×30 cycles, followed by a final 10 min extension step at 72° C.

PCR products were purified by phenol/chloroform and chloroform extraction before ligation with pT7 Blue (Novagen) according to manufacturers recommendations. Putative SBE clones were initially characterised by standard plasmid DNA purification methods and restriction digestion. Representative clones harbouring a range of different sized inserts were selected for sequencing.

Chromosomal Location of SBE Genes in Wheat

The Chinese Spring wheat nullisomic-tetrasomic lines as described in Sears (1966) were used for assignment of the SBE sequences chromosome locations. Ditelosomic lines (Sears, 1966) were used to determine the chromosome arm location. The Betzes barley ditelosomic addition lines in wheat are described in Islam (1983).

Figure 9A:
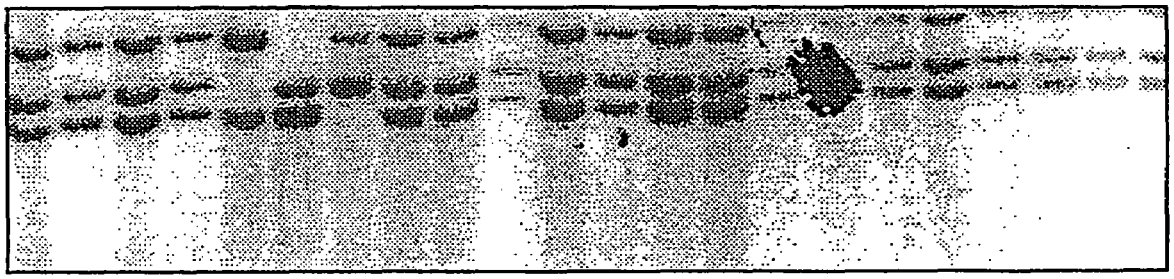
FIGS. 9a and 9b show hybridisation of clone B1 (SBEII-2) and clone B2 (SBEII-1), respectively, to HindIII-digested genomic DNA of Chinese Spring wheat nullisomic-tetrasomic lines.
Figure 9B:
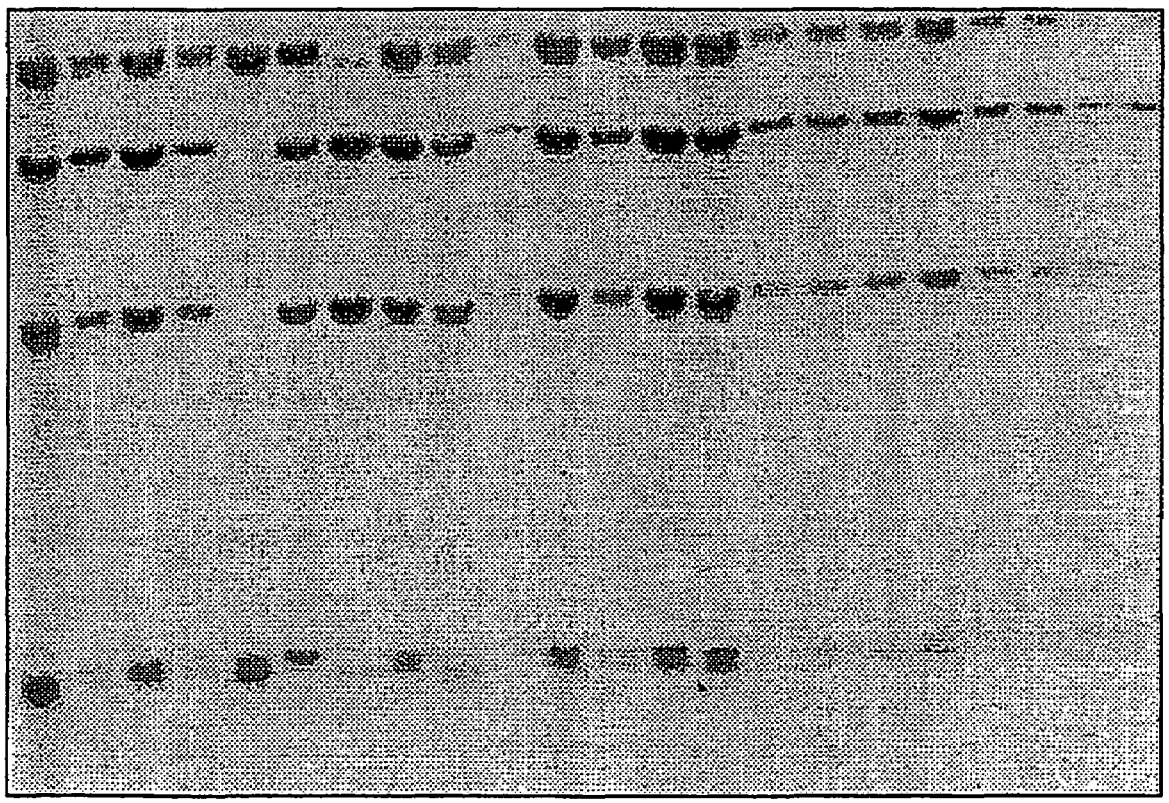

The chromosomal location of the two families of SBEII sequences (SBEII-1, SBEII-2) was determined by probing wheat nulli-tetra and ditelosomic stock lines with gel-purified inserts of the various clones. FIG. 9a shows the hybridisation obtained with an SBEII-2 (clone B1) probe on HindIII digested DNA. The euploid Chinese Spring gives 3 bands, one of which is missing in turn in the lines nullisomic for chromosomes 2A, 2B and 2D. The same blot was re-probed with a SBEII-1 specific probe (clone B2). This yields an entirely different hybridisation profile (FIG. 9b), demonstrating the specificity of the probe used. Again bands are missing in each of the lines nullisomic for 2A, 2B and 2D. the same banding pattern was observed using the SBEII-1 clones B2 and B4. Thus the SBEII sub-family 1 and 2 gene sequences lie on the wheat group 2 set of homeologous chromosomes.

Ditelosomic addition lines were used to identify the arm location of these genes (data not shown). This revealed that the SBEII-1 and SBEII-2 sequences are both located on the long arms of the homeologous group 2 chromosomes of wheat.

Barley addition lines were used to determine whether homologous sequences are present in barley. These showed that sequences homologous to the wheat SBEII-1 and SBEII-2 sequences are located on the long arms of barley chromosome 2H.

RNA Isolation and Northern Blotting

Wheat grains were harvested at appropriate intervals and frozen in liquid Nitrogen before grinding to a fine powder using either a Braun Mikrodismembrator™ or a pestle and mortar. Total RNA was isolated using the RNAqueous™

(Ambion Inc) Kit according to the manufacturers instructions, or with the following method. Frozen powdered grain was mixed with a 10× volume of 0.2M Tris-HCl pH9, 0.4M NaCl, 25 mM EDTA, 1% SDS, 1% PVPP, 0.25% Antifoam A, and 0.1M DTT. This mixture was extracted twice with an equal volume of phenol/chloroform/isoamyl alcohol (25:24:1), the nucleic acids precipitated from the aqueous phase by the addition of 0.8 volumes of isopropanol, and the resulting pellet dissolved in $H_2O$. The RNA was then selectively precipitated by the addition of 1 volume of 4M LiCl, incubated at 4° C. overnight, and the resulting pellet dissolved in sterile distilled $H_2O$. 15 μg of total RNA was electrophoresed on a 1% agarose, 2.21M Formaldehyde, 40 mM MOPS pH7.0, 10 mM sodium acetate, 1 mM EDTA gel, in a 40 mM MOPS pH7, 10 mM sodium acetate, 1 mM EDTA running buffer at 1 V/cm overnight. Gels were placed in a 50 ng/ml solution of Ethidium Bromide in water for 30 minutes, de-stained in water for 2 hours, and visualised and photographs under UV light. The gels were then washed briefly in sterile distilled $H_2O$, then blotted onto HyBond N+™ (Amersham International), according to standard protocols (Sambrook et al, 1989) overnight. Blots were then dismantled and airdried before UV fixing at 312 nm for 2 minutes.

Probe Isolation and Purification

5–10 μg of the plasmids pUN1 and pSR98-29 were digested with Sst1 (Life Technologies Ltd) according to the manufacturers instructions, to release fragments of approximately 0.8 kb (NptII) and 1 kb (SBEII-1) respectively. 5–10 μg of the plasmid pVT96-54 was digested with BamH1 to release a SBEII-2 fragment of approximately 1.2 kb. Digests were electrophoresed on 1% low melting point agarose gels. The gene specific fragments were excised and the DNA purified using a Wizard™ Gel Purification Kit (Promega).

Probe Labelling and Hybridization 25 ng of the appropriate probe (Maize Waxy promoter, NptII, Wheat SBEII-1 or Wheat SBEII-2 fragments) were radiolabelled using the Rediprime 11™ system (Amersham International) using $\alpha^{32}$PdCTP (Amersham International) according to manufacturers instructions. Blots were hybridized overnight at 65° C. in 0.6M NaCl, 20 mM Pipes, 4 mM $Na_2EDTA2H_2O$, 0.2% gelatin, 0.2% Ficoll 400, 0.2% PVP-360, 10 mM $Na_4P_2O_710H_2O$, 0.8% SDS, 0.5 mg/ml denatured salmon sperm DNA. Post hybridization washes were carried out in 30 mM NaCl, 2 Mm $NaH_2PO_4.2H_2O$, 0.2 mM $Na_2EDTA.2H_2O$, 0.1% SDS at room temperature for 7 minutes, then 65° C. for 10 minutes. Filters were exposed to Kodak BioMax MR™ (Amersham International) film at −70° C. Blots were stripped by washing in 15 mM NaCl, 1 mM $NaH_2PO_4.2H_2O$, 0.1 mM EDTA at 90° C. for 10 minutes, or until no counts above background remained.

Extension of the SBEII-1 3' Sequence Towards the 5' End of the Mature Peptide

We have exploited the sequence divergence between our wheat SBEII-1 and SBEII-2 sequences to design the SBEII-1 specific 3' primer, Sb4. This primer was used in conjunction with an SBEII specific 5' primer to extend the novel SBEII-1 sequence using a PCR-based approach.

Figure 11I:
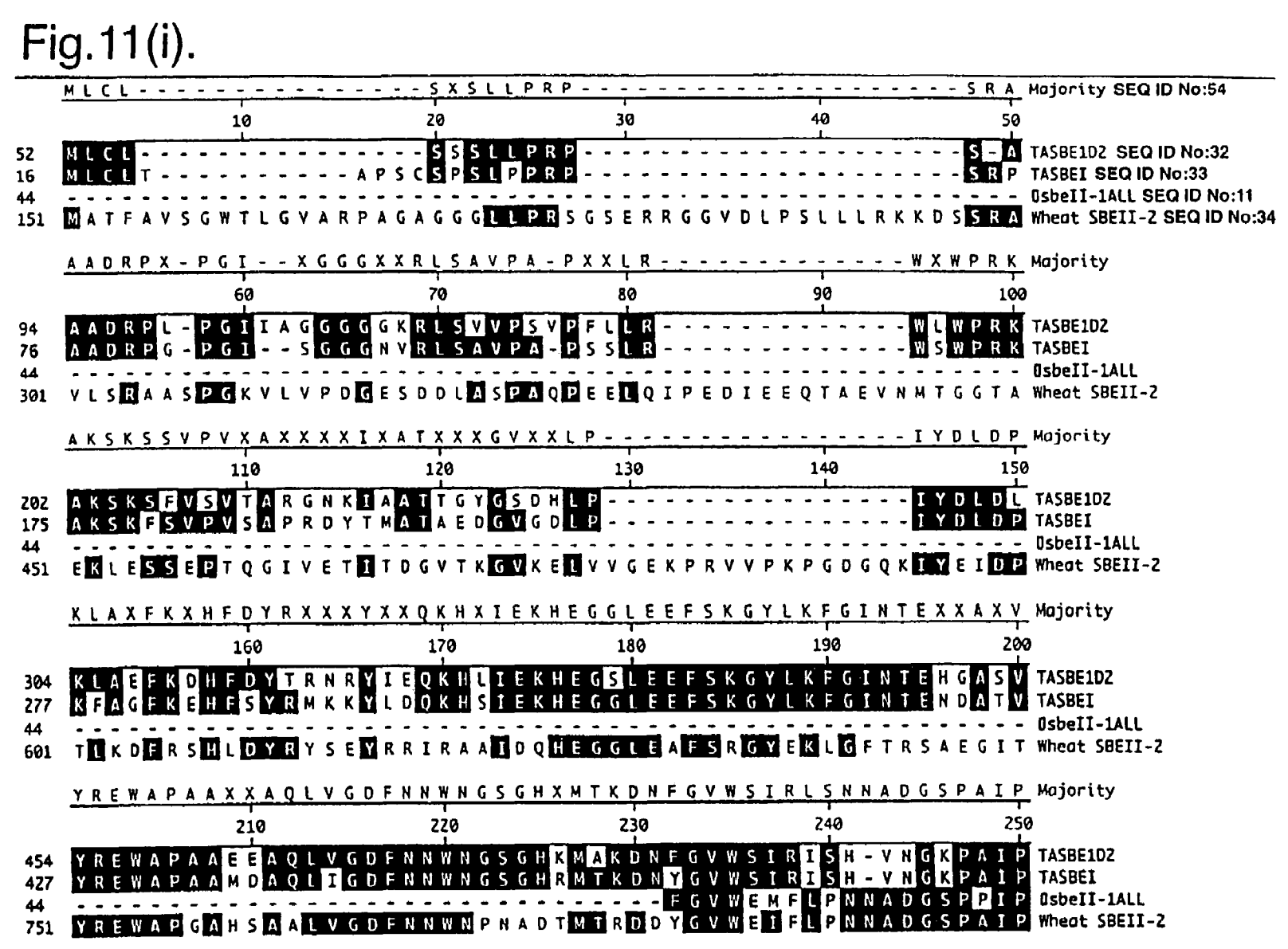
Figure 11II:
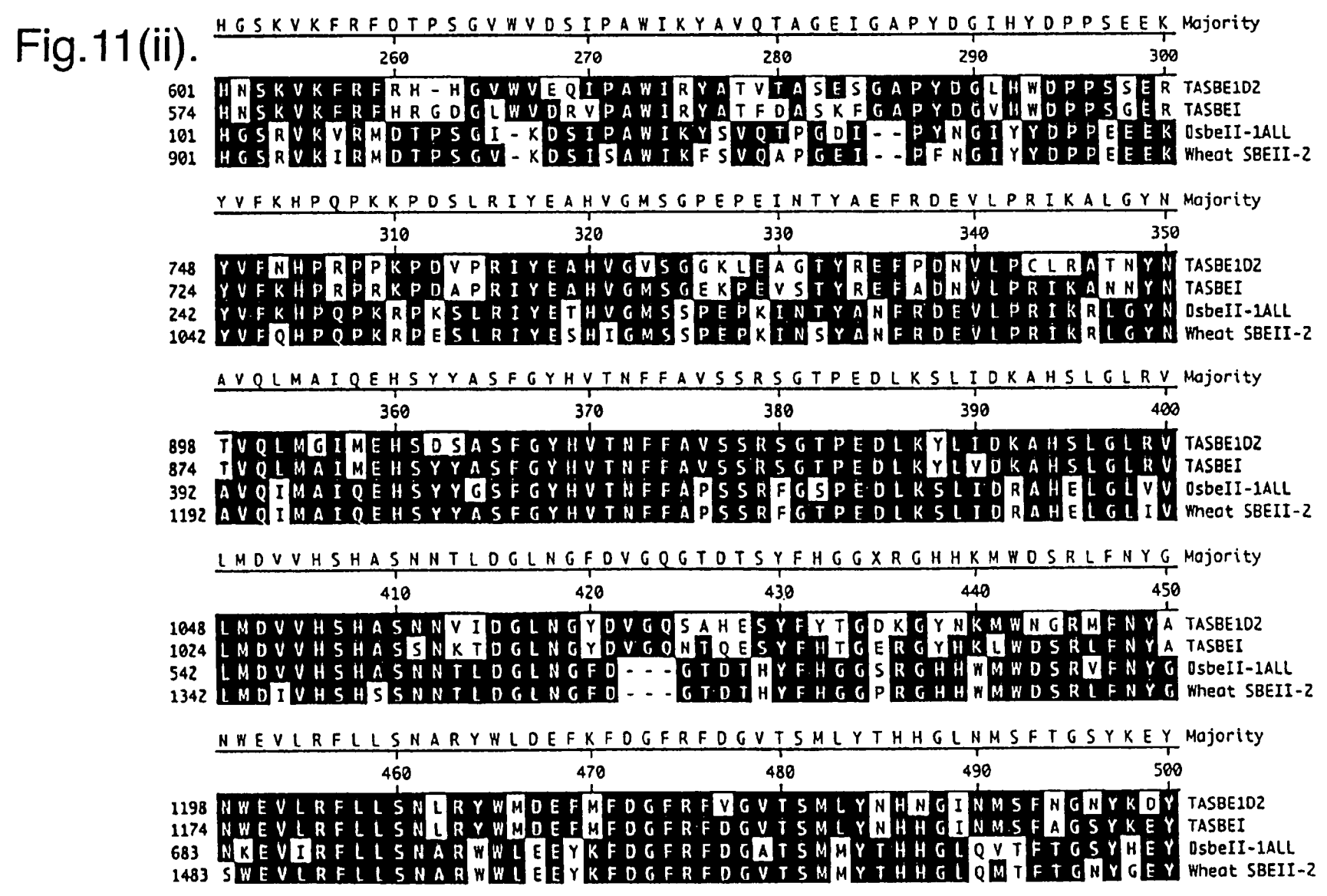
Figure 11III:
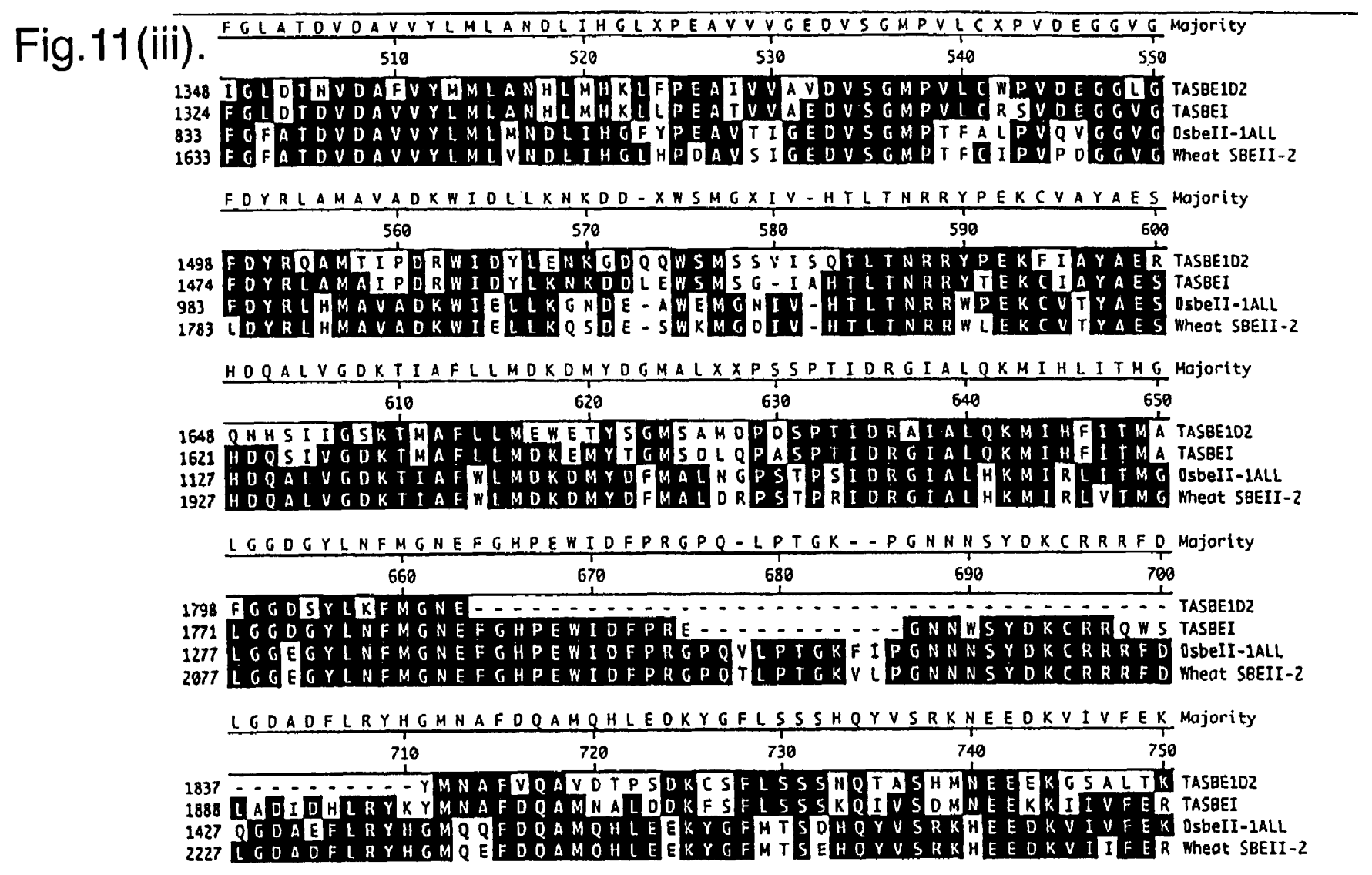
Figure 11IV:
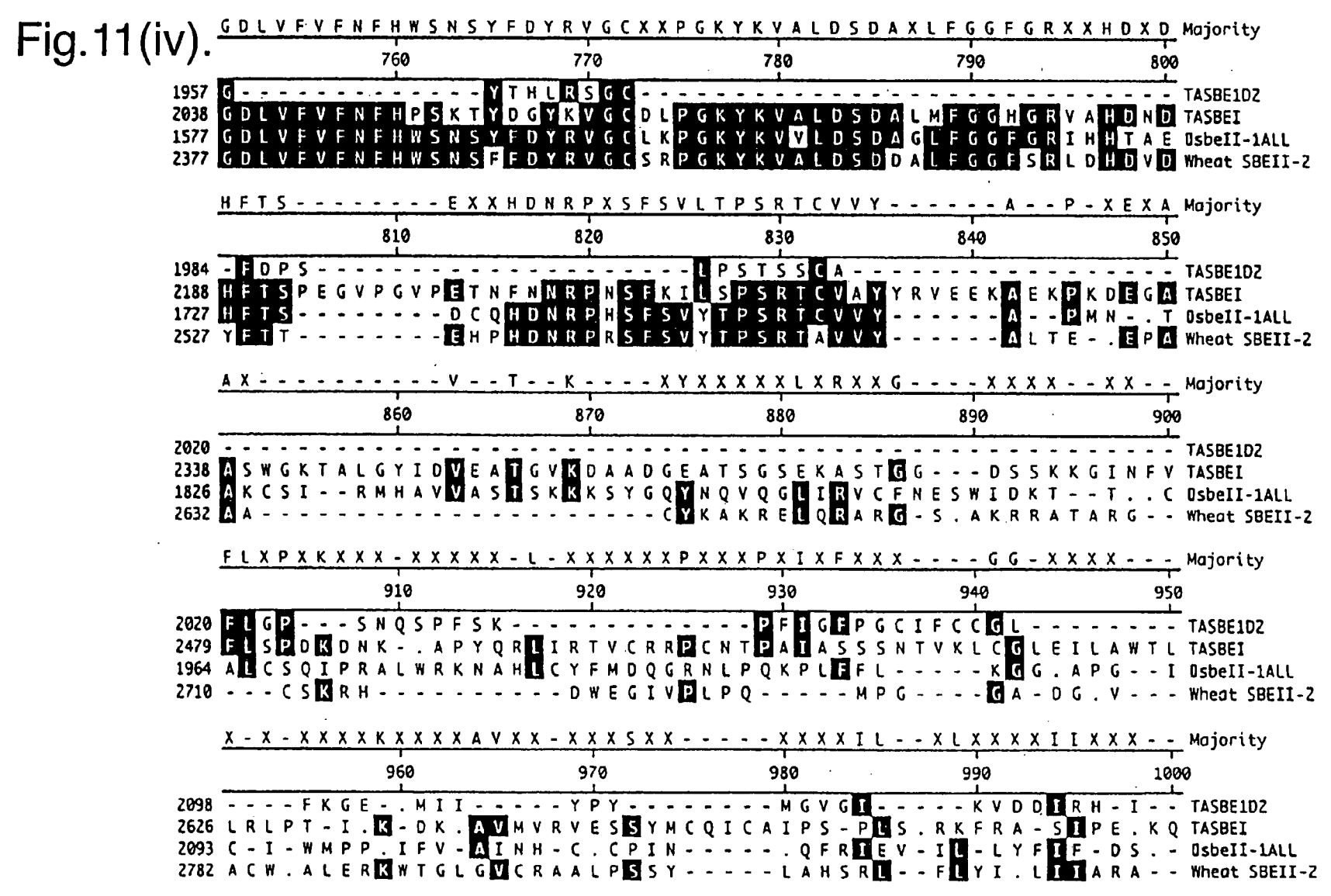

To extend the SBEII-1 3' sequence towards the 5' end of the mature peptide, a second conserved domain was identified and an oligonucleotide sense primer, AGSBEI, designed. PCR amplification from the endosperm first strand cDNA pool was carried out using the AGSBEI-Sb4 primer pair. Separation of the amplification products by electrophoresis through a 1% (w/v) agarose gel (data not shown) showed that the reaction yielded a distinct band of approx. 2.2 kb. The approx 2.2 kb amplification products were excised from the gel, ligated with PT7Blue and transformed into competent Novablue E. coli cells. Following overnight culture, nine putative recombinant clones were selected for further analysis. Screening of each of the selected clones using vector specific primers indicated that clones 5A1, 5A2, 5A5 and 5A9 harboured inserts of the predicted size. Of these clone 5A1 (which falls in sub-class C) was selected for sequencing (FIG. 10). The amino acid sequence of FIG. 10 corresponds to the OsbeII-1ALL sequence of FIG. 2. Although not full length the predicted open reading frame includes nucleotides 44 through to 1823 and encodes a 593 amino acid peptide. Based on similarities with the maize genes, it is estimated that this sequence is missing approximately 230 amino acids out of a predicted total of approximately 830 amino acids. On this basis, the partial sequence represents about 70% of the coding sequence. Multiple sequence alignment of this SBEII-1 sequence with recently published wheat SBEII-2 (Nair et al., 1997), SBEI (Rapenin et al., 1997) and SBE1-D2 (Rabman et al., 1997) sequences showed that the SBEII-1 sequence has similarity indices of 69.6%, 31.2% and 46.7% to SBEII-2, SBEI and SBEI-D2 respectively (FIGS. 11 and 11a). This demonstrates that the SBEII-1 sequence differs from the published wheat SBE sequences, and confirms the analysis of the 3' sequence alignment (FIG. 3). The increase in relative homology when compared to the values obtained following 3' sequence alignment results from the fact that the central domain of SBEs is highly conserved (Burton et al., 1995; Gao et al., 1997). However, it is clear that this cloned wheat SBEII-1 sequence is significantly different from previously published wheat SBE sequences and represents a novel sequence.

Full experimental details were as follows.

SBEII-1 sequences were extended toward the 5' end of the mature peptide by amplification from the endosperm cDNA pool using the SBEII-1 specific primer Sb4 [TTTTCTTCA-CAACGCCCTGGG] (SEQ ID No: 40) in conjunction with the primer AGSBEI [TGTTTGGGAGATCTTCCTCCC] (SEQ ID No: 41). AGSBEI was designed to be homologous to the GVWEIFLP (SEQ ID No: 42) motif which is conserved in all known SBE sequences and is situated toward the 5' end of the mature peptide coding sequence. PCR was carried out in a 50 μl reaction, comprising 5 μl of the cDNA pool, 50 pmol Sb4, 50 pmol SBEA1, 5 μl 5×Taq buffer, 4 μl 25 mM $Mg^{2+}$, 0.5 μl 20 mM dNTPs, and 1.25u Taq polymerase. All of the reaction components were mixed, before thermocycling at (94° C.-45 sec, 55° C.-30 sec, 72° C.-1 min 30 sec)×30 cycles, followed by a final 10 min extension step at 72° C. Amplification products were separated by electrophoresis through a 1% (w/v) agarose gel and specific amplification products of the predicted sue were excised from the gel., The DNA was eluted from the gel slice using QIAGEN's gel extraction kit according to the manufacturers recommendations before ligation with pT7 Blue (Novagen). Ligation was carried out in a 10 μl reaction volume comprising 7.5 μl purified amplification product, 1 μl 10× ligation buffer, 1 μl pT7Blue and 0.5 μl T4 DNA ligase (Amersham). The reaction components were mixed well before being placed at 4° C. overnight. Following overnight incubation, half of the ligation reaction was used to transform competent Novablue E. coli cells (Novagen). Transformed cells were plated out onto LB plates supplemented with X-gal (40 μgml$^{-1}$), IPTG (0.1 mM), Carbenicillin (100 μgml$^{-1}$), and Tetracycline (12.5 μgml$^{-1}$), before placing at 37° C. overnight. Putative recombinant clones were initially screened for the presence of an insert by colony PCR using the vector specific primers T7B and U19. Insert positive clones were then screened using an insert specific primer in conjunction with either 1B or U19 primers to determine the orientation of the insert within the multiple cloning site prior to sequencing.

Southern Blot Analysis

Southern analyses of the pre-made nulli-tetra and ditelosomic blots were carried out essentially as described in Jack et al (1994).

The SBEII-1 clones discussed above have been cloned into transformation vectors for transformation of wheat.

Northern Blot Analysis

Northern blots were prepared from total RNA from developing wheat grains of the cultivar Bobwhite. FIG. 12 shows a northern blot of RNA from wheat grains of the cultivar Bobwhite grown in the glasshouse as described and harvested between 5 and 29 days after anthesis. The blot was probed with the 1 kb Sac1 SBEII-1 fragment and subsequently (following blot stripping) with the 1.2 kb BamH1 SBEII-2 fragment, both fragments purified and labelled as described. In FIG. 12 panel A shows the Ethidium Bromide-stained RNA gel prior to northern transfer. Panel B shows the results of probing with the SBEII-1 probe and panel C shows the results of probing with the SBEII-2 probe. Comparing within and between panels B and C differences can be observed in the relative intensities of the signals at the different time points. In particular a relatively stronger signal intensity is observed with the SBEII-2 probe for the 5 day time point than with the SBEII-1 probe, indicating that the transcript profiles for SBEII-1 and SBEII-2 are distinct, suggesting that the two gene families (SBEII-1 and SBEII-2) are differentially expressed during grain development. The size of the transcripts observed for both SBEII-1 and SBEII-2 is approximately 3.5 kb. However the SBEII-2 transcript is slightly smaller than the SBEII-1 transcript.

Plasmid Constructions

Figure 13:
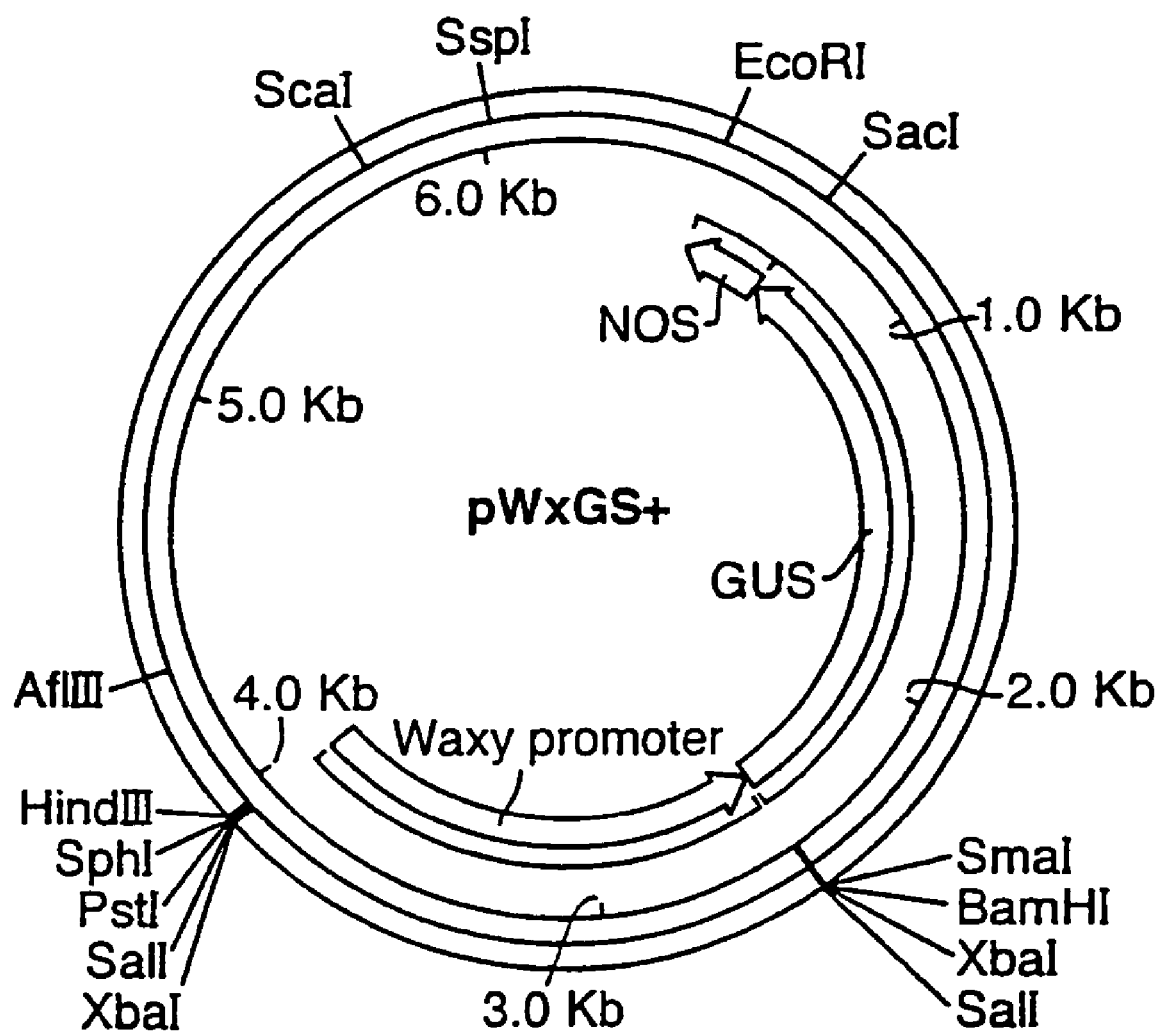
FIG. 13 is a restriction map of plasmid pWxGS+.
Figure 14:
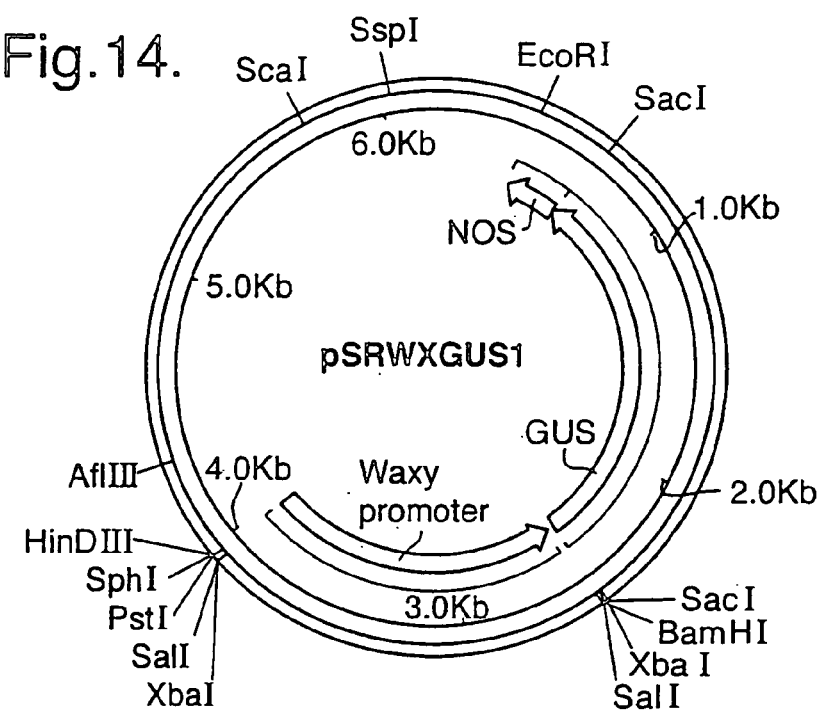
FIG. 14 is a restriction map of plasmid pSRWXGUS1.
Figure 15:
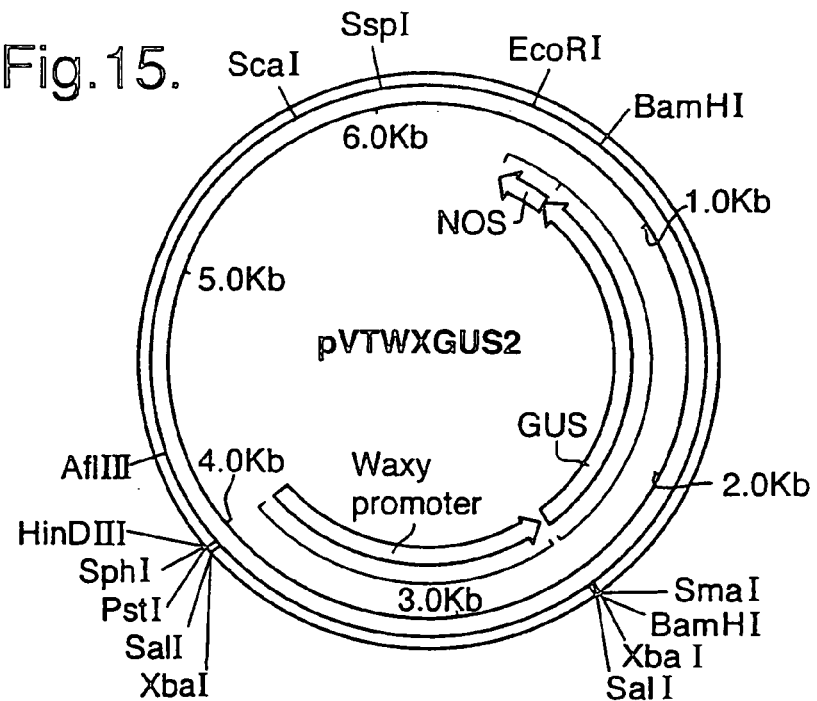
FIG. 15 is a restriction map of plasmid pVTWGUS2.

Standard molecular biology procedures (Sambrook et al, 1989) were used for plasmid constructions.

pWxGS+ (FIG. 13) comprising a maize granule bound starch synthase gene (Shure el al 1983) promoter-GUS-Nos fusion was obtained as a gift to Unilever Research from Sue Wessler (University of Georgia, Athens, USA) and may be obtained on request from that source. The promoter in pWxGS+ is approximately 1.5 kb in length and represents a truncated version of a similar, but larger promoter fragment described in Russell & Fromm (1997). The sequence of the promoter (HindIII-BarmH1 fragment) in pWxGS+ is presented in FIG. 13A (SEQ ID No: 55).

pSRWXGUS1 (FIG. 14) was produced by inserting a Sac 1 linker [d(pCGAGCTCG)0] (New England Biolabs [NEB]) (NEB catalogue No 1044) into the Sma1 site in pWxGS+.

pVTWXGUS2 (FIG. 15) was produced by inserting a BamH 1 linker [d(pCGGGATCCCG)] (SEQ ID No: 43) (NEB catalogue No. 1071) into the Ecl136II (an isoschizomer of Sac1 which gives blunt ends) site of pWxGS+

A Sac1 linker was inserted at the XbaI site (which had been blunted using Klenow+ dNTps) of the SBEII-1 Clone B6 in the plasmid pT7Blue to produce an intermediate clone. The SBE sequence was then purified from this intermediate clone as a Sac1 fragment and ligated into the Sac1 sites of pSRWXGUS1 replacing the GUS gene sequence to produce the plasmids pSR96-26 and pSR96-29 representing antisense and sense orientations of the SBEII-1 sequence downstream of the Waxy promoter, respectively.

A BamH1 linker was inserted at the XbaI site (which had been blunted using Klenow+ dNTps) of the SBEII-2 Clone B11 in pT7Blue to produce an intermediate clone. The SBE sequence was then purified from this intermediate as a BamH1 fragment and inserted into the BamH1 sites of pVTWXGUS2, replacing the GUS gene sequence, to produce the plasmids pVT96-50 and pVT96-53 representing antisense and sense orientations, respectively, of the SBEII-2 sequence downstream of the Waxy promoter.

pVT96-54. A BamH1 linker was inserted at the Xba1 site (which had been blunted using Klenow+ dNTPs) of the SBEII-2 clone B9 (equivalent to clone B1) in pT7Blue to produce an intermediate clone. The SBEII-2 sequence was then purified from this intermediate clone as a BamH 1 fragment and inserted into the BamH1 sites of pVTWX-GUS2, replacing the GUS gene sequence, to produce the plasmid pVT96-54.

Figure 16:
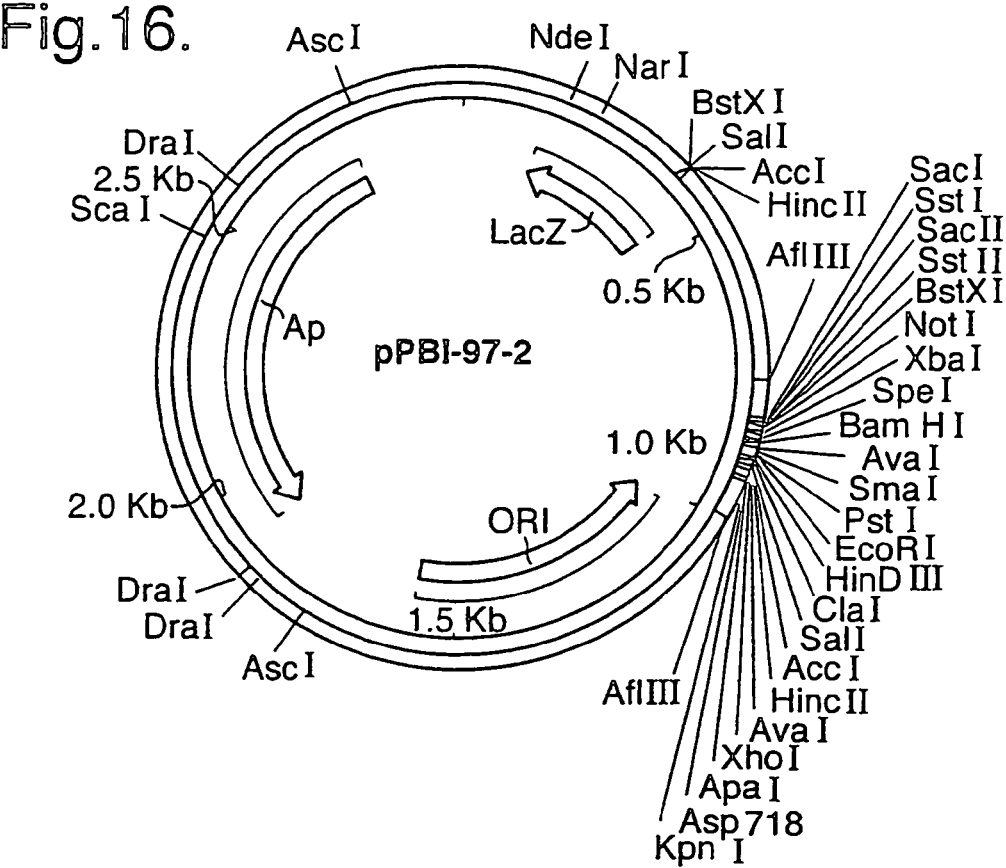
FIG. 16 is a restriction map of plasmid pPBI-97-2.
Figure 17:
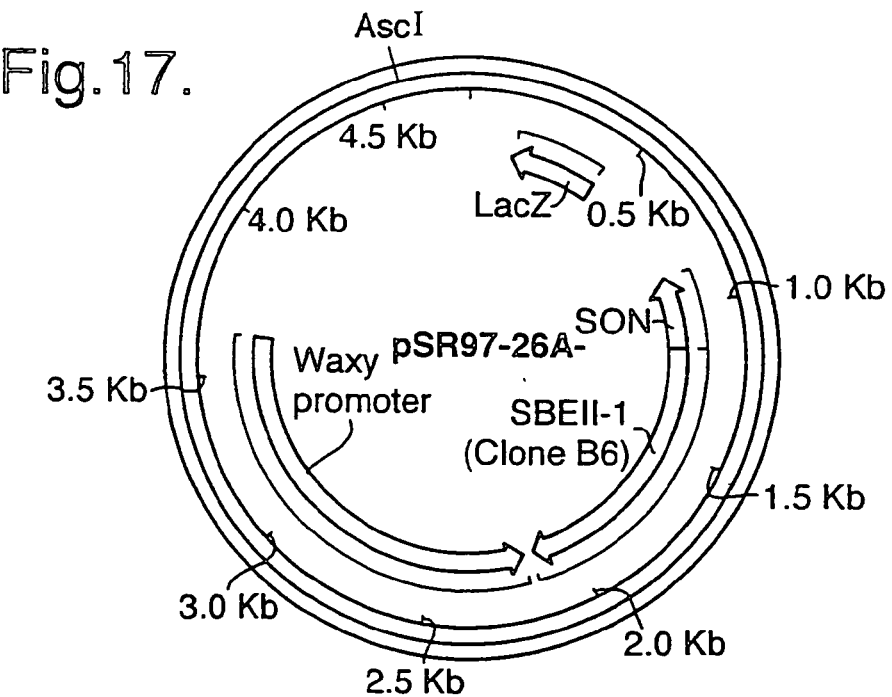
FIG. 17 is a restriction map of plasmid pSR97-26A-.
Figure 18:
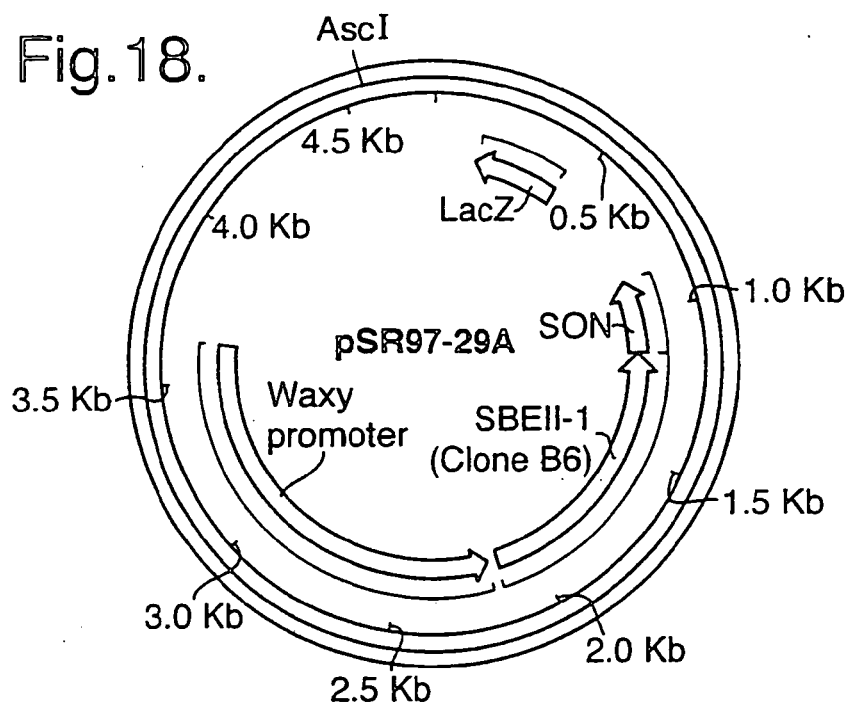
FIG. 18 is a restriction map of plasmid pSR97-29A-.
Figure 19:
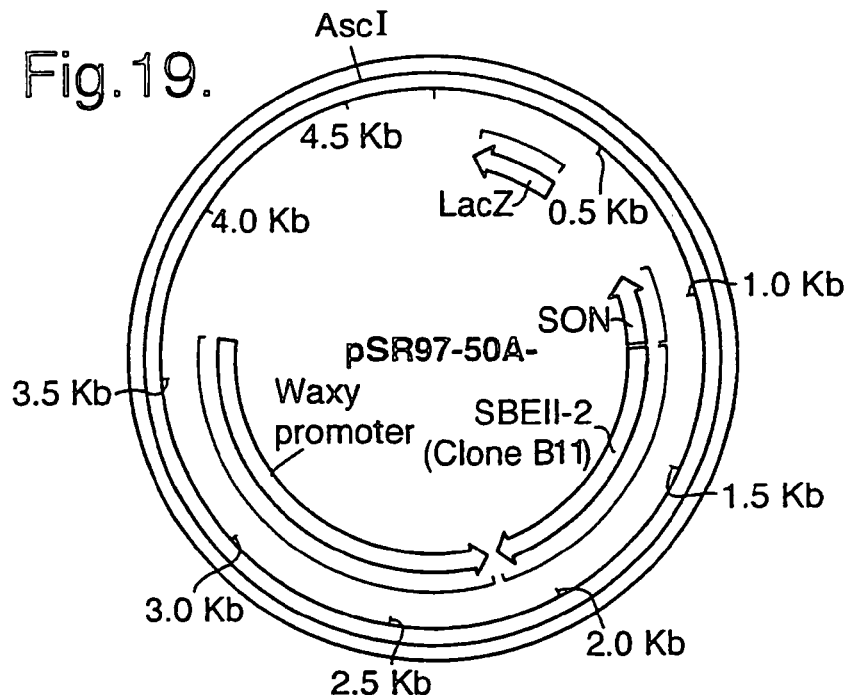
FIG. 19 is a restriction map of plasmid pSR97-50A-.
Figure 20:
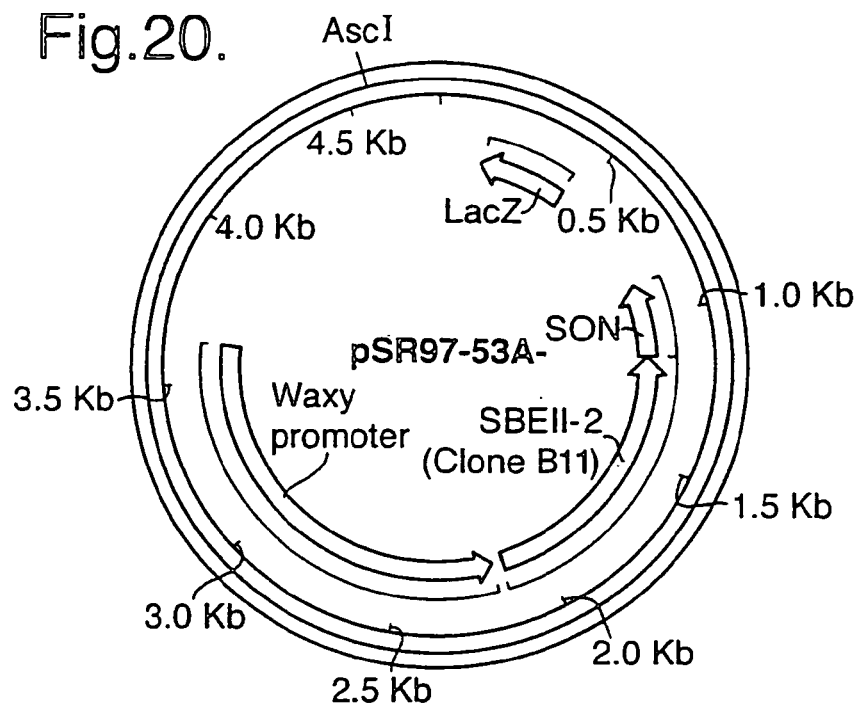
FIG. 20 is a restriction map of plasmid pSR97-53A-.
Figure 21:
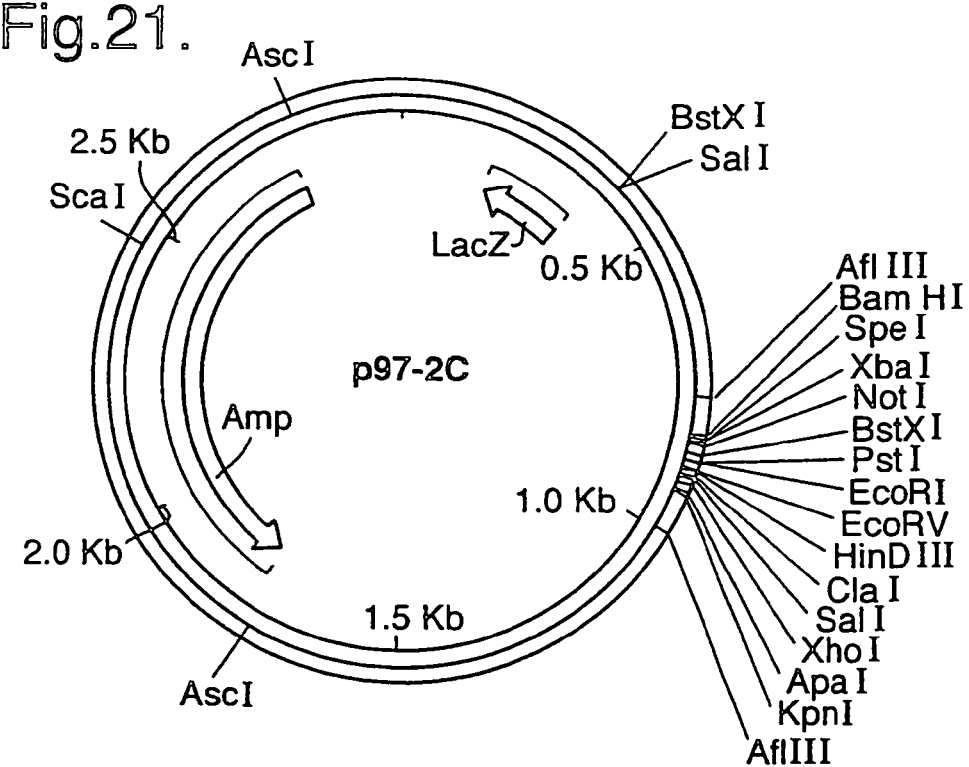
FIG. 21 is a restriction map of plasmid p97-2C.

The Waxy-SBE-NOS sequences in the plasmids pSR96-26 and pSR96-29 and pVT96-50 and pVT96-53 were purified as HindIII/EcoRI fragments and inserted into the EcoRI/HindIII sites of plasmid pPBI-97-2 (also known as p97-2) (FIG. 16). Plasmid pPBI-97-2 is described in European Patent Application No. 97305694.8 (published as WO 99/06570). Following removal of the ampicillin resistance marker gene the resulting plasmids were designated pSR97-26A- (clone B6 (SBEII-1, subclass A) in antisense orientation), pSR97-29A- (clone B6 in sense orientation), and pSR97-50A- (clone B11 (SBEII-2, sub-class A) in antisense orientation) and pSR97-53A- (clone B11 in sense orientation) as illustrated in FIGS. 17, 18, 19 and 20, respectively.

p97-2C (FIG. 21) was produced by digesting the polylinker sites Ecl136 II to SmaI in the plasmid pPBI97-2 (FIG. 16), ligating and selecting recombinants in which the polylinker region from SmaI to Ecl136 II had reinserted in the opposite orientation.

Figure 22:
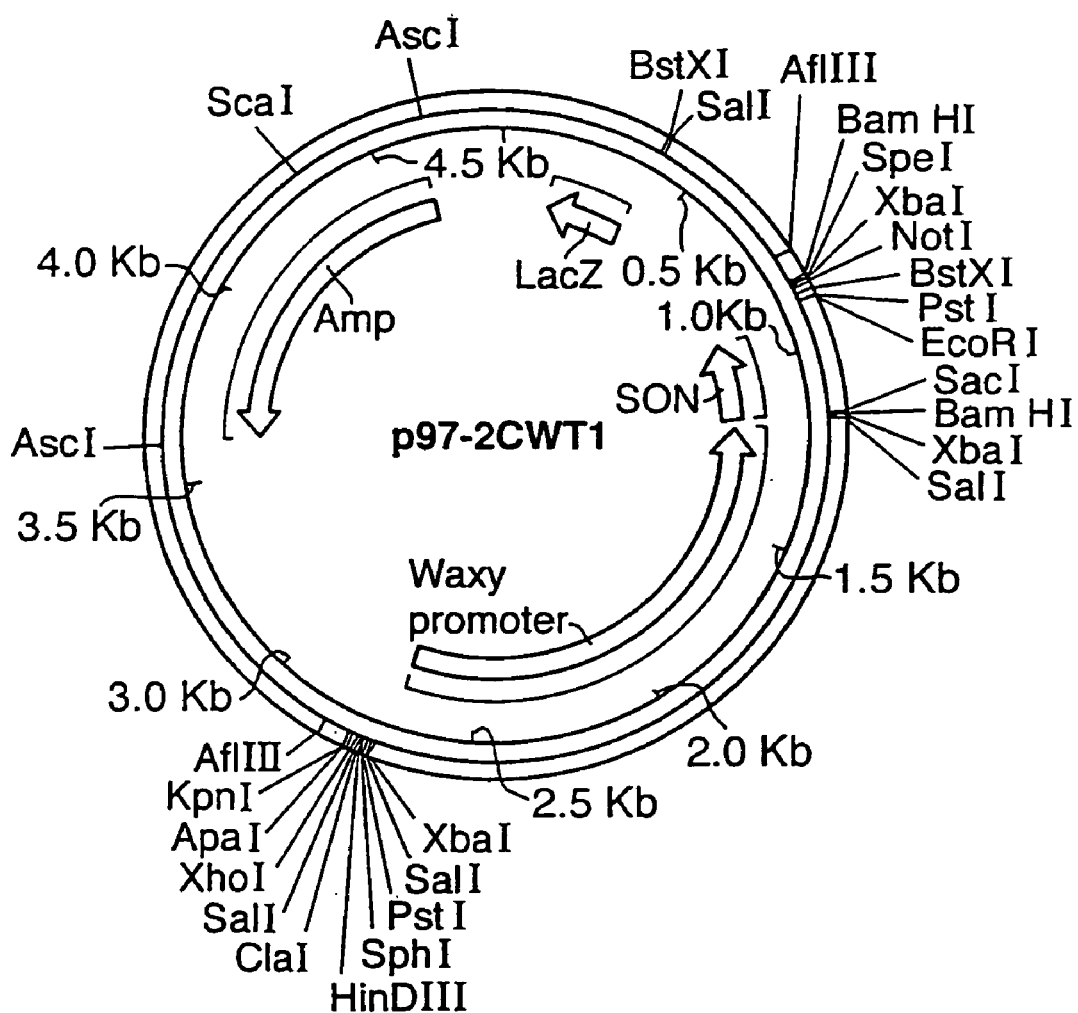
FIG. 22 is a restriction map of plasmid p97-2CWT1.
Figure 23:
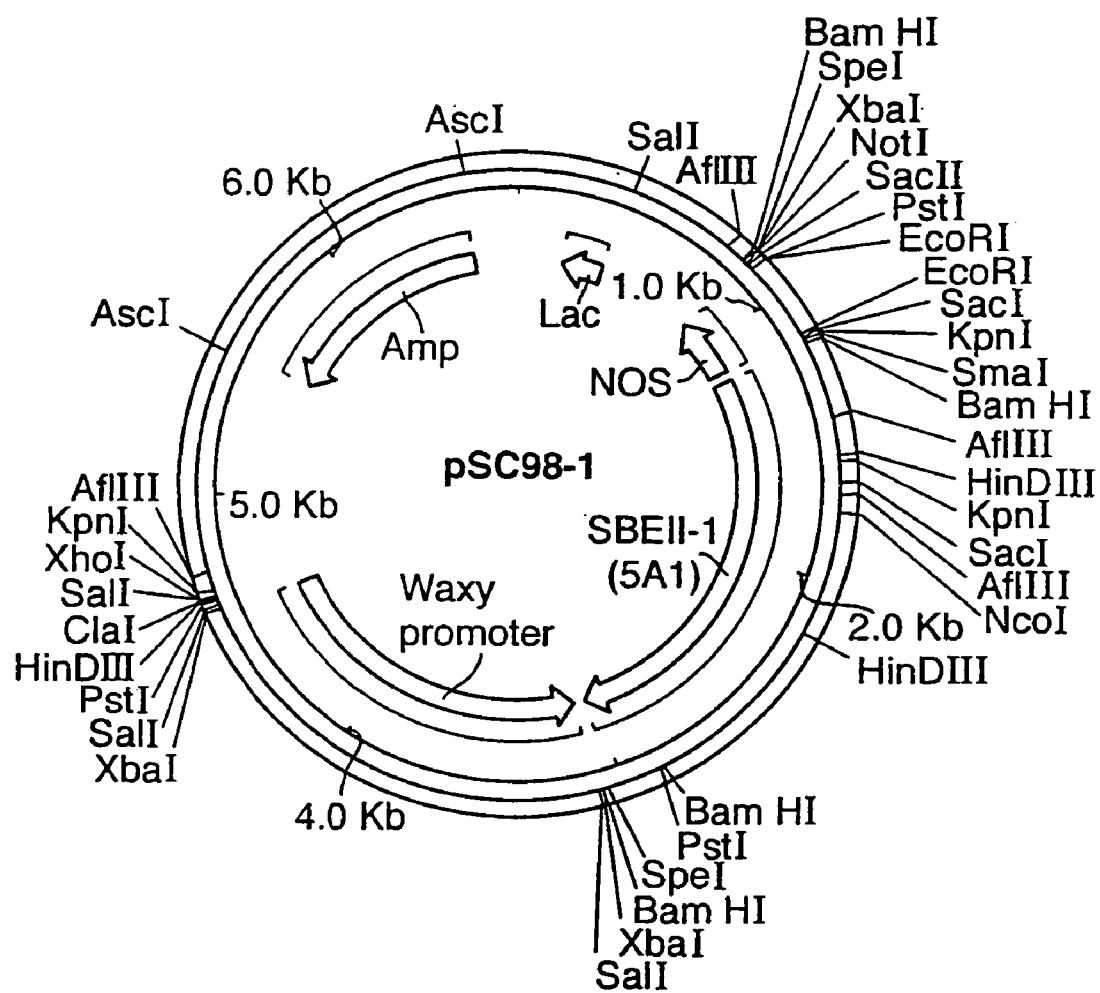
FIG. 23 is a restriction map of plasmid pSC98-1.
Figure 24:
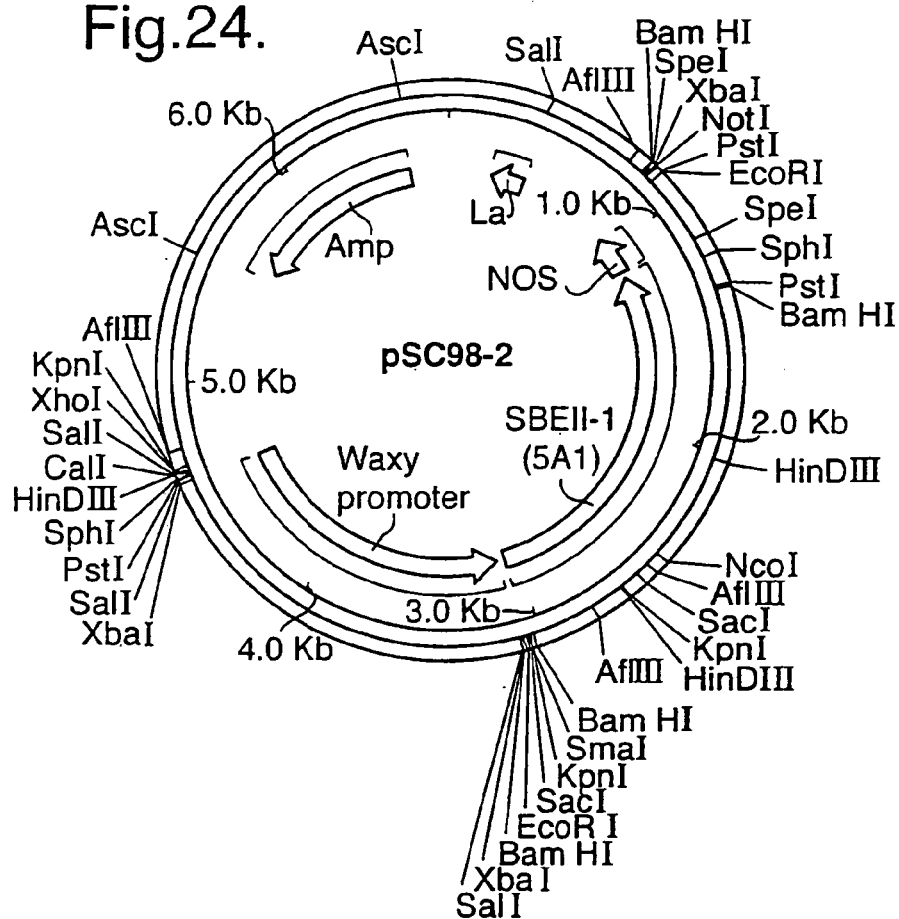
FIG. 24 is a restriction map of plasmid pSC98-2.

The Waxy-NOS sequences in pSRWXGUS1 were transferred as a HindIII/EcoRI fragment into the HindIII/EcoRI sites of plasmid p97-2C to produce the plasmid p97-2CWT1 (FIG. 22).

pSC98-1 and pSC98-2. The 5' extended SBEII-1 clone 5A1 in pT7Blue (comprising SBE sequence from coordinate 43 to 2003 bp in FIG. 10) was digested with EcoRI and Xba1, followed by 'in-fill' of overhangs using Klenow polymerase and dNTPs. The resulting blunt ended SBE fragment was gel purified and ligated to p97-2CWT1 (FIG. 22) which had been digested with Ecl136II and dephophorylated using calf intestinal phosphatase. The resulting recombinants were screened by restriction digest anaylsis and clones comprising both orientations of the SBE sequence (with respect to the waxy promoter) were identified. pSC98-1 (FIG. 23) is an antisense version and pSC98-2 (FIG. 24) is a sense version. Following removal of the ampicillin marker gene the resulting plasmids were designated pSC98-1A- and pSC98-2A- respectively.

Ubiquitin Promoter—NptII selection Construct:pUN1 pUN1 was made in the following way:

A SacI linker was inserted at the SmaI site of the plasmid pAHC25 (Christensen and Quail 1996) to produce an intermediate plasmid. The GUS gene was removed from this intermediate plasmid by digesting with SacI followed by self ligation and identification of recombinant molecules lacking the GUS sequence to produce the plasmid pPBI95-9. pPBI95-9was digested with EcoRI and following self ligation recombinant molecules lacking the Ubi-BAR sequences were identified. The resulting plasmid is designated pPBI96-23. An NptII sequence was amplified as a PCR product using the primers AG95-7:

5'GATGAGCTCCGTTTCGCATGATTGAACAAGATGG (SEQ ID No:44) and AG95-8: 5'GTCGAGCTCAGAAGAACTCGTCAAGAAGGC (SEQ ID No: 45), using pPBIBAG3 (Goldsbrough et al 1994 as template for the NptII sequence. The amplified product was cloned into the SstI site of pBluescript (Stratagene) and sequenced. The sequencing revealed that the NptII sequence was of the 'mutant' form rather than the wild-type as had been expected. The 'mutant' form carries a single base change which is flanked by unique Nco1 and Sph1 sites. The pBluescript clone was digested with Nco1 and Sph1 to remove the region containing the single base change. Two oligonucleotides, (Npt1:CCCGACGGCGAGGATCTCGTCGTGACC (SEQ ID No: 46) and Npt2: CATGGGTCACGACGAGATCCTCGCCGTCGGGCATG) (SEQ ID No: 47) were then annealed to each other to form an Nco1/Sph1 fragment. This was cloned into the Nco1/Sph1 digested Bluescript/Npt11 clone, and the resulting clone was sequenced to confirm that the gene was now of the wild type form.

Figure 25:
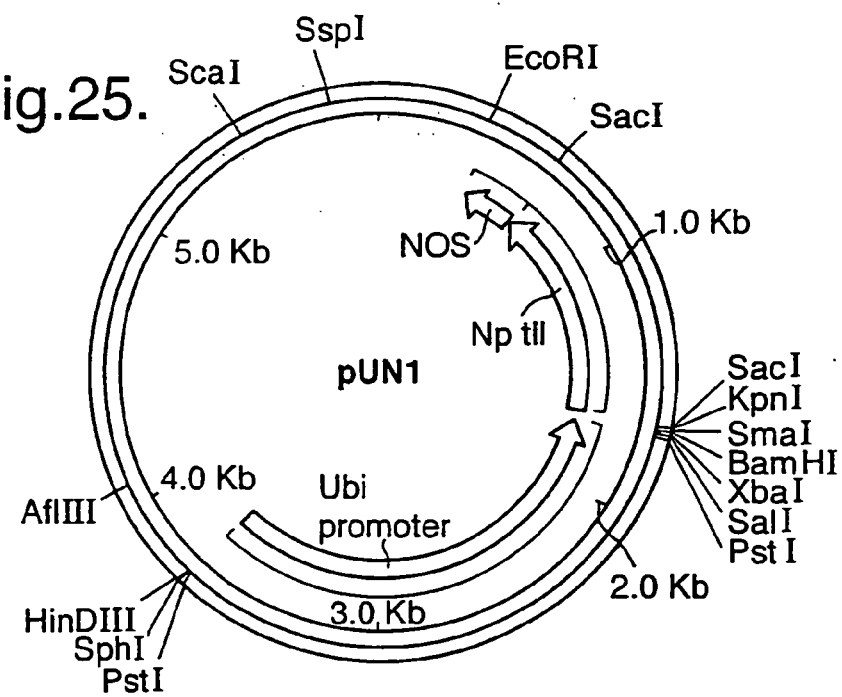
FIG. 25 is a restriction map of plasmid pUNI.
Figure 27:
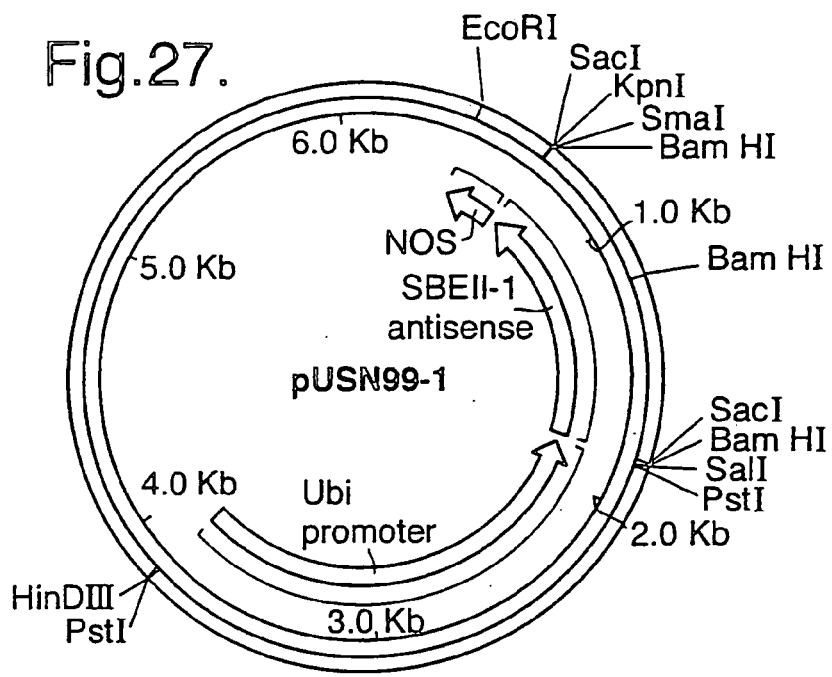
FIG. 27 is a restriction map of plasmid pUSN99-1.
Figure 28:
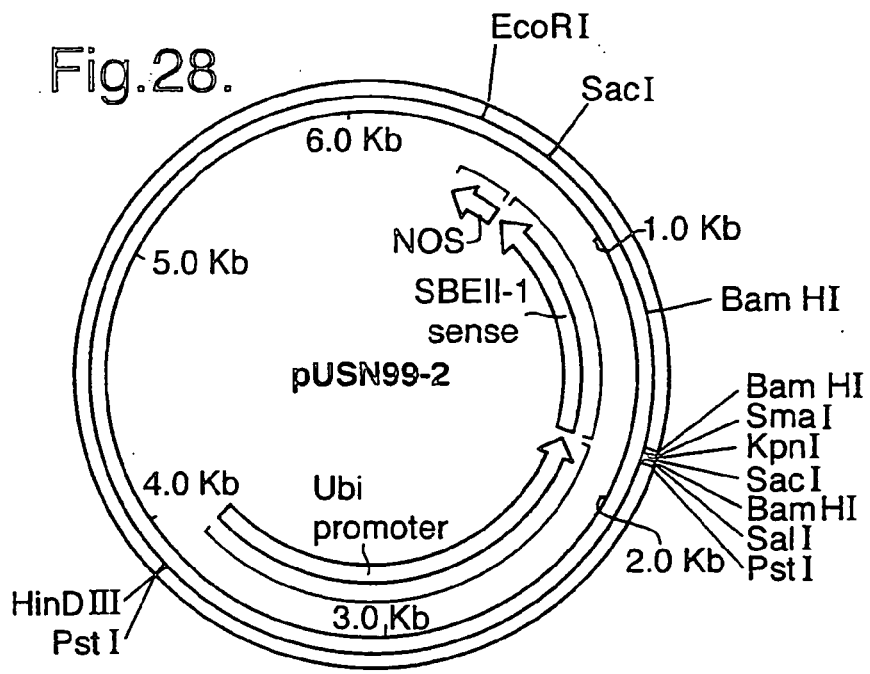
FIG. 28 is a restriction map of plasmid pUSN99-2.

The NptII sequences was then purified as a Sac1 fragment and inserted at the SacI site of pPBI96-23 to produce pUN1 (FIG. 25). pUN1 includes the wild-type ubiquitin promoter (Ubi promoter), which is also referred to as the ubiquitin regulatory system (abbreviated to URS). The orientation of the NptII sequence in pUN1 was determined by restriction digest analysis. The sequence of the NptII Sac1 fragment is presented in FIG. 26 (SEQ ID No: 35). pUSN99-1 and pUSN99-2. The SBEII-1 (clone B6) sequence was purified as a Sac1 fragment from the plasmid pSR96-26 and inserted at the Sac1 site of pPBI96-23 to produce the plasmids pUSN99-1 and pUSN99-2 (FIGS. 27 and 28) representing sense and antisense orientations of the SBEII-1 sequences respectively.

pPBI97-2BdUN1. pPBI92-2BdUN1 (also sometimes referred to as p97-2BdUN1) comprises a reconstituted ubiquitin regulatory system (referred to hereafter as a modified ubiquitin promoter or a modified ubiquitin regulatory system (mURS)) which lacks the two overlapping 'consensus heatshock elements' discussed in EP 0342926 and U.S. Pat. No. 5,614,399. The modified ubiquitin promoter was prepared via PCR amplification of two DNA fragments using maize genomic DNA as template, followed by ligation of the two fragments to produce a single fragment lacking the consensus heatshock (HS) elements. A Kpn1 restriction site was engineered in place of the HS elements. The primers used were designed from sequence information published by Liu et al 1995 (EMBL DNA database accession ZMU29159). To delete the HS elements and to replace with a diagnostic Kpn1 site the ubiquitin promoter and intron sequences were amplified as two fragments using the primer combinations HS1+Ubi3-3 and HS2+Ubi5-2, the sequences of which are given below. Primers Ubi5-2 and Ubi3-3 are homologous to sequences in the sequence published by Liu et al 1995. Primers HS1 and HS2 are homologous to sequences located immediately 3' and 5' respectively of the two overlapping HS elements in the ubiquitin promoter as described in EP 0342926 and U.S. Pat. No. 5,361,399. Both of these primers have a Kpn1 tail at their 5' ends.

Primers

```
HS1:
5-ATTAGGTACCGGACTTGCTCCGCTGTCGGC-3    (SEQ ID No: 48)

HS2:
5-TATAGGTACCGAGGCAGCGACAGAGATGCC-3    (SEQ ID No: 49)

Ubi5-2:
5-AGCTGAATCCGGCGGCATGGC-3             (SEQ ID No: 50)

Ubi3-3:
5-TGATAGTCTTGCCAGTCAGGG-3             (SEQ ID No: 51)
```

Figure 30:
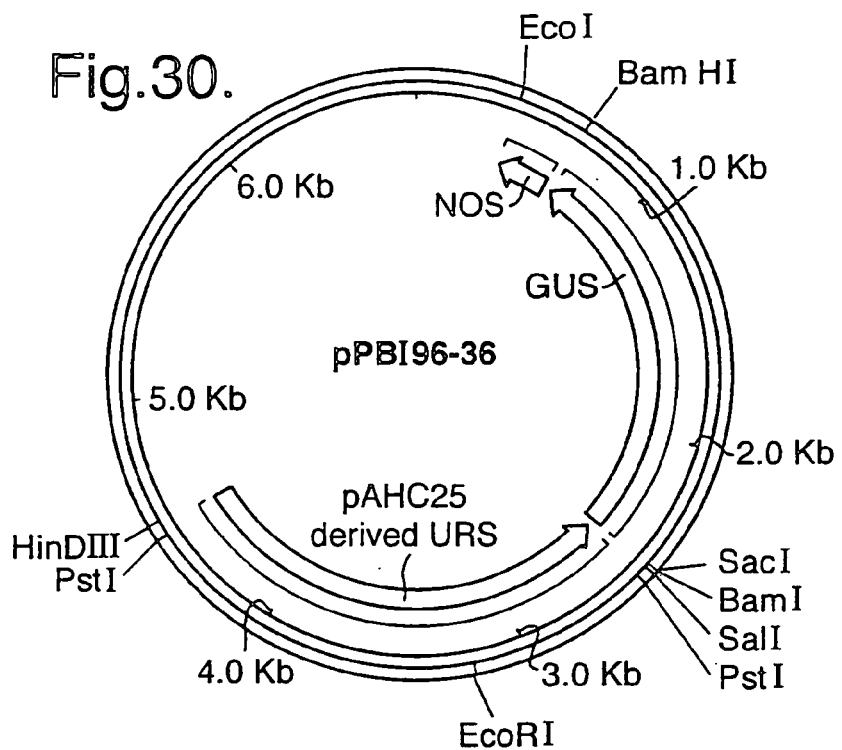
FIG. 30 is a restriction map of plasmid pPBI96-36.
Figure 31:
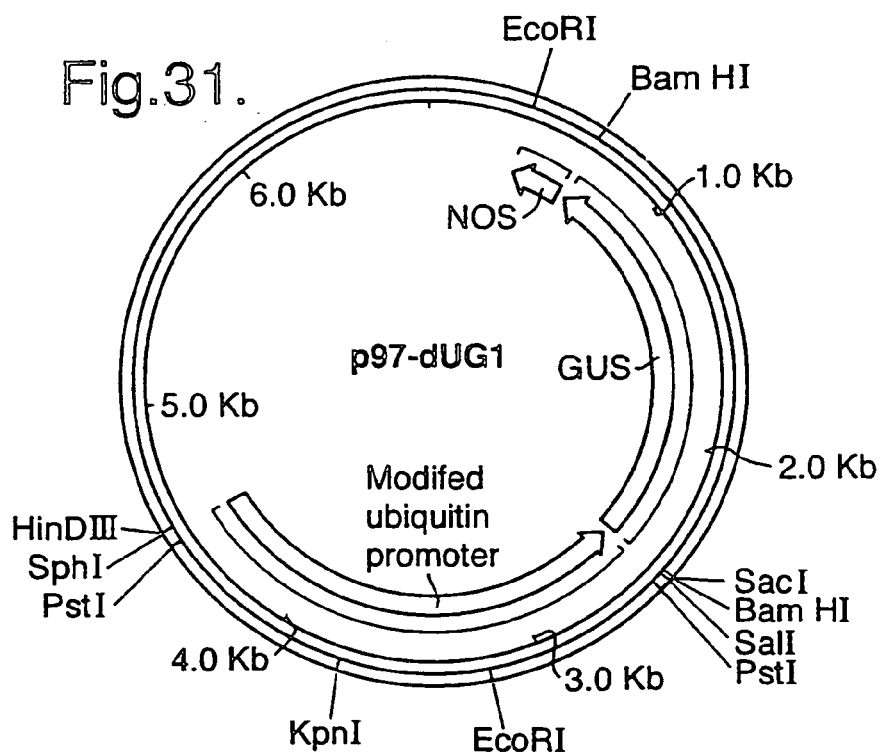
FIG. 31 is a restriction map of plasmid p97-dUG1.

The amplified products were subcloned into pGEM TEasy (Promega) to produce the plasmids p97-U1 and p97-U2. The full-length (approx. 2 Kb) modified ubiquitin promoter was reconstructed by subcloning the Kpn1-Sac1 fragment from p97-U1 into the Kpn1/Sac1 sites of p97-U2 to produce p97-U3. A partial restriction map of the predicted sequence (SEQ ID No: 52) of the cloned fragment in p97-U3 is presented in FIG. 29. (The modified ubiquitin promotor (or mURS) is the subject of a copending European Patent Application filed by the present applicants on the same day as the present application, under the reference C1235.01/M). The modified ubiquitin promoter was transferred as a PstI fragment from p97-U3 into plasmid pPBI96-36. The plasmid pBI96-36 (FIG. 30) comprises the GUS-Nos reporter gene fusion under the control of the wild-type ubiquitin promoter (derived from pAHC25) in a pUC plasmid backbone. The promoter replaces the wild-type ubicuitin regulatory system in pPBI96-36 to produce an intermediary plasmid p97-dUG1 (FIG. 31).

Construction of oPBI97-2BdUN1

Figure 32:
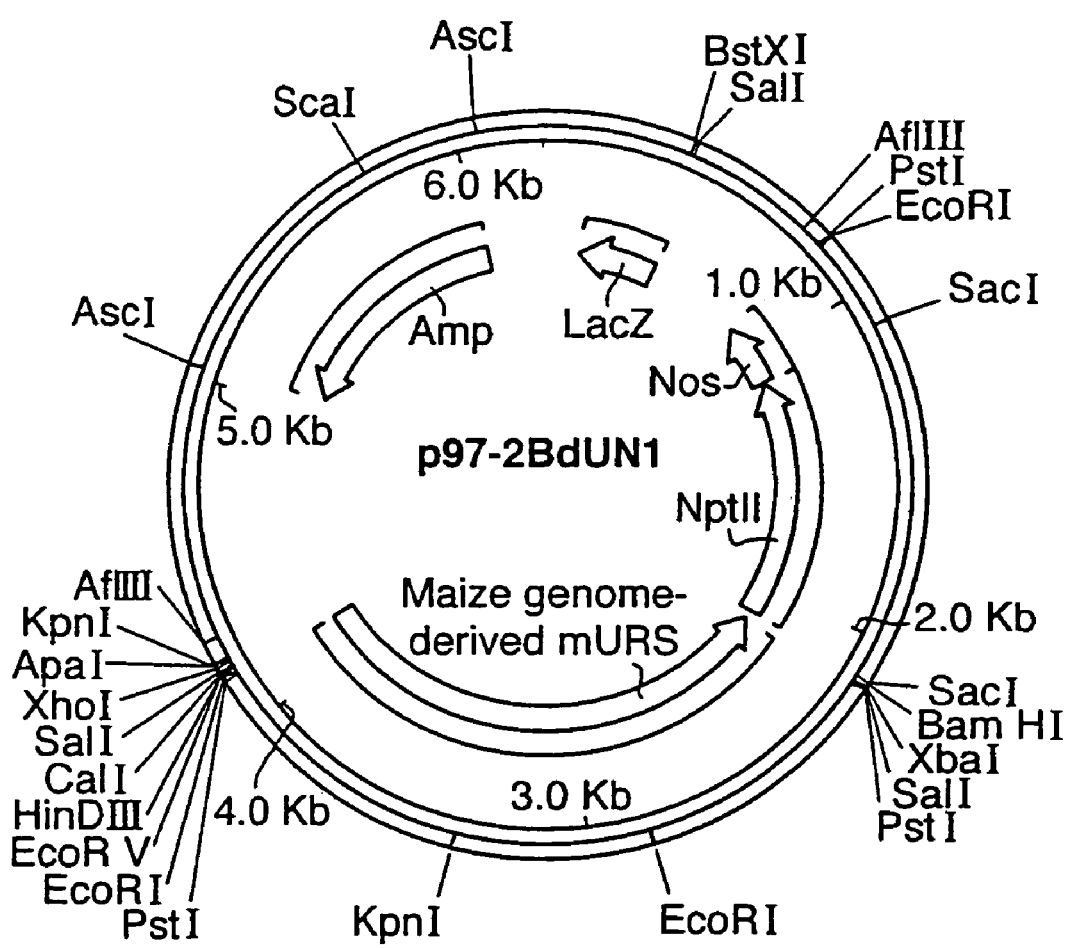
FIG. 32 is a restriction map of plasmid p97-2BdUN1.

The Ubi-Nos sequences in pPBI96-23 were transferred as an EcoRI-HindIII fragment into the EcoRI and HindIII sites of p97-2B (plasmid p97-2B is described in European Patent Application No. 97305694.8 published as WO 99/06570) to produce the plasmid p97-2BUbiNos. The modified ubiquitin promoter was purified as a HindIII/SacI fragment from p97-dUG1 (FIG. 31) and transferred into the HindIII and SacI sites of p97-2BUbiNos, replacing the wild-type ubiquitin promoter to produce p97-2BdUbiNos. The NptII sequence in pUN1 was purified as a SacI fragment and transferred into the SacI site of p97-2BdUbiNos to produce pPBI97-2BdUN1 (FIG. 32). Following removal of the ampicillin resistance marker using the method as described in WO 99/06570, the resulting plasmid as used for wheat transformation was designated p97-2BdUN1A- pCaineo pCaiNeo comprises the NptII gene under control of a CaMV35S promoter and maize Adh1 intron. The plasmid is described in Fromm et al 1986.

Transformation of Wheat

The following plasmid combinations (co-bombardments) have been used in the transformation of wheat plants:

TABLE 2

Plasmid combinations used in wheat transformation experiments.

| Starch gene construct/s | Selection marker construct |
| --- | --- |
| pWXGS+<br>pSR97-26A-antisense | pAHC25<br>pUN1<br>pUN1 or<br>p97-2BdUN1 |

TABLE 2-continued

Plasmid combinations used in wheat transformation experiments.

| Starch gene construct/s | Selection marker construct |
|---|---|
| pSR97-29A-sense | p97-2BdUN1 or pCaiNeo |
| pSC98-1A-antisense | p97-2BdUN1 |
| pUSN-1 sense | p97-2BdUN1 |
| pUSN-2 antisense | p97-2BdUN1 |
| pUSN-1 sense & pUSN-2 antisense | pUN1 |
| pSC98-2A-sense | p97-2BdUN1 |

The wheat transformation methods used and described here are largely based on those described by Barcelo and Lazzeri, 1995.

Embryo wheat plants of the spring cultivar Bobwhite and the winter cultivar Florida were grown in a glasshouse with 16 hr day length supplemented with lights to maintain a minimum light intensity of 500 umol $m^{-2}s^{-1}$ at 0.5M above flag leaf. Glasshouse temperatures were maintained at 19° C.+/−1° C. during the day and 14° C.+/−1° C. at night.

Immature embryos of wheat were harvested from developing grain. The seeds were harvested and embryos were cultured at approximately 12 days after anthesis when the embryos were approximately 1 mm in length. Seeds were first rinsed in 70% ethanol for 5 minutes and then sterilised in a 10% solution of Domestos bleach (Domestos is a Trade Mark) for 15 minutes followed by 6 washes with sterile distilled water. Following removal of the embryonic axis the embryos were placed axis surface face down on agargel (Sigma catalogue no. A-3301) solidified MM1 media. The general recipe for MM1 is given in Appendix 1, and the recipes for the various constituents in Appendix 2. The embryos were maintained in darkness for one to two days at 24° C.+/−1° C. prior to bombardment.

The plasmids pAHC25, pCAiNeo, pUN1 and p97-2BdUN1 were used to provide selection markers in the combinations with starch gene constructs as detailed in Table 2. pAHC25 (Christensen and Quail 1996) contains a chimeric Ubi-BAR gene which provides selection of transformants to phosphinothricin, the active ingredient in herbicides BASTA™ and Bialophos (see Block, M. de. et al 1987). The plasmids pCAiNeo (Fromm el al., 1986), pUN1 and p97-2BdUN1 contain chimeric promoter-NptII gene fusions and provide selection of transformants against a range of aminoglycoside antibiotics including kanamycin, neomycin, geneticin and paromycin.

Particle bombardments was used to introduce plasmids into plant cells. The following method was used to precipitate plasmid DNA onto 0.6 μm gold particles (BIO-RAD catalogue number 165-2262): A total of 5 μg of plasmid DNA was added to a 50 μl sonicated for one minute suspension of gold particle (@ 10 mg/ml) in a 1.5 ml microfuge tube. Following a brief vortex for three seconds 50 μl of a 0.5M solution of calcium chloride and 20 μl of a 0.05M solution of spermidine free base were added to the opposite sides of the microfuge tube lid. The tube contents were mixed together by closing the lid and tapping the calcium chloride and spermidine to the bottom of the tube. Following a vortex for three seconds the suspension was centrifuged at 13,000 rpm for 5 seconds. The supernatant was then removed and the pellet resuspended in 150 μl of absolute ethanol. This requires scraping the gold particles off the inside of the tube using a pipette tip. Following a further three second vortex, the sample was centrifuged again and the pellet resuspended in a total volume of 85 μl in absolute ethanol. The particles were vortexed briefly and sonicated for 5 seconds in a Camlab Trisonic T310 water bath sonicator to ensure fine dispersion. An aliquot of 5 μl of the DNA coated gold particles were placed in the centre of a macrocarrier (BIO-RAD catalogue no. 115-2335) and allowed to dry for 30 mins. Particle bombardment was performed by using a Biolisitic™ PDS-1000/He (BIO-RAD Instruments, Hercules Calif.) chamber which is illustrated schematically in FIG. 33, using helium pressure of 650 and 900 psi (rupture discs: BIO-RAD catalogue numbers 165-2327 and 165-2328 respectively).

Figure 33:
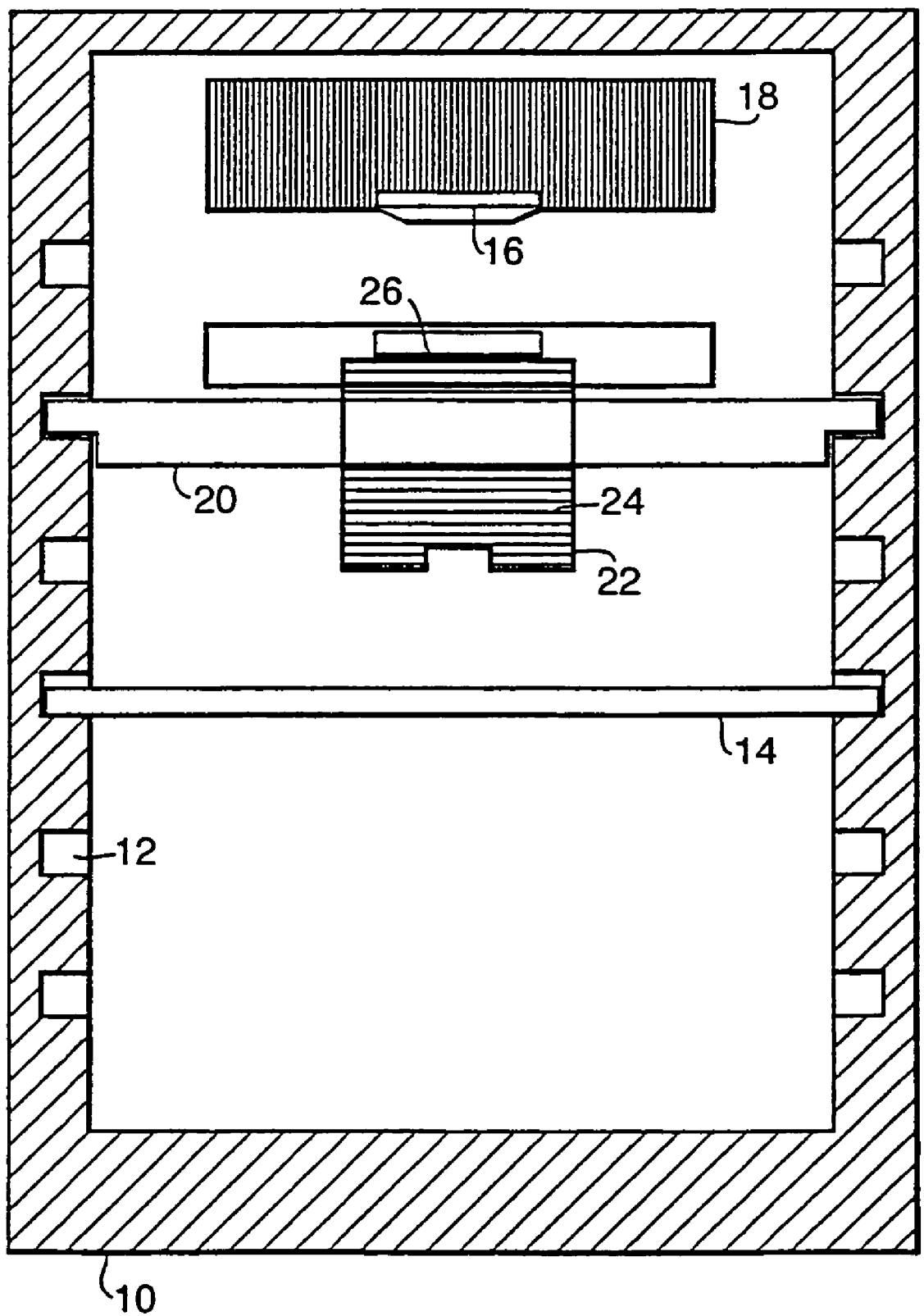
FIG. 33 is a schematic illustration of a particle bombardment chamber (not to scale)

Referring to FIG. 33, the illustrated vacuum chamber comprises a housing 10, the inner side walls of which include a series of recesses 12 for receiving shelves such as sample shelf 14 shown at the fourth level down from the top of the housing. A rupture disc 16 is supported in a He pressure shock tube 18 near the top of the housing. A support 20, resting in the second set of recesses 12 down from the top of the housing, carries unit 22 that includes a stopping screen and a number of rings 24, with 11 rings below the support 20 and 3–4 rings, above the support 20. Macrocarrier 26 is supported at the top of unit 22. The approximate distance from the rupture disc 16 to the macrocarrier 26 is 25 mm, with the approximate distance from the macrocarrier 26 to the stopping screen being 7 mm, and the approximate distance from the stopping screen to the sample shelf 14 being 67 mm. The top of unit 22 is about 21 mm from the bottom of the shock tube 18, and the bottom unit 22 is about 31 mm from the top of sample shelf 14.

Immature embryos were bombarded between 1 and 2 days after culture. For bombardment the immature embryos were grouped into a circular area of approximately 1 cm in diameter comprising 20–100 embryos, axis side face down on the MM1 media. The Petri dish (not shown) containing the tissue was placed in the chamber on shelf 14, on the fourth shelf level down from the top, as illustrated in FIG. 33. The air in the chamber was then evacuated to a vacuum of 28.5 inches of Hg. The macrocarrier 26 was accelerated with a helium shock wave using rupture membranes that burst when the He pressure in the shock tube 18 reaches 650 or 900 psi. Within 1 hour after bombardment the bombarded embryos were plated on MM1 media at 10 embryos per 9 cm petri dish and then maintained in constant darkness at 24° C. for 2–3 weeks. During this period somatic embryogenic callus was produced on the bombarded embryos.

After 2–3 weeks the embryos were transferred onto agar-solidified regeneration media, known as R media, and incubated under 16 hr daylength at 24° C. The general recipe for R media is given in Appendix 1. Embryos were transferred on fresh plates at 2–3 week intervals. The composition of the regeneration media varied depending on which selection regime was to be used. For transformants bombarded with the BAR gene the 3 amino solution was omitted and PPT (phosphinothricin) at 1 mg/L, rising to 3 mg/L over a period of three 2–3 week transfers was used for selection. For selection of transformants using the NptII gene three different regimes were used: 1) Geneticin (GIBCO-BRL catalogue no. 10131-019) was incorporated (at 50 mg/L) immediately on transfer to regeneration media and maintained at 50 mg/L on subsequent transfers to regeneration media. 2) & 3) Embryos were first transferred to regeneration media without selection for 12 days and 2–3 weeks, respectively, and thereafter transferred on to media containing Geneticin at 50 mg/L. After 2–3 passages on regeneration media regenerating shoots were transferred to individual culture tubes containing 15 ml of regeneration media at half salt strength with selection at 3 mg/L PPT or 35 mg/L geneticin depending on whether the BAR gene of NptII gene had been used in the original bombardments. Following root formation the regenerated plants were transferred to soil and the glasshouse.

Genomic DNA Isolation and Southern Analyses

Southern analyses of primary transformants and progeny material were carried out as follows: Freeze dried leaf tissues were ground briefly in a Kontes™ pestle and mortar, and genomic DNA extracted as described in Fulton et al, 1995. 5 µg of DNA were digested with an appropriate restriction enzyme according to the manufacturers instructions, and electrophoresed overnight on a 1% agarose gel, after which the gel was then photographed, washed and blotted onto Hybond N+™ (Amersham International) according to the method of Southern using standard procedures (Sambrook et al 1989). Following blotting, the filters were air dried, baked at 65° C. for 1–2 hours and TV fixed at 312 nm for 2 minutes.

Probe preparation and labelling for the Southern analyses of transformed material was carried out as described above.

GUS histochemistry was performed essentially as described in Jefferson (1987).

Evaluation of the Ubiquitin Promoter for Constitutive Expression of Associated Transgenes.

Figure 34:
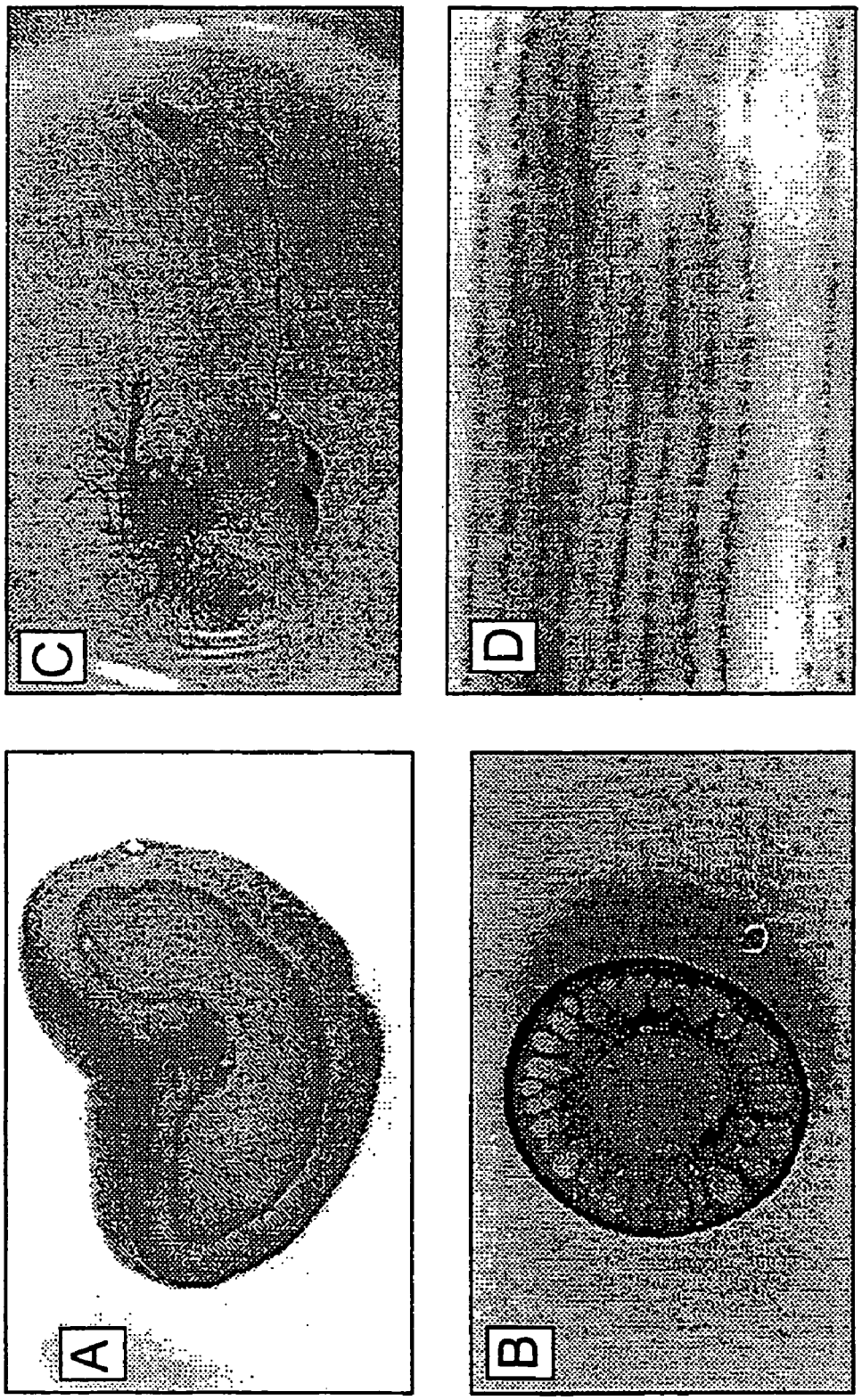
FIG. 34 shows histochemical localisation of Ubi-GUS expression in seed (panel A), stem (panel B), floral (panel C) and leaf tissues (panel D) of wheat transformed with plasmid pAHC25.
Figure 35:
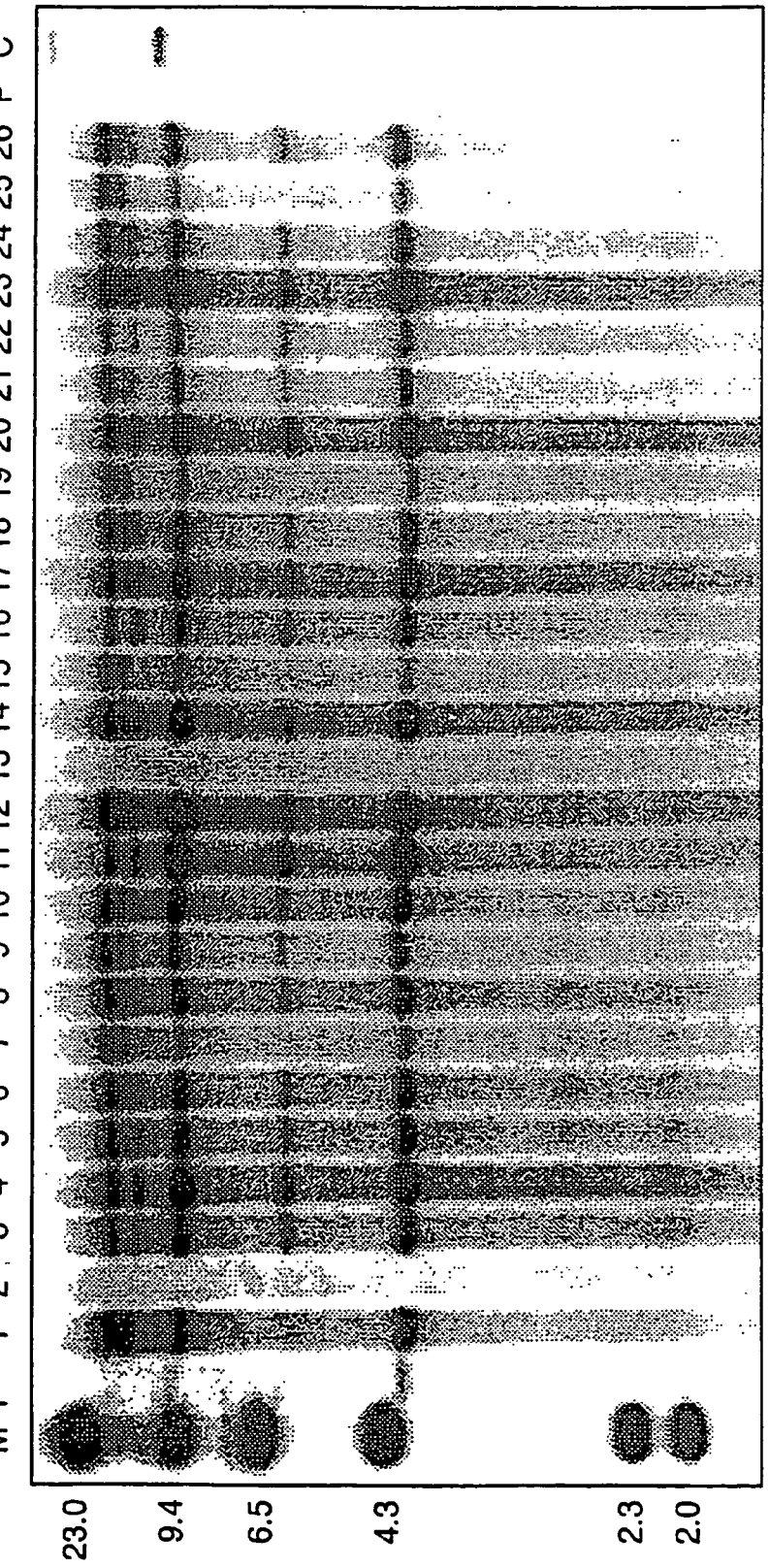
FIG. 35 is a Southern blot of 26 progeny plants of transformant BW 119 which had been transformed with pAHC25.

The plasmid pAHC25 (Christensen and Quail, 1996) was transformed into wheat as described in previous sections. Transformants were selected on the basis of resistance to phosphinothricin. Southern blot analyses were carried out on the primary transformants to confirm integration of the plasmid sequences (data not shown). GUS histochemical analyses were also carried out and demonstrated that the ubiquitin promoter is capable of mediating high levels of GUS expression in a range of wheat tissues. FIGS. 34A, B, C & D show histochemical localisation of GUS expression in the seed, stem, floral and leaf tissues respectively. Southern blot and GUS histochemical analyses were also carried out on self progeny from primary transformants to confirm that the transformation system used is capable of producing transgenic plants which stably transmit the integrated plasmid sequences to progeny plants. FIG. 35 shows a Southern blot of 26 progeny plants of transformant BW119 which had been transformed with pAHC25. In this example genomic DNA from the progeny plants was digested with the restriction enzyme Sac1 and the blot was probed with the GUS gene coding sequence. The Southern blot results are suggestive of the presence of two independently segregating integration loci, each comprising concatamers of pAHC25 plasmid sequences.

Evaluation of the Maize Waxy Promoter for Endosperm-Specific Expression of Associated Transgenes.

The plasmids pWxGS+ and pUN1 were co-transformed into wheat as described in previous sections. Transformants were selected on the basis of resistance to geneticin. Southern blot analyses were carried out on the primary transformants to confirm integration of the plasmid sequences (data not shown). Gus histochemical analyses were also carried out to determine the expression profile mediated by the maize waxy promoter. The majority of the transformants that expressed GUS exhibited expression specifically in endosperm tissue, demonstrating the suitability of this promoter for mediating endosperm expression of associated transgenes. FIG. 36A & B shows endosperm specific expression of GUS in seeds from two independent transformants. We did not observe GUS expression in pollen grains as was seen by Russell and Fromm (1997), however the construct they used also incorporated the maize hsp 70 intron which may conceivably have influenced expression both quantitatively and qualitatively.

Transformation of Wheat With Starch Gene Constructs.

Figure 37:
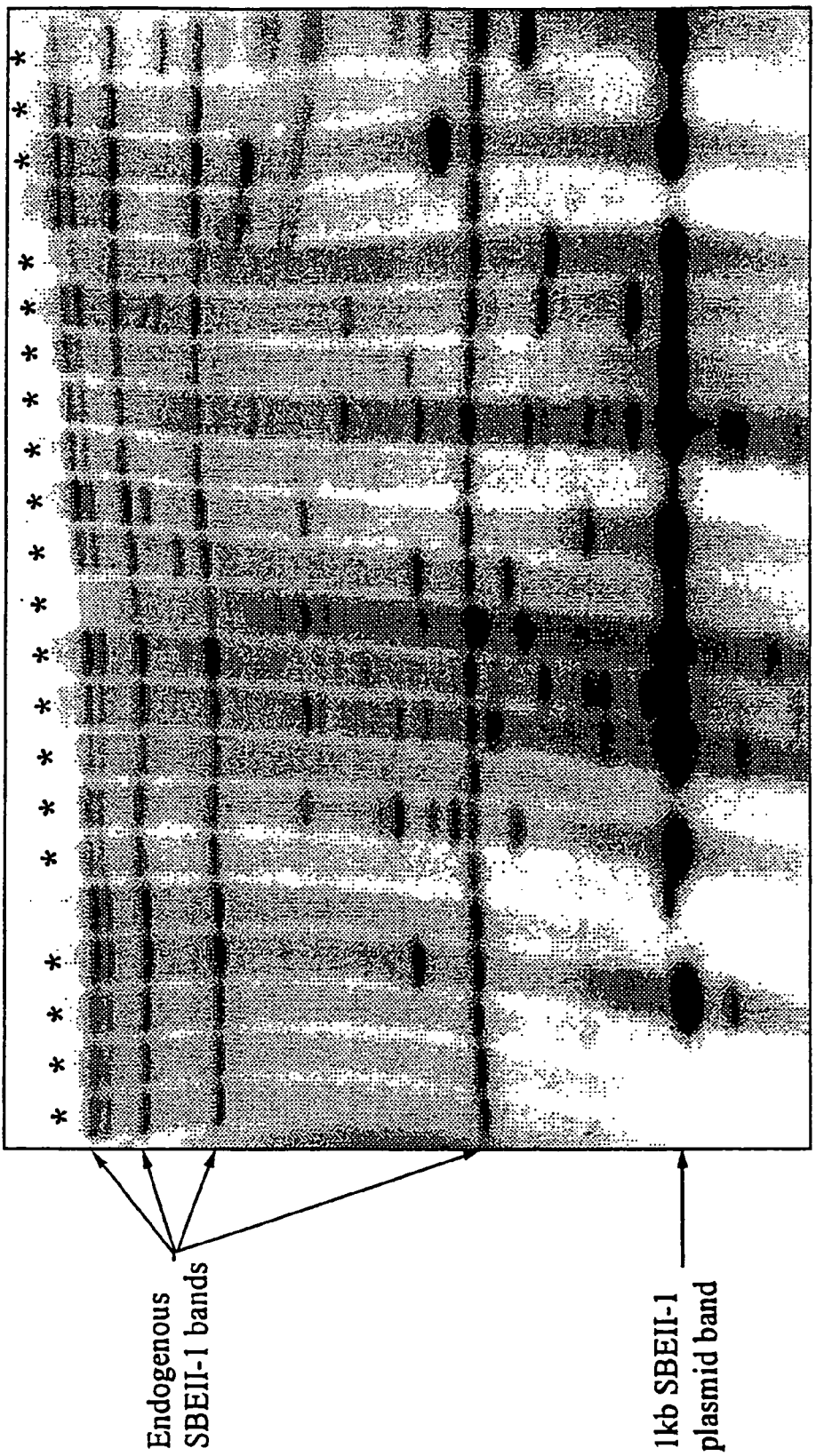
FIG. 37 is a Southern blot of genomic DNA of putative primary transformants digested with Sac1 and probed with the 1 kb Sac1 SBEII-1 probe.

The various construct combinations detailed in Table 2 were co-transformed into wheat using the procedures as described in previous sections. Transformants were selected on the basis of resistance to geneticin. The primary transformants were confirmed positive by Southern blot analysis. Blots were sequentially probed with an NptII coding sequence probe and a SBE coding region probe. FIG. 37 shows an example of a Southern blot which comprises 22 putative transformants which had been co-bombarded with pSR97-29A- or pSR97-26A- and pUN1 or p97-2BdUN1. Genomic DNAs on this blot had been digested with Sac1. The blot was first probed with the NptII probe. Lanes marked with an asterisk correspond to transformants which give a positive signal with the NptII probe. The blot shown in FIG. 37 was probed with the SBEII-1 1 kb Sac1 fragment. The Sac1 digest is expected to release a 1 kb SBEII-1 hybridising band from both pSR97-29A- and pSR97-26A- plasmid sequences, and the intensity of this band will vary depending on the copy number of inserted plasmid sequences. As can be seen in FIG. 37 several additional SBEII-1 hybridising bands are also observed. Five of these bands are present in all lanes and result from hybridisation to endogenous wheat SBEII-1 sequences. The additional bands of varying size which are observed in the majority of lanes which show the 1 kb hybridising band most likely result from integration events in which one or more copies of the plasmid had been linearised within the 1 kb SBEII-1 sequence prior to integration. In the example shown in FIG. 37, of the 20 NptII positive plants, 16 were found to be co-transformed with the SBEII-1 sequences, representing a co-transformation efficiency of 80%.

Differential Scanning Calorimetry (DSC)

When heated, an aqueous suspension of starch in excess water undergoes a co-operative endothermic transition known as gelatinisation, as discussed above, entailing a melting of the starch crystallites. Differential scanning calorimetry (DSC) measures the amount of energy (heat) absorbed or released by a sample as it is heated, cooled or held in a constant (isothermal) temperature. DSC has been widely used to study the gelatinisation and retrogradation of starch.

DSC analyses were carried out on single grains or pools of 5 grains from primary transformants generated through transformation using each of the gene construct combinations detailed in Table 2.

Two different sample preparation and DSC methodologies were used:

Method 1:

Individual seed samples were crushed and ground using a pestle and mortar. The resulting bran was then separated and samples weighed into 50 µm aluminium DSC pans. Water, three times by weight, was added and the sample pans sealed. Analyses were performed using a Perkin-Elmer DSC-7 Robotic™ system equipped with an Intercooler II™, for sub-ambient conditions. Samples were heated from 25° C. to 80° C. at a heating rate of 5° C. min$^{-1}$. Gelatinisation enthalpy, onset and peak and end temperatures were recorded. The thermograms were analysed using the Perkin-Elmer software programs (Thermal Analysis Software 7). Gelatinisation enthalpy is expressed in Joules (J)/gram (g) of sample.

Method 2:

Pools of 5 seeds from a single primary transformant, or single seeds from primary transformants, were milled using a Cemotec 1090™ Sample Mill. The milled sample was then passed through a 250 micron sieve to separate the bran from endosperm. Approximately 5 mg of the sieved samples was then accurately weighed into 50 μl aluminium DSC pans. Water, three times by weight, was added and the sample pans sealed. Analyses were performed using a Perkin-Elmer Pyris 1™ DSC equipped with autosampler and Intracooler IP. Samples were heated from 40° C. to 85° C. at a heating rate of 10° C. per minute. The thermograms were analysed using the Perkin-Elmer software programs (Pyris Software for Windows v 3.5). Gelatinisation enthalpy, onset and peak and end temperatures were recorded.

Using method 1, DSC analyses were performed on individual mature grains of primary transformants, transformed with the plasmid combinations pSR97-26A-/pUN1, pSR97-26A-/p97-2BdUN1 and pSR97-29A-/p97-2BdUN1. Data obtained were compared to data from control material which had been transformed with one of the NptII selectable marker plasmids, but did not contain any of the 'starch' plasmids. Table 3 summarises the average onset, peak, end and enthalpy values for the selected material. The majority of samples showed similar values to the control material. However, as can be seen from Table 3 onset, peak and end temperatures were higher for a number of the transgenic samples compared to the control material. For example, transformant BW 326 exhibits a 6.7° C., 4.9° C. and 4.6° C. increase in onset, peak and end temperatures (respectively) compared to the control sample.

Using method 2 a further series of DSC analyses were carried out on pools of 5 grains from primary transformants, transformed with the plasmid combinations pSC98–1A-/p97-2BdUN1, pUSN-1/p97-2BdUN1, pUSN-2/p97-2BdUN1 and pUSN-1/pUSN-2/pUN1. obtained were compared to data from control material which had been transformed with one of the NptII selectable marker plasmids, but did not contain any of the 'starch' plasmids. Table 4 summaries the onset, peak, end and enthalpy values for the selected pooled samples. In many cases there is evidence that the 'starch' transgenic material shows onset, peak and end temperatures which are greater than those observed for the control material. For example, transformant BW727 exhibits a 9.8° C., 8.7° C. and 9.1° C. increase in onset, peak and end temperatures (respectively) compared to the BW control sample 3, and a 7.6° C., 6.8° C. and 7.8° C. increase in onset, peak and end temperatures (respectively) compared to the BW control sample 2.

TABLE 3

Results of DSC analyses on single grains using method 1. Data shown are the averages of between 2 and 6 individual grain samples ($T_o$, $T_p$ and $T_f$ are onset, peak and end temperatures respectively).

| Plasmid combination | Line Code | $T_o$ (° C.) | $T_p$ (° C.) | $T_f$ (° C.) | ΔH (J/g) |
|---|---|---|---|---|---|
| BW control sample 1 | | 55.2 | 59.7 | 66.5 | 4.66 |
| pSR97-26A-/pUN1 | BW283 | 57.1 | 60.4 | 65.0 | 2.12 |
| | BW135 | 57.2 | 62.1 | 68.6 | 4.86 |
| | BW324 | 57.8 | 62.1 | 69.1 | 5.33 |
| | BW325 | 58.4 | 61.8 | 68.7 | 3.90 |
| | BW326 | 61.9 | 64.6 | 71.1 | 2.46 |
| | BW348 | 60.7 | 63.4 | 69.7 | 3.76 |
| pSR97-26A-/p97-2BdUN1 | F227 | 57.4 | 61.4 | 67.3 | 2.65 |
| pSR97-29A-/p97-2BdUN1 | F310 | 62.1 | 63.7 | 69.2 | 6.75 |
| | F312 | 59.0 | 62.3 | 66.8 | 1.16 |
| | BW335 | 56.2 | 60.8 | 69.1 | 4.63 |
| | BW353 | 59.5 | 62.7 | 70.8 | 3.21 |
| | BW354 | 55.4 | 61.7 | 68.9 | 4.28 |
| | BW355 | 57.9 | 61.5 | 68.0 | 3.95 |
| | BW357 | 55.3 | 60.6 | 68.0 | 3.74 |
| | BW363 | 56.7 | 62.5 | 67.9 | 1.13 |
| | BW367 | 59.0 | 62.5 | 68.2 | 2.17 |
| | BW369 | 57.9 | 60.9 | 65.9 | 1.04 |
| | BW370 | 53.7 | 59.4 | 67.5 | 6.00 |
| | BW375 | 57.2 | 61.5 | 70.0 | 4.14 |
| | BW376 | 54.0 | 58.1 | 68.0 | 3.39 |
| | BW377 | 53.4 | 60.9 | 69.2 | 2.60 |
| | BW380 | 54.6 | 61.6 | 67.6 | 2.16 |
| | BW390 | 56.8 | 61.2 | 68.5 | 1.29 |
| | BW399 | 57.4 | 62.7 | 67.9 | 1.77 |
| | BW400 | 60.6 | 63.6 | 68.1 | 0.64 |
| | BW341 | 51.6 | 59.0 | 66.4 | 1.97 |

TABLE 4

Results of DSC analyses on pools of 5 grains using method 2. $T_o$, $T_p$ and $T_f$ are onset, peak and end temperatures respectively

| Plasmid combination | Line Code | $T_o$ (° C.) | $T_p$ (° C.) | $T_f$ (° C.) | ΔH (J/g) |
|---|---|---|---|---|---|
| F control sample 1 | | 60.1 | 63.9 | 68.0 | 6.30 |
| BW control sample 2 | | 59.3 | 64.0 | 68.4 | 5.94 |
| BW control sample 3 | | 57.08 | 62.09 | 67.08 | 4.28 |
| pSC98-1A-/p97-2BdUN1 | BW449 | 59.3 | 62.9 | 67.9 | 3.95 |
| | BW477 | 57.7 | 63.6 | 70.6 | 8.30 |
| | F492 | 62.3 | 66.4 | 70.2 | 7.60 |
| | F494 | 63.6 | 67.3 | 71.0 | 5.73 |
| | BW511 | 59.6 | 63.8 | 67.2 | 0.98 |
| | BW518 | 60.2 | 64.9 | 69.2 | 3.57 |
| | BW519 | 58.4 | 63.6 | 68.5 | 4.13 |
| | BW527 | 58.7 | 63.7 | 69.0 | 6.38 |
| | BW549 | 59.9 | 64.8 | 69.3 | 4.48 |
| | BW550 | 60.2 | 64.6 | 68.9 | 5.06 |
| | BW552 | 60.8 | 62.9 | 67.9 | 3.74 |
| | BW553 | 59.5 | 63.9 | 67.5 | 3.60 |
| | BW555 | 61.0 | 66.1 | 68.2 | 5.43 |
| | BW557 | 62.7 | 66.9 | 71.0 | 5.08 |
| | BW559 | 61.6 | 65.9 | 70.8 | 5.08 |
| | BW563 | 61.4 | 65.1 | 69.4 | 1.90 |
| | BW564 | 59.4 | 64.5 | 73.2 | 7.08 |
| | BW576 | 61.8 | 65.6 | 69.3 | 2.65 |
| | BW587 | 61.3 | 65.4 | 69.4 | 5.36 |
| | BW614 | 63.9 | 67.9 | 71.8 | 5.83 |
| | BW618 | 61.3 | 65.6 | 69.7 | 3.54 |
| | BW583a | 58.9 | 63.7 | 68.0 | 3.54 |
| | BW631 | 61.5 | 65.6 | 69.7 | 4.52 |
| | BW633 | 61.9 | 66.0 | 70.2 | 5.12 |
| | BW634a | 60.8 | 64.9 | 70.2 | 5.10 |
| | BW637a | 62.8 | 67.2 | 72.0 | 5.16 |
| | BW639 | 61.8 | 65.1 | 68.9 | 2.15 |
| | BW640a | 62.2 | 66.7 | 71.0 | 3.23 |
| | BW642 | 63.2 | 67.2 | 70.9 | 4.90 |
| | BW698 | 62.9 | 67.0 | 70.9 | 4.48 |
| | BW700a | 63.8 | 67.6 | 71.2 | 3.41 |
| | BE524a | 59.4 | 64.3 | 68.9 | 4.05 |
| pUSN-1/p97-2BdUN1 | BW622 | 59.0 | 64.1 | 68.7 | 4.32 |
| | BW628 | 56.2 | 63.3 | 66.0 | 6.09 |
| | BW645 | 57.5 | 65.6 | 69.5 | 5.97 |

TABLE 4-continued

Results of DSC analyses on pools of 5 grains using method 2. $T_o$, $T_p$ and $T_f$ are onset, peak and end temperatures respectively

| Plasmid combination | Line Code | $T_o$ (° C.) | $T_p$ (° C.) | $T_f$ (° C.) | ΔH (J/g) |
|---|---|---|---|---|---|
| | BW646 | 61.6 | 66.4 | 67.7 | 3.99 |
| | BW647 | 61.3 | 65.4 | 69.0 | 3.47 |
| | BW648 | 59.8 | 64.4 | 68.8 | 4.65 |
| | BW649 | 61.3 | 65.6 | 70.1 | 5.07 |
| | BW656 | 59.9 | 64.6 | 69.2 | 5.38 |
| | BW660 | 62.0 | 67.3 | 71.0 | 4.23 |
| | BW661 | 61.5 | 65.8 | 69.6 | 3.88 |
| | BW664 | 61.1 | 66.1 | 70.8 | 4.81 |
| | BW665 | 61.6 | 66.5 | 69.4 | 5.25 |
| | BW667 | 63.0 | 67.1 | 70.8 | 3.91 |
| | BW672 | 63.0 | 68.1 | 71.9 | 5.43 |
| | BW673A | 63.1 | 67.7 | 71.6 | 4.83 |
| | BW675 | 62.1 | 66.4 | 71.3 | 10.97 |
| | BW676 | 59.8 | 67.3 | 71.2 | 4.21 |
| | BW678 | 63.0 | 66.3 | 69.3 | 1.20 |
| | BW680 | 60.8 | 65.3 | 70.1 | 4.94 |
| | BW701 | 62.3 | 67.5 | 72.2 | 4.70 |
| | BW706 | 63.0 | 67.3 | 71.3 | 4.94 |
| | BW707 | 60.9 | 65.8 | 70.0 | 4.77 |
| | BW708 | 61.7 | 65.5 | 68.8 | 6.11 |
| | BW726 | 62.6 | 67.5 | 71.3 | 5.44 |
| | BW755 | 60.8 | 65.8 | 70.6 | 5.18 |
| | BW702 | 61.9 | 67.0 | 71.0 | 4.44 |
| | BW756 | 62.3 | 66.1 | 69.7 | 4.83 |
| pUSN-2/p97-2BdUN1 | BW625 | 62.7 | 68.2 | 73.8 | 4.27 |
| | BW653 | 60.4 | 65.3 | 70.1 | 6.52 |
| | BW704 | 60.9 | 66.2 | 70.2 | 4.19 |
| | BW718 | 61.3 | 66.9 | 71.2 | 4.15 |
| | BW719 | 62.2 | 67.2 | 71.7 | 5.32 |
| | BW722 | 64.8 | 67.5 | 70.0 | 2.14 |
| | BW740 | 63.4 | 67.9 | 72.3 | 5.67 |
| | BW741 | 62.6 | 66.9 | 70.5 | 5.30 |
| | BW742 | 64.6 | 67.9 | 72.0 | 6.66 |
| | BW752 | 62.3 | 66.3 | 70.0 | 4.63 |
| pUSN-1/pUSN-2/pUN1 | BW685 | 62.6 | 65.5 | 69.0 | 2.60 |
| | BW686A | 61.9 | 66.3 | 70.2 | 4.45 |
| | BW714 | 63.0 | 67.6 | 71.3 | 3.53 |
| | BW727 | 66.9 | 70.8 | 76.2 | 5.19 |
| | BW728 | 62.0 | 66.3 | 70.4 | 5.70 |
| | BW731 | 63.3 | 67.9 | 73.0 | 4.90 |
| | BW732 | 63.5 | 66.8 | 70.8 | 4.11 |
| | BW748 | 62.1 | 67.4 | 71.9 | 5.38 |
| | BW794 | 62.8 | 67.5 | 71.8 | 5.17 |

APPENDIX 1

| Constituent | Volume of stock per liter of 2x concentrated media |
|---|---|
| Recipe for 2x concentrated MM1 media | |
| Macrosalts MS (10X stock) | 200 ml |
| Microsalts L (1000x stock) | 2 ml |
| FeNaEDTA MS (100x stock) | 20 ml |
| [Sigma catalogue F-0518] | |
| Modified Vits MS (x1000) | 1 ml |
| 3 amino acid solution (25x stock) | 40 ml |
| myo inositol | 0.2 g |
| (Sigma catalogue number I-3011) | |
| sucrose | 180 g |
| AgNO$_3$ (20 mg/ml stock) | 1 ml |
| Added after filter sterilisation | |
| Picloram (1 m/ml stock) | 4 ml |
| Added after filter sterilisation | |
| Filter sterilise and add to an equal volume of moulten 2x agargel (10 g/L). | |
| Recipe for 2x concentrated R media | |
| Macrosalts L7 (10X stock) | 200 ml |
| Microsalts L (1000x stock) | 2 ml |

APPENDIX 1-continued

| Constituent | Volume of stock per liter of 2x concentrated media |
|---|---|
| FeNaEDTA MS (100x stock) | 20 ml |
| Vits/Inositol L2 (200x stock) | 10 ml |
| 3 amino acid solution (25x stock) | 40 ml |
| Maltose | 60 g |
| 2,4-D (1 mg/ml stock) | 200 μl |
| added after filter sterilisation | |
| Zeatin cis trans mixed isomers | 2 ml |
| (Melford labs catalogue no. Z-0917) | |
| (5 mg/ml stock) added after filter | |
| sterilisation | |
| Filter sterilise and add to an equal volume of moulten 2x agar (16 g/liter) | |

APPENDIX 2

Recipes for constituents of MM1 and R media

Microsalts L (1000x stock)

| | per 100 ml |
|---|---|
| MnSO$_4$•7H$_2$O | 1.34 g |
| H$_3$BO$_3$ | 0.5 g |
| ZnSO$_4$•7H$_2$O | 0.75 g |
| KI | 75 mg |
| Na$_2$MoO$_4$•2H$_2$O | 25 mg |
| CuSO$_4$•5H$_2$O | 2.5 mg |
| CoCl$_2$•6H$_2$O | 2.5 mg |

Filter sterilise through a 22 μm membrane filter
Store at 4° C.

Macrosalts MS (10X stock)

| | per liter |
|---|---|
| NH$_4$NO$_3$ | 16.5 g |
| KNO$_3$ | 19.0 g |
| KH$_2$PO$_4$ | 1.7 g |
| MgSO$_4$•7H$_2$O | 3.7 g |
| CaCl$_2$•2H$_2$O | 4.4 g |

NB: Dissolve CaCl$_2$ before mixing with other components
NB: Make up KH$_2$PO$_4$ separately in sterile H$_2$0, and add last.
Store solution at 4° C. after autoclaving Modified MS Vits (1000x stock)

| | Per 100 ml |
|---|---|
| Thiamine HCl | 10 mg |
| Pyridoxine HCl | 50 mg |
| Nicotinic acid | 50 mg |

Store solution in 10 ml aliquots at −20° C.

3 amino acid solution (25x stock)

| | Per liter |
|---|---|
| L-Glutamine | 18.75 g |
| L-Proline | 3.75 g |
| L-Asparagine | 2.5 g |

Store solution in 40 ml aliquots at −20° C.

Macrosalts L7 (10x stock)

| | per liter |
|---|---|
| NH$_4$NO$_3$ | 2.5 g |
| KNO$_3$ | 15.0 g |
| KH$_2$PO$_4$ | 2.0 g |

APPENDIX 2-continued

Recipes for constituents of MM1 and R media

| | |
|---|---|
| MgSO$_4$•7H$_2$O | 3.5 g |
| CaCl$_2$•2H$_2$O | 4.5 g |

NB: Dissolve CaCl$_2$ before mixing with other components
NB: Make up KH$_2$PO$_4$ separately in 50 ml H$_2$0 and add last
Store solution at 4° C. after autoclaving Vits/Inositol (200x stock)

| 200x Stock | Per 100 ml |
|---|---|
| Inositol | 4.0 g |
| Thiamine HCl | 0.2 g |
| Pyridoxine HCl | 0.02 g |
| Nicotinic acid | 0.02 g |
| Ca-pantothenate | 0.02 g |
| Ascorbic acid | 0.02 g |

Store solution in 40 ml aliquots at −20° C.

REFERENCES

Atwell, W. A., Hood, L. F., Lineback, D. R., VarriaDo-Marston, E., and Zobel, H. F. (1988). The terminology and methodology associated with basic starch penomena. Cereal Foods World 33, 306–311.

Baba, T., Kimura, K., Mizuno, K., Etoh, H., Ishida, Y., Shida, O., and Arai, Y. (1991). Sequence conservation of the catalytic regions of amylolytic enzymes in maize branching enzyme-I. Biochem. Biophys. Res. Comm. 181(1): 87–94.

Barcelo P., and Lazzeri, P. (1995). Transformation of cereals by microprojectile bombardment of immature inflorescence and scutellum tissues. Methods in Molecular Biology—Plant Gene Transfer and Expression Protocols (vol 49), 113–123. Jones H [ed] Humana Press Inc., Totowa, N.J.

Block, M. de et al. (1987). EMBO J 6:2513–2518

Boyer, C. D. and Priess, J. (1978). Multiple forms of (1-4)-α-D-Glucan, (1-4)-α-D-Glucan 6-glycosyl transferase from developing Zea mays L. kernals. Carbohydrate Res 61:321–334.

Burton, R. A., Bewley; J. D., Smith, A. M., Bhattacharyya, M. K., Tatge, H., Ring, S., Bull, V., Hamilton, W. D. O., and Martin, C. (1995). Starch branching enzymes belonging to distinct enzyme families are differentially expressed during pea embryo development. Plant J 7:1–13

Christensen, A. H., and Quail, P. H. (1996). Transgenic research, 5:213–218.

Donovan, J. W. (1979). Phase transitions of the starch-water system. Biopolym. 18, 263–275.

Fisher, D. K., Boyer, C. D., and Hannah, L. C. (1993). Starch branching enzyme II from maize endosperm. Plant Physiol. 102:1045–1046.

Fisher, D. K., Gao, M., Kim, K-N., Boyer, C. D., and Guiltinan, M. J. (1996). Two closely related cDNAs encoding starch branching enzyme from Arabidopsis thaliana. Plant Mol. Biol. 30:97–108

Fromm M E, Taylor L P & Walbot V. (1986). Stable transformation of maize after gene transfer by electroporation. Nature 319: 791–793, Fulton, T. M., Chunwongse, J., and Tanksley, S. D. (1995). Miniprep Protocol for Extraction of DNA from Tomato and other Herbaceous Plants, Plant Molecular Biology Reporter, 13 (3), pages 225–227.

Gao, M., Fisher, D. K., Kim, K-N., Shannon, J. C., and Guiltinan, M. J. (1997). Independent genetic control of maize starch-branching enzymes IIa and IIb: Isolation and characterisation of a Sbe2a cDNA. Plant Physiol. 114: 69–78.

Gaun, H. P., and Preiss, J. (1993). Differentiation of the properties of the branching isoenzymes from maize (Zea mays). Plant Physiol. 102: 1269–1273.

Goldsbrough A P, Beizile F, Yoder J I (1994). Complementation of the tomato anthocyanin without (αw) mutant using the dihydroflavonol 4-reductase gene. Plant Physiology 105, 491–496.

Islam, A. K. M. R. (1983). Ditelosomic additions of barley chromosomes to wheat. In Proc. 6th Int. Wheat Genet. Symp. 233–238. Kyoto, Japan.

Jack, P. L., Dimitrijevic, T. A. F., and Mayes S. (1994) Assessment of nuclear, mitochondrial and chloroplast RFLP markers in oil palm (Elaris guineensis Jacq.) Theor. Appl. Genet. 90:643–649.

Jefferson R A (1987). Assaying chimaeric genes in plants: The GUS gene fusion system. Plant Molecular Biology Reporter 5 (4) 387–405.

Kennedy, J. F. and Cabalda, V. M. B. (1991). Bioactive carbohydrates in food. Chemistry in Britain, November, 1017–1019, 1026.

Khoshnoodi, J., Ek, B., Rask, L., and Larsson, H. (1993). Characterisation of the 97 and 103 kDa forms of starch branching enzyme from potato tubers. FEBS 332 (1,2): 132–138.

Kossmann, J., Vimser, R. G. F., Muller-Rober, B., Willmitzer, L., and Sonnewald, U. (1991). Cloning and expression anayslis of a potato cDNA that encodes branching enzyme: evidence for co-expression of starch biosynthetic genes. Mol. Gren. Genet 230: 39–44.

Liu et al (1995). Biochem Cell Biol 73: 19–30.

Martin, C., and Smith, A. M. (1995). Starch biosynthesis. Plant Cell 7:971–985.

Matzke & Matzke (1995). Plant Physiol. 107, 679–685.

Mizuno, K., Kawasaki, T., Shinada, H., Satoh, H., Kobayashi, E., Okumura, S., Arai, Y., and Baba, T. (1993). Alteration of the structural properties of starch components by the lack of an isoform of starch branching enzyme in rice seeds. J. Biol. Chem. 268(25): 19084–19091.

Morell, M. K., Rahman, S., Abrahams, S. L., and Appels, R. (1995). The biochemistry and molecular biology of starch synthesis in cereals. Auist. J. Plant Physiol. 22: 647–660.

Morell, M., Blennow, A., Kosar-Hashermi, B., and Samuel, M. S. (1997). Differential expression and properties of starch branching enzyme isoforms in developing wheat endosperm. Plant Physiol. 113:201–208.

Mousley, C. G. (1994). PhD Thesis, Wye College, University of London.

Nair, R. B., Baga, M., Scoles, G. J., Kartha, K. K., and Chibbar, R. N. (1997). Isolation, characterisation and expression analysis of a starch branching enzyme II cDNA from wheat. Plant Sci. 122:153–163.

Nakamura, Y., Takeichi, T., Kawaguchi, K., and Yamanouchi, H. (1992). Purification of two forms of starch branching enzyme (Q-ernme) from developing rice endosperm. Physiol. Plant 84: 329–335.

Nakamura, Y., and Yamanouchi, H. (1992). Nucleotide sequence of a cDNA encoding starch-branching enzyme, or Q-enzyme I, from rice endosperm. Plant Physiol. 99:1265–1266.

Preiss, J. (1991). Biology and molecular biology of starch synthesis and regulation. In Oxford Surveys Plant Mol. Cell Biol. 7:59–114.

Rahman, S., Abrahams, S., Abbott, D., Mukai, Y., Samuel, M., Morrell, M., and Appels, R. (1997). A complex arrangement of genes at a starch branching enzyme I locus in the D-genome donor of wheat. Genome 40:465–474.

Rapellin, A et al 1997. Isolation of a starch branching enzyme I cDNA from a wheat endosperm library. EMBL database accession Y12320.

Russell, D. A. and Fromm, M. E. (1977). Tissue-specific expression in transgenic maize of four endosperm promoters from maize and rice. Transgenic Research 6: 157–168.

Sambrook J, Fritsch E F, Maniatis T (1989) Molecular Cloning: A Laboratory Manual, 2nd ed. Cold Spring Harbour Laboratory Press, Cold Spring Harbour, N.Y.

Salehuzzaman, S. N. I. M., Jacobsen, E., and Visser, R. G. F. (1992). Cloning, partial sequencing and expression of a cDNA coding for branching enzyme in cassava. Plant Mol. Biol. 20:809–819.

Sears, E. R. (1966). In Chromosome manipulations and plant genetics Edited by R. Riley and K. R. Lavis, Oliver and Boyd, Edinburgh. pp29–45.

Sheehy et al (1988) PNAS 85, 9905–8809.

Smith, A. M. (1988). Major differences in isoforms of starch-branching enzyme between developing embryos of round- and wrinkled-seeded peas (*Pisum sativum* L.). Planta 175:270–279.

Shure, M et al 1983. Cell 35: 225–233.

Sun, C., Sathish, P., Deiber, A., and Jansson, C. (1995). Multiple starch branching enzymes in barley endosperm. In Photosynthesis from light to biosphere. P. Mathis (ed.) Vol. V:317–320.

Sun, C., Sathish, P., Ahlandsberg, S., and Jansson, C. (1998). The two genes encoding starch-branching enzymes IIa and IIb are differentially expressed in Barley. Plant Physiol. 118:37–49 (earliest electronic publication date 10th Sep. 1998).

Svegmark, K. and Hermansson, A-M. (1990). Shear induced changes in the viscoelastic behaviour of heat treated potato starch dispersions. Carboyd. Polym. 13, 29–45.

Takeda, Y., Gaun, H. P., and Preiss, J. (1993). Branching of amylose by the branching isoenzymes of maize endosperm. Carbohydrate Res. 240:252–263.

Van der Krol et al, Mol Gen. Genet. 220, 204–212.

---

The invention claimed is:

1. An isolated nucleotide sequence comprising SEQ ID NO:3.

2. A nucleic acid construct comprising a nucleotide sequence comprising SEQ ID NO:3.

3. A construct according to claim 2, wherein the sequence is operably linked, in sense or antisense orientation, to a promoter sequence.

4. An expression vector comprising a construct according to any one of claims 2 or 3.

5. A host cell into which has been introduced a construct according to any one of claims 2 or 3.

6. A method of altering the starch characteristics of a wheat plant, comprising introducing into the genome of the wheat plant a sequence comprising SEQ ID NO:3 operably linked to a suitable promoter which is active in the wheat plant.

7. A method according to claim 6, wherein the sequence is linked in the antisense orientation to the promoter.

8. A method according to any one of claims 6 or 7, wherein the altered starch characteristics relate to the starch content and/or starch composition of the plant.

9. A wheat plant, or progeny of said wheat plant, altered by the method of any one of claims 6 or 7 and comprising the introduced sequence.

10. A part or cell of a wheat plant according to claim 9.

11. A storage organ from a wheat plant according to claim 9.

12. A wheat plant according to claim 9, or part or cell thereof, containing starch having an elevated gelatinisation onset and/or peak temperature as measured by DSC compared to starch from an unaltered plant.

13. A method of making altered starch, comprising altering a wheat plant by the method of any one of claims 6 or 7, and extracting therefrom starch having altered properties compared to starch extracted from unaltered wheat plants.

* * * * *